(12) United States Patent
Bretschneider et al.

(10) Patent No.: US 8,946,124 B2
(45) Date of Patent: Feb. 3, 2015

(54) SUBSTITUTED 3-(BIPHENYL-3-YL)-8,8-DIFLUORO-4-HYDROXY-1-AZASPIRO[4.5]DEC-3-EN-2-ONES FOR THERAPY AND HALOGEN-SUBSTITUTED SPIROCYCLIC KETOENOLS

(75) Inventors: Thomas Bretschneider, Lohmar (DE); Reiner Fischer, Monheim (DE); Stefan Lehr, Lyons (FR); Elmar Gatzweiler, Bad Nauheim (DE); Ulrich Görgens, Ratingen (DE); Isolde Häuser-Hahn, Leverkusen (DE); Ines Heinemann, Hofheim (DE); Arnd Voerste, Köln (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/000,147

(22) PCT Filed: Feb. 14, 2012

(86) PCT No.: PCT/EP2012/052521
§ 371 (c)(1),
(2), (4) Date: Oct. 28, 2013

(87) PCT Pub. No.: WO2012/110519
PCT Pub. Date: Aug. 23, 2012

(65) Prior Publication Data
US 2014/0045696 A1    Feb. 13, 2014

Related U.S. Application Data

(60) Provisional application No. 61/443,852, filed on Feb. 17, 2011.

(30) Foreign Application Priority Data

Feb. 17, 2011 (EP) ...................... 11154805
Aug. 4, 2011 (DE) .......................... 10 2011 080 405

(51) Int. Cl.
*A01N 43/08* (2006.01)
*A01N 43/38* (2006.01)
*C07D 209/54* (2006.01)
*C07D 307/94* (2006.01)
(Continued)

(52) U.S. Cl.
CPC .............. *A01N 43/38* (2013.01); *C07D 209/54* (2013.01); *A61K 31/403* (2013.01); *A61K 45/06* (2013.01); *A01N 43/12* (2013.01)
USPC ............ 504/138; 504/140; 548/408; 549/265

(58) Field of Classification Search
CPC .............................. C07D 209/54; C07D 307/94
USPC .................... 548/408; 549/265; 504/138, 140
See application file for complete search history.

(56) References Cited

U.S. PATENT DOCUMENTS 2,842,476 A    7/1958  Schreiber
4,245,432 A    1/1981  Dannelly
(Continued)

FOREIGN PATENT DOCUMENTS

AL     521334 A1    1/1993
CA    1165071       2/1984
(Continued)

OTHER PUBLICATIONS

"Addition Des Reactifs Nucleophiles Sur La Triple Liason Nitrile", Ann Chim., 1970, t. 5, No. 1, 11-27.
(Continued)

*Primary Examiner* — Shawquia Jackson
(74) *Attorney, Agent, or Firm* — Miles and Stockbridge

(57) ABSTRACT

The invention relates to novel compounds of the formula (I)

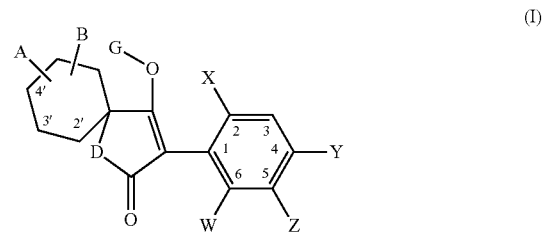

in which W, X, Y, Z, A, B, D and G have the meanings given above,
to a plurality of processes and intermediates for their preparation, and to their use as pesticides and/or herbicides and/or fungicides.
The invention also relates to selective herbicidal compositions comprising, firstly, the halogen-substituted spirocyclic ketoenols and, secondly, a crop plant compatibility-improving compound.
The present invention furthermore relates to the boosting of the action of crop protection compositions comprising, in particular, halogen-substituted spirocyclic ketoenols, through the addition of ammonium salts or phosphonium salts and optionally penetrants, to the corresponding compositions, to processes for producing them and to their application in crop protection as pesticides and/or fungicides and/or for preventing unwanted plant growth.
The invention also relates to substituted 3-(biphenyl-3-yl)-8,8-difluoro-4-hydroxy-1-azaspiro[4.5]dec-3-en-2-ones of the formula (Ia) for therapeutic purposes, to pharmaceutical compositions and to their use in therapy, in particular for the prophylaxis and therapy of tumor disorders.

13 Claims, 1 Drawing Sheet

(51) Int. Cl.
*A61K 31/403* (2006.01)
*A61K 45/06* (2006.01)
*A01N 43/12* (2006.01)

(56) References Cited

U.S. PATENT DOCUMENTS

| | | | |
|---|---|---|---|
| 4,272,417 A | 6/1981 | Barke |
| 4,623,727 A | 11/1986 | Hubele |
| 4,639,266 A | 1/1987 | Heubach |
| 4,808,430 A | 2/1989 | Kouno |
| 4,844,734 A | 7/1989 | Iwasaki |
| 4,881,966 A | 11/1989 | Nyffeler |
| 4,886,000 A | 12/1989 | Holter et al. |
| 4,888,049 A | 12/1989 | Iwasaki |
| 4,891,057 A | 1/1990 | Sohn |
| 4,902,340 A | 2/1990 | Hubele |
| 4,944,790 A | 7/1990 | Moser |
| 4,985,063 A | 1/1991 | Fischer et al. |
| 5,013,659 A | 5/1991 | Bedbrook |
| 5,045,560 A | 9/1991 | Fischer et al. |
| 5,094,681 A | 3/1992 | Kramer |
| 5,116,836 A | 5/1992 | Fischer et al. |
| 5,215,570 A | 6/1993 | Burckhardt |
| 5,225,434 A | 7/1993 | Bertram et al. |
| 5,258,527 A | 11/1993 | Krauskopf et al. |
| 5,262,383 A | 11/1993 | Fischer |
| 5,314,863 A | 5/1994 | Loher |
| 5,380,852 A | 1/1995 | Schutze |
| 5,401,700 A | 3/1995 | Sohn |
| 5,462,912 A | 10/1995 | Hioki |
| 5,462,913 A | 10/1995 | Fischer et al. |
| 5,500,367 A | 3/1996 | Hain |
| 5,504,057 A | 4/1996 | Fischer et al. |
| 5,508,436 A | 4/1996 | Fischer |
| 5,516,750 A | 5/1996 | Willms |
| 5,538,937 A | 7/1996 | Hasebe |
| 5,567,671 A | 10/1996 | Fischer et al. |
| 5,589,469 A | 12/1996 | Fischer et al. |
| 5,602,078 A | 2/1997 | Fischer et al. |
| 5,610,122 A | 3/1997 | Fischer |
| 5,616,536 A | 4/1997 | Fischer et al. |
| 5,622,917 A | 4/1997 | Fischer et al. |
| 5,677,449 A | 10/1997 | Fischer et al. |
| 5,683,965 A | 11/1997 | Bachmann |
| 5,689,046 A | 11/1997 | Schroder |
| 5,700,758 A | 12/1997 | Rosch |
| 5,705,476 A | 1/1998 | Hoffarth |
| 5,739,079 A | 4/1998 | Holdgrun |
| 5,759,837 A | 6/1998 | Kuhajda et al. |
| 5,792,755 A | 8/1998 | Sagenmuller |
| 5,811,374 A | 9/1998 | Bertram |
| 5,830,825 A | 11/1998 | Fischer |
| 5,830,826 A | 11/1998 | Fischer |
| 5,847,211 A | 12/1998 | Fischer et al. |
| 5,876,739 A | 3/1999 | Turnblad |
| 5,972,839 A | 10/1999 | Ziemer |
| 5,985,647 A | 11/1999 | Hain |
| 5,994,274 A | 11/1999 | Fischer et al. |
| 6,110,872 A | 8/2000 | Lieb et al. |
| 6,114,374 A | 9/2000 | Lieb et al. |
| 6,133,296 A | 10/2000 | Lieb et al. |
| 6,140,358 A | 10/2000 | Lieb et al. |
| 6,200,932 B1 | 3/2001 | Fischer et al. |
| 6,235,680 B1 | 5/2001 | Ziemer |
| 6,251,827 B1 | 6/2001 | Ziemer |
| 6,251,830 B1 | 6/2001 | Fischer et al. |
| 6,255,342 B1 | 7/2001 | Lieb et al. |
| 6,271,180 B2 | 8/2001 | Lieb et al. |
| 6,288,102 B1 | 9/2001 | Hagemann et al. |
| 6,316,486 B1 | 11/2001 | Lieb et al. |
| 6,358,887 B1 | 3/2002 | Fischer et al. |
| 6,359,151 B2 | 3/2002 | Lieb et al. |
| 6,380,246 B1 | 4/2002 | Lieb et al. |
| 6,388,123 B1 | 5/2002 | Lieb et al. |
| 6,417,370 B1 | 7/2002 | Lieb et al. |
| 6,451,843 B1 | 9/2002 | Lieb et al. |
| 6,469,196 B2 | 10/2002 | Fischer et al. |
| 6,472,419 B1 | 10/2002 | Fischer et al. |
| 6,486,343 B1 | 11/2002 | Lieb et al. |
| 6,504,036 B1 | 1/2003 | Lieb et al. |
| 6,511,942 B1 | 1/2003 | Turberg et al. |
| 6,589,976 B1 | 7/2003 | Fischer et al. |
| 6,596,873 B1 | 7/2003 | Lieb et al. |
| 6,602,823 B1 | 8/2003 | Röchling |
| 6,608,211 B1 | 8/2003 | Hagemann et al. |
| 6,645,914 B1 | 11/2003 | Woznica et al. |
| 6,670,488 B1 | 12/2003 | Hagemann et al. |
| 6,716,832 B2 | 4/2004 | Lieb et al. |
| 6,746,990 B2 | 6/2004 | Fischer et al. |
| 6,759,548 B2 | 7/2004 | Fischer et al. |
| 6,858,741 B2 | 2/2005 | Lieb et al. |
| 6,861,391 B1 | 3/2005 | Fischer et al. |
| 6,900,341 B2 | 5/2005 | Hagemann et al. |
| 6,933,261 B2 | 8/2005 | Lieb et al. |
| 6,939,888 B2 | 9/2005 | Fischer et al. |
| 7,105,471 B2 | 9/2006 | Lieb et al. |
| 7,109,370 B2 | 9/2006 | Hagemann et al. |
| 7,256,158 B2 | 8/2007 | Lieb et al. |
| 7,288,676 B2 | 10/2007 | Lieb et al. |
| 7,432,225 B2 | 10/2008 | Fischer et al. |
| 7,638,547 B2 | 12/2009 | Himmler et al. |
| 7,718,186 B2 | 5/2010 | Fischer et al. |
| 7,718,706 B2 | 5/2010 | Lieb et al. |
| 7,727,933 B2 | 6/2010 | Fischer et al. |
| 7,754,654 B2 | 7/2010 | Fischer et al. |
| 7,776,791 B2 | 8/2010 | Fischer et al. |
| 7,888,285 B2 | 2/2011 | Fischer et al. |
| 7,897,543 B2 | 3/2011 | Bretschneider et al. |
| 7,897,803 B2 | 3/2011 | Himmler et al. |
| 7,915,282 B2 | 3/2011 | Ruther et al. |
| 7,947,704 B2 | 5/2011 | Bretschneider et al. |
| 8,013,172 B2 | 9/2011 | Fischer et al. |
| 8,039,014 B2 | 10/2011 | Fischer et al. |
| 8,058,210 B2 | 11/2011 | Lieb et al. |
| 8,067,458 B2 | 11/2011 | Fischer et al. |
| 8,138,119 B2 | 3/2012 | Fischer et al. |
| 8,138,350 B2 | 3/2012 | Jeschke et al. |
| 8,173,697 B2 | 5/2012 | Fischer et al. |
| 8,193,120 B2 | 6/2012 | Ruther et al. |
| 8,314,254 B2 | 11/2012 | Fischer et al. |
| 8,334,300 B2 | 12/2012 | Ruther et al. |
| 8,383,853 B2 | 2/2013 | Fischer et al. |
| 8,389,443 B2 | 3/2013 | Fischer et al. |
| 8,410,289 B2 | 4/2013 | Fischer et al. |
| 8,435,549 B2 | 5/2013 | Fischer et al. |
| 8,507,537 B2 | 8/2013 | Fischer et al. |
| 2001/0004629 A1 | 6/2001 | Lieb et al. |
| 2002/0010204 A1 | 1/2002 | Lieb et al. |
| 2002/0022575 A1 | 2/2002 | Fischer et al. |
| 2002/0188136 A1 | 12/2002 | Lieb et al. |
| 2003/0045432 A1 | 3/2003 | Fischer et al. |
| 2003/0096806 A1 | 5/2003 | Lieb et al. |
| 2003/0144504 A1 | 7/2003 | Fischer et al. |
| 2003/0171219 A1 | 9/2003 | Lieb et al. |
| 2003/0176428 A1 | 9/2003 | Schneidersmann |
| 2003/0199572 A1 | 10/2003 | Lieb et al. |
| 2003/0216260 A1 | 11/2003 | Ruther et al. |
| 2003/0224939 A1 | 12/2003 | Miles |
| 2003/0228984 A1 | 12/2003 | Hagemann et al. |
| 2004/0019061 A1 | 1/2004 | Fischer et al. |
| 2004/0102327 A1 | 5/2004 | Hagemann et al. |
| 2004/0116744 A1 | 6/2004 | Furuya |
| 2004/0127365 A1 | 7/2004 | Lieb |
| 2004/0167031 A1 | 8/2004 | Lieb et al. |
| 2004/0224844 A1 | 11/2004 | Bickers |
| 2005/0009880 A1 | 1/2005 | Cottrell |
| 2005/0037922 A1 | 2/2005 | Bickers |
| 2005/0038021 A1 | 2/2005 | Lieb et al. |
| 2005/0049145 A1 | 3/2005 | Bickers |
| 2005/0054535 A1 | 3/2005 | Fischer et al. |
| 2005/0096386 A1 | 5/2005 | Cottrell |
| 2005/0164883 A1 | 7/2005 | Maetzke |
| 2005/0164885 A1 | 7/2005 | Lieb et al. |
| 2005/0187111 A1 | 8/2005 | Hagemann et al. |

(56) References Cited

U.S. PATENT DOCUMENTS

| | | |
|---|---|---|
| 2005/0256000 A1 | 11/2005 | Schaper |
| 2006/0122061 A1 | 6/2006 | Lieb et al. |
| 2006/0160847 A1 | 7/2006 | Fischer et al. |
| 2006/0166829 A1 | 7/2006 | Fischer et al. |
| 2007/0015664 A1 | 1/2007 | Fischer et al. |
| 2007/0032539 A1 | 2/2007 | Himmler |
| 2007/0043219 A1 | 2/2007 | Himmler |
| 2007/0066617 A1 | 3/2007 | Mita |
| 2007/0129252 A1 | 6/2007 | Fischer et al. |
| 2007/0129407 A1 | 6/2007 | Koyanagi |
| 2007/0225167 A1 | 9/2007 | Fischer et al. |
| 2007/0225170 A1 | 9/2007 | Fischer et al. |
| 2007/0244007 A1 | 10/2007 | Fischer et al. |
| 2007/0275858 A1 | 11/2007 | Fischer et al. |
| 2007/0298968 A1 | 12/2007 | Bretschneider et al. |
| 2007/0298969 A1 | 12/2007 | Fischer et al. |
| 2008/0081807 A1 | 4/2008 | Lieb et al. |
| 2008/0167188 A1 | 7/2008 | Fischer et al. |
| 2008/0220973 A1 | 9/2008 | Fischer et al. |
| 2008/0269052 A1 | 10/2008 | Rosinger |
| 2008/0269059 A1 | 10/2008 | Ziemer |
| 2008/0305955 A1 | 12/2008 | Bretschneider et al. |
| 2008/0318776 A1 | 12/2008 | Fischer et al. |
| 2009/0029858 A1 | 1/2009 | Fischer et al. |
| 2009/0076282 A1 | 3/2009 | Toriyabe |
| 2009/0111847 A1 | 4/2009 | Li |
| 2009/0209513 A1 | 8/2009 | Fischer |
| 2009/0215624 A1 | 8/2009 | Fischer et al. |
| 2009/0227563 A1 | 9/2009 | Fischer |
| 2009/0239906 A1 | 9/2009 | Fischer et al. |
| 2009/0247551 A1 | 10/2009 | Jeschke |
| 2009/0253749 A1 | 10/2009 | Jeschke |
| 2009/0259046 A1 | 10/2009 | Hamamoto |
| 2009/0298828 A1 | 12/2009 | Fischer et al. |
| 2009/0305891 A1 | 12/2009 | Fischer et al. |
| 2010/0004127 A1 | 1/2010 | Fischer et al. |
| 2010/0009850 A1 | 1/2010 | Fischer et al. |
| 2010/0022527 A1 | 1/2010 | Heimbach et al. |
| 2010/0056598 A1 | 3/2010 | Himmler et al. |
| 2010/0087320 A1 | 4/2010 | Lieb et al. |
| 2010/0130578 A1 | 5/2010 | Fischer |
| 2010/0168226 A1 | 7/2010 | Fischer |
| 2010/0174084 A1 | 7/2010 | Fischer et al. |
| 2010/0234229 A1 | 9/2010 | Fischer et al. |
| 2010/0240705 A1 | 9/2010 | Jeschke |
| 2010/0240924 A1 | 9/2010 | Fischer et al. |
| 2010/0256195 A1 | 10/2010 | Fischer |
| 2010/0261608 A1 | 10/2010 | Fischer et al. |
| 2010/0261934 A1 | 10/2010 | Fischer et al. |
| 2010/0267964 A1 | 10/2010 | Fischer et al. |
| 2010/0279873 A1 | 11/2010 | Fischer et al. |
| 2010/0298145 A1 | 11/2010 | Bretschneider |
| 2010/0311593 A1 | 12/2010 | Fischer et al. |
| 2011/0086762 A1 | 4/2011 | Fischer et al. |
| 2011/0092368 A1 | 4/2011 | Fischer et al. |
| 2011/0130284 A1 | 6/2011 | Fischer |
| 2011/0143943 A1 | 6/2011 | Ruther et al. |
| 2011/0183849 A1 | 7/2011 | Ruther et al. |
| 2011/0190493 A1 | 8/2011 | Bretschneider et al. |
| 2011/0195842 A1 | 8/2011 | Bretschneider et al. |
| 2011/0195998 A1 | 8/2011 | Goto |
| 2011/0212949 A1 | 9/2011 | Bretschneider |
| 2011/0213160 A1 | 9/2011 | Bretschneider et al. |
| 2011/0230346 A1 | 9/2011 | Fischer |
| 2011/0230351 A1 | 9/2011 | Fischer |
| 2011/0263424 A1 | 10/2011 | Bretschneider et al. |
| 2011/0306499 A1 | 12/2011 | Bretschneider et al. |
| 2012/0012833 A1 | 1/2012 | Shirasawa |
| 2012/0015807 A1 | 1/2012 | Fischer et al. |
| 2012/0178927 A1 | 7/2012 | Fischer et al. |
| 2012/0238450 A1 | 9/2012 | Ruther et al. |

FOREIGN PATENT DOCUMENTS

| | | |
|---|---|---|
| DE | 4014420 | 4/1991 |
| DE | 102005059892 | 6/2007 |
| DE | 102005059892 A1 | 6/2007 |
| DE | 102010008642 | 8/2011 |
| DE | 102010008643 | 8/2011 |
| EP | 0036106 | 9/1983 |
| EP | 0086750 | 7/1987 |
| EP | 0262399 A2 | 4/1988 |
| EP | 0346620 | 12/1989 |
| EP | 355599 A1 | 2/1990 |
| EP | 377893 A2 | 7/1990 |
| EP | 0174562 | 1/1991 |
| EP | 0269806 | 2/1991 |
| EP | 415211 A2 | 3/1991 |
| EP | 0191736 | 7/1991 |
| EP | 442073 A2 | 8/1991 |
| EP | 442077 A2 | 8/1991 |
| EP | 0454782 A1 | 11/1991 |
| EP | 456063 A2 | 11/1991 |
| EP | 0193259 | 12/1991 |
| EP | 0268554 | 12/1991 |
| EP | 0142924 | 4/1992 |
| EP | 0309862 | 8/1992 |
| EP | 0131624 | 9/1992 |
| EP | 0221044 | 9/1992 |
| EP | 0242246 | 11/1992 |
| EP | 0365484 | 1/1993 |
| EP | 0539588 | 5/1993 |
| EP | 0333131 | 10/1993 |
| EP | 0094349 | 4/1994 |
| EP | 596298 A2 | 5/1994 |
| EP | 613884 A2 | 9/1994 |
| EP | 613885 A2 | 9/1994 |
| EP | 0664081 | 7/1995 |
| EP | 0668267 A1 | 8/1995 |
| EP | 0595130 | 7/1996 |
| EP | 0242236 | 8/1996 |
| EP | 0257993 | 11/1996 |
| EP | 0492366 | 3/1997 |
| EP | 0528156 | 3/1997 |
| EP | 0453086 | 9/1997 |
| EP | 0647637 | 1/1999 |
| EP | 0681865 | 3/2000 |
| EP | 0464461 | 11/2000 |
| EP | 1066258 A1 | 1/2001 |
| EP | 0582198 | 2/2006 |
| FR | 2600494 | 12/1987 |
| GB | 2266888 A | 11/1993 |
| JP | 6087254 | 5/1985 |
| JP | 2000053670 | 2/2000 |
| JP | 2002205984 | 7/2002 |
| JP | 2008110953 | 5/2008 |
| JP | 2010018586 | 1/2010 |
| WO | WO-8402919 | 8/1984 |
| WO | WO-8706766 | 11/1987 |
| WO | WO-9008324 | 7/1990 |
| WO | WO-9107874 | 6/1991 |
| WO | WO-9108202 | 6/1991 |
| WO | WO-9113972 | 9/1991 |
| WO | WO-9119806 | 12/1991 |
| WO | WO-9200377 | 1/1992 |
| WO | WO-9211376 | 7/1992 |
| WO | WO-9214827 | 9/1992 |
| WO | WO-9216108 | 10/1992 |
| WO | 9501971 A1 | 1/1995 |
| WO | WO-9507897 | 3/1995 |
| WO | WO-9517817 | 7/1995 |
| WO | 9520572 A1 | 8/1995 |
| WO | 9526954 A1 | 10/1995 |
| WO | WO-9620196 | 7/1996 |
| WO | 9625395 A1 | 8/1996 |
| WO | 9635664 A1 | 11/1996 |
| WO | 9701535 A1 | 1/1997 |
| WO | 9702243 A1 | 1/1997 |
| WO | 9736868 A1 | 10/1997 |
| WO | 9743275 A2 | 11/1997 |
| WO | WO-9745016 | 12/1997 |

(56) References Cited

FOREIGN PATENT DOCUMENTS

| | | |
|---|---|---|
| WO | 9805638 A2 | 2/1998 |
| WO | 9806721 A1 | 2/1998 |
| WO | WO-9813361 | 4/1998 |
| WO | 9825928 A1 | 6/1998 |
| WO | WO-9827049 | 6/1998 |
| WO | WO-9835553 | 8/1998 |
| WO | WO-9838856 | 9/1998 |
| WO | WO-9900020 | 1/1999 |
| WO | 9916748 A1 | 4/1999 |
| WO | WO-9916744 | 4/1999 |
| WO | 9924437 A1 | 5/1999 |
| WO | 9943649 A1 | 9/1999 |
| WO | 9948869 A1 | 9/1999 |
| WO | 9955673 A1 | 11/1999 |
| WO | WO-0035278 | 6/2000 |
| WO | 0117972 A2 | 3/2001 |
| WO | 0123354 A2 | 4/2001 |
| WO | 0174770 A1 | 10/2001 |
| WO | WO-0202532 | 1/2002 |
| WO | WO-0228186 | 4/2002 |
| WO | WO-0234048 | 5/2002 |
| WO | WO-02096882 | 12/2002 |
| WO | 03013249 A1 | 2/2003 |
| WO | 03062244 A1 | 7/2003 |
| WO | WO-03059065 | 7/2003 |
| WO | WO-03106457 | 12/2003 |
| WO | 2004007448 A1 | 1/2004 |
| WO | 2004024688 A1 | 3/2004 |
| WO | WO-0280675 | 5/2004 |
| WO | 2004065366 A1 | 8/2004 |
| WO | 2004080962 A1 | 9/2004 |
| WO | WO-2004084631 | 10/2004 |
| WO | WO-2004099160 | 11/2004 |
| WO | 2004111042 A1 | 12/2004 |
| WO | WO-2005015994 | 2/2005 |
| WO | WO-2005016001 | 2/2005 |
| WO | WO-2005035486 | 4/2005 |
| WO | 2005044791 A2 | 5/2005 |
| WO | 2005044796 A1 | 5/2005 |
| WO | 2005048710 A1 | 6/2005 |
| WO | 2005049569 A1 | 6/2005 |
| WO | 2005066125 A1 | 7/2005 |
| WO | WO-2005077934 | 8/2005 |
| WO | 2005089118 A2 | 9/2005 |
| WO | WO-2005085216 | 9/2005 |
| WO | 2005092897 A2 | 10/2005 |
| WO | WO-2005112630 | 12/2005 |
| WO | 2006000355 A1 | 1/2006 |
| WO | 2006024411 A2 | 3/2006 |
| WO | 2006029799 A1 | 3/2006 |
| WO | WO-2006043635 | 4/2006 |
| WO | 2006056281 A1 | 6/2006 |
| WO | 2006056282 A1 | 6/2006 |
| WO | WO-2006056433 | 6/2006 |
| WO | 2006089633 A2 | 8/2006 |
| WO | WO-2006100288 | 9/2006 |
| WO | WO-2007023719 | 3/2007 |
| WO | WO-2007023764 | 3/2007 |
| WO | 2007039286 A1 | 4/2007 |
| WO | WO-2007040280 | 4/2007 |
| WO | 2007048545 A2 | 5/2007 |
| WO | WO-2007057407 | 5/2007 |
| WO | WO-2007068427 | 6/2007 |
| WO | WO-2007068428 | 6/2007 |
| WO | 2007073856 A2 | 7/2007 |
| WO | WO-2007027777 | 7/2007 |
| WO | WO-2007075459 | 7/2007 |
| WO | 2007096058 A1 | 8/2007 |
| WO | WO-2007101369 | 9/2007 |
| WO | WO-2007115643 | 10/2007 |
| WO | WO-2007115644 | 10/2007 |
| WO | WO-2007115646 | 10/2007 |
| WO | 2007121868 A1 | 11/2007 |
| WO | 2007140881 A1 | 12/2007 |
| WO | WO-2007149134 | 12/2007 |
| WO | WO-2008009360 | 1/2008 |
| WO | WO-2008009379 | 1/2008 |
| WO | 2008022725 A1 | 2/2008 |
| WO | 2008067873 A1 | 6/2008 |
| WO | 2008067910 A1 | 6/2008 |
| WO | 2008067911 A1 | 6/2008 |
| WO | WO-2008066153 | 6/2008 |
| WO | WO-2008083950 | 7/2008 |
| WO | WO-2008104503 | 9/2008 |
| WO | 2008138551 A2 | 11/2008 |
| WO | WO-2008131860 | 11/2008 |
| WO | WO-2008131861 | 11/2008 |
| WO | 2009015801 A1 | 2/2009 |
| WO | 2009039975 A1 | 4/2009 |
| WO | 2009049851 A1 | 4/2009 |
| WO | 2009115262 A1 | 9/2009 |
| WO | WO-2010005692 | 1/2010 |
| WO | WO-2010006713 | 1/2010 |
| WO | 2010052161 A2 | 5/2010 |
| WO | 2010063378 A1 | 6/2010 |
| WO | 2010063380 A1 | 6/2010 |
| WO | 2010063670 A1 | 6/2010 |
| WO | 2010066780 A1 | 6/2010 |
| WO | WO-2010069502 | 6/2010 |
| WO | WO-2010074747 | 7/2010 |
| WO | WO-2010074751 | 7/2010 |
| WO | 2010102758 A2 | 9/2010 |
| WO | WO-2010133337 | 11/2010 |
| WO | 2010135914 A1 | 12/2010 |
| WO | 2011067131 A1 | 6/2011 |
| WO | 2011067135 A1 | 6/2011 |
| WO | 2011067203 A1 | 6/2011 |
| WO | 2011067240 A1 | 6/2011 |
| WO | WO-2011098440 | 8/2011 |
| WO | WO-2011098443 | 8/2011 |

OTHER PUBLICATIONS

"Amino-Acids of the Cyclohexane Series. Part I.", J. Chem. Soc. 1961, 4372-4379.

Baur Peter, "Polydisperse Ethoxylated Fatty Alcohol Surfacants as Accelerators of Cuticular Penetration. 1. Effects of Ethoxy Chain Length and the Size of the Penetrants", Pestic. Sci. vol. 51, 1997, 131-152.

Bhattacharya Bhabatosh, "Isoquinoline Derivatives: part XVIII—Formation of I-Alkyl-(or alkaryl or aryl)-3-methyl-7-chloro-(or 5-chloro)-isoquinolines", Indian J. Chem. 6, 1968, 341-345.

Braun Hans-Peter, "The General Mitochondrial processing Peptidase from Potato is an Integral Part of Cytochrome C Reductase of the Respiratory Chain", The EMBO Journal vol. 11, No. 9, 1992, 3219-3227.

Campbell, Alexander C., "Synthesis of (E)- and (Z)-Pulvinones", J. Chem. Soc. Perkin Trans. I, 1985, 1567-1576.

Chemie der Pflanzenschutzund Schaedlin Gsbekaempfungsmittel vol. 2, 1970, 401-412.

Christou Paul, "Transformation Technology", Trends in Plant Science, vol. 1, No. 12, Dec. 1996.

"Cyclisierung Von N-Acylalanin- und N-Acylglycinestern", Liebigs Ann. Chem. 1985, 1095-1098.

"D.7.1.5. Reaktionen von Carbonsauren und Carbonsauredarivaten mit Basen", Organikum, Berlin, 1977.

Edward, John T., "Stereochemistry of the Bucherer-Bergs and Strecker Reactions of 4-tert-Butylcyclohexanone", Can. J. Chem. vol. 53, 1975, 3339-3350.

"European Search Report for European Application No. 11154805.3, dated Jun. 24, 2011", 1-2.

Fustero Santos, "Solution-, Solid-Phase, and Fluorous Synthesis of B,B-Difluorinated Cyclic Quaternary a-Amino Acid Derivatives: A Comparative Study", Chem. Eur. J., vol. 14, 2008, 7019-7029.

"Glossary of Common Names and Abbreviations of Herbicides ", Weed Research, vol. 26, 1986, 441-445.

Klingman Glenn, "5. Surface Active Agents", Weed Control as a Science, 1961, 81-91.

Lieb Folker, "2-(Chlorocarbonyl)-2-Mesitylketene, a new Building Block For the Synthesis of 4-Hydroxy-3-Mesityl Tetronic acids", Tetrahedron vol. 57, 2001, 4133-4137.

(56) References Cited

OTHER PUBLICATIONS

Sonnewald Uwe, "Transgenic Tobacco Plants Expressing Yeast-Derived Invertase in Either the Cytosol, Vacuole or Apoplast: a Powerful Tool for Studying Sucrose Metabolism and Sink/Source Interactions", The Plant Journal, vol. 1, No. 1, 1991, 95-106.

Sonntag Norman, "The Reactions of Aliphatic Acid Chlorides", Chemical Reviews, 52, 1953, 237-416.

Suzuki Seikichi, "Studies on Antiviral AgentslV. Biological Activity of Tenuazonic Acid Derivatives", Chem. Pharm. Bull.vol. 15, No. 8, 1967, 1120-1122.

"Synthesis and Insecticidal Activity of Novel N-Oxydihydropyrolle Derivatives with a Substituted Spirocyclohexyl Group", Biosci. Biotechnol. Ciochem. vol. 67, No. 6, 2003, 1230-1238.

"The use of Herbicides in Potato", Weed Control Handbook, 5, 1968, 101-103.

"Use of Molecular Sieves in the Methyl Esterification of Carboxylic Acids", Chem. Ind. 1968, 1-2.

Wolter, Frank P., "rbcS Genes in Solanum Tuberosum: Conservation of Transit Peptide and Exon Shuffling During Evolution", Proc. Natl. Acad. Sci., vol. 85, Feb. 1988, 846-850.

International Search Report for PCT/EP2012/052521 Mailed Jun. 26, 2012.

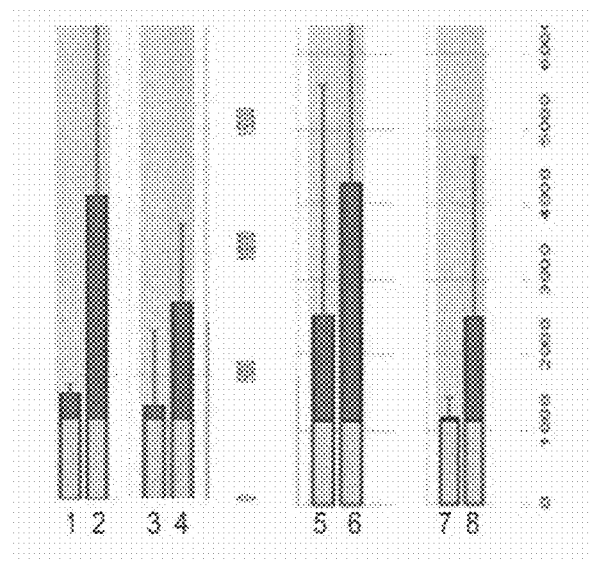

SUBSTITUTED 3-(BIPHENYL-3-YL)-8,8-DIFLUORO-4-HYDROXY-1-AZASPIRO[4.5]DEC-3-EN-2-ONES FOR THERAPY AND HALOGEN-SUBSTITUTED SPIROCYCLIC KETOENOLS

CROSS REFERENCE TO RELATED APPLICATIONS

This application is a §371 National Stage Application of PCT/EP2012/052521, filed Feb. 14, 2012, which claims priority to European Application No. 11154805.3, filed Feb. 17, 2011, U.S. Provisional Application No. 61/433,852, filed Feb. 17, 2011, and German Application No. 10 2011 080 405.6, filed Aug. 4, 2011.

BACKGROUND OF THE INVENTION

1. Field of the Invention

The present invention relates to substituted 3-(biphenyl-3-yl)-8,8-difluoro-4-hydroxy-1-azaspiro[4.5]dec-3-en-2-ones of the formula (Ia) for therapeutic purposes, to pharmaceutical compositions comprising the compounds according to the invention and to their use in therapy, in particular for the prophylaxis and/or therapy of tumor disorders.

2. Description of Related Art

Acetyl-CoA carboxylases (ACCs) play a key role in cellular fatty acid homeostasis. ACCs are biotin-containing enzymes which catalyze the carboxylation of acetyl-CoA to malonyl-CoA in an ATP-dependent manner (Kim, 1997; Harwood, 2005; Tong, 2005). This reaction, which proceeds as two half-reactions, a biotin carboxylase (BC) reaction and a carboxyltransferase (CT) reaction, is the first introductory step of fatty acid biosynthesis and is the rate-determining step of the pathway. Two human ACC isoforms, ACC1 and ACC2, which are encoded by two different genes, are known (LuTFI ABU-ELHEIGA et al, 1995, Jane WIDMER, et al. 1996). ACC1 is expressed in lipogenic tissue (liver, fatty tissue), localized in the cytosole and fills the malonyl-CoA pool which serves as C2 unit donor for the de novo synthesis of long-chain fatty acids by FASN and subsequent chain extension. ACC2 is expressed mainly in oxidative tissues (liver, heart, skeletal muscle) (Bianchi et al., 1990; Kim, 1997), is associated with mitochondria and regulates a second malonyl-CoA pool. This regulates fatty acid oxidation by inhibiting carnitine palmityltransferase I, the enzyme which facilitates entry of long-chain fatty acids into the mitochondria for β oxidation (Milgraum L Z, et al., 1997, Widmer J. et al., 1996). Both enzymes show very high sequence homology and are regulated in a similar manner by a combination of transcriptional, translational and posttranslational mechanisms. Both in humans and in animals, ACC activity is highly controlled by a number of dietary, hormonal and other physiological mechanisms such as forward allosteric activation by citrate, feedback inhibition by long-chain fatty acids, reversible phosphorylation and/or inactivation or modulation of enzyme production by modified gene expression.

ACC1 knockout mice are embryonally lethal (Swinnen, et al., 2006, Abu-Elheiga, et al. 2005). ACC2 knockout mice show reduced malonyl-CoA concentrations in skeletal and heart muscle, increased fatty acid oxidation in the muscle, reduced liver fat levels, reduced amounts of total body fat, increased levels of UCP3 in the skeletal muscle (as an indication of higher energy expenditure), a reduced body weight, reduced plasma concentrations of free fatty acids, reduced plasma glucose levels, reduced amounts of tissue glycogen, and they are protected against diet-induced diabetes and obesity (Abu-Elheiga et al., 2001, 2003; Oh et al., 2005).

In addition to the involvement in fatty acid synthesis in lipogenic tissues and fatty acid oxidation in oxidative tissues, in many tumor cells an upregulation of ACC and an increased lipogenesis was observed (Swinnen, et al., 2004, Heemers, et al., 2000, Swinnen, et al., 2002, Rossi, et al., 2003, Milgraum, et al., 1997, Yahagi, et al., 2005). With very high probability, this phenotype contributes to the development and progression of tumors; however, the regulatory mechanisms involved still have to be clarified.

EP0454782 and U.S. Pat. No. 5,759,837 protect the use of fatty acid synthesis inhibitors for inhibiting tumor cell growth. Cyclic ketoenols have not been disclosed.

A number of substances capable of inhibiting plant and/or insect ACC have been discovered.

The PCT patent application PCT/EP99/01787, published as WO 99/48869, which corresponds to the European Patent EP 1 066 258 B1, refers to novel arylphenyl-substituted cyclic ketoenols, to a plurality of processes for their preparation and to their use as pesticides and herbicides.

3-Acylpyrrolidine-2,4-diones have already been described as having pharmaceutical properties (S. Suzuki et al. Chem. Pharm. Bull. 15 1120 (1967)). Furthermore, N-phenylpyrrolidine-2,4-diones have been synthesized by R. Schmierer and H. Mildenberger (Liebigs Ann. Chem. 1985, 1095). A biological activity of these compounds has not been described.

EP-A-0 262 399 and GB-A-2 266 888 disclose compounds of a similar structure (3-arylpyrrolidine-2,4-diones) of which, however, no herbicidal, insecticidal or acaricidal activity has become known. Unsubstituted bicyclic 3-arylpyrrolidine-2,4-dione derivatives (EP-A-355 599, EP-A-415 211 and JP-A-12-053 670) and substituted monocyclic 3-arylpyrrolidine-2,4-dione derivatives (EP-A-377 893 and EP-A-442 077) are known to have herbicidal, insecticidal or acaricidal activity.

Additionally known are polycyclic 3-arylpyrrolidine-2,4-dione derivatives (EP-A-442 073) and 1H-arylpyrrolidinedione derivatives (EP-A-456 063, EP-A-521 334, EP-A-596 298, EP-A-613 884, EP-A-613 885, WO 95/01 971, WO 95/26 954, WO 95/20 572, EP-A-0 668 267, WO 96/25 395, WO 96/35 664, WO 97/01 535, WO 97/02 243, WO 97/36 868, WO 97/43275, WO 98/05638, WO 98/06721, WO 98/25928, WO 99/24437, WO 99/43649, WO 99/48869, WO 99/55673, WO 01/17972, WO 01/23354, WO 01/74770, WO 03/013249, WO 03/062244, WO 2004/007448, WO 2004/024 688, WO 04/065366, WO 04/080962, WO 04/111042, WO 05/044791, WO 05/044796, WO 05/048710, WO 05/049569, WO 05/066125, WO 05/092897, WO 06/000355, WO 06/029799, WO 06/056281, WO 06/056282, WO 06/089633, WO 07/048,545, DEA 102 00505 9892, WO 07/073,856, WO 07/096,058, WO 07/121,868, WO 07/140,881, WO 08/067,873, WO 08/067,910, WO 08/067,911, WO 08/138,551, WO 09/015,801, WO 09/039,975, WO 09/049,851, WO 09/115,262, WO10/052,161, WO 10/063,378, WO 10/063,670, WO10/063,380, WO10/066,780, WO10/102,758, WO2010/135914, WO2011/067131, WO2011/067135, WO2011/067203 and WO2011/067240.

Furthermore known are ketal-substituted 1H-arylpyrrolidine-2,4-diones from WO 99/16748 and (spiro)-ketal-substituted N-alkoxyalkoxy-substituted arylpyrrolidinediones from JP-A-14 205 984 and Ito M. et. al., Bioscience, Biotechnology and Biochemistry 67, 1230-1238, (2003). Moreover, WO 06/024411 discloses herbicidal compositions comprising ketoenols.

WO 2008/022725 discloses 4'-biphenyl-substituted tetronic acid derivatives for the therapy of viral disorders.

WO 2005/089118 and WO2007/039286 disclose, in a general manner, nitrogen-containing bicyclic structures for therapy; however, 5"-biphenyl-substituted cyclic ketoenols are not specifically mentioned.

Surprisingly, it has now been found that a specific subgroup of the aryl-substituted cyclic ketoenols described in the prior art also inhibit human ACC and are suitable for the therapy of disorders.

Here, it was unforseeable whether and which of the structures known as insecticides or herbicides achieve the object of the invention, that is represent structures which can be used in the therapy of human disorders.

The applicant is not aware that 3-(biphenyl-3-yl)-8,8-difluoro-4-hydroxy-1-azaspiro[4.5]dec-3-en-2-ones of the formula (Ia) according to the present invention have been described in the prior art for the therapy of disorders, in particular not for the therapy of tumor disorders.

SUMMARY

Based on this prior art, it is an object of the present invention to provide structures for the therapy of disorders.

BRIEF DESCRIPTION OF THE DRAWING

FIG. 1 represent embodiments as described herein.

DETAILED DESCRIPTION OF A PREFERRED EMBODIMENT

In particular, the structures according to the invention should be suitable for the prophylaxis and therapy of tumor disorders and have advantages over the structures known in the prior art.

Of particular interest here are compounds which are selective against human ACC2, that is compounds which inhibit human ACC1 more strongly than human ACC2.

What is to be provided are in particular structures for the therapy of disorders which strongly inhibit human ACC1. The structures sought should inhibit human ACC1 more strongly than human ACC2, that is they should be selective against human ACC2.

Preferably, the structures provided for the therapy of disorders should additionally also have one, even better more or best of all all of the following properties:
according to a single measurement or even better according to the mean of a plurality of measurements, they inhibit human ACC1 with an IC50 of less than 300 nM, even better less than 200 nM and even better still of less than 100 nM in the assay described,
according to a single measurement or even better according to the mean of a plurality of measurements, they inhibit human ACC2 with an IC50 of greater than 0.5 µM, even better greater than 1.5 µM and even better still of greater than 2 µM in the assay described,
according to a single measurement or even better according to the mean of a plurality of measurements, the ratio of the IC50 for the inhibition of human ACC2 to the IC50 for the inhibition of human ACC1 is at least a factor of 8, even better at least a factor of 15 and even better still at least a factor of 20.
according to a single measurement or even better according to the mean of a plurality of measurements, they inhibit tumor cell proliferation of MCF7 cell lines with an IC50 of less than 250 nM, even better less than 100 nM and even better still of less than 50 nM in the assay described,
according to a single measurement or even better according to the mean of a plurality of measurements, they have a log P/D value of less than 3, even better less than 2.5 in the assay described,
according to a single measurement or even better according to the mean of a plurality of measurements, they have a log MA value of less than 3, even better less than 2.5, even better still less than 2 in the assay described,
according to a single measurement or even better according to the mean of a plurality of measurements, they have an HSA protein binding constant of greater than 1 µmol/l in the assay described,
according to a single measurement or even better according to the mean of a plurality of measurements, they have a free fraction of greater than 0.1%, even better greater than 0.2%, with respect to binding to human plasma protein in the assay described.
according to a single measurement or even better according to the mean of a plurality of measurements, they have a ratio of the free fractions with respect to binding to mouse plasma protein and human plasma protein of a factor of less than 15, even better less than 10,
they have a ratio of the free fractions with respect to plasma protein binding of various species which leads to an acceptable estimated human dose,
they have pharmacokinetic parameters which lead to an acceptable estimated human dose and which allow administration as a medicament,
they have low clearance,
they have high bioavailability,
they have a moderate to high distribution volume,
they have an acceptable relative bioavailability which leads to an acceptable estimated human dose and which allows administration as a medicament,
they have an estimated human half-life of not more than two weeks,
they have an in-vivo activity in the PC3 xenograft mouse model,
they have an activity in the PC3 xenograft mouse model with plasma levels which lead to an acceptable estimated human dose,
their estimated human daily dose is less than 2 g, even better less than 1 g, per patient.

Surprisingly, it has now been found that compounds of the formula (Ia)

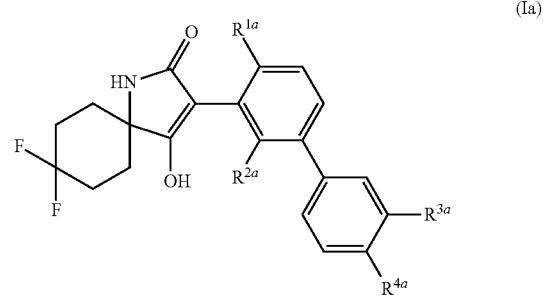

(Ia)

where
$R^{1a}$ represents a methyl group or a chlorine atom and
$R^{2a}$ represents a hydrogen atom or a methyl group and
$R^{3a}$ represents a hydrogen or a fluorine atom and
$R^{4a}$ represents a chlorine or fluorine atom
and their salts
are particularly suitable for the therapy of disorders and achieve the object of the invention.

Here, it was unforseeable whether and which of the structures known as insecticides or herbicides achieve the object of the invention, that is represents a structure which can be used in the therapy of human disorders.

It was even less forseeable whether and which of the structures known as insecticides or herbicides inhibit human ACC, and even less whether and which shows selectivity against one of the human isoforms.

From the large group of the cyclic ketoenols known as insecticides, fungicides or herbicides, the compounds of the formula (Ia) surprisingly distinguish themselves by good enzyme inhibition of human ACCs. Here, the compounds according to the invention have increased selectivity against ACC2 and inhibit in particular ACC1. This property was unforseeable and qualifies the compounds according to the invention for a therapy with reduced side effects. Unwanted side effects are probably caused by simultaneous inhibition of human ACC2s, whereas the effects are based mainly on the inhibition of human ACC1s.

The present invention also embraces the use of the physiologically acceptable salts of the compounds according to the invention.

The present invention also embraces the use of the tautomeric forms of the compounds of the formula (Ia) according to the invention, for example

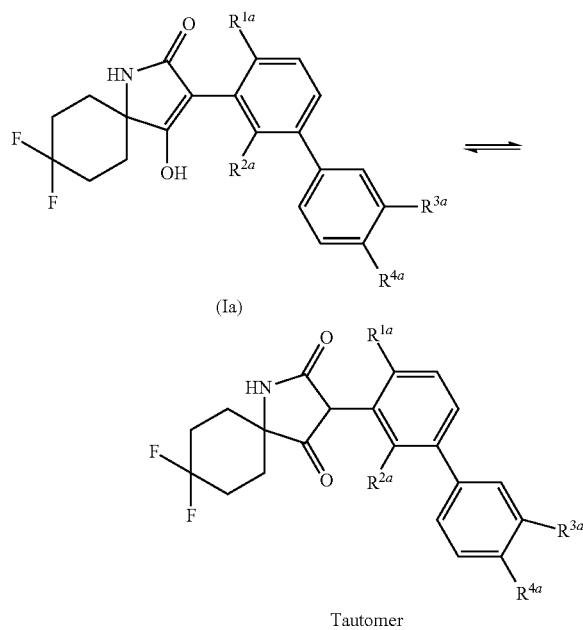

(Ia)

Tautomer

Physiologically acceptable salts of the compounds of the formula (Ia) according to the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

The present invention furthermore provides medicaments comprising the compounds of the formula (Ia) according to the invention and at least one or more further active compounds, in particular for the prophylaxis and/or therapy of tumor disorders.

The compounds of the formula (Ia) according to the invention can act systemically and/or locally. For this purpose, it can be administered in a suitable manner, for example by the oral, parenteral, pulmonal, nasal, sublingual, lingual, buccal, rectal, dermal, transdermal, conjunctival, otic route, or as an implant or stent.

The compounds of the formula (Ia) according to the invention can be administered in administration forms suitable for these administration routes.

Suitable administration forms for oral administration are those which work according to the prior art, which release the compounds according to the invention rapidly and/or in a modified manner and which contain the compounds of the formula (Ia) according to the invention in crystalline and/or amorphized and/or dissolved form, for example tablets (uncoated or coated tablets, for example with gastric juice-resistant or retarded-dissolution or insoluble coatings which control the release of the compound according to the invention), tablets or films/wafers which disintegrate rapidly in the oral cavity, films/lyophilizates or capsules (for example hard or soft gelatin capsules), sugar-coated tablets, granules, pellets, powders, emulsions, suspensions, aerosols or solutions.

Parenteral administration can be accomplished with avoidance of an absorption step (for example by an intravenous, intraarterial, intracardiac, intraspinal or intralumbar route) or with inclusion of an absorption (for example by an intramuscular, subcutaneous, intracutaneous, percutaneous or intraperitoneal route). Administration forms suitable for parenteral administration include preparations for injection and infusion in the form of solutions, suspensions, emulsions, lyophilizates or sterile powders.

Suitable administration forms for the other administration routes are, for example, pharmaceutical forms for inhalation (including powder inhalers, nebulizers), nasal drops, solutions or sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (for example patches), milk, pastes, foams, dusting powders, implants or stents.

The compounds of the formula (Ia) according to the invention can be converted into the administration forms mentioned. This can be accomplished in a manner known per se by mixing with inert nontoxic pharmaceutically suitable auxiliaries. These auxiliaries include carriers (for example microcrystalline cellulose, lactose, mannitol), solvents (e.g. liquid polyethylene glycols), emulsifiers and dispersing or wetting agents (for example sodium dodecylsulfate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and flavor and/or odor correctants.

The present invention further provides medicaments which comprise the compounds of the formula (Ia) according to the invention, typically together with one or more inert, nontoxic, pharmaceutically suitable auxiliaries, and for the use thereof for the aforementioned purposes.

The compounds of the formula (Ia) according to the invention are formulated to pharmaceutical preparations in a manner known per se by converting the active compound or the active compounds with the auxiliaries customary in the art of pharmaceutical formulation into the desired administration form.

Suitable for use as auxiliaries are, for example, carriers, fillers, disintegrants, binders, humectants, glidants, absorbants and adsorbants, diluents, solvents, cosolvents, emulsifiers, solubilizers, taste correctants, colorants, preservatives, stabilizers, wetting agents, salts for modifying osmotic pressure or buffers.

Reference should be made to Remington's Pharmaceutical Science, 15th ed. Mack Publishing Company, East Pennsylvania (1980).

The pharmaceutical formulations can be present
in solid form, for example as tablets, sugar-coated tablets, pills, suppositories, capsules, transdermal systems or
in semi-solid form, for example as ointments, creams, gels, suppositories, emulsions or
in liquid form, for example as solutions, tinctures, suspensions or emulsions.

Auxiliaries for the purpose of the invention are, for example, salts, saccharides (mono-, di-, tri-, oligo- and/or polysaccharides), proteins, amino acids, peptides, fats, waxes, oils, hydrocarbons and derivatives thereof, where the auxiliaries may be of natural origin or synthetic or partially synthetic.

Suitable for oral or peroral administration are in particular tablets, sugar-coated tablets, capsules, pills, powders, granules, pastilles, suspensions, emulsions or solutions.

Suitable for parenteral administration are in particular suspensions, emulsions and especially solutions.

The present invention relates to the compounds of the formula (Ia) according to the invention. They can be used for the prophylaxis and therapy of human disorders, in particular tumor disorders.

The compounds of the formula (Ia) according to the invention can be used in particular for inhibiting or reducing cell proliferation and/or cell division and/or to induce apoptosis.

The compounds according to the invention of the formula (Ia) are suitable in particular for the prophylaxis and/or therapy of hyper-proliferative disorders such as, for example,
  psoriasis,
  keloids and other skin hyperplasias,
  benign prostate hyperplasias (BPH),
  solid tumors and
  hematological tumors.

Solid tumors which can be treated in accordance with the invention are, for example, tumors of the breast, the respiratory tract, the brain, the reproductive organs, the gastrointestinal tract, the urogenital tract, the eye, the liver, the skin, the head and the neck, the tyroid gland, the parathyroid gland, the bones and the connective tissue and metastases of these tumors.

Hematological tumors which can be treated are, for example,
  multiple myelomas
  lymphomas or
  leukemias Breast tumors which can be treated are, for example:
  breast carcinomas with positive hormone receptor status
  breast carcinomas with negative hormone receptor status
  Her-2 positive breast carcinomas
  hormone receptor and Her-2 negative breast carcinomas
  BRCA-associated breast carcinomas
  inflammatory breast carcinoma.

Tumors of the respiratory tract which can be treated are, for example,
  non-small-cell bronchial carcinomas and
  small-cell bronchial carcinomas.

Tumors of the brain which can be treated are, for example,
  gliomas,
  glioblastomas,
  astrocytomas,
  meningiomas and
  medulloblastomas.

Tumours of the male reproductive organs which can be treated are, for example:
  prostate carcinomas,
  malignant testicular tumors and
  penis carcinomas.

Tumours of the female reproductive organs which can be treated are, for example:
  endometrial carcinomas
  cervix carcinomas
  ovarial carcinomas
  vaginal carcinomas
  vulvar carcinomas Tumors of the gastrointestinal tract which can be treated are, for example:
  colorectal carcinomas
  anal carcinomas
  stomach carcinomas
  pancreas carcinomas
  esophagus carcinomas
  gall bladder carcinomas
  carcinomas of the small intestine
  salivary gland carcinomas
  neuroendocrine tumors
  gastrointestinal stroma tumors Tumors of the uorgenital tract which can be treated are, for example:
  urinary bladder carcinomas
  kidney cell carcinomas
  carcinomas of the renal pelvis and lower urinary tract Tumours of the eye which can be treated are, for example:
  retinoblastomas
  intraocular melanomas Tumours of the liver which can be treated are, for example:
  hepatocellular carcinomas
  cholangiocellular carcinomas Tumours of the skin which can be treated are, for example:
  malignant melanomas
  basaliomas
  spinaliomas
  Kaposi sarcomas
  Merkel cell carcinomas Tumours of the head and neck which can be treated are, for example:
  larynx carcinomas
  carcinomas of the pharynx and the oral cavity Sarcomas which can be treated are, for example:
  soft tissue sarcomas
  osteosarcomas Lymphomas which can be treated are, for example:
  non-Hodgkin lymphomas
  Hodgkin lymphomas
  cutaneous lymphomas
  lymphomas of the central nervous system
  AIDS-associated lymphomas Leukemias which can be treated are, for example:
  acute myeloid leukemias
  chronic myeloid leukemias
  acute lymphatic leukemias
  chronic lymphatic leukemias
  hairy cell leukemias Advantageously, the compounds of the formula (Ia) according to the invention can be used for the prophylaxis and/or therapy of:
breast carcinomas, in particular hormone receptor-negative, hormone receptor-positive or BRCA-associated breast carcinomas, and also
pancreas carcinomas, renal cell carcinomas, hepatocellular carcinomas, malignant melanomas and other skin tumors, non-small-cell bronchial carcinomas, endometrial carcinoma,
colorectal carcinomas and prostate carcinomas.

Particularly advantageously, the compounds of the formula (Ia) according to the invention can be used for the prophylaxis and/or therapy of breast carcinomas, in particular hormone receptor-positive breast carcinomas, colorectal carcinomas, prostate carcinomas, in particular androgen receptor-negative prostate carcinomas, or non-small-cell bronchial carcinomas.

These disorders are well-characterized in man, but also exist in other mammals.

The present application provides the compounds of the formula (Ia) according to the invention, in particular the compounds:
3-(3',4'-Difluoro-4-methylbiphenyl-3-yl)-8,8-difluoro-4-hydroxy-1-azaspiro[4.5]dec-3-en-2-one
3-(4'-Chloro-2,4-dimethylbiphenyl-3-yl)-8,8-difluoro-4-hydroxy-1-azaspiro[4.5]dec-3-en-2-one
3-(4,4'-Dichlorobiphenyl-3-yl)-8,8-difluoro-4-hydroxy-1-azaspiro[4.5]dec-3-en-2-one
8,8-Difluoro-3-(4'-fluoro-4-methylbiphenyl-3-yl)-4-hydroxy-1-azaspiro[4.5]dec-3-en-2-one
3-(4'-Chloro-4-methylbiphenyl-3-yl)-8,8-difluoro-4-hydroxy-1-azaspiro[4.5]dec-3-en-2-one
3-(4'-Chloro-3'-fluoro-4-methylbiphenyl-3-yl)-8,8-difluoro-4-hydroxy-1-azaspiro[4.5]dec-3-en-2-one The present application furthermore provides the compounds of the formula (Ia) according to the invention for use as medicaments, in particular for the prophylaxis and/or therapy of tumor disorders.

The present application furthermore provides compounds of the formula (Ia) according to the invention for the prophylaxis and/or therapy of breast carcinomas, pancreas carcinomas, renal cell carcinomas, hepatocellular carcinomas, malignant melanomas and other skin tumors, non-small-cell bronchial carcinomas, endometrial carcinomas, colorectal carcinomas or prostate carcinomas.

The present application furthermore provides compounds of the formula (Ia) according to the invention for the prophylaxis and/or therapy of breast carcinomas, in particular hormone receptor-positive breast carcinomas, colorectal carcinomas, prostate carcinomas, in particular androgen receptor-negative prostate carcinomas, or non-small-cell bronchial carcinomas.

The invention further provides the use of the compounds of the formula (Ia) according to the invention for preparing a medicament.

The present application furthermore provides the use of the compounds of the formula (Ia) according to the invention for preparing a medicament for the prophylaxis and/or therapy of tumor disorders.

The present application furthermore provides the use of the compounds of the formula (Ia) according to the invention for preparing a medicament for the prophylaxis and/or therapy of breast carcinomas, pancreas carcinomas, renal cell carcinomas, hepatocellular carcinomas, malignant melanomas and other skin tumors, non-small-cell bronchial carcinomas, endometrial carcinomas, colorectal carcinomas or prostate carcinomas.

The present application furthermore provides the use of the compounds of the formula (Ia) according to the invention for preparing a medicament for the prophylaxis and/or therapy of breast carcinomas, in particular hormone receptor-positive breast carcinomas, colorectal carcinomas, prostate carcinomas, in particular androgen receptor-negative prostate carcinomas, or non-small-cell bronchial carcinomas.

The present application furthermore provides the use of the compounds of the formula (Ia) according to the invention for the prophylaxis and/or therapy of tumor disorders.

The present application furthermore provides the use of the compounds of the formula (Ia) according to the invention for the prophylaxis and/or therapy of breast carcinomas, pancreas carcinomas, renal cell carcinomas, hepatocellular carcinomas, malignant melanomas and other skin tumors, non-small-cell bronchial carcinomas, endometrial carcinomas, colorectal carcinomas or prostate carcinomas.

The present application furthermore provides the use of the compounds of the formula (Ia) according to the invention for the prophylaxis and/or therapy of breast carcinomas, in particular hormone receptor-positive breast carcinomas, colorectal carcinomas, prostate carcinomas, in particular androgen receptor-negative prostate carcinomas, or non-small-cell bronchial carcinomas.

The present application furthermore provides pharmaceutical formulations in the form of tablets comprising one of the compounds of the formula (Ia) according to the invention for the prophylaxis and/or therapy of breast carcinomas, pancreas carcinomas, renal cell carcinomas, hepatocellular carcinomas, malignant melanomas and other skin tumors, non-small-cell bronchial carcinomas, endometrial carcinomas, colorectal carcinomas or prostate carcinomas.

The present application furthermore provides pharmaceutical formulations in the form of tablets comprising one of the compounds of the formula (Ia) according to the invention for the prophylaxis and/or therapy of breast carcinomas, in particular hormone receptor-positive breast carcinomas, colorectal carcinomas, prostate carcinomas, in particular androgen receptor-negative prostate carcinomas, or non-small-cell bronchial carcinomas.

The invention further provides the use of the compounds of the formula (Ia) according to the invention for treating disorders associated with proliferative processes.

The compounds of the formula (Ia) according to the invention can be employed by themselves or, if required, in combination with one or more other pharmacologically active substances, as long as this combination does not lead to undesirable and unacceptable side effects. Accordingly, the present invention further provides medicaments comprising a compound according to the invention and one or more further active compounds, in particular for the prophylaxis and/or therapy of the disorders mentioned above.

For example, the compounds of the formula (Ia) according to the invention can be combined with known antihyperproliferative, cytostatic or cytotoxic substances for treatment of cancer disorders. Indicated is in particular the combination of the compounds according to the invention with other substances customarily used for cancer therapy, or else with radiotherapy.

Suitable active compounds in the combination which may be mentioned by way of example are:
afinitor, aldesleukin, alendronic acid, alfaferone, alitretinoin, allopurinol, aloprim, aloxi, altretamine, aminoglutethimide, amifostine, amrubicin, amsacrine, anastrozole, anzmet, aranesp, arglabin, arsenic trioxide, aromasin, 5-azacytidine, azathioprine, BCG or tice-BCG, bestatin, betamethasone acetate, betamethasone sodium phosphate, bexarotene, bleomycin sulfate, broxuridine, bortezomib, busulfan, calcitonin, campath, capecitabine, carboplatin, casodex, cefesone, celmoleukin, cerubidin, chlorambucil, cisplatin, cladribin, clodronic acid, cyclophosphamide, cytarabine, dacarbazine, dactinomycin, daunoxome, decadron, decadron phosphate, delestrogen, denileukin diftitox, depomedrol, deslorelin, dexrazoxane, diethylstilbestrol, diflucan, docetaxel, doxifluridine, doxorubicin, dronabinol, DW-166HC, eligard, elitek, ellence, emend, epirubicin, epoetin-alfa, epogen, eptaplatin, ergamisol, estrace, estradiol, estramustine sodium phosphate, ethinylestradiol, ethyol, etidronic acid, etopophos, etoposide, fadrozole, farstone, filgrastim, finasteride, fligrastim, floxuridine, fluconazole, fludarabin, 5-fluorodeoxyuridine monophosphate, 5-fluorouracil (5-FU), fluoxymesterone, flutamide, formestane, fosteabine, fotemustine, fulvestrant, gammagard, gemcitabine, gemtuzumab, gleevec, gliadel, goserelin, granisetron hydrochloride, histrelin, hycamtin, hydrocortone, erythro-hydroxynonyladenine, hydroxyurea, ibritumomab tiuxetan, idarubicin, ifosfamide, interferon-alpha, interferon-alpha-2, interferon-alpha-2a, interferon-alpha-2β, interferon-alpha-n1, interferon-alpha-n3, interferon-beta, interferon-gamma-1a, interleukin-2, intron A, iressa, irinotecan, kytril, lapatinib, lentinan sulfate, letrozole, leucovorin, leuprolide, leuprolide acetate, levamisole, levofolic acid calcium salt, levothroid, levoxyl, lomustine, lonidamine, marinol, mechlorethamine, mecobalamin, medroxyprogesterone acetate, megestrol acetate, melphalan, menest, 6-mercaptopurine, mesna, methotrexate, metvix, miltefosine, minocycline, mitomycin C, mitotane, mitoxantrone, modrenal, myocet, nedaplatin, neulasta, neumega, neupogen, nilutamide, nolvadex, NSC-631570, OCT-43, octreotide, ondansetron hydrochloride, orapred, oxaliplatin, paclitaxel, pediapred, pegaspargase, pegasys, pentostatin, picibanil, pilocarpine hydrochloride, pirarubicin, plicamycin, porfimer sodium, prednimustine, prednisolone, prednisone, premarin, procarbazine, procrit, raltitrexed, RDEA119, rebif, rhenium-186 etidronate, rituximab, roferon-A, romurtide, salagen, sandostatin, sargramostim, semustine, sizofiran, sobuzoxane, solu-medrol, streptozocin, strontium-89 chloride, synthroid, tamoxifen, tamsulosin, tasonermin, tastolactone, taxoter, teceleukin, temozolomide, teniposide, testosterone propionate, testred, thioguanine, thiotepa, thyrotropin, tiludronic acid, topotecan, toremifen, tositumomab, tastuzumab, teosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin-stimalamer, zofran; ABI-007, acolbifen, actimmune, affinitak, aminopterin, arzoxifen, asoprisnil, atamestane, atrasentan, BAY 43-9006 (sorafenib), avastin, CCI-779, CDC-501, celebrex, cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon-gamma, intron-PEG, ixabepilone, keyhole limpet hemocyanine, L-651582, lanreotide, lasofoxifen, libra, lonafarnib, miproxifen, minodronate, MS-209, liposomal MTP-PE, MX-6, nafarelin, nemorubicin, neovastat, nolatrexed, oblimersen, onko-TCS, osidem, paclitaxel polyglutamate, pamidronate disodium, PN-401, QS-21, quazepam, R-1549, raloxifen, ranpirnas, 13-cis-retic acid, satraplatin, seocalcitol, T-138067, tarceva, taxoprexin, thymosin-alpha-1, tiazofurin, tipifarnib, tirapazamine, TLK-286, toremifen, transMID-107R, valspodar, vapreotide, vatalanib, verteporfin, vinflunin, Z-100, zoledronic acid and combinations of these.

In a preferred embodiment, the compounds according to the invention can be combined with antihyperproliferative agents, which can be, by way of example—without this list being conclusive:
aminoglutethimide, L-asparaginase, azathioprine, 5-azacytidine, bleomycin, busulfan, carboplatin, carmustine, chlorambucil, cisplatin, colaspase, cyclophosphamide, cytarabine, dacarbazine, dactinomycin, daunorubicin, diethylstilbestrol, 2',2'-difluorodeoxycytidine, docetaxel, doxorubicin (adriamycin), epirubicin, epothilone and its derivatives, erythro-hydroxynonyladenine, ethinylestradiol, etoposide, fludarabin phosphate, 5-fluorodeoxyuridine, 5-fluorodeoxyuridine monophosphate, 5-fluorouracil, fluoxymesterone, flutamide, hexamethylmelamine, hydroxyurea, hydroxyprogesterone caproate, idarubicin, ifosfamide, interferon, irinotecan, leucovorin, lomustine, mechlorethamine, medroxyprogesterone acetate, megestrol acetate, melphalan, 6-mercaptopurine, mesna, methotrexate, mitomycin C, mitotane, mitoxantrone, paclitaxel, pentostatin, N-phosphonoacetyl L-aspartate (PALA), plicamycin, prednisolone, prednisone, procarbazine, raloxifen, semustine, streptozocin, tamoxifen, teniposide, testosterone propionate, thioguanine, thiotepa, topotecan, trimethylmelamine, uridine, vinblastine, vincristine, vindesine and vinorelbine.

In a promising manner, the compounds of the formula (Ia) according to the invention can also be combined with biological therapeutics such as antibodies (for example Avastin, Rituxan, Erbitux, Herceptin) and recombinant proteins.

The compounds of the formula (Ia) according to the invention can also achieve positive effects in combination with other therapies directed against angiogenesis, for example with Avastin, axitinib, regorafenib, recentin, sorafenib or sunitinib. Combinations with inhibitors of the proteasome and of mTOR and antihormones and steroidal metabolic enzyme inhibitors are particularly suitable because of their favorable profile of side effects.

In general, the following aims can be pursued with the combination of the compounds of the formula (Ia) according to the invention with other cytostatically or cytotoxically active agents:
improved efficacy in slowing the growth of a tumor, in reducing its size or even in the complete elimination thereof, compared with treatment with an individual active compound;
the possibility of using the chemotherapeutics used in a lower dosage than in the case of monotherapy;
the possibility of a more tolerable therapy with fewer side effects compared with individual administration;
the possibility of treatment of a broader spectrum of tumors;
the achievement of a higher rate of response to the therapy;
a longer survival time of the patient compared with present-day standard therapy.

In addition, the compounds according to the invention can also be used in conjunction with radiotherapy and/or surgical intervention.

1. SYNTHESIS ROUTES FOR COMPOUNDS OF THE FORMULA (IA)

The compounds of the formula (Ia) according to the invention can be prepared via synthesis route A and/or B.
Synthesis Route A
The aryl bromide derivative of the formula (IIa)

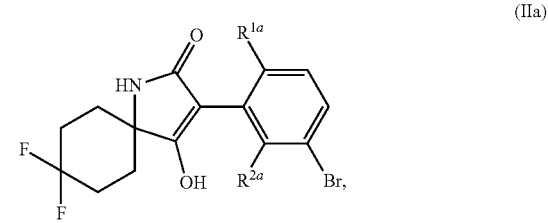

(IIa)

in which $R^{1a}$ and $R^a$ have the meanings mentioned above is reacted in a Suzuki coupling with compounds of the formula (IIIa)

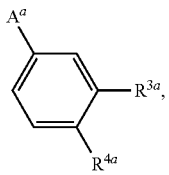

(IIIa)

in which $R^{3a}$ and $R^{4a}$ have the meanings mentioned above and $A^a$ represents —B(OH)$_2$, a boronic ester, preferably boronic acid pinacol ester, or —BF$_3^-$K$^+$.

The Suzuki couplings are generally carried out in inert solvents, in the presence of a catalyst, if appropriate in the presence of an additional reagent, preferably in a temperature range of from room temperature to 130° C. at atmospheric pressure. The reactions can also be carried out in a closed vessel with heating in a microwave oven.

Catalysts are, for example, palladium catalysts customary for Suzuki reaction conditions; preference is given to catalysts such as dichlorobis(triphenylphosphine)palladium, tetrakistriphenylphosphinepalladium(0), palladium on carbon, palladium(II) acetate, palladium(II) acetate/tricyclohexylphosphine, palladium(II) acetoacetonate/tri-tert-butylphosphonium tetrafluoroborate, dichloro[1,1'-bis(diphenylphosphino)ferrocene]palladium/dichloromethane complex or palladium(II) acetate with a ligand such as dicyclohexyl[2', 4',6'-tri(propan-2-yl)biphenyl-2-yl]phosphane. Additional reagents are, for example, potassium acetate or cesium acetate, cesium carbonate, potassium carbonate or sodium carbonate, potassium tert-butoxide, cesium fluoride, potassium phosphate or sodium hydroxide or potassium hydroxide, preference is given to additional reagents such as cesium carbonate and/or aqueous sodium hydroxide solution.

Inert solvents are, for example, ethers such as dioxane, tetrahydrofuran or 1,2-dimethoxyethane, hydrocarbons such as benzene, xylene or toluene, or carboxamides such as dimethylformamide, dimethylacetamide or N-methylpyrrolidone, or alkyl sulfoxides such as dimethyl sulfoxide, or mixtures of the solvents with alcohols such as methanol or ethanol and/or water; preference is given to 1,2-dimethoxyethane.

The compound of the formula (IIa) can be prepared by reacting the compounds of the formula (IVa)

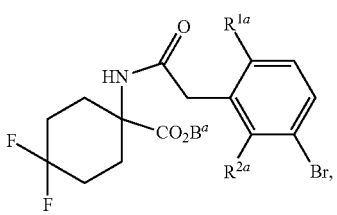

(IVa)

in which $R^{1a}$ and $R^{2a}$ have the meanings mentioned above and $B^a$ represents C$_1$-C$_6$-alkyl, preferably ethyl or methyl, under Dieckmann concensation conditions.

The Dieckmann condensations are generally carried out in inert solvents in the presence of a base, preferably in a temperature range of from room temperature to 130° C. at atmospheric pressure. Bases are, for example, alkali metal alkoxides or alkaline earth metal alkoxides such as sodium tert-butoxide or potassium tert-butoxide, sodium methoxide or sodium ethoxide; preference is given to potassium tert-butoxide.

Inert solvents are, for example, ethers such as dioxane, tetrahydrofuran or 1,2-dimethoxyethane, hydrocarbons such as benzene, xylene or toluene, or carboxamides such as dimethylformamide, dimethylacetamide or N-methylpyrrolidone, or alkyl sulfoxides such as dimethyl sulfoxide, or alcohols such as methanol or ethanol; preference is given to dimethylformamide.

The compounds of the formula (IVa) can be prepared by reacting compounds of the formula (Va) or a salt of compounds of the formula (Va)

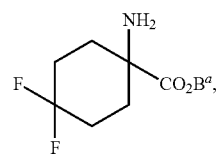

(Va)

in which $B^a$ has the meanings given above, with compounds of the formula (VIa)

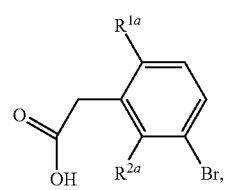

(VIa)

in which $R^{1a}$ and $R^{2a}$ have the meanings given above, under amide coupling conditions.

The reaction is generally carried out in inert solvents by reacting the compounds of the formula (VIa) initially with thionyl chloride or an equivalent reagent known to the person skilled in the art and in the second step with compounds of the formula (Va) or a salt of the compounds of the formula (Va) in the presence of a base such as triethylamine or potassium carbonate.

In an alternative process, the reaction can be carried out in inert solvents in the presence of a dehydrating agent, if appropriate in the presence of a base, preferably in a temperature range from –30° C. to 50° C. at atmospheric pressure.

Inert solvents are, for example, halogenated hydrocarbons such as dichloromethane or trichloromethane, hydrocarbons, such as benzene or toluene, nitromethane, tetrahydrofuran, 1,4-dioxane, dimethylformamide or acetonitrile. It is also possible to use mixtures of the solvents. Particular preference is given to acetonitrile, dichloromethane, dimethylformamide, tetrahydrofuran or toluene.

Bases are, for example, alkali metal carbonates such as, for example, sodium carbonate or potassium carbonate, or sodium bicarbonate or potassium bicarbonate, or organic bases such as trialkylamines, for example triethylamine, N-methylmorpholine, N-methylpiperidine, 4-dimethylaminopyridine or diisopropylethylamine.

Suitable dehydrating agents are, for example, carbodiimides such as, for example, N,N'-diethyl-, N',N',-dipropyl-, N,N'-diisopropyl-, N,N'-dicyclohexylcarbodiimide, N-(3- dimethylaminoisopropyl)-N'-ethylcarbodiimide hydrochloride (EDC), N-cyclohexylcarbodiimide-N'-propyloxymethylpolystyrene (PS-carbodiimide) or carbonyl compounds such as carbonyl diimidazole, or 1,2-oxazolium compounds such as 2-ethyl-5-phenyl-1,2-oxazolium 3-sulfate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or bis-(2-oxo-3-oxazolidinyl)phosphoryl chloride, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or benzotriazol-1-yloxytris(pyrrolidino)phosphonium hexafluorophosphate (PyBOP), or N-hydroxysuccinimide, or mixtures of these, with bases.

Preferably, the condensation is carried out with PyBOP, TBTU or with EDC in the presence of HOBt.

The process described above is illustrated by the synthesis scheme below:

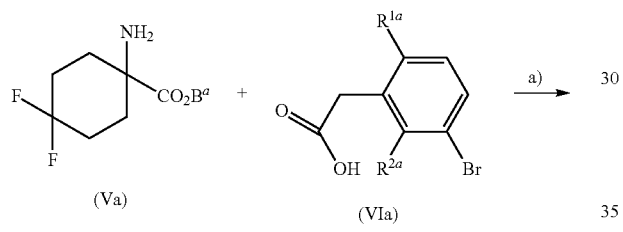

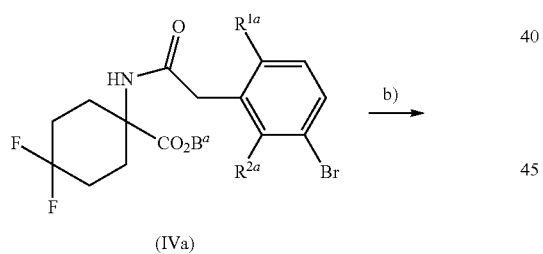

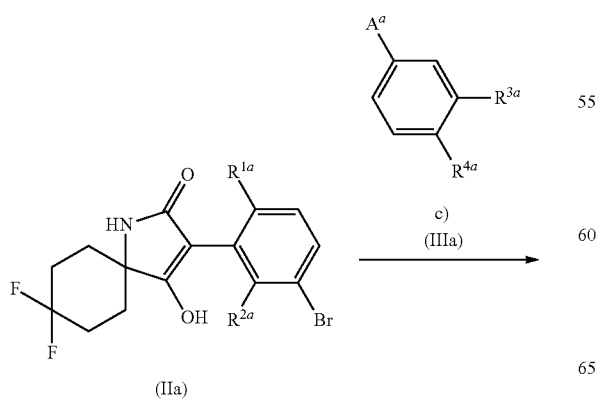

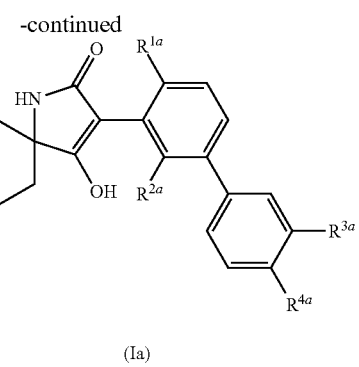

a): 1. $SOCl_2$, 80° C., 2. triethylamine, dichloromethane, room temperature;
b): KOtBu, DMF, 80° C;
c): cat. dichloro[1,1'-bis(diphenylphosphino)ferrocene]palladium/dichloromethane complex, $Cs_2CO_3$, 1,2-dimethoxyethane/water, reflux.

Synthesis Route B

Alternatively, the compounds of the formula (Ia) according to the invention can be prepared by reacting a compound of the formula (VIIa)

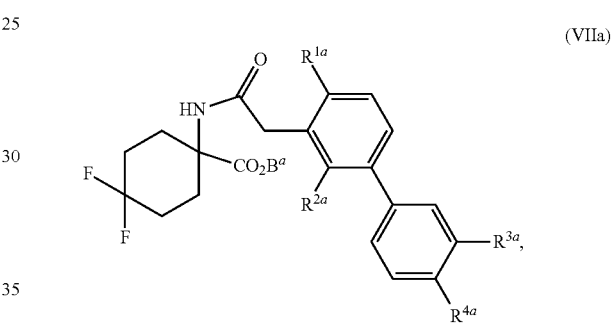

in which $R^{1a}$, $R^{2a}$, $R^{3a}$, $R^{4a}$ and $B^a$ have the meanings given above under the conditions indicated above in a Dieckmann condensation.

The compounds of the formula (VIIa) can be prepared by reacting compounds of the formula (Va) or a salt of compounds of the formula (Va) in which B has the meaning given above with compounds of the formula (VIIIa)

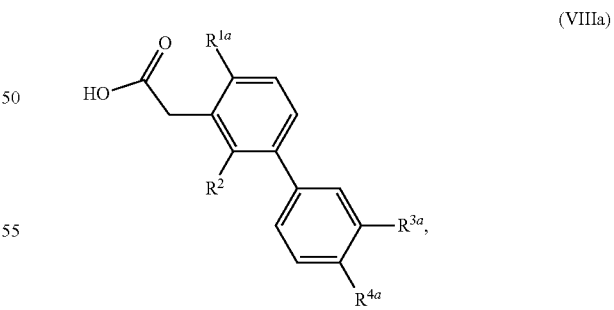

in which $R^{1a}$, $R^{2a}$, $R^{3a}$ and $R^{4a}$ have the meanings given above under the amide coupling conditions indicated above.

The compounds of the formula (VIIIa) can be prepared by reacting the compounds of the formula (VIa) in which $R^{1a}$ and $R^{2a}$ have the meanings given above in a Suzuki reaction under the conditions indicated above with compounds of the formula (IIIa) in which $R^{3a}$, $R^{4a}$ and $A^a$ have the meanings given above.

The process described above is illustrated by the synthesis scheme below:

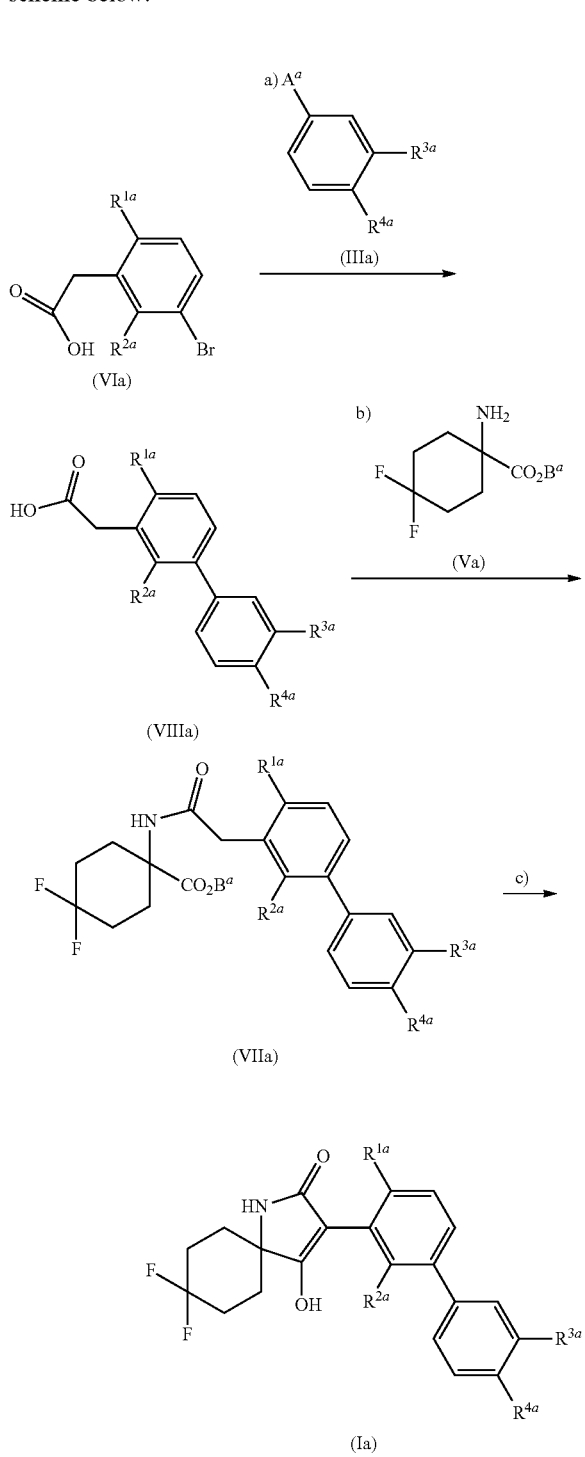

a): cat. palladium(II) acetylacetonate, cat. tri-tert-butylphosphonium tetrafluoroborate, NaOH, THF/water;
b): 1. SOCl₂, 80° C., 2. K₂CO₃, acetonitrile, room temperature;
c): KOtBu, DMF, room temperature.

The compounds of the formula (Va) or salts of compounds of the formula (Va) required for synthesis routes A and B, in which $B^a$ has the meaning given above, can be prepared by esterifying the compound of the formula (IXa) or a salt of the compound of the formula (IXa)

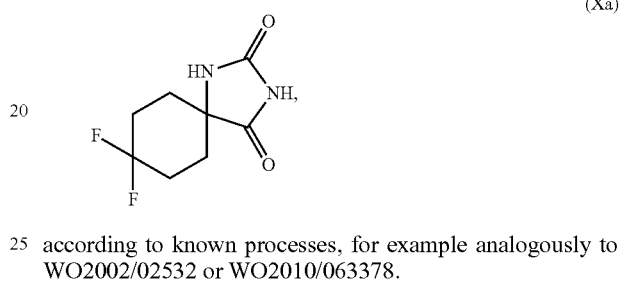

according to known processes, for example analogously to WO2002/02532 or WO2010/063378.

The compound of the formula (IXa) or salts of the compound of the formula (IXa) can be prepared by cleaving the compound of the formula (Xa)

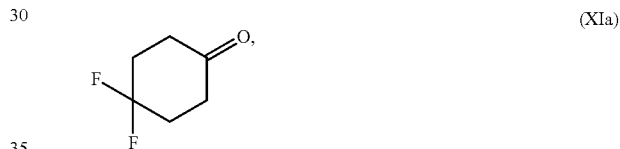

according to known processes, for example analogously to WO2002/02532 or WO2010/063378.

The compound of the formula (Xa) can be prepared by reacting the compound of the formula (XIa)

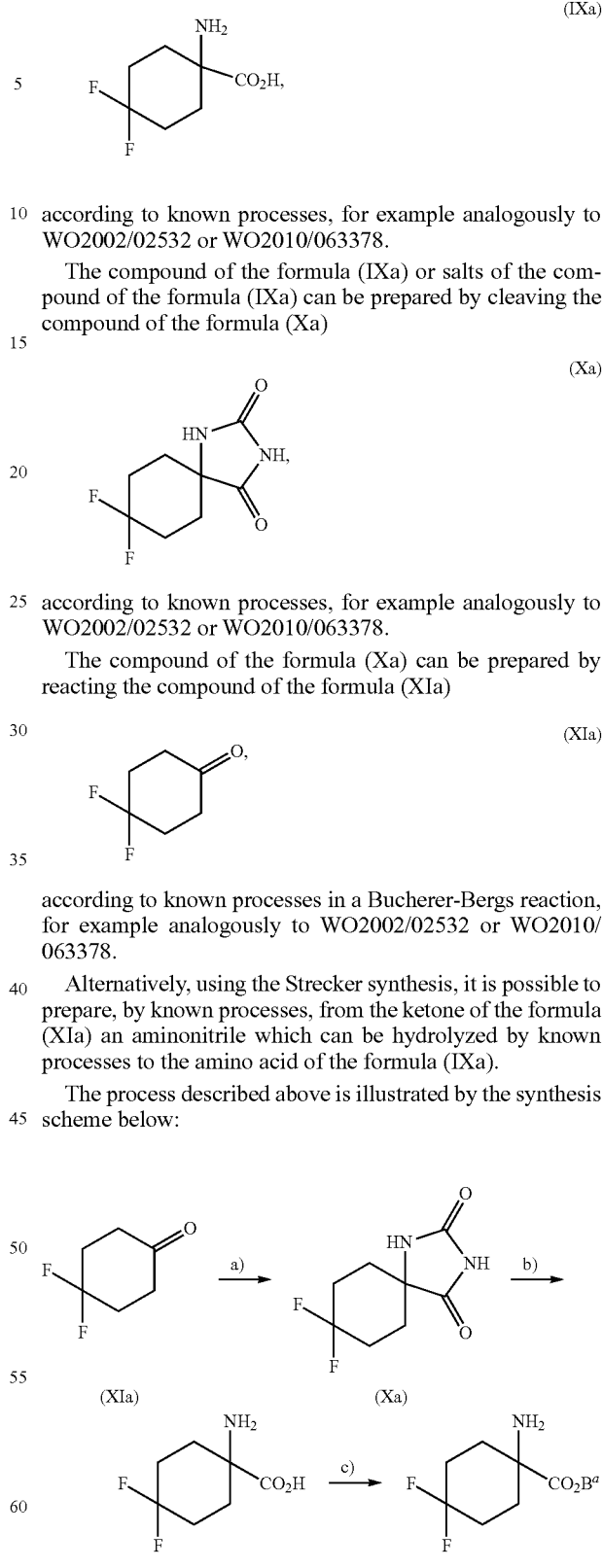

according to known processes in a Bucherer-Bergs reaction, for example analogously to WO2002/02532 or WO2010/063378.

Alternatively, using the Strecker synthesis, it is possible to prepare, by known processes, from the ketone of the formula (XIa) an aminonitrile which can be hydrolyzed by known processes to the amino acid of the formula (IXa).

The process described above is illustrated by the synthesis scheme below:

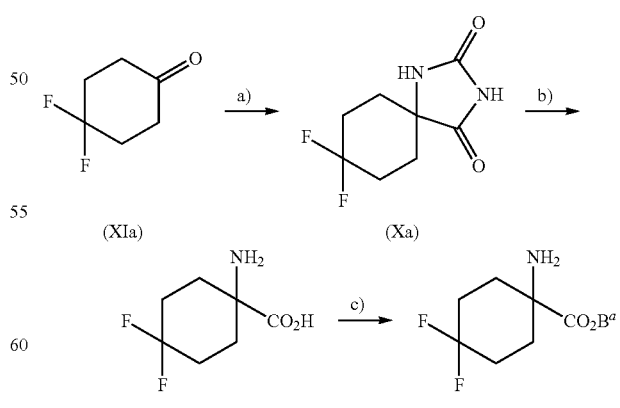

a): NaCN, (NH₄)₂CO₃, water/ethanol, 60° C.;
b): KOH or NaOH, water, reflux;
c): SOCl₂, e.g. methanol, 40° C. to reflux.

ABBREVIATIONS AND ACRONYMS

DMA dimethylacetamide
DMF dimethylformamide
DMSO dimethyl sulfoxide
ELSD evaporative light scattering detector
ESI electrospray ionization (in MS)
m.p. melting point
h hour(s)
HPLC high-pressure, high-performance liquid chromatography
LC-MS liquid chromatography-coupled mass spectrometry
min minute(s)
MS mass spectrometry
neg negative
NMR nuclear magnetic resonance spectrometry
pos positive
RP reversed-phase (in chromatography)
RT room temperature
$R_t$ retention time (in HPLC)
tert tertiary
THF tetrahydrofuran
UPLC ultra-performance liquid chromatography
LC-MS and HPLC Methods:
Method 1 (UPLC-MS):

Instrument: Waters Acquity UPLC-MS SQD 3001; column: Acquity UPLC BEH C18 1.7 50×2.1 mm; mobile phase A: water+0.1% formic acid, mobile phase B: acetonitrile; gradient: 0-1.6 min 1-99% B, 1.6-2.0 min 99% B; flow rate 0.8 ml/min; temperature: 60° C.; injection: 2 μl; DAD scan: 210-400 nM; ELSD.

Method 2 (UPLC-MS):

Instrument: Waters Acquity UPLC-MS SQD; column: Acquity UPLC BEH C18 1.7 50×2.1 mm; mobile phase A: water+0.05% formic acid, mobile phase B: acetonitrile+0.05% formic acid; gradient: 0-1.6 min 1-99% B, 1.6-2.0 min 99% B; flow rate 0.8 ml/min; temperature: 60° C.; injection: 2 μl; DAD scan: 210-400 nm; ELSD.

2. PREPARATION OF THE COMPARATIVE EXAMPLES AND WORKING EXAMPLES

Starting Materials and Intermediates

Example 1A (4'-Chloro-3'-fluoro-4-methylbiphenyl-3-yl)acetic acid

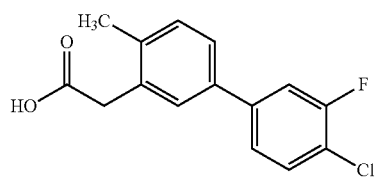 [SMILES: Cc1ccc(-c2ccc(Cl)c(F)c2)cc1CC(=O)O]

Under argon, 33.5 g (192 mmol) of (4-chloro-3-fluorophenyl)boronic acid were added to a solution of 40.0 g (175 mmol) of (5-bromo-2-methylphenyl)acetic acid (EP 1791816 and WO 2006/29799) in a mixture of 437 ml (437 mmol) of degassed 1N aqueous sodium hydroxide solution, 160 ml of degassed water and 160 ml of degassed tetrahydrofuran. The mixture was stirred for 10 minutes, 507 mg (1.75 mmol) of tri-tert-butylphosphonium tetrafluoroborate and 532 mg (1.75 mmol) of palladium(II) acetylacetonate were added and the mixture was stirred at room temperature for 20 h. Toluene and water were then added, the pH was adjusted to 1-2 with concentrated aqueous hydrogen chloride solution, the mixture was stirred for 10 minutes, the phases were separated, the aqueous phase was extracted twice with toluene and the combined organic phases were dried over sodium sulfate, filtered and concentrated. The residue was stirred in 300 ml of a 6/1 mixture of n-hexane/tert-butyl methyl ether for 30 minutes, filtered off with suction, washed with n-hexane and dried under reduced pressure. This gave 38.0 g (78% of theory) of the title compound.

$^1$H NMR (300 MHz, DMSO-$d_6$): δ [ppm]=2.27 (s, 3H), 3.67 (s, 2H), 7.27 (d, 1H), 7.49-7.59 (m, 3H), 7.61-7.75 (m, 2H), 12.4 (s, 1H).

LC-MS (method 1): $R_t$=1.31 min; MS (ESIneg): m/z=277 [M−H]⁻.

Example 2A 8,8-Difluoro-1,3-diazaspiro[4.5]decane-2,4-dione

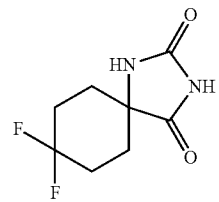

33.0 g of ammonium carbonate and 3.50 g of sodium cyanide were initially charged in 100 ml of water. Starting at room temperature, 7.70 g of 4,4'-difluorocyclohexanone were added dropwise and the reaction mixture was stirred at 55° C. to 60° C. for 24 hours and then at 0 to 5° C. for two hours, and the precipitate was filtered off with suction, washed with a little ice-water and dried. This gave 10.1 g (88% of theory) of the title compound.

$^1$H NMR (400 MHz, CD$_3$OD): δ [ppm]=1.77-1.84 (m, 2H), 1.93-2.09 (m, 4H), 2.17-2.28 (m, 2H).

Example 3A

1-Amino-4,4-difluorocyclohexanecarboxylic acid

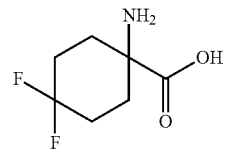

Under nitrogen gas, 4.10 g of the compound of Example 2A were suspended in 100 ml of 30% strength aqueous potassium hydroxide solution, and the mixture was stirred at reflux overnight. The mixture was concentrated to about 25% of the volume and, at 0-10° C., adjusted to pH 5.5 using concentrated aqueous hydrogen chloride solution. The solution was concentrated and dried. The residue (4.30 g) was used directly for the esterification.

Example 4A

Methyl 1-amino-4,4-difluorocyclohexanecarboxylate hydrochloride

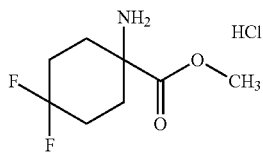

Under argon, 4.30 g of the compound from Example 3A were initially charged in 100 ml of methanol at 0 to 5° C. 10 ml of thionyl chloride were added dropwise, and the mixture was stirred at 0° C. for 30 minutes and at 70° C. for 24 h. The mixture was then cooled to 5° C. and the precipitate was filtered off with suction. The solution was concentrated using a rotary evaporator and the residue was crystallized using methyl tert-butyl ether. This gave 5.20 g (quantitative, still contains salts) of the title compound.

1H NMR (400 MHz, DMSO-$d_6$): δ [ppm]=1.97-2.33 (m, 6H), 2.14-2.17 (m, 2H), 3.78 (s, 3H), 9.00 (s, 3H).

Example 5A

Methyl 1-{[(4'-chloro-3'-fluoro-4-methylbiphenyl-3-yl)acetyl]amino}-4,4-difluorocyclohexanecarboxylate

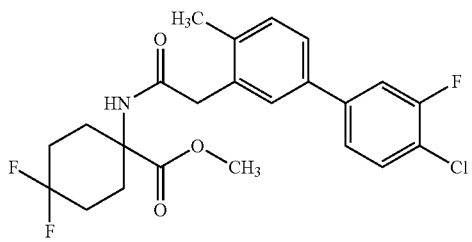 [SMILES: COC(=O)C1(NC(=O)Cc2cc(-c3ccc(Cl)c(F)c3)ccc2C)CCC(F)(F)CC1]

6.06 g (21.7 mmol) of the compound from Example 1A were dissolved in 7.5 ml (103 mmol) of thionyl chloride. The reaction mixture was stirred at 80° C. for 1 h and then concentrated. The residue was dissolved in 30 ml of acetonitrile. Ethyl acetate and saturated aqueous sodium bicarbonate solution were added to 5.00 g (21.8 mmol) of the compound from Example 4A. The phases were separated, the aqueous phase was extracted repeatedly with ethyl acetate and the combined organic phases were dried over sodium sulfate, filtered and concentrated. 140 ml of acetonitrile and 8.76 g (63.4 mmol) of potassium carbonate were added to the residue. With ice-cooling, the solution of the acid chloride was added dropwise, and the mixture was stirred at room temperature overnight. The mixture was then added to ice-water and extracted repeatedly with dichloromethane, and the combined organic phases were washed repeatedly with 1N aqueous hydrogen chloride solution and saturated aqueous sodium bicarbonate solution, dried over sodium sulfate, filtered and concentrated. This gave 8.22 g (83% of theory) of the title compound, which were converted without further purification.

$^1$H NMR (400 MHz, DMSO-$d_6$): δ [ppm]=1.85-2.06 (m, 6H), 2.08-2.18 (m, 2H), 2.28 (s, 3H), 3.55 (s, 3H), 3.60 (s, 2H), 7.25 (d, 1H), 7.48-7.54 (m, 2H), 7.58 (d, 1H), 7.62-7.73 (m, 2H), 8.50 (s, 1H).

LC-MS (method 2): $R_t$=1.42 min; MS (ESIpos): m/z=454 [M+H]$^+$.

Example 6A

Methyl 1-{[(4'-chloro-4-methylbiphenyl-3-yl)acetyl]amino}-4,4-difluorocyclohexanecarboxylate

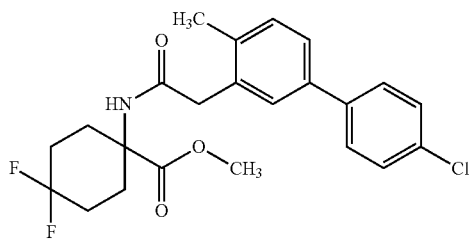

2.53 g (11 mmol) of the compound from Example 4A were initially charged in 50 ml of absolute tetrahydrofuran (THF). 3.07 ml of triethylamine were added dropwise at 20° C., the mixture was stirred for 5 min, and 2.61 g (10 mmol) of (4'-chloro-4-methylbiphenyl-3-yl)acetic acid (EP 2029531 A1 and US 2009/298828 A1) were added. After 15 min, a further 2.3 ml of triethylamine were added, followed immediately by the dropwise addition of 0.58 ml (6.2 mmol) of phosphorus oxychloride, and the mixture was stirred under reflux for 30 min. The mixture was concentrated under reduced pressure and the residue was purified by means of flash chromatography on silica gel using the mobile phase n-hexane/ethyl acetate 1:1. This gave 3.6 g (73% of theory) of the title compound of melting point 186° C.

$^1$H NMR (400 MHz, DMSO-$d_6$): δ [ppm]=1.87-2.07 (m, 6H), 2.11-2.15 (m, 2H), 2.28 (s, 3H), 3.55 (s, 3H), 3.60 (s, 2H), 7.23-7.25 (d, 1H), 7.43-7.45 (dd, 1H), 7.49-7.52 (m, 3H), 7.63-7.66 (m, 2H), 8.49 (s, 1H).

Example 7A

Methyl 4,4-difluoro-1-{[(4'-fluoro-4-methylbiphenyl-3-yl)acetyl]amino}cyclohexanecarboxylate

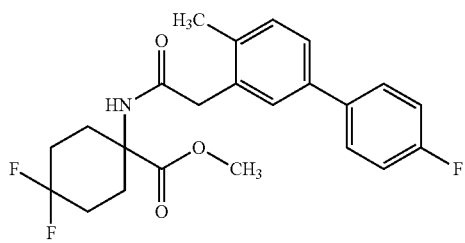 [SMILES: COC(=O)C1(NC(=O)Cc2cc(-c3ccc(F)cc3)ccc2C)CCC(F)(F)CC1]

2.53 g (11 mmol) of the compound from Example 4A were initially charged in 50 ml of absolute tetrahydrofuran (THF). At 20° C., 3.07 ml of triethylamine were added dropwise, the mixture was stirred for 5 min and 2.44 g (10 mmol) of (4'-fluoro-4-methylbiphenyl-3-yl)acetic acid were added. After 15 min, a further 2.3 ml of triethylamine were added, followed immediately by the dropwise addition of 0.58 ml (6.2 mmol) of phosphorus oxychloride, and the mixture was stirred under reflux for 30 min. The mixture was concentrated under reduced pressure and the residue was purified by means of flash chromatography on silica gel using the mobile phase n-hexane/ethyl acetate 1:1. This gave 2.84 g (60% of theory) of the title compound of melting point 187° C.

$^1$H NMR (400 MHz, DMSO-$d_6$): δ [ppm]=1.88-2.14 (m, 8H), 2.27 (s, 3H), 3.54 (s, 3H), 3.59 (s, 2H), 7.22-7.29 (m, 3H), 7.40-7.42 (m, 1H), 7.48-7.49 (m, 1H), 7.63-7.66 (m, 2H), 8.48 (s, 1H).

Example 8A

Methyl 1-{[(4,4'-dichlorobiphenyl-3-yl)acetyl]amino}-4,4-difluorocyclohexanecarboxylate

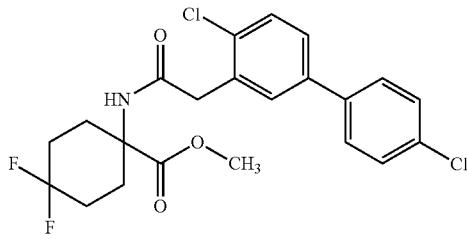 [SMILES: COC(=O)C1(NC(=O)Cc2cc(-c3ccc(Cl)cc3)ccc2Cl)CCC(F)(F)CC1]

2.53 g (11 mmol) of the compound from Example 4A were initially charged in 50 ml of absolute tetrahydrofuran (THF). 3.07 ml of triethylamine were added dropwise at 20° C., the mixture was stirred for 5 min, and 2.81 g (10 mmol) of (4,4'-dichlorobiphenyl-3-yl)acetic acid (EP 1943218 A1 and US 2009/215624 A1) were added. After 15 min, a further 2.3 ml of triethylamine were added, followed immediately by the dropwise addition of 0.58 ml (6.2 mmol) of phosphorus oxychloride, and the mixture was stirred under reflux for 30 min. The mixture was concentrated under reduced pressure and the residue was purified by means of flash chromatography on silica gel using the mobile phase n-hexane/ethyl acetate 1:1. This gave 3.3 g (59% of theory) of the title compound of melting point 146-147° C.

$^1$H NMR (400 MHz, DMSO-$d_6$): δ [ppm]=1.89-2.17 (m, 8H), 3.56 (s, 3H), 3.74 (s, 2H), 7.49-7.59 (m, 4H), 7.67-7.71 (m, 3H), 8.56 (s, 1H).

Example 9A

Methyl 1-{[(4'-chloro-2,4-dimethylbiphenyl-3-yl)acetyl]amino}-4,4-difluorocyclohexanecarboxylate

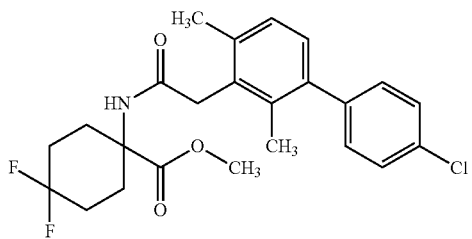 [SMILES: COC(=O)C1(NC(=O)Cc2c(C)ccc(-c3ccc(Cl)cc3)c2C)CCC(F)(F)CC1]

2.53 g (11 mmol) of the compound from Example 4A were initially charged in 50 ml of absolute tetrahydrofuran (THF). At 20° C., 3.07 ml of triethylamine were added dropwise, the mixture was stirred for 5 min and 2.75 g (10 mmol) of (4'-chloro-2,4-dimethylbiphenyl-3-yl)acetic acid were added. After 15 min, a further 2.3 ml of triethylamine were added, followed immediately by the dropwise addition of 0.58 ml (6.2 mmol) of phosphorus oxychloride, and the mixture was stirred under reflux for 30 min. The mixture was concentrated under reduced pressure and the residue was purified by means of flash chromatography on silica gel using the mobile phase n-hexane/ethyl acetate 1:1. This gave 2.59 g (53% of theory) of the title compound of melting point 179-183° C.

$^1$H NMR (400 MHz, DMSO-$d_6$): δ [ppm]=1.89-2.15 (m, 8H), 2.11 (s, 3H), 2.28 (s, 3H), 3.55 (s, 3H), 3.68 (s, 2H), 6.94-6.96 (d, 1H), 7.05-7.07 (d, 1H), 7.26-7.28 (m, 2H), 7.46-7.48 (m, 2H), 8.46 (s, 1H).

Example 10A

Methyl 1-{[(5-bromo-2-methylphenyl)acetyl]amino}-4,4-difluorocyclohexanecarboxylate

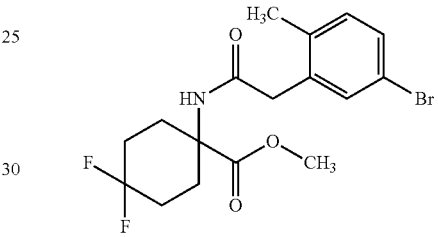

36.5 ml (500 mmol) of thionyl chloride were added to 22.91 g (100 mmol) of (5-bromo-2-methylphenyl)acetic acid (EP 1791816 A1 and WO 2006/29799 A1), and the mixture was stirred at 80° C. until the evolution of gas was complete and then concentrated. The residue was dissolved in 100 ml of tetrahydrofuran (THF) (solution A). 25.3 g (110 mmol) of the compound from Example 4A were initially charged in 308 ml of THF, 21.3 ml of triethylamine were added dropwise at 20° C., solution A was then added dropwise with cooling and the mixture was stirred at room temperature until the reaction had gone to completion. The precipitate is filtered off with suction and washed with THF, the filtrate is concentrated under reduced pressure and the residue is recrystallized from methyl tert-butyl ether. This gave 33.6 g (83% of theory) of the title compound.

$^1$H NMR (400 MHz, DMSO-$d_6$): δ [ppm]=1.91-2.02 (m, 6H), 2.09-2.13 (m, 2H), 2.19 (s, 3H), 3.54 (s, 2H), 3.58 (s, 3H), 7.11-7.13 (d, 1H), 7.31-7.33 (dd, 1H), 7.39-7.40 (d, 1H), 8.54 (s, 1H).

Example 11A 3-(5-Bromo-2-methylphenyl)-8,8-difluoro-4-hydroxy-1-azaspiro[4.5]dec-3-en-2-one

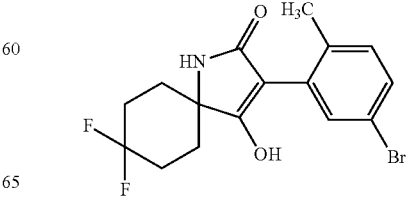

11.0 g (27.2 mmol) of the compound from Example 10A were initially charged in a solution of 22 ml of DMA (N,N-dimethylacetamide), a solution of 10 ml of DMA and 3.54 g (1.1 eq.) of potassium tert-butoxide was added dropwise at 20-30° C. and the mixture was stirred at 30° C. for a further 1 h. The mixture was poured into 200 ml of water and the mixture was adjusted to pH 2 using aqueous 1N hydrochloric acid, the resulting precipitate was filtered off with suction, washed with water and dried in a vacuum drying cabinet at 50° C. The product was suspended in hot methyl tert-butyl ether, n-hexane was added and the mixture was filtered off with suction and dried. This gave 11.0 g (97% of theory) of the title compound in a purity of 89%.

$^1$H NMR (400 MHz, DMSO-$d_6$): δ [ppm]=1.53-1.56 (m, 2H), 1.92-2.23 (m, 6H), 2.11 (s, 3H), 7.17-7.19 (d, 1H), 7.24 (d, 1H), 7.36-7.40 (dd, 1H), 8.80 (s, 1H), 11.2 (s, 1H).

Starting Materials and Intermediates for Comparative Examples

Example 12A

Methyl 1-{[(5-bromo-2-methylphenyl)acetyl]amino}cyclohexanecarboxylate

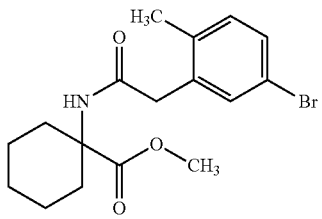 [SMILES: COC(=O)C1(NC(=O)Cc2cc(Br)ccc2C)CCCCC1]

2.06 g (9.00 mmol) of (5-bromo-2-methylphenyl)acetic acid (described in EP 1791816 and WO 2006/29799) were dissolved in 3.7 ml (51.3 mmol) of thionyl chloride. The reaction mixture was stirred at 80° C. for 2 h and then concentrated. The residue was dissolved in 20 ml of dichloromethane. 2.09 g (10.8 mmol) of methyl 1-aminocyclohexanecarboxylate hydrochloride were dissolved in 25 ml of dichloromethane, 55 mg (0.45 mmol) of 4-dimethylaminopyridine and 3.1 ml (22.5 mmol) of triethylamine were added and the mixture was stirred at room temperature for 0.5 h. The solution of the acid chloride was added dropwise, and the mixture was stirred at room temperature for 36 h. The mixture was then diluted with diluted with dichloromethane, washed with water, 1N aqueous hydrogen chloride solution and saturated aqueous sodium bicarbonate solution, dried, filtered and concentrated. This gave 2.80 g (84% of theory) of the title compound.

$^1$H NMR (300 MHz, DMSO-$d_6$): δ [ppm]=1.15-1.31 (m, 1H), 1.37-1.58 (m, 5H), 1.59-1.73 (m, 2H), 1.86-1.99 (m, 2H), 2.19 (s, 3H), 3.51 (s, 2H), 3.54 (s, 3H), 7.10 (d, 1H), 7.30 (dd, 1H), 7.39 (d, 1H), 8.26 (s, 1H).

LC-MS (method 1): $R_t$=1.30 min; MS (ESIpos): m/z=368 [M+H]$^+$.

Example 13A 3-(5-Bromo-2-methylphenyl)-4-hydroxy-1-azaspiro[4.5]dec-3-en-2-one

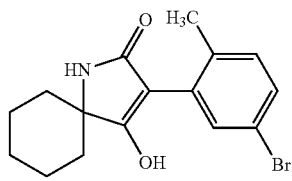 [SMILES: Cc1ccc(Br)cc1C1=C(O)C2(CCCCC2)NC1=O]

1.71 g (15.2 mmol) of potassium tert-butoxide were added to 2.80 g (7.60 mmol) of the compound from Example 12A in 15 ml of N,N-dimethylformamide. The reaction mixture was heated at 80° C. for 15 minutes. After cooling, water was added and aqueous hydrogen chloride solution was added dropwise. The precipitate was filtered off with suction, washed with water and dried. This gave 2.33 g (90% of theory) of the title compound.

$^1$H NMR (400 MHz, DMSO-$d_6$): δ [ppm]=1.09-1.27 (m, 1H), 1.30-1.41 (m, 2H), 1.51-1.72 (m, 5H), 1.76-1.90 (m, 2H), 2.11 (s, 3H), 7.17 (d, 1H), 7.22 (d, 1H), 7.36 (dd, 1H), 8.19 (s, 1H), 10.87 (s, 1H).

LC-MS (method 1): $R_t$=1.09 min; MS (ESIpos): m/z=336 [M+H]$^+$.

Example 14A

Methyl cis-1-{[(5-bromo-2-methylphenyl)acetyl]amino}-4-(trifluoromethyl)cyclohexanecarboxylate

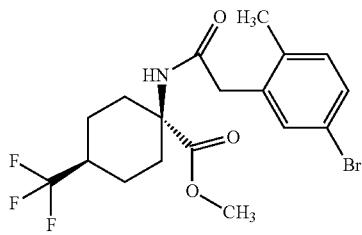 [SMILES: COC(=O)[C@]1(NC(=O)Cc2cc(Br)ccc2C)CC[C@@H](C(F)(F)F)CC1]

Under nitrogen, 19.0 g (82.9 mmol) of (5-bromo-2-methylphenyl)acetic acid (EP 1791816 A1 and WO 2006/29799 A1) were dissolved in 97 ml (1327 mmol) of thionyl chloride. The reaction mixture was stirred at 80° C. for four hours and at room temperature overnight and then concentrated under reduced pressure. Drying under fine vacuum gave 20.5 g (100% of theory) of the title compound as a brownish oil. At room temperature, 10.00 g (38.22 mmol) of methyl cis-1-amino-4-(trifluoromethyl)cyclohexanecarboxylate hydrochloride (EP 1220841 A2 and WO 2001/23354 A3), 9.67 g (95.54 mmol) of triethylamine and 233 mg (1.91 mmol) of N,N-dimethylaminopyridine were dissolved in 95 ml of dichloromethane. A solution of 9.46 g (38.22 mmol) of (5-bromo-2-methylphenyl)acetyl chloride in 95 ml of dichloromethane was then added dropwise to the mixture. The resulting reaction mixture was stirred at room temperature overnight. For work-up, the mixture was diluted with dichloromethane and the organic phase was washed with aqueous saturated sodium bicarbonate solution and with aqueous 5% strength citric acid. After drying over sodium sulfate, the mixture was concentrated by evaporation and the residue was purified by chromatography on silica gel (mobile phase: dichloromethane/methanol gradient). Evaporation and drying gave 8.84 g (53% of theory) of the title compound which were used without further characterization in the next step.

Example 15A (5s,8s)-3-(5-Bromo-2-methylphenyl)-4-hydroxy-8-(trifluoromethyl)-1-azaspiro[4.5]dec-3-en-2-one

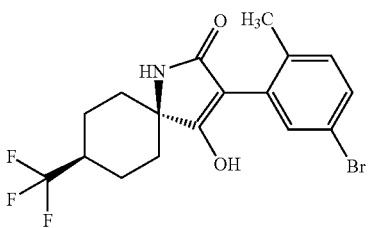 [SMILES: Cc1ccc(Br)cc1C1=C(O)[C@]2(CC[C@H](C(F)(F)F)CC2)NC1=O]

4.53 g (40.34 mmol) of potassium tert-butoxide were added to 8.80 g (20.17 mmol) of methyl cis-1-{[(5-bromo-2-methylphenyl)acetyl]amino}-4-(trifluoromethyl)cyclohexanecarboxylate (Example 14A) in 100 ml of N,N-dimethylformamide. The reaction mixture was stirred at 80° C. for 60 minutes. For work-up, the cold reaction mixture was poured into 800 ml of ice-water and acidified with aqueous hydrochloric acid. The crude product was filtered off and purified by silica gel chromatography (mobile phase: hexane/ethyl acetate gradient). Drying gave 5.23 g (64% of theory) of the title compound.

$^1$H NMR (400 MHz, DMSO-$d_6$): δ [ppm]=1.40-1.50 (m, 2H), 1.58-1.72 (m, 2H), 1.77-1.86 (m, 2H), 1.86-1.96 (m, 2H), 2.07 (s, 3H), 2.12-2.28 (m, 1H), 7.14 (d, 1H), 7.19 (d, 1H), 7.33 (dd, 1H), 8.33 (s, 1H), 11.01 (s, 1H).

LC-MS (method 3): $R_t$=1.18 min; MS (ESIpos): m/z=406 [M+H]$^+$.

Example 16A

Methyl cis-1-{[(4'-chloro-4-methylbiphenyl-3-yl)acetyl]amino}-4-(trifluoromethyl)cyclohexanecarboxylate

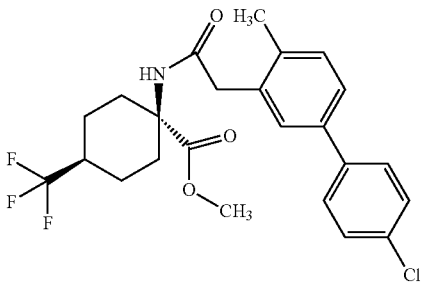 [SMILES: COC(=O)[C@]1(NC(=O)Cc2cc(-c3ccc(Cl)cc3)ccc2C)CC[C@@H](C(F)(F)F)CC1]

5.00 g (19.18 mmol) of (4'-chloro-4-methylbiphenyl-3-yl)acetic acid (EP 2029531 A1 and US 2009/298828 A1) were dissolved in 36.51 g (306.84 mmol) of thionyl chloride. The reaction mixture was stirred at 80° C. for four hours and then concentrated under reduced pressure. Drying under fine vacuum gave 5.4 g (100% of theory) of (4'-chloro-4-methylbiphenyl-3-yl)acetyl chloride as a brownish oil. At room temperature, 5.00 g (19.09 mmol) of methyl cis-1-amino-4-(trifluoromethyl)cyclohexanecarboxylate hydrochloride (EP 1220841 A2 and WO 2001/23354 A3), 4.83 g (47.73 mmol) of triethylamine and 117 mg (0.955 mmol) of N,N-dimethylaminopyridine were dissolved in 40 ml of dichloromethane. A solution of 5.33 g (19.09 mmol) of (4'-chloro-4-methylbiphenyl-3-yl)acetyl chloride in 40 ml of dichloromethane was then added dropwise to the mixture. The resulting reaction mixture was stirred at room temperature overnight. For work-up, the mixture was diluted with dichloromethane and the organic phase was washed with aqueous 5% strength citric acid. After drying over sodium sulfate, the mixture was concentrated by evaporation and the residue was purified by chromatography on silica gel (mobile phase: hexane/ethyl acetate gradient). Concentration and drying gave 6.36 g (71% of theory) of the title compound.

$^1$H NMR (300 MHz, DMSO-$d_6$): δ [ppm]=1.35-1.80 (m, 6H), 2.05-2.18 (m, 2H), 2.24 (s, 3H), 2.25-2.40 (m, 1H), 3.49 (s, 3H), 3.56 (s, 2H), 7.19 (d, 1H), 7.40 (dd, 1H), 7.42-7.52 (m, 3H), 7.56-7.65 (m, 2H), 8.34 (s, 1H).

LC-MS (method 1): $R_t$=1.50 min; MS (ESIpos): m/z=468 [M+H]$^+$.

COMPARATIVE EXAMPLES

For Working Example 1-1

V.1-a (5s,8s)-3-(4'-Chloro-3'-fluoro-4-methylbiphenyl-3-yl)-4-hydroxy-8-(trifluoromethyl)-1-azaspiro[4.5]dec-3-en-2-one

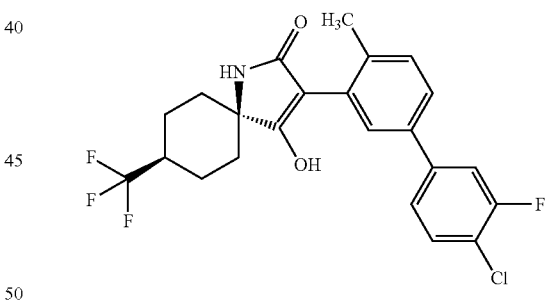

Under argon, 1.01 g (1.24 mmol) of dichloro[1,1'-bis(diphenylphosphino)ferrocene]palladium/dichloromethane complex were added to 5.00 g (12.4 mmol) of the compound from Example 15A in 500 ml of degassed 1,2-dimethoxyethane. The mixture was stirred at room temperature for 5 minutes, and 3.24 g (18.5 mmol) of (4-chloro-3-fluorophenyl)boronic acid and a solution of 14.1 g (43.3 mmol) of cesium carbonate in 30 ml of degassed water was then added. The reaction mixture was heated under reflux for 2 h. After cooling, 10 ml of concentrated aqueous hydrogen chloride solution were added, the aqueous phase was separated off, magnesium sulfate was added, the mixture was filtered through silica gel, the filter cake was washed with ethyl acetate and the mixture was concentrated. Purification of the crude product by chromatography on silica gel (mobile phase: hexane/ethyl acetate gradient) and crystallization from ethyl acetate gave 2.48 g (44% of theory) of the title compound.

$^1$H NMR (300 MHz, DMSO-d$_6$): δ [ppm]=1.45-1.57 (m, 2H), 1.62-1.79 (m, 2H), 1.81-2.05 (m, 4H), 2.19 (s, 3H), 2.20-2.33 (m, 1H), 7.32 (d, 1H), 7.41 (d, 1H), 7.49-7.58 (m, 2H), 7.64 (t, 1H), 7.70 (dd, 1H), 8.33 (s, 1H), 10.95 (s, 1H).

LC-MS (method 1): R$_t$=1.34 min; MS (ESIpos): m/z=454 [M+H]$^+$.

V.1-b=Table 1, line 3, p. 41 and Table 2, line 3, p. 44 of WO08/067,911

3-(4'-Chloro-3'-fluoro-4-methylbiphenyl-3-yl)-4-hydroxy-1-azaspiro[4.5]dec-3-en-2-one

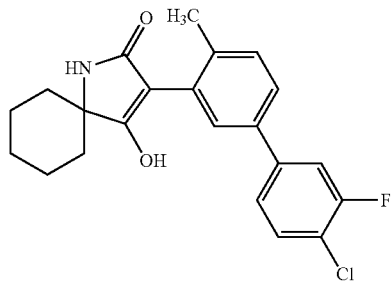 [SMILES: Cc1ccc(-c2ccc(Cl)c(F)c2)cc1C1=C(O)C2(CCCCC2)NC1=O]

Under argon, 36.4 mg (0.05 mmol) of dichloro[1,1'-bis(diphenylphosphino)ferrocene]palladium complex were added to 150 mg (0.45 mmol) of the compound from Example 13A in 15 ml of degassed 1,2-dimethoxyethane. The mixture was stirred at room temperature for 5 minutes, and 117 mg (0.67 mmol) of (4-chloro-3-fluorophenyl)boronic acid and a solution of 509 mg (1.56 mmol) of cesium carbonate in 0.9 ml of degassed water was then added. Under microwave irradiation, the reaction mixture was heated at 150° C. for 10 minutes. After cooling, 0.3 ml of concentrated aqueous hydrogen chloride solution were added, magnesium sulfate was added, the mixture was filtered through silica gel, the filter cake was washed with ethyl acetate and the mixture was concentrated. Purification of the crude product by HPLC chromatography (C18 phase, mobile phase: water/acetonitrile gradient/0.1% formic acid) gave 43.7 mg (25% of theory) of the title compound.

$^1$H NMR (300 MHz, DMSO-d$_6$): 1.11-1.28 (m, 1H), 1.33-1.44 (m, 2H), 1.52-1.73 (m, 5H), 1.78-1.92 (m, 2H), 2.19 (s, 3H), 7.31 (d, 1H), 7.40 (d, 1H), 7.49-7.57 (m, 2H), 7.64 (t, 1H), 7.70 (dd, 1H), 8.14 (s, 1H), 10.77 (s, 1H).

LC-MS (method 1): R$_t$=1.30 min; MS (ESIpos): m/z=386 [M+H]$^+$.

For Working Example 1-2

V.2-a (5s,8s)-3-(4'-Chloro-4-methylbiphenyl-3-yl)-4-hydroxy-8-(trifluoromethyl)-1-azaspiro[4.5]dec-3-en-2-one

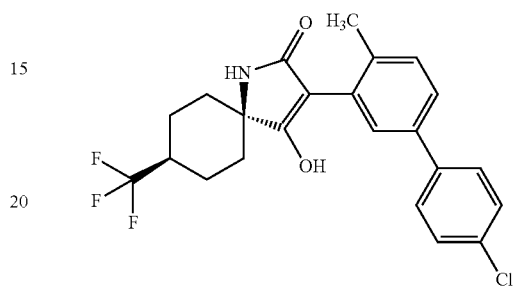

3.05 g (27.18 mmol) of potassium tert-butoxide were added to 6.36 g (13.59 mmol) of methyl cis-1-{[(4'-chloro-4-methylbiphenyl-3-yl)acetyl]amino}-4-(trifluoromethyl)cyclohexanecarboxylate (Example 16A) in 68 ml of N,N-dimethylformamide. The reaction mixture was stirred at 80° C. for 60 minutes. For work-up, the cold reaction mixture was poured into 800 ml of ice-water and acidified with aqueous hydrochloric acid. The crude product was filtered off, dried and purified by chromatography on silica gel (hexane/ethyl acetate gradient). Evaporation gave 4.1 g (69% of theory) of the title compound.

$^1$H NMR (400 MHz, DMSO-d$_6$): δ [ppm]=1.40-1.55 (m, 2H), 1.58-1.77 (m, 2H), 1.78-2.02 (m, 4H), 2.15 (s, 3H), 2.17-2.30 (m, 1H), 7.27 (d, 1H), 7.32 (d, 1H), 7.42-7.51 (m, 3H), 7.58-7.66 (m, 2H), 8.29 (s, 1H), 10.90 (s, 1H).

LC-MS (method 1): R$_t$=1.32 min; MS (ESIpos): m/z=436 [M+H]$^+$.

V.2-b=Example I-1-a18 of WO03/059065

3-(4'-Chloro-4-methylbiphenyl-3-yl)-4-hydroxy-1-azaspiro[4.5]dec-3-en-2-one

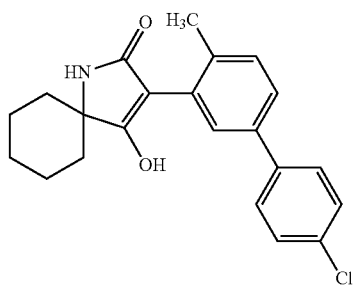 [SMILES: Cc1ccc(-c2ccc(Cl)cc2)cc1C1=C(O)C2(CCCCC2)NC1=O]

$^1$H NMR (300 MHz, DMSO-d$_6$): 1.10-1.29 (m, 1H), 1.33-1.43 (m, 2H), 1.52-1.73 (m, 5H), 1.78-1.92 (m, 2H), 2.19 (s, 3H), 7.29 (d, 1H), 7.35 (d, 1H), 7.45-7.52 (m, 3H), 7.62-7.68 (m, 2H), 8.10 (br. s., 1H), 10.82 (br. s, 1H).

Table V gives an overview of the comparative examples which the applicant considers to be the closest prior art

TABLE V

| Ex. | Structure/Name | Disclosed in |
|---|---|---|
| V.1-a | | |
| V.1-b | | Table 1, line 3, p. 41 and Table 2, line 3, p. 44 of WO08/067911 |
| V.2-a | | |
| V.2-b | | Example I-1-a18 of WO03/059065 |

WORKING EXAMPLES

Example 1-1

3-(4'-Chloro-3'-fluoro-4-methylbiphenyl-3-yl)-8,8-difluoro-4-hydroxy-1-azaspiro[4.5]dec-3-en-2-one

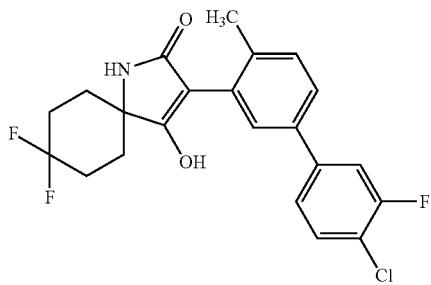 [SMILES: Cc1ccc(-c2ccc(Cl)c(F)c2)cc1C1=C(O)C2(CCC(F)(F)CC2)NC1=O]

Under nitrogen, 2.23 g (19.9 mmol) of potassium tert-butoxide were added to 8.19 g (18.0 mmol) of the compound from Example 5A in 80 ml of N,N-dimethylformamide. The reaction mixture was stirred at room temperature for 15 minutes. The reaction mixture was then added to ice-water, 1N aqueous hydrogen chloride solution was added dropwise until a pH of 1-2 had been reached, the mixture was stirred for 30 minutes and filtered off with suction, the filter cake was washed with water and the precipitate was dried. For further purification, the product was dissolved in 1N aqueous sodium hydroxide solution, precipitated by acidification with aqueous 1 N hydrochloric acid, stirred for 30 minutes, washed with water, filtered off and dried. This gave 7.50 g (97% of theory) of the title compound.

$^1$H NMR (400 MHz, DMSO-$d_6$): δ [ppm]=1.50-1.62 (m, 2H), 2.05-2.31 (m, 6H), 2.20 (s, 3H), 7.32 (d, 1H), 7.41 (d, 1H), 7.49-7.57 (m, 2H), 7.64 (t, 1H), 7.69 (dd, 1H), 8.32 (s, 1H), 11.08 (s, 1H).

LC-MS (method 1): $R_t$=1.26 min; MS (ESIpos): m/z=422 [M+H]$^+$.

Example 1-2

3-(4'-Chloro-4-methylbiphenyl-3-yl)-8,8-difluoro-4-hydroxy-1-azaspiro[4.5]dec-3-en-2-one

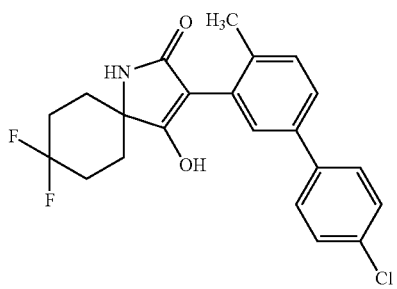 [SMILES: Cc1ccc(-c2ccc(Cl)cc2)cc1C1=C(O)C2(CCC(F)(F)CC2)NC1=O]

Under argon and at 20 to 30° C., 3.31 g (28.0 mmol) of potassium tert-butoxide in 10 ml of N,N-dimethylacetamide were added to 11.1 g (25.5 mmol) of the compound from Example 6A in 22 ml of N,N-dimethylacetamide. The reaction mixture was stirred at 30° C. for 3 h. The reaction mixture was then added to 250 ml of ice-water, 1N aqueous hydrogen chloride solution was added dropwise until a pH of 2 had been reached and the precipitate was filtered off with suction and washed with water. For further purification, the product was taken up in methylene chloride and extracted with 50 ml of 1N aqueous sodium hydroxide solution, the aqueous phase was acidified with aqueous 1 N hydrochloric acid, filtered off with suction, washed with water and, for purification, suspended in 25 ml of hot acetonitrile on an ultrasonic bath, filtered off with suction, washed and dried. This gave 5.70 g (55% of theory) of the title compound.

$^1$H NMR (400 MHz, DMSO-$d_6$): δ=1.54-1.56 (d, 2H), 2.07-2.33 (m, 6H), 2.19 (s, 3H), 7.29-7.31 (d, 1H), 7.36 (d, 1H), 7.48-7.53 (m, 3H), 7.64-7.71 (m, 2H), 8.28 (s, 1H), 11.5 (s, 1H).

LC-MS (method 2): $R_t$=1.24 min; MS (ESIpos): m/z=404 [M+H]$^+$.

Example 1-3

8,8-Difluoro-3-(4'-fluoro-4-methylbiphenyl-3-yl)-4-hydroxy-1-azaspiro[4.5]dec-3-en-2-one

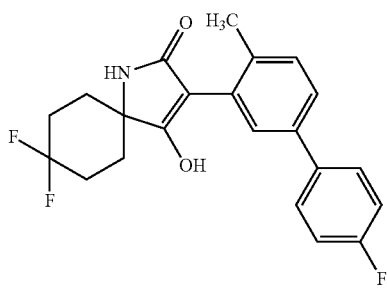 [SMILES: Cc1ccc(-c2ccc(F)cc2)cc1C1=C(O)C2(CCC(F)(F)CC2)NC1=O]

2.80 g (5.94 mmol) of the compound from Example 7A were initially charged in a solution of 8 ml of DMA (N,N-dimethylacetamide), a solution of 5 ml of DMA and 1.75 g (2.5 eq.) of potassium tert-butoxide was added dropwise at 20° C. and the mixture was stirred at room temperature for 4 h. The mixture was poured into 200 ml of water and the reaction was adjusted to pH 2 using concentrated aqueous hydrochloric acid, and the resulting residue was filtered off with suction. Purification by flash column chromatography (silica gel; ethyl acetate/n-hexane 1:1) gave 1.07 g (44% of theory) of the title compound.

$^1$H NMR (400 MHz, DMSO-$d_6$): δ [ppm]=1.55-1.57 (m, 2H), 2.07-2.30 (m, 6H), 2.19 (s, 3H), 7.24-7.34 (m, 4H), 7.45-7.47 (dd, 1H), 7.63-7.67 (m, 2H), 8.28 (s, 1H), 11.05 (s, 1H).

LC-MS (method 1): $R_t$=1.21 min; MS (ESIpos): m/z=388 [M+H]$^+$.

Example 1-4

3-(4,4'-Dichlorobiphenyl-3-yl)-8,8-difluoro-4-hydroxy-1-azaspiro[4.5]dec-3-en-2-one

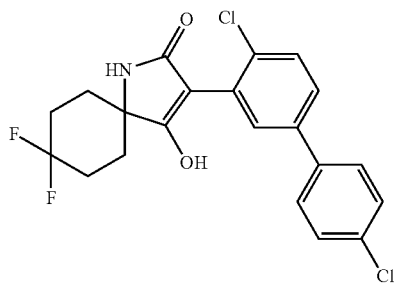 [SMILES: O=C1NC2(CCC(F)(F)CC2)C(O)=C1c1cc(-c2ccc(Cl)cc2)ccc1Cl]

3.20 g (5.74 mmol) of the compound from Example 8A were initially charged in a solution of 14 ml of DMA (N,N-dimethylacetamide), a solution of 9 ml of DMA and 1.69 g (2.5 eq.) of potassium tert-butoxide was added dropwise at 20° C. and the mixture was stirred at room temperature for 4 h. The mixture was poured into 200 ml of water and the reaction was adjusted to pH 2 using concentrated aqueous hydrochloric acid, and the resulting residue was filtered off with suction. Purification by flash column chromatography (silica gel; ethyl acetate/n-hexane 1:1) gave 1.50 g (52% of theory) of the title compound of melting point m.p. 156° C.

$^1$H NMR (300 MHz, DMSO-$d_6$): δ [ppm]=1.50-1.62 (m, 2H), 2.02-2.24 (m, 6H), 7.50-7.57 (m, 4H), 7.58-7.65 (m, 1H), 7.66-7.72 (m, 2H), 8.37 (s, 1H), 11.4 (s, 1H).

LC-MS (method 1): $R_t$=1.28 min; MS (ESIpos): m/z=424 [M+H]$^+$.

Example 1-5

3-(4'-Chloro-2,4-dimethylbiphenyl-3-yl)-8,8-difluoro-4-hydroxy-1-azaspiro[4.5]dec-3-en-2-one

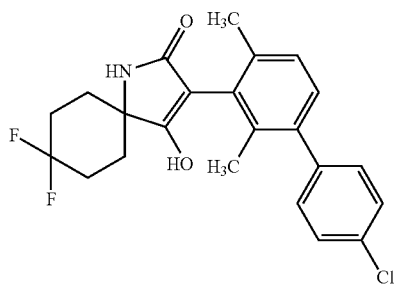 [SMILES: Cc1ccc(-c2ccc(Cl)cc2)c(C)c1C1=C(O)C2(CCC(F)(F)CC2)NC1=O]

2.55 g (5.29 mmol) of the compound from Example 9A were initially charged in a solution of 5 ml of DMA (N,N-dimethylacetamide), a solution of 5 ml of DMA and 1.88 g (3 eq.) of potassium tert-butoxide was added dropwise at 20° C. and the mixture was stirred at room temperature for 24 h. The mixture was poured into 200 ml of water and the reaction was adjusted to pH 2 using concentrated aqueous hydrochloric acid, and the resulting residue was filtered off with suction. Purification by flash column chromatography (silica gel; ethyl acetate/n-hexane 2:1) gave 0.87 g (31% of theory) of the title compound.

$^{1}$H NMR (400 MHz, DMSO-$d_6$): δ [ppm]=1.55 (m, 2H), 2.07-2.33 (m, 6H), 1.98 (d, 3H), 2.13 (s, 3H), 7.03-7.05 (d, 1H), 7.11-7.13 (d, 1H), 7.28-7.31 (m, 2H), 7.46-7.49 (m, 2H), 8.22 (s, 1H), 10.95 (s, 1H).

LC-MS (method 1): $R_t$=1.31 min; MS (ESIpos): m/z=418 [M+H]$^{+}$.

Example 1-6

3-(3',4'-Difluoro-4-methylbiphenyl-3-yl)-8,8-difluoro-4-hydroxy-1-azaspiro[4.5]dec-3-en-2-one

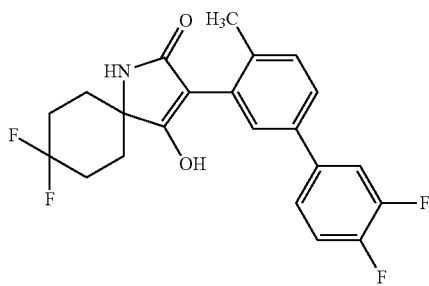 [SMILES: Cc1ccc(-c2ccc(F)c(F)c2)cc1C1=C(O)C2(CCC(F)(F)CC2)NC1=O]

0.74 g (2.0 mmol) of the compound from Example 11A was initially charged in 5 ml of ethylene glycol dimethyl ether, 14.5 ml of 2M aqueous sodium carbonate solution were added dropwise and 10 mg of bis(trisphenylphosphine)palladium(II) chloride were added. 0.35 g (2.2 mmol) of 3,4-difluorophenylboronic acid was then added, and the mixture was stirred under reflux overnight. After cooling, the mixture was acidified with 1N aqueous hydrochloric acid and extracted with ethyl acetate, and the extract was dried and concentrated. Purification was carried out by MPLC separation on silica gel using the mobile phase hexane/ethyl acetate 1/1. This gave 0.7 g (70% of theory) of the title compound. 395 mg were then purified again by HPLC [column: Chromatorex C18, 10 μm, 125 mm×30 mm; mobile phase: water/acetonitrile gradient with addition of 0.1% formic acid]. This gave 121 mg of the title compound.

$^{1}$H-NMR (400 MHz, DMSO-$d_6$): δ [ppm]=1.49-1.63 (m, 2H), 2.02-2.35 (m, 9H), 7.31 (d, 1H), 7.38 (d, 1H), 7.43-7.57 (m, 3H), 7.65-7.77 (m, 1H), 8.37 (s, 1H), 11.08 (s, 1H).

LC-MS (method 2): $R_t$=1.20 min; MS (ESIpos): m/z=406 [M+H]$^{+}$.

3. ASSAYS 3.1 Human ACC Enzyme Assays

The ACC1 and ACC2 inhibition data were obtained using the two assays described below. In most cases, a common serial dilution series of the test substances was prepared for the two measurements, and several substance plate copies were then made from this dilution series using a 384-well 50-nl capillary pipettor (Hummingbird™ from Genomics Solutions). These were then in each case used in the ACC1 and the ACC2 assay such that, for optimum comparibility, the two enzyme inhibition measurements were carried out using copies of the same substance dilution series.

Human ACC1 Enzyme Assay

The hACC1-inhibitory activity of the substances of this invention was measured using the hACC1 assay described in the paragraphs below.

Essentially, the enzyme activity is measured by quantifying the adenosine diphosphate (ADP) formed as a byproduct of the enzyme reactions using the ADP-Glo™ detection system from Promega. In this test, initially the adenosine triphosphate (ATP) not consumed in the enzyme reaction is converted quantitatively with an adenylate cyclase ("ADP-GLO reagent") into cAMP, the adenylate cyclase is then stopped and ("kinase detection reagent") the ADP formed is subsequently converted into ATP, which is converted in a luciferase-based reaction into a glow luminescence signal.

The enzyme used was C-terminally FLAG-tagged recombinant human ACC1 (acetyl-coenzyme A carboxylase alpha transcript variant 1) (GenBank Accession No. NM_198834), (amino acids 39-end), expressed in baculovirus-infected insect cells (Hi5) and purified by anti-FLAG affinity chromatography.

For the assay, 50 nl of a 100-times concentrated solution of the test substance in DMSO were pipetted into a white low-volume 384-well microtiter plate (Greiner Bio-One, Frickenhausen, Germany), 2.5 μl of a solution of hACC1 in assay buffer [50 mM HEPES/NaOH pH 7.5, 2 mM $MgCl_2$, 2 mM potassium citrate, 12 mM $NaHCO_3$, 2 mM dithiothreitol (DTT), 0.005% (w/v) bovine serum albumin (BSA)] were added and the mixture was incubated for 15 min to allow prebinding of the substances to the enzyme prior to the enzyme reaction. The enzyme reaction was then started by addition of 2.5 μl of a solution of adenosine triphosphate (ATP, 100 μM=>final concentration in 5 μl of assay volume: 50 μM) and acetyl-CoA (20 μM=>final concentration in 5 μl assay volume: 10 μM) in assay buffer, and the resulting mixture was incubated at 22° C. for the reaction time of 45 min. The concentration of the hACC1 was adjusted to the respective activity of the enzyme and set such that the assay was carried out in the linear range. Typical concentrations were in the range of 1.75 ng/μl. The reaction was stopped by addition of 2.5 μl of the "ADP-GLO reagent" (1:1.5-times diluted), and the resulting mixture was incubated at 22° C. for 1 h to convert the unreacted ATP completely into cAMP. 2.5 μl of the "kinase detection reagent" were then added (1.2-times more concentrated than recommended by the manufacturer), the resulting mixture was incubated at 22° C. for 1 h and the luminescence was then measured using a suitable measuring instrument (Viewlux or Topcount from Perkin-Elmer or Pherastar from BMG Labtechnologies). The amount of light emitted was taken as a measure for the amount of ADP formed and thus for the enzyme activity of the hACC1. The data were normalized (enzyme reaction without inhibitor=0% inhibition, all other assay components but no enzyme=100% inhibition). Usually, the test substances were tested on the same microtiter plates at 10 different concentrations in the range from 20 μM to 1 nM (20 μM, 6.7 μM, 2.2 μM, 0.74 μM, 0.25 μM, 82 nM, 27 nM, 9.2 nM, 3.1 nM and 1 nM, the dilution series were prepared before the assay based on the 100-times concentrated solution by serial 1:3 dilutions) in two replications for each concentration, and the $IC_{50}$ values were calculated with a 4-parameter fit using an inhouse software.

Human ACC2 Enzyme Assay

The hACC2-inhibitory activity of the substances of this invention was measured using the hACC2 assay described in the paragraphs below.

Essentially, the enzyme activity is measured by quantifying the adenosine diphosphate (ADP) formed as a byproduct of the enzyme reactions using the ADP-Glo™ detection system from Promega. In this test, initially the adenosine triphosphate (ATP) not consumed in the enzyme reaction is converted quantitatively with an adenylate cyclase ("ADP-GLO reagent") into cAMP, the adenylate cyclase is then stopped and ("kinase detection reagent") the ADP formed is subsequently converted into ATP, which is converted in a luciferase-based reaction into a glow luminescence signal.

The enzyme used was C-terminally FLAG-tagged recombinant human ACC2 (acetyl-coenzyme A carboxylase 2, GenBank Accession No. NP_001084), (amino acids 27-end), expressed in baculovirus-infected insect cells (Hi5) and purified by anti-FLAG affinity chromatography.

For the assay, 50 nl of a 100-times concentrated solution of the test substance in DMSO were pipetted into a white low-volume 384-well microtiter plate (Greiner Bio-One, Frickenhausen, Germany), 2.5 µl of a solution of hACC2 in assay buffer [50 mM HEPES/NaOH pH 7.5, 2 mM MgCl$_2$, 2 mM potassium citrate, 12 mM NaHCO$_3$, 2 mM dithiothreitol (DTT), 0.005% (w/v) bovine serum albumin (BSA)] were added and the mixture was incubated for 15 min to allow prebinding of the substances to the enzyme prior to the enzyme reaction. The enzyme reaction was then started by addition of 2.5 µl of a solution of adenosine triphosphate (ATP, 100 µM=>final concentration in 5 µl of assay volume: 50 µM) and acetyl-CoA (20 µM=>final concentration in 5 µl assay volume: 10 µM) in assay buffer, and the resulting mixture was incubated at 22° C. for the reaction time of 45 min. The concentration of the hACC2 was adjusted to the respective activity of the enzyme and set such that the assay was carried out in the linear range. Typical concentrations were in the range of 2 ng/µl. The reaction was stopped by addition of 2.5 µl of the "ADP-GLO reagent" (1:1.5-times diluted), and the resulting mixture was incubated at 22° C. for 1 h to convert the unreacted ATP completely into cAMP. 2.5 µl of the "kinase detection reagent" were then added (1.2-times more concentrated than recommended by the manufacturer), the resulting mixture was incubated at 22° C. for 1 h and the luminescence was then measured using a suitable measuring instrument (Viewlux or Topcount from Perkin-Elmer or Pherastar from BMG Labtechnologies). The amount of light emitted was taken as a measure for the amount of ADP formed and thus for the enzyme activity of the hACC2. The data were normalized (enzyme reaction without inhibitor=0% inhibition, all other assay components but no enzyme=100% inhibition). Usually, the test substances were tested on the same microtiter plates at 10 different concentrations in the range from 20 µM to 1 nM (20 µM, 6.7 µM, 2.2 µM, 0.74 µM, 0.25 µM, 82 nM, 27 nM, 9.2 nM, 3.1 nM and 1 nM, the dilution series were prepared before the assay based on the 100-times concentrated solution by serial 1:3 dilutions) in two replications for each concentration, and the IC$_{50}$ values were calculated with a 4-parameter fit using an inhouse software.

3.2 Cell Assays

In accordance with the invention, the substances were tested in cell-based assays for the ability of the substances of inhibiting tumor cell proliferation after a 96-hour incubation with the substance. Cell viability was tested using the Cell-Titer-Glo® luminescent cell viability assay (Promega). The cells were sown at a density of 2000-5000 cells/well (depending on the cell line) in 100 µl growth medium on 96-well microtiter plates. For each cell line examined, cells were sown on a separate plate to determine the luminescence at t=0 hours and t=96 hours. After overnight incubation at 37° C., the luminescence values for the t=0 samples were determined. The dose plates for the t=96 hours points in time were treated with substances diluted with growth medium. The cells were then incubated at 37° C. for 96 hours, and the luminescence values for the t=96 hours samples were then determined. For data analysis, the t=0 values were subtracted from the t=96 hours values for treated and untreated samples. The differences in luminescence in percent between substance-treated samples and control values were used to determine the growth inhibition in percent.

The substances were tested in the following cell lines which represent the stated indications in an exemplary manner:

| Cell line | Source | Indication |
|---|---|---|
| MCF7 | ATCC | hormone receptor-positive breast carcinoma |
| KM12 | NCI | colorectal carcinoma |
| PC3 | DMSZ | androgen receptor-negative prostate carcinoma |
| H460 | ATCC | non-small-cell bronchial carcinoma |

ATCC: American Type Culture Collection
NCI: National Cancer Institute
DMSZ: Deutsche Sammlung von Mikroorganismen und Zellkulturen GmbH

3.3 Analysis of the ACC1 Expression in Tumor Tissue and Normal Tissue

The ACC1 expression was determined using a microarray. To this end, the RNA of various tumor tissues and the corresponding normal tissues was isolated. The method made use of Trizol RNA extraction reagent (Invitrogen) and subsequent purification using the RNeasy mini kit (Qiagen). Moreover, a DNase I (Qiagen) digestion was carried out to eliminate genomic DNA. For quality control, the total RNA was analyzed with the aid of an RNA LabChip on an Agilent Bioanalyzer 2100 Platform (Agilent Technologies), and the RNA concentration was determined using the Peqlab NanoDrop system. For hybridization, the one-cycle eukaryotic target labeling assay from Affymetrix was used, and the array was then read on an AffymetrixGeneChip 3000 scanner (Affymetrix). Evaluation and quality control were carried out using the Expressionist Pro 4.0 Refiner (GeneData) software.

3.4 Assays for Determining the Octanol/Water Distribution Coefficient (log P/D) Membrane Affinity (log MA) and Protein Binding to Human Serum Albumin (K$_d$ HSA)

Assay for Determining the Octanol/Water Distribution Coefficient (log P/D):

The distribution coefficient octanol/water P or D is a key parameter for estimating membrane penetration and permeability. It is defined as the ratio of the equilibrium concentrations of a substance in the two-phase system octanol/water.

$$P/D = \frac{c_{octanol}}{c_{water}}$$

P=partition
D=distribution
c(octanol)=concentration of the substance in the octanol phase
c(water)=concentration of the substance in the aqueous phase It is usually stated in form of the decadic logarithm (log P or log D).

log P describes the distribution behavior of a substance exclusively present in its neutral form. logD describes the distribution behavior of a substance at a certain pH; depending on the ionisation constant pKa of the substance, some of the substance may be present in ionic form, and some in neutral form.

The log P/D of the active compounds was determined using an isocratic HPLC method (HPLC=high performance liquid chromatography) (literature: OECD Guideline for Testing of Chemicals No. 117). The method is based on the correlation of the HPLC retention time of the test substance to that of reference substances with known distribution coefficients.

The test substance was employed as a 10 mM solution in DMSO (DMSO=dimethyl sulfoxide). 10 µl of this solution were made up to 100 µl with a methanol/water mixture in a ratio of 7+3.

The nine reference substances were dissolved individually in methanol. The concentration is shown in Table 1. 100 µl each of the stock solutions were added to an HPLC vial and mixed with 300 µl of water.

TABLE 1

| Reference substance | log P | Approximate retention time [min] | Molar mass | Stock sol. weighted in [mg/10 ml] |
|---|---|---|---|---|
| acetanilide | 1.0 | 0.8 | 135.2 | 12 |
| 4-methylbenzyl alcohol | 1.6 | 0.9 | 122.2 | 15 |
| methyl benzoate | 2.1 | 1.1 | 136.2 | 18 |
| ethyl benzoate | 2.6 | 1.4 | 150.2 | 19 |
| naphthalene | 3.6 | 2.1 | 128.2 | 3 |
| 1,2,4-trichlorobenzene | 4.2 | 3.4 | 181.5 | 14 |
| 2,6-diphenylpyridine | 4.9 | 4.6 | 231.3 | 5 |
| triphenylamine | 5.7 | 8.0 | 245.3 | 8 |
| DDT | 6.2 | 10.3 | 354.5 | 10 |

A formamide solution was used to determine the hold-up time. To this end, 7 mg of formamide were dissolved in 10 ml of methanol. 100 µl of this stock solution were mixed with 500 µl of methanol and 200 µl of water.

All solutions were chromatographed using a flow rate of 1.00 ml/min.

Chromatographic Conditions:

| | |
|---|---|
| HPLC system | Waters Alliance HT 2790 |
| UV detector | DAD Waters 996 |
| MS detector | MS Micromass ZQ |
| HPLC Software | MassLynx 4.1 from Waters |
| Column | Spherisorb ODS 3 µm 4.6 × 60 mm |
| Mobile phase | methanol + water with 0.01M ammonium acetate (0.77 g/liter) 75 + 25, pH 7.0 |

Injection Volumes:

| | |
|---|---|
| formamide | 5 µl |
| references | 5 µl |
| test substance | 15 µl |

Injection Protocol:

formamide, references, test substance 1, test substance 2, . . . , formamide, references.

Evaluation of the retention times was carried out in a diode array detector (DAD) at 200-400 nm. Via the molecular mass, the identity of the test substance was checked using the downstream mass spectrometer.

The HPLC run was evaluated using the Waters software Masslynx 4.1.

The log P/D values were calculated using the software "POW Determination" (proprietary development).

Assays for Determining Membrane Affinity log MA and Protein Binding to Human Serum Albumin (HSA):

Determination of membrane affinity and protein binding to human serum albumin (HSA) was carried out via Transil technology (literature: A. Loidl-Stahlhofen, A. Eckert, T. Hartmann, M. Schöttner J Pharm Sci 90, 599-606 (2001). Transil® (commercially available from Sovicell in Leipzig, Germany) are glass beads (diameter 10-12 µm) coated with a double-layer membrane of phosphatidylcholine (MA-Transil) or covalently attached human serum albumin (HSA-Transil).

To determine the log MA and the protein binding constant to HSA, the commercially available TRANSIL Intestinal Absorption & HSA Binding Combined Assay Kit was used. This is a 96-well microtiter plate (96 well-MTP) which is filled with Transil and can be used to determine MA-Transil and HSA-Transil binding of in each case eight active compounds. For each active compound, the Transil plate provides a row of 12 wells. Two wells serve as reference and are only filled with buffer pH 7.4. Five further wells contain MA-Transil in various increasing concentrations, the five remaining wells contain HSA-Transil in various increasing concentrations.

To determine binding of an active compound to Transil, the supernatant of the wells with Transil was quantified against the reference solution without Transil via HPLC-MS coupling (HPLC-MS=high performance liquid chromatography/mass spectrometry).

This is how the individual steps of the assay were carried out:

From the internal substance store, the active compounds were delivered in a 96-well MTP. This plate is referred to as mother plate. Each well contained 30 µl of a 10 mmol solution of active compound in DMSO (dimethyl sulfoxide). Two wells at the start (well A1) and at the end of the plate (well H12) were filled with 30 µl of a 10 mmol solution of warfarin in DMSO. Warfarin, whose membrane affinity and binding to HSA is known, serves to check whether the measurement is correct. The mother plate was used to prepare a daughter plate with a 1 to 4000 dilution with a mixture of buffer pH 7.4 and DMSO in a ratio of 1+1. The active compound concentration of each well was 2.5 µmol/liter, the volume of each well was 400 µl.

Using a Hamilton pipetting robot Microlab STAR, the 96 active compounds from the daughter plate were divided onto 12 Transil plates in total. From each well of the daughter plate, 12 times 20 µl were removed. The concentration of each well of the Transil plate was 0.25 µmol/liter, which corresponds to a dilution of 1 to 10. The DMSO content was 5%.

The filled Transil plates were each resuspended for two minutes, then allowed to stand at room temperature for at least two minutes and then centrifuged at 600 rotations per minute for five minutes. The pipetting robot was then used to remove 20 µl of supernatant from each well of the Transil plate and to transfer these to a separate microtiter plate. Here, the supernatants of in each case four Transil plates were pooled in a microtiter plate, so that at the end there were three pooled microtiter plates with in each case 80 µl of solution and an active compound concentration of 62.5 nM per well.

Prior to quantification of the active compounds by HPLC-MS, an optimization has to be carried out for each active compound where by way of a single injection daughter ion and optimum electrical voltages are determined. To this end, the pipetting robot prepared a dilution of the mother plate of 1 to 10 000 000 in an acetonitrile/water mixture in a ratio of 8+2 in a separate microtiter plate.

This microtiter plate was measured by HPLC-MS using the software Discovery Quant Optimize from AB Sciex. The three pooled microtiter plates were measured by HPLC-MS using the software Discovery Quant Analyze from AB Sciex.

Chromatographic Conditions:
HPLC-MS system: Agilent 1200 Rapid resolution HPLC
  Sciex Triple Quad 5500 mass spectrometer (from AB Sciex)
  PAL Autosampler DLW Option
Software: Analyst 1.4 (from AB Sciex)
  Discovery Quant Optimize (from AB Sciex)
  Discovery Quant Analyze (from AB Sciex)
Optimization:
Column: capillary
Injection volume: 5 µl
Flow rate: 0 min→22 80 µl/min
  0-0.19 min→80 µl/min
  0.20-0.65 min→30 µl/min
  0.66-0.7 min→150 µl/min
Mobile phase: A=acetonitrile+0.05% formic acid
  B=water+0.05% formic acid
  isocratic A:B 8+2
Analysis:
Column: Poroshell 120 SB-C18 2.7 µm 3×30 mm
Injection volume: 2 µl
Flow rate: 1 ml/min
Mobile phase: gradient
  A=acetonitrile+0.05% formic acid
  B=water+0.05% formic acid
  0 min→95% A, 5% B
  0-1.0 min→5% A, 95% B increasing in a linear manner
  1.0-2.2 min→5% A, 95% B isocratic
  2.21-2.3 min→95% A, 5% β isocratic

3.5 Determination of Plasma Protein Binding by Equilibrium Dialysis

The binding of test substances to plasma proteins is determined by equilibrium dialysis by means of the Ht-dialysis apparatus (96-well) made of Teflon and a semipermeable membrane (regenerated cellulose, MWCO 12-14K). This separates 150 µl each of a plasma side and a buffer side (50 mM phosphate buffer). The test substance is added in 2 concentrations (usually 3 and 0.3 µM) to the plasma side and binds to plasma proteins. The unbound fraction of the test substance passes through the membrane and is distributed on either side until equilibrium is established (after approx. 6-8 h at 37° C.). The substance concentration on the buffer side and the plasma side is determined by LC-MS analysis. For this, both sides are brought by dilution with buffer or plasma to the same matrix (10% plasma) and then precipitated with methanol. The free (unbound) fraction (fu) is calculated from the quotient of the buffer and plasma concentration. Stability tests and recovery tests are run concurrently as controls. In addition, the substance in buffer is dialysed against buffer, to check the nonspecific binding to apparatus and membrane and establishment of equilibrium. Because during incubation the osmotic pressure of the plasma proteins leads to dilution of the plasma (volume shift), this possible error is determined by weighing blank plasma samples and is included in the calculation of fu. Establishment of equilibrium and plasma stability should have a value not lower than 80% and the recovery should be at least 30%. A free fraction of <1% is regarded as high, between 1 and 10% as moderate and >10% as low plasma protein binding.

3.6 Pharmacokinetic Parameters

Determination of the Pharmacokinetic Parameters of a Test Substance in the Rat and in the Dog For this, the test substances were applied in dissolved form both for intravenous, and for intragastric application, wherein compatible solubilizers such as PEG400 and/or ethanol were used in a compatible amount.

Intravenous Administration:

The test substances were applied at a dose of 0.1-1 mg/kg. Administration was as a bolus injection in the male rat and as an infusion in the female dog (15 min). At various time points after the bolus injection, and before and after the 15-minute infusion, blood samples of about 100-150 µl were removed via a catheter either from the jugular vein (rat) or from the saphenous vein (dog). Lithium-heparin was added as anticoagulant to the blood samples and they were stored in a refrigerator until required for further processing. After centrifugation of the samples for 15 min at 3000 rpm, an aliquot of 100 µl was taken from the supernatant (plasma) and was precipitated by adding 400 µl of cold ACN or methanol (absolute). The precipitated samples were frozen-out at 20° C. overnight, then centrifuged again at 3000 rpm for 15 min, before 150 µl of the clear supernatant were removed to determine the concentration. The analysis was effected by means of an Agilent 1200 HPLC system with connected LCMS/MS detection.

Calculation of the PK parameters (using PK calculation software, e.g. WinNonLin®): CLplasma: total plasma clearance of the test substance (in 1*kg/h); CLblood: total blood clearance of the test substance (in 1*kg/h), where (CLblood=CLplasma*Cp/Cb); Vss: apparent steady-state distribution volume (in 1/kg); t1/2: half-life within a specified interval (here: terminal t1/2, in h); AUCnorm: area under the plasma concentration time profile from time point zero extrapolated to infinity divided by the dose normalized for body weight (in kg*l/h); AUC(0-tn)norm: integrated area under the plasma concentration time profile from time point zero until the last time point at which a plasma concentration was measurable, divided by the dose normalized for body weight (in kg*l/h); Cmax: maximum concentration of the test substance in the plasma (in µg/l); Cmax,norm: maximum concentration of the test substance in the plasma divided by the dose normalized for body weight (in kg/l); Cb/Cp: ratio of the blood to plasma concentration distribution.

Intragastric Administration:

The test substances were administered to fasting male rats or female dogs at a dose of 0.3-1 mg/kg intragastrically as a bolus using a feeding tube. At various time points after administration, blood samples of about 100-150 µl were removed via a catheter either from the jugular vein (rat) or from the saphenous vein (dog). Lithium-heparin was added as anticoagulant to the blood samples and they were stored in a refrigerator until required for further processing. After centrifugation of the samples for 15 min at 3000 rpm, an aliquot of 100 µl was taken from the supernatant (plasma) and was precipitated by adding 400 µl of cold ACN or methanol (absolute). The precipitated samples were frozen-out at −20° C. overnight, then centrifuged at 3000 rpm for 15 min, before 150 µl of the clear supernatant were removed to determine the concentration. The analysis was effected by means of an Agilent 1200 HPLC system with connected LCMS/MS detection.

Calculation of the PK Parameters (Using PK Calculation Software, e.g. WinNonLin®):

AUCnorm: area under the plasma concentration time profile from time point zero extrapolated to infinity divided by the dose normalized for body weight (in kg*l/h); AUC(0-tn) norm: integrated area under the plasma concentration time profile from time point zero until the last time point at which a plasma concentration was measurable, divided by the dose normalized for body weight (in kg*l/h); Cmax: maximum concentration of the test substance in the plasma (in µg/l); Cmax,norm: maximum concentration of the test substance in the plasma divided by the dose normalized for body weight (in kg/l); t1/2: half-life within a specified interval (here: terminal t1/2, in h); Fobs %: observed oral bioavailability, AUC (0-tn)norm after i.g. administration divided by AUC(0-tn) norm after i.v. administration. tmax: time point at which the maximum concentration of the test substance is measured in the plasma.

To calculate the relative bioavailability of a test substance, the AUC(0-tn)norm after i.g. administration of a suspension of a microcrystalline substance is divided by the AUC(0-tn) norm after administration of a substance solution.

3.7 In-Vivo Efficacy

Xenograft Model

Xenograft models in immunosuppressed mice were used to determine the antitumor activity in living organisms.

To this end, initially the maximum tolerable dose (MTD) was determined using the following protocol: Over a period of 3 weeks, a defined dose of the test substance was administered daily orally to female nude mice (NMRI-nude (nu/nu) mice, Taconic M&B A/S), and the mice were observed daily for mortality and body weight. The MTD was defined as the highest dose which could be administered without any animal dying during the treatment phase, and without any body weight loss of more than 10% compared to the initial weight.

Xenograft models in which the test substances were administered in their MTD or, if it was not possible to determine this beforehand, in the highest dose that could be formulated in the standard vehicle, and in some cases also in lower doses were then used to determine the antitumor activity. Use was made primarily of a prostate carcinoma model with hormone-independent human PC-3 cells in male nude mice (NMRI-nude (nu/nu) mice, Taconic M&B A/S). To this end, 3 million tumor cells (suspended in medium+Matrigel) 1:1, final 0.1 ml) were injected subcutaneously into the side of each animal. When the tumors extended to an area of 20-30 mm$^2$, the mice were randomized into therapy groups and therapy was initiated. The therapy was then continued until an average tumor size of 130-160 mm$^2$ had been reached in the control group, which had only been given the vehicle of the test substance, or in one of the treatment groups, with tumor area and body weight being measured 2-3 times per week. At this point in time, the experiment was terminated in all groups and the prepared tumors were weighed.

The T/C value was calculated as primary success parameter using the effect on the final tumor weight: mean tumor weight in the treatment group divided by mean of the tumor weight in the vehicle group.

4. RESULTS 4.1. Enzyme Assay

Table 2 summarizes the results of the working examples and comparative examples from the enzyme assays. For the exact determination of the selectivity, measurements of the inhibition of ACC1 and ACC2 (in each case IC50 determinations) were compared in each case pair by pair, with copies of the same substance dilution series being used in the two assays. If either the ACC1 or the ACC2 IC50 determination was not evaluated owing to an insufficient data quality, both measurements were disregarded and were not listed in the table. The selectivity of the inhibition of ACC1 vs. the inhibition of ACC2 was then determined as a mean of the selectivities observed in the individual measurements.

TABLE 2

| Example | Measurement No. | Preparation No. | ACC 1 IC50 [µmol/l] | ACC 2 IC50 [µmol/l] | Ratio of IC50s ACC2/ACC1 (respective measurement) | Selectivity ACC1 vs. ACC2 (mean of the individual measurements ± standard deviation) |
|---|---|---|---|---|---|---|
| 1-1 | 1 | 1 | 0.053 | 2.780 | 52.7 | 33.8 ± 15.3 |
|  | 2 | 1 | 0.054 | 3.239 | 59.9 |  |
|  | 3 | 1 | 0.117 | 3.371 | 28.8 |  |
|  | 4 | 1 | 0.125 | 2.112 | 16.9 |  |
|  | 5 | 2 | 0.069 | 2.515 | 36.3 |  |
|  | 6 | 2 | 0.095 | 3.744 | 39.6 |  |
|  | 7 | 3 | 0.058 | 0.957 | 16.5 |  |
|  | 8 | 3 | 0.097 | 1.914 | 19.7 |  |
| 1-2 | 1 | 1 | 0.068 | 2.35 | 34.7 | 13.4 ± 4.5 |
|  | 2 | 1 | 0.080 | 2.07 | 26.1 |  |
|  | 3 | 2 | 0.099 | 2.45 | 24.6 |  |
|  | 4 | 2 | 0.109 | 2.79 | 25.5 |  |
|  | 5 | 3 | 0.075 | 0.65 | 9.1 |  |
|  | 6 | 3 | 0.065 | 1.28 | 19.7 |  |
|  | 7 | 2 | 0.135 | 1.23 | 9.1 |  |
|  | 8 | 2 | 0.153 | 1.74 | 11.4 |  |
| 1-3 | 1 | 1 | 0.166 | >20 | >120.8 | >101.8 ± 19.0 |
|  | 2 | 1 | 0.241 | >20 | >82.8 |  |
| 1-4 | 1 | 1 | 0.121 | 5.48 | 45.5 | 39.7 ± 5.7 |
|  | 2 | 1 | 0.091 | 3.11 | 34.0 |  |
| 1-5 | 1 | 1 | 0.218 | 2.70 | 12.4 | 12.4 |
| 1-6 | 1 | 1 | 0.133 | 3.87 | 29.1 | 51.9 ± 22.8 |
|  | 2 | 1 | 0.107 | 8.03 | 74.7 |  |
| V.1-a | 1 | 1 | 0.067 | 0.580 | 8.6 | 9.4 ± 0.8 |
|  | 2 | 1 | 0.059 | 0.610 | 10.3 |  |
| V.1-b | 1 | 0.043 | 1.95 | 45.9 | 45.9 | 46.9 |

TABLE 2-continued

| Example | Measurement No. | Preparation No. | ACC 1 IC50 [μmol/l] | ACC 2 IC50 [μmol/l] | Ratio of IC50s ACC2/ACC1 (respective measurement) | Selectivity ACC1 vs. ACC2 (mean of the individual measurements ± standard deviation) |
|---|---|---|---|---|---|---|
| V.2-a | 1 | 1 | 0.109 | 1.22 | 11.2 | 9.8 ± 1.4 |
|  | 2 | 1 | 0.111 | 0.94 | 8.4 |  |
| V.2-b | 1 | 1 | 0.208 | 2.40 | 11.5 | 12.8 ± 1.3 |
|  | 2 | 1 | 0.196 | 2.76 | 14.1 |  |

These data show that the compounds according to the invention strongly inhibit human ACC and have marked selectivity against human ACC2. This property was unknown, not obvious and could not be determined without undue experimentation.

4.2 Cell Assays

Table 3 summarizes the results of the working examples and comparative examples from the cell assays.

TABLE 3

| Example | KM12 IC50 (μmol/l) | PC3 IC50 (μmol/l) | H460 IC50 (μmol/l) | MCF7 IC50 [μm/l] |
|---|---|---|---|---|
| 1-1 | 0.028 | 0.039 | 0.131 | 0.022 |
| 1-2 | 0.058 | 0.050 | 0.134 | 0.030 |
| 1-3 | 0.578 | 0.476 | 0.678 | 0.209 |
| 1-4 | 0.319 | 0.231 | 0.481 | 0.086 |
| 1-5 | 0.668 | 0.506 | 0.769 | 0.205 |
| 1-6 | 0.257 | 0.158 | 0.371 | 0.045 |
| V.1-a | 0.245 | 0.398 | 0.573 | 0.030 |
| V.1-b |  |  |  | 0.022 |
| V.2-a | 0.037 | 0.038 | 0.057 | 0.035 |
| V.2-b |  |  |  | 0.041 |

4.3 ACC1 Expression in Tumor Tissue and Normal Tissue

The ACC1 expression in tumor tissue and corresponding normal tissue was determined by microarray (FIG. 1). In breast carcinomas, colorectal carcinomas, bronchial carcinomas and pancreas carcinomas, the expression of ACC1 was significantly upregulated compared to normal tissue.

4.4 Octanol/Water Distribution Coefficient (log P/D), Membrane Affinity (log MA) and Protein Binding to Human Serum Albumin ($K_d$ HSA)

Table 4 shows the log P/D, log MA and $K_d$ HSA values determined

Evaluation of the HPLC peaks was carried out using Discovery Quant Analyze. The results (log MA and binding constant to HSA $K_d$) were calculated using an Excel workbook provided by Sovicell.

TABLE 4

| Example | logP/D pH 7.4 | logMA | $K_d$ HSA [μmol/l] |
|---|---|---|---|
| 1-1 | 1.9 (n = 3) | 1.87 (1.7-2, n = 3) | 3.04 (2.23-3.64, n = 3) |
| V.1-a | 2.55 (2.4-2.7, n = 2) | 2.55 (2.4-2.7, n = 2) | 1.43 (1.16-1.7, n = 2) |
| V.1-b | 2.8 (2.7-2.9, n = 5) | 2.55 (2.4-2.9, n = 4) | 3.5 (2.52-4.27, n = 4) |
| 1-2 | 1.73 (1.5-1.9, n = 3) | 1.83 (1.7-1.9, n = 3) | 3.86 (2.81-5.39, n = 3) |
| V.2-a | 2.23 (1.8-2.5, n = 3) | 2.38 (2.0-2.7, n = 4) | 3.07 (2.38-2.8, n = 3) |
| V.2-b | 2.77 (2.7-2.9, n = 4) | 2.05 (1.9-2.2, n = 2) | 3.22 (2.35-4.1, n = 2) |

4.5 Plasma Protein Binding by Equilibrium Dialysis

Table 5 shows binding to plasma proteins of man, mouse and rat, determined by equilibrium analysis.

TABLE 5

| Example | fu [%] (human) | fu [%] (mouse) | fu [%] (rat) | fu (mouse)/fu (human) |
|---|---|---|---|---|
| 1-1 | 0.35 (0.33-0.37, n = 3) | 1.84 (1.02-2.71, n = 4) | 0.27 (0.26-0.28, n = 3) | 5 |
| V.1-a | 0.05 (n = 1) | 1.9 (n = 1) | — | 39 |
| V.1-b | 0.4 (0.40-0.41, n = 2) | 7.46 (7.35-7.57, n = 2) | 6.12 (5.61-6.64, n = 2) | 19 |
| 1-2 | 0.42 (n = 1) | 3.49 (2.96-4.02, n = 2) | — | 8 |
| V.2-a | 0.07 (n = 1) | 2.41 (n = 1) | — | 34 |
| V.2-b | 0.36 (n = 1) | 2.81 (1.29-3.87, n = 6) | 0.71 (0.14-2.92, n = 8) | 8 |

4.6 Pharmacokinetic Parameters

Pharmacokinetic Parameters Obtained from Rats.

Table 6 shows the pharmacokinetic parameters obtained from rats.

TABLE 6

| Example | $CL_{plasma}$ [l/h/kg] | $CL_{blood}$ [l/h/kg] | $t^{1/2}$ [h] | Vss [l/kg] | F [%] |
|---|---|---|---|---|---|
| 1-1 | 0.010 | 0.022 | 40 | 0.55 | 95 |
| V.1-a | — | — | — | — | — |
| V.1-b | — | — | — | — | — |
| 1-2 | 0.006 | 0.012 | 52 | 0.36 | 123 |
| V.2-a | — | — | — | — | — |
| V.2-b | — | — | — | — | — |

4.7 In-Vivo Efficacy

Maximum Tolerated Dose (MTD) in the Mouse

Example 1-1 was administered to female nude mice (NMRI nu/nu):
Dosage see Table 7
Administration route: per os
Vehicle: PEG400/ethanol/Solutol HS 15 (70/5/25, v/v/v)
  (Solutol HS15: polyoxyethylene ester of 12-hydroxystearic acid)
Administration volume:10 ml/kg
Protocol: see Table 7

The treatment phase was followed by an observation phase of 21 days. The deaths that occurred during this period and the effect on the body weight are summarized in Table 1.

TABLE 7

| Substance | Dose (mg/kg) | Protocol | Maximum change in body weight (%) | Deaths |
|---|---|---|---|---|
| 1-1 | 12.5 | 21 days, 1 administration per day | plus 11 | 0 of 4 |
| 1-1 | 25 | 21 days, 1 administration per day | plus 12 | 0 of 4 |
| 1-1 | 50 | 21 days, 1 administration per day | plus 6 | 0 of 4 |
| 1-1 | 75 | 21 days, 1 administration per day | plus 8 | 0 of 4 |
| 1-1 | 100 | 21 days, 1 administration per day | plus 14 | 0 of 4 |
| 1-1 | 50 | 21 days, 2 administrations per day | plus 11 | 0 of 4 |

Accordingly, the MTD for a 21-day treatment with administration once per day is higher than 100 mg/kg.

Accordingly, the MTD for a 21-day treatment with administration twice per day is higher than 50 mg/kg.

In-Vivo Efficacy in the PC3 Xenograft Model in the Mouse

Example 1-1 was subsequently administered to male nude mice (NMRI nu/nu) in the PC-3 prostate carcinoma xenograft model:
Dosage see Table 8
Administration route: per os
Vehicle: PEG400/ethanol/Solutol HS 15 (70/5/25, v/v/v)
Administration volume: 10 ml/kg
Protocol: see Table 8
Number of mice: 9

TABLE 8

| Substance | Dose (mg/kg) | Protocol | T/C | Maximum change in body weight (%) | Deaths |
|---|---|---|---|---|---|
| 1-1 | 40 | 17 days, 2 administrations per day | 0.26 | minus 2 | 0 of 9 |
| 1-1 | 80 day 1-3 70 from day 4 onwards | 17 days, 2 administrations per day | 0.26 | minus 7 | 0 of 9 |

The therapeutic efficacy was defined as a T/C of <=0.50. Good tolerability was defined as a maximum change in body weight of <=minus 10% and 100% survival of the test animals. Since, following administration of 80 mg/kg and administration 2 times per day there was a reduction in body weight of more than 10% in individual animals after 3 days, from day 4 onward the dosage was reduced to 70 mg/kg and administration 2 times per day.

Accordingly, at 40 mg/kg and administration 2 times per day, therapeutic efficacy and good tolerability were observed.

Accordingly, at 80 mg/kg for the first 3 days followed by 70 mg/kg (administration in each case 2 times per day), therapeutic efficacy and good tolerability were observed.

Prediction of Human Pharmacokinetic Parameters and Human Therapeutic Dosage

The human pharmacokinetic (PK) parameters (Table 9) were predicted based on the in vivo PK parameters obtained for rats (single species scaling), taking into account the interspecies differences in the free fraction (fu) in the plasma. The effective AUC (area under curve) was determined based on the measured plasma concentration time profile for in vivo efficacy in the PC3 tumor model of the mouse (nu/nu mouse). The therapeutic human dosage was determined using the predicted human clearance (CL), assuming 100% bioavailability (F=1) and using the effective AUC in the animal model according to the formula below:

TABLE 9

$$\text{Dosage} = \text{AUC} \times \frac{fu_{mouse}}{fu_{human}} \times \frac{\text{CL}}{F}$$

| Example | Dosage (mouse) [mg/kg] | ther. AUC (mouse) [mg * h/l] | fu (mouse/ human) | calc. AUC (human) [mg * h/l] | pred. CL (human) [l/h/kg] | pred. dosage (human) [mg/kg] | pred. dosage (human) [mg/patient] |
|---|---|---|---|---|---|---|---|
| 1-1 | 40 [2 × per day] | 376 | 4 | 1882 | 0.003 | 5.6 | 395 |
|  | 80 [2 × per day] | 6085 |  | 3041 |  | 9.1 | 639 |
| V.1-a | — | — | — | — | — | — | — |
| V.1-b | — | — | — | — | — | — | — |
| 1-2 | — | — | — | — | — | — | — |
| V.2-a | — | — | — | — | — | — | — |
| V.2-b | — | — | — | — | — | — | — | ther. = therapeutic
calc. = calculated
pred. = predicted (fu-corrected)

The present invention also relates to novel halogen-substituted spirocyclic ketoenols of the formula (I), to a plurality of processes for their preparation and to their use as pesticides and/or herbicides and/or fungicides. The invention also provides selective herbicidal compositions comprising, firstly, the halogen-substituted spirocyclic ketoenols and, secondly, a crop plant compatibility-improving compound.

The present invention furthermore relates to the boosting of the action of crop protection compositions comprising, in particular, halogen-substituted spirocyclic ketoenols, through the additon of ammonium salts or phosphonium salts and optionally penetrants, to the corresponding compositions, to processes for producing them and to their application in crop protection as insecticides and/or acaricides and/or nematicides and/or fungicides and/or for preventing unwanted plant growth.

3-Acylpyrrolidine-2,4-diones have already been described as having pharmaceutical properties (S. Suzuki et al. Chem. Pharm. Bull. 15 1120 (1967)). Furthermore, N-phenylpyrrolidine-2,4-diones have been synthesized by R. Schmierer and H. Mildenberger (Liebigs Ann. Chem. 1985, 1095). A biological activity of these compounds has not been described.

EP-A-0 262 399 and GB-A-2 266 888 disclose compounds of a similar structure (3-arylpyrrolidine-2,4-diones) of which, however, no herbicidal, insecticidal or acaricidal activity has become known. Unsubstituted bicyclic 3-arylpyrrolidine-2,4-dione derivatives (EP-A-355 599, EP-A-415 211 and JP-A-12-053 670) and substituted monocyclic 3-arylpyrrolidine-2,4-dione derivatives (EP-A-377 893, EP-A-442 077 and WO 10/066,780) are known to have herbicidal, insecticidal or acaridical activity.

Additionally known are polycyclic 3-arylpyrrolidine-2,4-dione derivatives (EP-A-442 073) and 1H-arylpyrrolidinedione derivatives (EP-A-456 063, EP-A-521 334, EP-A-596 298, EP-A-613 884, EP-A-613 885, WO 95/01 971, WO 95/26 954, WO 95/20 572, EP-A-0 668 267, WO 96/25 395, WO 96/35 664, WO 97/01 535, WO 97/02 243, WO 97/36 868, WO 97/43275, WO 98/05638, WO 98/06721, WO 98/25928, WO 99/24437, WO 99/43649, WO 99/48869, WO 99/55673, WO 01/17972, WO 01/23354, WO 01/74770, WO 03/013249, WO 03/062244, WO 2004/007448, WO 2004/024 688, WO 04/065366, WO 04/080962, WO 04/111042, WO 05/044791, WO 05/044796, WO 05/048710, WO 05/049569, WO 05/066125, WO 05/092897, WO 06/000355, WO 06/029799, WO 06/056281, WO 06/056282, WO 06/089633, WO 07/048,545, DEA 102 00505 9892, WO 07/073,856, WO 07/096,058, WO 07/121,868, WO 07/140,881, WO 08/067,873, WO 08/067,910, WO 08/067,911, WO 08/138,551, WO 09/015,801, WO 09/039,975, WO 09/049,851, WO 09/115,262, WO 10/052,161, WO 10/102,758, WO 10/063,378, WO 10/063,670, WO 11/098,440, WO 11/098,443, WO 11/067,135, WO 11/067,240). Furthermore known are ketal-substituted 1H-arylpyrrolidine-2,4-diones from WO 99/16748 and (spiro)-ketal-substituted N-alkoxyalkoxy-substituted arylpyrrolidinediones from JP-A-14 205 984 and Ito M. et. al., Bioscience, Biotechnology and Biochemistry 67, 1230-1238, (2003). The addition of safeners to ketoenols is also known in principle from WO 03/013249. Moreover, WO 06/024411 discloses herbicidal compositions comprising ketoenols. Pharmaceutical action has hitherto been disclosed in WO 2011/098433, DE-A-102010008642, DE-A-102010008643 and DE application number 102010008640.

It is known that certain substituted $\Delta^3$-dihydrofuran-2-one derivatives have herbicidal properties (cf. DE-A-4 014 420). The synthesis of the tetronic acid derivatives used as starting materials (such as, for example, 3-(2-methylphenyl)-4-hydroxy-5-(4-fluorophenyl)-$\Delta^3$-dihydrofuran-(2)) has also been described in DE-A-4 014 420. Compounds of a similar structure are known from the publication Campbell et al., J. Chem. Soc., Perkin Trans. 1, 1985, (8) 1567-76, without any insecticidal and/or acaricidal activity being mentioned. 3-Aryl-$\Delta^3$-dihydrofuranone derivatives having herbicidal, acaricidal and insecticidal properties are furthermore known from: EP-A-528 156, EP-A-647 637, WO 95/26 954, WO 96/20 196, WO 96/25 395, WO 96/35 664, WO 97/01 535, WO 97/02 243, WO 97/36 868, WO 98/05 638, WO 98/06 721, WO 99/16 748, WO 98/25 928, WO 99/43 649, WO 99/48 869, WO 99/55 673, WO 01/23354, WO 01/74 770, WO 01/17 972, WO 04/024 688, WO 04/080 962, WO 04/111 042, WO 05/092 897, WO 06/000 355, WO 06/029 799, WO 07/048,545, WO 07/073,856, WO 07/096,058, WO 07/121, 868, WO 07/140,881, WO 08/067,911, WO 08/083,950, WO 09/015,801, WO 09/039,975, WO 10/133,337, WO 10/135, 914 and WO 11/098,440).

4-Hydroxy-3-mesityltetronic acids are also described in the publication Tetrahedron 57, 2001, 4133-4137.

Also known are biphenyl-substituted 1H-pyrrolidinedione derivatives having fungicidal action (WO 03/059065).

However, the activity and the activity spectrum of these compounds are, in particular at low application rates and concentrations, not always entirely satisfactory. Furthermore, the plant compatibility of these compounds with respect to the crop plants is not always sufficient. Moreover, the toxicological properties and/or environmental properties of these compounds are not always completely satisfactory.

This invention now provides novel compounds of the formula (I)

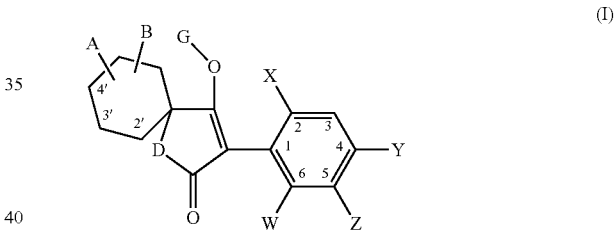

(I)

in which

W represents hydrogen, halogen, alkyl, alkenyl, alkynyl, optionally substituted cycloalkyl, alkoxy, alkenyloxy, haloalkyl, haloalkoxy or cyano, X represents halogen, alkyl, alkenyl, alkynyl, optionally substituted cycloalkyl, alkoxy, alkenyloxy, alkylthio, alkylsulfinyl, alkylsulfonyl, haloalkyl, haloalkoxy, haloalkenyloxy, nitro or cyano, Y and Z independently of one another represent hydrogen, alkyl, alkenyl, alkynyl, optionally substituted cycloalkyl, alkoxy, halogen, haloalkyl, haloalkoxy, cyano, nitro or in each case optionally substituted aryl or hetaryl, A represents halogen, B represents halogen or a bond to the adjacent carbon atom, with the proviso that A and B are located in the 3'- and/or 4'-position, D represents NH or oxygen, G represents hydrogen (a) or represents one of the groups

(b)

(c) 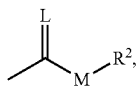

(d) 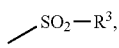

(e) 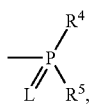

(f) E, or (g) 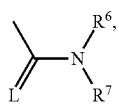

in which

E represents a metal ion or an ammonium ion,

L represents oxygen or sulfur,

M represents oxygen or sulfur, $R^1$ represents in each case optionally halogen- or cyano-substituted alkyl, alkenyl, alkoxyalkyl, alkylthioalkyl or polyalkoxyalkyl or represents in each case optionally halogen-, alkyl- or alkoxy-substituted cycloalkyl or heterocyclyl or represents in each case optionally substituted phenyl, phenylalkyl, hetaryl, phenoxyalkyl or hetaryloxyalkyl, $R^2$ represents in each case optionally halogen- or cyano-substituted alkyl, alkenyl, alkoxyalkyl or polyalkoxyalkyl or represents in each case optionally substituted cycloalkyl, phenyl or benzyl, $R^3$, $R^4$ and $R^5$ independently of one another represent in each case optionally halogen-substituted alkyl, alkoxy, alkylamino, dialkylamino, alkylthio, alkenylthio or cycloalkylthio or represent in each case optionally substituted phenyl, benzyl, phenoxy or phenylthio, $R^6$ and $R^7$ independently of one another represent hydrogen, represent in each case optionally halogen- or cyano-substituted alkyl, cycloalkyl, alkenyl, alkoxy, alkoxyalkyl, represent in each case optionally substituted phenyl or benzyl, or together with the N atom to which they are attached form an optionally substituted cycle which optionally contains oxygen or sulfur.

Depending inter alia on the nature of the substituents, the compounds of the formula (I) can be present as optical isomers or isomer mixtures of varying composition which, if desired, can be separated in a customary manner. The present invention provides both the pure isomers and the isomer mixtures, their preparation and use and compositions comprising them. For the sake of simplicity, however, compounds of the formula (I) are always referred to below, although both the pure compounds and also, if appropriate, mixtures having different proportions of isomeric compounds are meant.

Taking into consideration the various meanings (a), (b), (c), (d), (e), (f) and (g) of group G, the following principal structures (I-1-a) to (I-1-g) result if D is NH, (I-1-a) 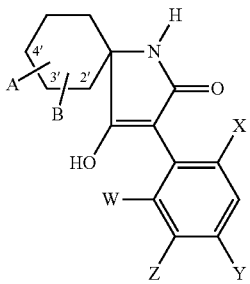

(I-1-b) 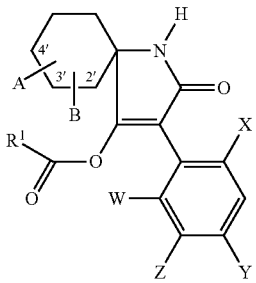

(I-1-c) 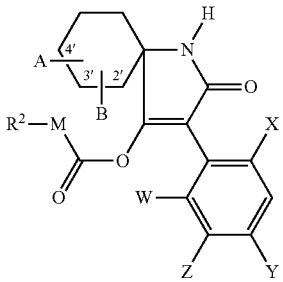

(I-1-d) 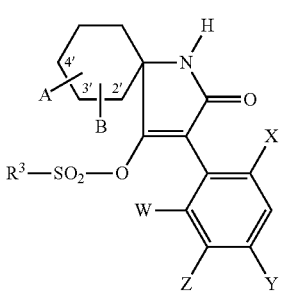

(I-1-e) 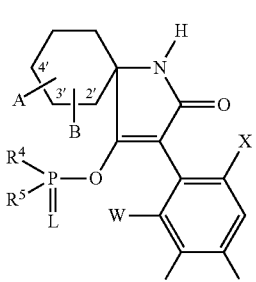

-continued

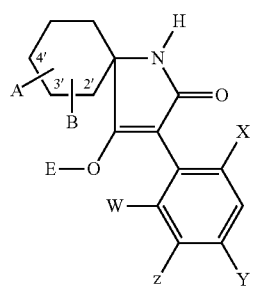
(I-1-f)

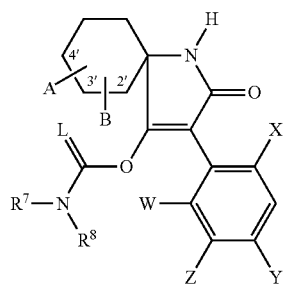
(I-1-g)

in which
A, B, E, L, M, W, X, Y, Z, $R^1$, $R^2$, $R^3$, $R^4$, $R^5$, $R^6$ and $R^7$ have the meanings given above.

Taking into consideration the various meanings (a), (b), (c), (d), (e), (f) and (g) of group G, the following principal structures (I-2-a) to (I-2-g) result if D is oxygen,

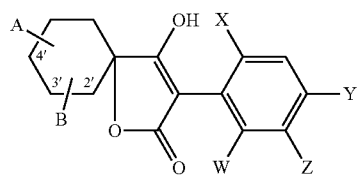
(I-2-a)

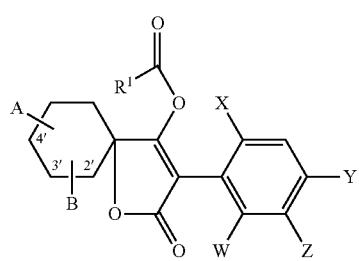
(I-2-b)

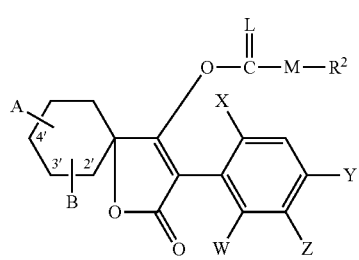
(I-2-c)

-continued

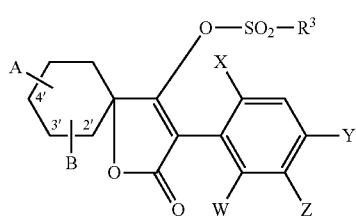
(I-2-d)

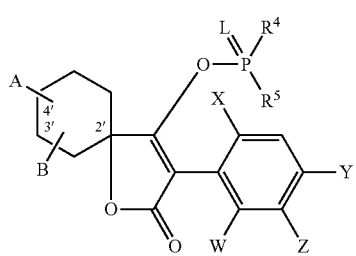
(I-2-e)

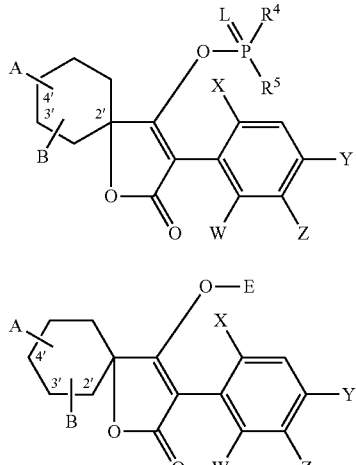
(I-2-f)

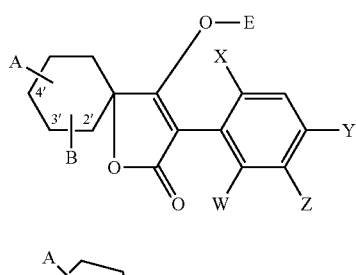
(I-2-g)

in which
A, B, E, L, M, W, X, Y, Z, $R^1$, $R^2$, $R^3$, $R^4$, $R^5$, $R^6$ and $R^7$ have the meaning given above.

Furthermore, it has been found that the novel compounds of the formula (I) are obtained by one of the processes described below:

(A) Substituted 3-phenylpyrrolidine-2,4-diones or their enols of the formula (I-1-a)

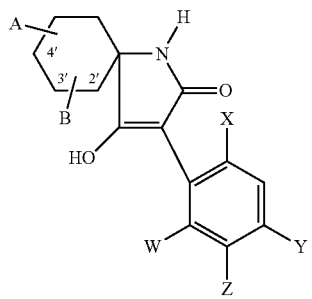
(I-1-a)

in which
A, B, W, X, Y and Z have the meanings given above,
are obtained when
N-acylamino acid esters of the formula (II)

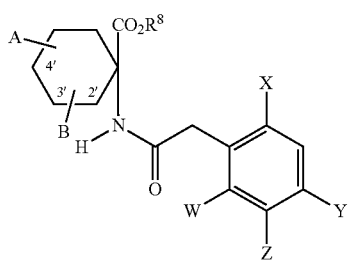
(II)

in which
A, B, W, X, Y and Z have the meanings given above,
and
$R^8$ represents alkyl (preferably $C_1$-$C_6$-alkyl),
are condensed intramolecularly in the presence of a diluent and in the presence of a base.
(B) Moreover, it has been found that substituted 3-phenyl-4-hydroxy-$\Delta^3$-dihydrofuranone derivatives of the formula (I-2-a)

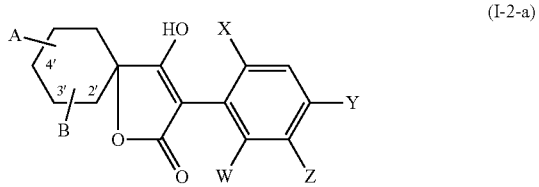
(I-2-a)

in which
A, B, W, X, Y and Z have the meanings given above,
are obtained when
carboxylic esters of the formula (III)

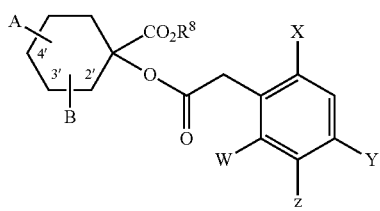
(III)

in which
A, B, W, X, Y, Z and $R^8$ have the meanings given above,
are condensed intramolecularly in the presence of a diluent and in the presence of a base.
Moreover, it has been found
(C) that the compounds of the formulae (I-1-b) and (I-2-b) shown above in which $R^1$, A, B, D, W, X, Y and Z have the meanings given above are obtained when the respective compounds of the formulae (I-1-a) and (I-2-a) shown above in which A, B, D, W, X, Y and Z have the meanings given above are in each case α) reacted with compounds of the formula (IV)

(IV)

in which
$R^1$ has the meaning given above and
Hal represents halogen (in particular chlorine or bromine)
or
β) with carboxylic anhydrides of the formula (V)

$R^1$—CO—O—CO—$R^1$ (V)

in which
$R^1$ has the meaning given above
if appropriate in the presence of a diluent and if appropriate in the presence of an acid binder;
(D) that the compounds of the formulae (I-1-c) and (I-2-c) shown above in which $R^2$, A, B, D, M, W, X, Y and Z have the meanings given above and L represents oxygen are obtained when the respective compounds of the formulae (I-1-a) and (I-2-a) shown above in which A, B, D, W, X, Y and Z have the meanings given above are in each case reacted with chloroformic esters or chloroformic thioesters of the formula (VI)

$R^2$-M-CO—Cl (VI)

in which
$R^2$ and M have the meanings given above,
if appropriate in the presence of a diluent and if appropriate in the presence of an acid binder;
(E) that compounds of the formulae (I-1-c) and (I-2-c) shown above in which $R^2$, A, B, D, M, W, X, Y and Z have the meanings given above and L represents sulfur are obtained when the respective compounds of the formulae (I-1-a) and (I-2-a) shown above in which A, B, D, W, X, Y and Z have the meanings given above are in each case
reacted with chloromonothioformic esters or chlorodithioformic esters of the formula (VII)

(VII)

in which
M and $R^2$ have the meanings given above,
if appropriate in the presence of a diluent and if appropriate in the presence of an acid binder,
(F) that compounds of the formulae (I-1-d) and (I-2-d) shown above in which $R^3$, A, B, D, W, X, Y and Z have the meanings given above are obtained when the respective compounds of the formulae (I-1-a) and (I-2-a) shown above in which A, B, D, W, X, Y and Z have the meanings given above are in each case
reacted with sulfonyl chlorides of the formula (VIII)

$R^3$—$SO_2$—Cl (VIII)

in which
$R^3$ has the meaning given above and
if appropriate in the presence of a diluent and if appropriate in the presence of an acid binder,
(G) that compounds of the formulae (I-1-e) and (I-2-e) shown above in which L, $R^4$, $R^5$, A, B, D, W, X, Y and Z have the meanings given above are obtained when the respective compounds of the formulae (I-1-a) and (I-2-a) shown above in which A, B, D, W, X, Y and Z have the meanings given above are in each case
reacted with phosphorus compounds of the formula (IX)

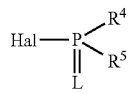

in which
L, R⁴ and R⁵ have the meanings given above and
Hal represents halogen (in particular chlorine or bromine), if appropriate in the presence of a diluent and if appropriate in the presence of an acid binder,
(H) that compounds of the formulae (I-1-f) and (I-2-f) shown above in which E, A, B, D, W, X, Y and Z have the meanings given above are obtained when the respective compounds of the formulae (I-1-a) and (I-2-a) in which A, B, D, W, X, Y and Z have the meanings given above are in each case reacted with metal compounds or amines of the formulae (X) or (XI)

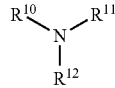

in which
Me represents a monovalent or divalent metal (preferably an alkali metal or alkaline earth metal such as lithium, sodium, potassium, magnesium or calcium),
t represents the number 1 or 2 and
$R^{10}$, $R^{11}$, $R^{12}$ independently of one another represent hydrogen or alkyl (preferably $C_1$-$C_8$-alkyl),
if appropriate in the presence of a diluent,
(I) that compounds of the formulae (I-1-g) and (I-2-g) shown above in which L, R⁶, R⁷, A, B, D, W, X, Y and Z have the meanings given above are obtained when the respective compounds of the formulae (I-1-a) and (I-2-a) shown above in which A, B, D, W, X, Y and Z have the meanings given above are in each case
α) reacted with isocyanates or isothiocyanates of the formula (XII)

in which
R⁶ and L have the meanings given above,
if appropriate in the presence of a diluent and if appropriate in the presence of a catalyst, or
β) with carbamoyl chlorides or thiocarbamoyl chlorides of the formula (XIII)

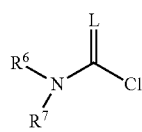

in which
L, R⁶ and R⁷ have the meanings given above,
if appropriate in the presence of a diluent and if appropriate in the presence of an acid binder,
(Jα) that compounds of the formulae (I-1) and (I-2) shown above in which A, B, D, G, W, X, Y and Z have the meaning given above are obtained when compounds of the formulae (I-1') and (I-2') in which A, B, D, G, W, X and Y have the meaning given above and Z' preferably represents bromine or iodine

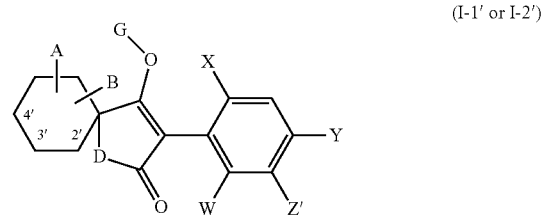

and
(Jβ) that compounds of the formulae (I-1) and (I-2) shown above in which A, B, D, G, W, X, Y and Z have the meaning given above are obtained when compounds of the formulae (I-1") and (I-2") in which A, B, D, G, W, X and Z have the meaning given above and Y' preferably represents bromine or iodine

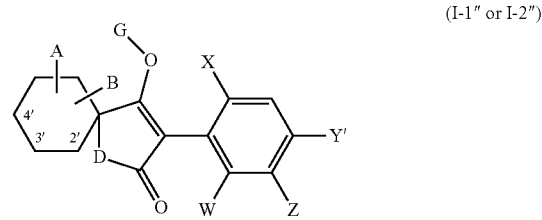

are coupled with (het)aryl derivatives capable of coupling, for example phenylboronic acids of the formulae (XIVα) and (XIVβ)

or esters thereof, in the presence of a solvent, in the presence of a catalyst (for example Pd complexes) and in the presence of a base (for example sodium carbonate, potassium phosphate),
(K) that compounds of the formulae (I-1) and (I-2) shown above in which A, B, G, W, X, Y and Z have the meaning given above are obtained when compounds of the formulae (I-1") and (I-2") in which A, B, G, W, X and Z have the meaning given above and Y' preferably represents bromine or iodine

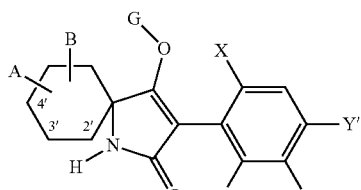
(I-1″)

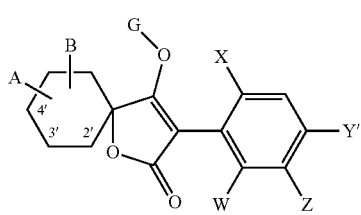
(I-2″)

are reacted with halogenated alcohols, for example trifluoroethanol of the formula (XV)

Y—OH      (XV)

in the presence of a solvent in the presence of a copper salt (for example Cu—I-J) and in the presence of a base (for example potassium tert-butoxide, sodium hydride) to exchange the bromine or iodine atom.

Furthermore it has been found that the novel compounds of the formula (I) have very good activity as pesticides, preferably as insecticides, acaricides, nematicides, fungicides and herbicides, are additionally frequently highly compatible with plants, especially crop plants, and/or have favorable toxicological and/or environmentally relevant properties.

Surprisingly, it has now also been found that certain substituted cyclic ketoenols, when used together with the crop plant compatibility-improving compounds (safeners/antidotes) described below, efficiently prevent damage to the crop plants and can be used in a particularly advantageous manner as broad-spectrum combination preparations for the selective control of unwanted plants in crops of useful plants, such as, for example, in cereals, but also in corn, soybeans and rice.

The invention also provides selective herbicidal compositions comprising an effective amount of an active compound combination comprising, as components, a') at least one compound of the formula (I) in which A, B, D, G, W, X, Y and Z have the meaning given above
and
(b') at least one crop plant compatibility-improving compound (safener).

The safeners are preferably selected from the group consisting of:
S1) compounds of the formula (S1)

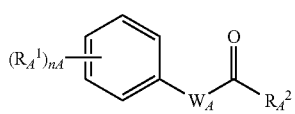
(S1)

where the symbols and indices have the following meanings:
$n_A$ is a natural number from 0 to 5, preferably from 0 to 3;
$R_A^1$ is halogen, $(C_1-C_4)$-alkyl, $(C_1-C_4)$-alkoxy, nitro or $(C_1-C_4)$-haloalkyl;

$W_A$ is an unsubstituted or substituted divalent heterocyclic radical from the group of the partially unsaturated or aromatic five-membered heterocycles having 1 to 3 ring heteroatoms of the N or O type, where at least one nitrogen atom and at most one oxygen atom is present in the ring, preferably a radical from the group of $(W_A^1)$ to $(W_A^4)$,

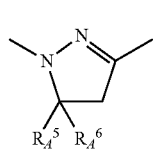
$(W_A^1)$

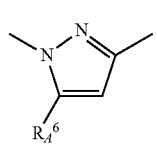
$(W_A^2)$

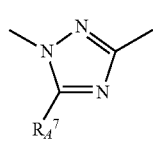
$(W_A^3)$

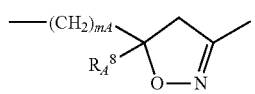
$(W_A^4)$

MA is 0 or 1;
$R_A^2$ is $OR_A^3$, $SR_A^3$ or $NR_A^3R_A^4$ or a saturated or unsaturated 3- to 7-membered heterocycle having at least one nitrogen atom and up to 3 heteroatoms, preferably from the group of O and S, which is joined to the carbonyl group in (S1) via the nitrogen atom and is unsubstituted or substituted by radicals from the group of $(C_1-C_4)$-alkyl, $(C_1-C_4)$-alkoxy or optionally substituted phenyl, preferably a radical of the formula $OR_A^3$, $NHR_A^4$ or $N(CH_3)_2$, especially of the formula $OR_A^3$;
$R_A^3$ is hydrogen or an unsubstituted or substituted aliphatic hydrocarbyl radical preferably having a total of 1 to 18 carbon atoms;
$R^4$ is hydrogen, $(C_1-C_6)$-alkyl, $(C_1-C_6)$-alkoxy or substituted or unsubstituted phenyl;
$R_A^5$ is H, $(C_1-C_8)$-alkyl, $(C_1-C_8)$-haloalkyl, $(C_1-C_4)$-alkoxy-$(C_1-C_8)$-alkyl, cyano or $COOR_A^9$, where $R_A^9$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_{12})$-cycloalkyl or tri-$(C_1-C_4)$-alkylsilyl;
$R_A^6$, $R_A^7$, $R_A^8$ are identical or different and are hydrogen, $(C_1-C_8)$-alkyl, $(C_1-C_8)$-haloalkyl, $(C_3-C_{12})$-cycloalkyl or substituted or unsubstituted phenyl;
preferably:
a) compounds of the dichlorophenylpyrazoline-3-carboxylic acid type (S1$^a$), preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds as described in WO-A-91/07874;
b) derivatives of dichlorophenylpyrazolecarboxylic acid (S1$^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole- 3-carboxylate (S1-3), ethyl 1-(2,4-dichlorophenyl)-5-(1,1-dimethylethyl)pyrazole-3-carboxylate (S1-4) and related compounds as described in EP-A-333 131 and EP-A-269 806;

c) derivatives of 1,5-diphenylpyrazole-3-carboxylic acid (S1$^c$), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds as described in EP-A-268 554, for example;

d) compounds of the triazolecarboxylic acid type (S1$^d$), preferably compounds such as fenchlorazole (ethyl ester), i.e. ethyl 1-(2,4-dichlorophenyl)-5-trichloromethyl-(1H)-1,2,4-triazole-3-carboxylate (51-7), and related compounds as described in EP-A-174 562 and EP-A-346 620;

e) compounds of the 5-benzyl- or 5-phenyl-2-isoxazoline-3-carboxylic acid or of the 5,5-diphenyl-2-isoxazoline-3-carboxylic acid type (S1$^e$), preferably compounds such as ethyl 5-(2,4-dichlorobenzyl)-2-isoxazoline-3-carboxylate (51-8) or ethyl 5-phenyl-2-isoxazoline-3-carboxylate (S1-9) and related compounds as described in WO-A-91/08202, or 5,5-diphenyl-2-isoxazolinecarboxylic acid (S1-10) or ethyl 5,5-diphenyl-2-isoxazolinecarboxylate (S1-11) ("isoxadifen-ethyl") or n-propyl 5,5-diphenyl-2-isoxazolinecarboxylate (S1-12) or ethyl 5-(4-fluorophenyl)-5-phenyl-2-isoxazoline-3-carboxylate (S1-13), as described in patent application WO-A-95/07897.

S2) Quinoline derivatives of the formula (S2)

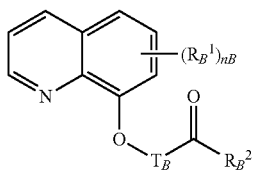

(S2)

where the symbols and indices have the following meanings:

$R_B^1$ is halogen, $(C_1-C_4)$-alkyl, $(C_1-C_4)$-alkoxy, nitro or $(C_1-C_4)$-haloalkyl;

$n_B$ is a natural number from 0 to 5, preferably 0 to 3;

$R_B^2$ is $OR_B^3$, $SR_B^3$ or $NR_B^3 R_B^4$ or a saturated
or unsaturated 3- to 7-membered heterocycle having at least one nitrogen atom and up to 3 heteroatoms, preferably from the group of O and S, which is joined to the carbonyl group in (S2) via the nitrogen atom and is unsubstituted or substituted by radicals from the group of $(C_1-C_4)$-alkyl, $(C_1-C_4)$-alkoxy or optionally substituted phenyl, preferably a radical of the formula $OR_B^3$, $NHR_B^4$ or $N(CH_3)_2$; especially of the formula $OR_B^3$;

$R_B^3$ is hydrogen or an unsubstituted or substituted aliphatic hydrocarbyl radical preferably having a total of 1 to 18 carbon atoms;

$R_B^4$ is hydrogen, $(C_1-C_6)$-alkyl, $(C_1-C_6)$-alkoxy or substituted or unsubstituted phenyl;

$T_B$ is a $(C_1$ or $C_2)$-alkanediyl chain which is unsubstituted or substituted by one or two $(C_1-C_4)$-alkyl radicals or by $[(C_1-C_3)$-alkoxy]carbonyl;

preferably:

a) compounds of the 8-quinolinoxyacetic acid type (S2$^a$), preferably 1-methylhexyl (5-chloro-8-quinolinoxy)acetate ("cloquintocet-mexyl") (S2-1), 1,3-dimethylbut-1-yl (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (S2-6), allyl (5-chloro-8-quinolinoxy)acetate (S2-7), 2-(2-propylideneiminoxy)-1-ethyl (5-chloro-8-quinolinoxy)acetate (S2-8), 2-oxoprop-1-yl (5-chloro-8-quinolinoxy)acetate (S2-9) and related compounds, as described in EP-A-86 750, EP-A-94 349 and EP-A-191 736 or EP-A-0 492 366, and also (5-chloro-8-quinolinoxy)acetic acid (S2-10), hydrates and salts thereof, for example the lithium, sodium, potassium, calcium, magnesium, aluminum, iron, ammonium, quaternary ammonium, sulfonium or phosphonium salts thereof, as described in WO-A-2002/34048;

b) compounds of the (5-chloro-8-quinolinoxy)malonic acid type (S2$^b$), preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds, as described in EP-A-0 582 198.

S3) Compounds of the formula (S3)

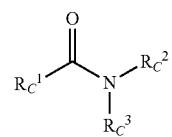

(S3)

where the symbols and indices have the following meanings:

$R_C^1$ is $(C_1-C_4)$-alkyl, $(C_1-C_4)$-haloalkyl, $(C_2-C_4)$-alkenyl, $(C_2-C_4)$-haloalkenyl, $(C_3-C_7)$-cycloalkyl, preferably dichloromethyl;

$R_C^2$, $R_C^3$ are identical or different and are hydrogen, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_1-C_4)$-alkylcarbamoyl-$(C_1-C_4)$-alkyl, $(C_2-C_4)$-alkenylcarbamoyl-$(C_1-C_4)$-alkyl, $(C_1-C_4)$-alkoxy-$(C_1-C_4)$-alkyl, dioxolanyl-$(C_1-C_4)$-alkyl, thiazolyl, furyl, furylalkyl, thienyl, piperidyl, substituted or unsubstituted phenyl, or $R_C^2$ and $R_C^3$ together form a substituted or unsubstituted heterocyclic ring, preferably an oxazolidine, thiazolidine, piperidine, morpholine, hexahydropyrimidine or benzoxazine ring;

preferably:
active compounds of the dichloroacetamide type, which are frequently used as pre-emergence safeners (soil-acting safeners), for example "dichlormid" (N,N-diallyl-2,2-dichloroacetamide) (S3-1), "R-29148" (3-dichloroacetyl-2,2,5-trimethyl-1,3-oxazolidine) from Stauffer (S3-2), "R-28725" (3-dichloroacetyl-2,2-dimethyl-1,3-oxazolidine) from Stauffer (S3-3), "benoxacor" (4-dichloroacetyl-3,4-dihydro-3-methyl-2H-1,4-benzoxazine) (S3-4), "PPG-1292" (N-allyl-N-[(1,3-dioxolan-2-yl)methyl]dichloroacetamide) from PPG Industries (S3-5), "DKA-24" (N-allyl-N-[(allylaminocarbonyl)methyl]dichloroacetamide) from Sagro-Chem (S3-6), "AD-67" or "MON 4660" (3-dichloroacetyl-1-oxa-3-azaspiro[4,5]decane) from Nitrokemia or Monsanto (S3-7), "TI-35" (1-dichloroacetylazepane) from TRI-Chemical RT (S3-8), "diclonon" (dicyclonone) or "BAS145138" or "LAB145138" (S3-9) (3-dichloroacetyl-2,2,5-trimethyl-1,3-diazabicyclo[4.3.0]nonane) from BASF, "furilazole" or "MON 13900" ((RS)-3-dichloroacetyl-5-(2-furyl)-2,2-dimethyloxazolidine) (S3-10); and the (R) isomer thereof (S3-11).

S4) N-Acylsulfonamides of the formula (S4) and salts thereof

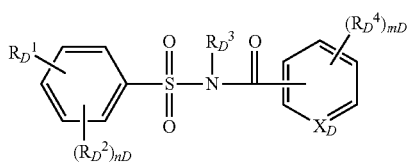

where the symbols and indices have the following meanings:

$X_D$ is CH or N;

$R_D^1$ is CO—$NR_D^5 R_D^6$ or NHCO—$R_D^7$;

$R_D^2$ is halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulfonyl, $(C_1-C_4)$-alkoxycarbonyl or $(C_1-C_4)$-alkylcarbonyl;

$R_D^3$ is hydrogen, $(C_1-C_4)$-alkyl, $(C_2-C_4)$-alkenyl or $(C_2-C_4)$-alkynyl;

$R_D^4$ is halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkylsulfinyl, $(C_1-C_4)$-alkylsulfonyl, $(C_1-C_4)$-alkoxycarbonyl or $(C_1-C_4)$-alkylcarbonyl;

$R_D^5$ is hydrogen, $(C_1-C_6)$-alkyl, $(C_3-C_6)$-cycloalkyl, $(C_2-C_6)$-alkenyl, $(C_2-C_6)$-alkynyl, $(C_5-C_6)$-cycloalkenyl, phenyl or 3- to 6-membered heterocyclyl containing $v_D$ heteroatoms from the group of nitrogen, oxygen and sulfur, where the seven latter radicals are each substituted by $v_D$ substituents from the group of halogen, $(C_1-C_6)$-alkoxy, $(C_1-C_6)$-haloalkoxy, $(C_1-C_2)$-alkylsulfinyl, $(C_1-C_2)$-alkylsulfonyl, $(C_3-C_6)$-cycloalkyl, $(C_1-C_4)$-alkoxycarbonyl, $(C_1-C_4)$-alkylcarbonyl and phenyl, and in the case of cyclic radicals also $(C_1-C_4)$-alkyl and $(C_1-C_4)$-haloalkyl;

$R_D^6$ is hydrogen, $(C_1-C_6)$-alkyl, $(C_2-C_6)$-alkenyl or $(C_2-C_6)$-alkynyl, where the three latter radicals are each substituted by $v_D$ radicals from the group of halogen, hydroxyl, $(C_1-C_4)$-alkyl, $(C_1-C_4)$-alkoxy and $(C_1-C_4)$-alkylthio, or $R_D^5$ and $R_D^6$ together with the nitrogen atom which bears them form a pyrrolidinyl or piperidinyl radical;

$R_D^7$ is hydrogen, $(C_1-C_4)$-alkylamino, di-$(C_1-C_4)$-alkylamino, $(C_1-C_6)$-alkyl, $(C_3-C_6)$-cycloalkyl, where the 2 latter radicals are substituted by $v_D$ substituents from the group of halogen, $(C_1-C_4)$-alkoxy, $(C_1-C_6)$-haloalkoxy and $(C_1-C_4)$-alkylthio, and in the case of cyclic radicals also $(C_1-C_4)$-alkyl and $(C_1-C_4)$-haloalkyl;

$n_D$ is 0, 1 or 2;

$m_D$ is 1 or 2;

$v_D$ is 0, 1, 2 or 3;

among these, preference is given to compounds of the N-acylsulfonamide type, for example of the formula (S4$^a$) below, which are known, for example, from WO-A-97/45016

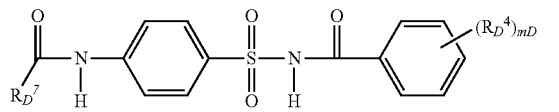

in which $R_D^7$ is $(C_1-C_6)$-alkyl, $(C_3-C_6)$-cycloalkyl, where the 2 latter radicals are substituted by $v_D$ substituents from the group of halogen, $(C_1-C_4)$-alkoxy, $(C_1-C_6)$-haloalkoxy and $(C_1-C_4)$-alkylthio, and in the case of cyclic radicals also $(C_1-C_4)$-alkyl and $(C_1-C_4)$-haloalkyl;

$R_D^4$ is halogen, $(C_1-C_4)$-alkyl, $(C_1-C_4)$-alkoxy, $CF_3$;

$m_D$ is 1 or 2;

$v_D$ is 0, 1, 2 or 3;

and acylsulfamoylbenzamides, for example of the formula (S4$^b$) below, which are known, for example, from WO-A-99/16744,

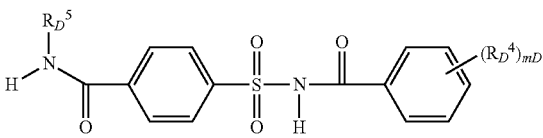

for example those in which $R_D^5$=cyclopropyl and $(R_D^4)$=2-OMe ("cyprosulfamide", S4-1), $R_D^5$=cyclopropyl and $(R_D^4)$=5-Cl-2-OMe (S4-2), $R_D^5$=ethyl and $(R_D^4)$=2-OMe (S4-3), $R_D^5$=isopropyl and $(R_D^4)$=5-Cl-2-OMe (S4-4) and $R_D^5$=isopropyl and $(R_D^4)$=2-OMe (S4-5), and compounds of the N-acylsulfamoylphenylurea type, of the formula (S4$^c$), which are known, for example, from EP-A-365484,

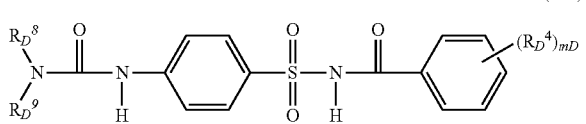

in which $R_D^8$ and $R_D^9$ are each independently hydrogen, $(C_1-C_8)$-alkyl, $(C_3-C_8)$-cycloalkyl, $(C_3-C_6)$-alkenyl, $(C_3-C_6)$-alkynyl, $R_D^4$ is halogen, $(C_1-C_4)$-alkyl, $(C_1-C_4)$-alkoxy, $CF_3$ $m_D$ is 1 or 2;

for example

1-[4-(N-2-methoxybenzoylsulfamoyl)phenyl]-3-methylurea, 1-[4-(N-2-methoxybenzoylsulfamoyl)phenyl]-3,3-dimethylurea, 1-[4-(N-4,5-dimethylbenzoylsulfamoyl)phenyl]-3-methylurea.

S5) Active compounds from the class of the hydroxyaromatics and aromatic-aliphatic carboxylic acid derivatives (S5), for example ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicyclic acid, 2-hydroxycinnamic acid, 1,2-dihydro-2-oxo-6-trifluoromethylpyridine-3-carboxamide, 2,4-dichlorocinnamic acid, as described in WO-A-2004/084631, WO-A-2005/015994, WO-A-2005/016001.

S6) Active compounds from the class of the 1,2-dihydroquinoxalin-2-ones (S6), for example 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-[2-(diethylamino)ethyl]-6,7-dimethyl-3-thiophen-2-ylquinoxalin-2(1H)-one, 1-(2-methylsulfonylaminoethyl)-3-(2-thienyl)-1,2-dihydroquinoxalin-2-one, as described in WO-A-2005/112630.

S7) Compounds of the formula (S7), as described in WO-A-1998/38856,

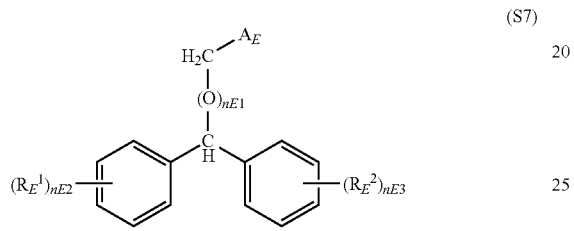

where the symbols and indices have the following meanings:

$R_E^1$, $R_E^2$ are each independently of one another halogen, $(C_1-C_4)$-alkyl, $(C_1-C_4)$-alkoxy, $(C_1-C_4)$-haloalkyl, $(C_1-C_4)$-alkylamino, di-$(C_1-C_4)$-alkylamino, nitro;

$A_E$ is $COOR_E^3$ or $COSR_E^4$ $R_E^3$, $R_E^4$ are each independently of one another hydrogen, $(C_1-C_4)$-alkyl, $(C_2-C_6)$-alkenyl, $(C_2-C_4)$-alkynyl, cyanoalkyl, $(C_1-C_4)$-haloalkyl, phenyl, nitrophenyl, benzyl, halobenzyl, pyridinylalkyl and alkylammonium, $n_E^1$ is 0 or 1

$n_E^2$, $n_E^3$ are each independently of one another 0, 1 or 2, preferably:
diphenylmethoxyacetic acid, ethyl diphenylmethoxyacetate, methyl diphenylmethoxyacetate (CAS reg. no. 41858-19-9) (S7-1).

S8) Compounds of the formula (S8), as described in WO-A-98/27049,

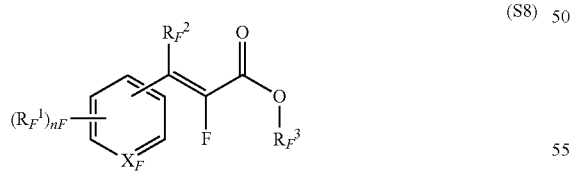

in which $X_F$ is CH or N, $n_F$ in the case that $X_F=N$ is an integer from 0 to 4 and in the case that $X_F=CH$ is an integer from 0 to 5, $R_F^1$ is halogen, $(C_1-C_4)$-alkyl, $(C_1-C_4)$-haloalkyl, $(C_1-C_4)$-alkoxy, $(C_1-C_4)$-haloalkoxy, nitro, $(C_1-C_4)$-alkylthio, $(C_1-C_4)$-alkylsulfonyl, $(C_1-C_4)$-alkoxycarbonyl, optionally substituted phenyl, optionally substituted phenoxy, $R_F^2$ is hydrogen or $(C_1-C_4)$-alkyl, $R_F^3$ is hydrogen, $(C_1-C_8)$-alkyl, $(C_2-C_4)$-alkenyl, $(C_2-C_4)$-alkynyl, or aryl, where each of the aforementioned carbon-containing radicals is unsubstituted or substituted by one or more, preferably up to three identical or different radicals from the group consisting of halogen and alkoxy; or salts thereof preferably compounds in which $X_F$ is CH, $n_F$ is an integer from 0 to 2, $R_F^1$ is halogen, $(C_1-C_4)$-alkyl, $(C_1-C_4)$-haloalkyl, $(C_1-C_4)$-alkoxy, $(C_1-C_4)$-haloalkoxy, $R_F^2$ is hydrogen or $(C_1-C_4)$-alkyl, $R_F^3$ is hydrogen, $(C_1-C_8)$-alkyl, $(C_2-C_4)$-alkenyl, $(C_2-C_4)$-alkynyl, or aryl, where each of the aforementioned carbon-containing radicals is unsubstituted or substituted by one or more, preferably up to three identical or different radicals from the group consisting of halogen and alkoxy; or salts thereof.

S9) Active compounds from the class of the 3-(5-tetrazolylcarbonyl)-2-quinolones (S9), for example 1,2-dihydro-4-hydroxy-1-ethyl-3-(5-tetrazolylcarbonyl)-2-quinolone (CAS reg. no.: 219479-18-2), 1,2-dihydro-4-hydroxy-1-methyl-3-(5-tetrazolylcarbonyl)-2-quinolone (CAS reg. no. 95855-00-8), as described in WO-A-1999/000020.

S10) Compounds of the formulae (S10$^a$) or (S10$^b$) as described in WO-A-2007/023719 and WO-A-2007/023764,

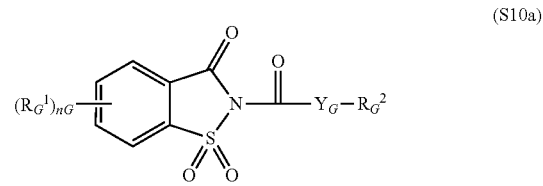

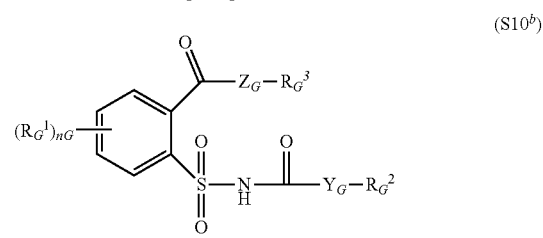

in which $R_G^1$ is halogen, $(C_1-C_4)$-alkyl, methoxy, nitro, cyano, $CF_3$, $OCF_3$, $Y_G$, $Z_G$ are each independently of one another O or S, $n_G$ is an integer from 0 to 4, $R_G^2$ is $(C_1-C_{16})$-alkyl, $(C_2-C_6)$-alkenyl, $(C_3-C_6)$-cycloalkyl, aryl; benzyl, halobenzyl, $R_G^3$ is hydrogen or $(C_1-C_6)$-alkyl.

S11) Active compounds of the type of the oxyimino compounds (S11), which are known as seed dressings, such as, for example, "oxabetrinil" ((Z)-1,3-dioxolan-2-ylmethoxyimino(phenyl)acetonitrile) (S11-1), which is known as seed dressing safener for millet against metolachlor damage, "fluxofenim" (1-(4-chlorophenyl)-2,2,2-trifluoro-1-ethanone O-(1,3-dioxolan-2-ylmethyl)oxime) (S11-2), which is known as seed dressing safener for millet against metolachlor damage, and "cyometrinil" or "CGA-43089" ((Z)-cyanomethoxy-imino(phenyl)acetonitrile) (S11-3), which is known as seed dressing safener for millet against metolachlor damage.

S12) Active compounds from the class of the isothiochromanones (S12), for example methyl [(3-oxo-1H-2-benzothiopyran-4(3H)-ylidene)methoxy]acetate (CAS reg. no. 205121-04-6) (S12-1) and related compounds from WO-A-1998/13361.

S13) One or more compounds from group (S13):

"naphthalic anhydride" (1,8-naphthalenedicarboxylic anhydride) (S13-1), which is known as seed dressing safener for corn against thiocarbamate herbicide damage, "fenclorim" (4,6-dichloro-2-phenylpyrimidine) (S13-2), which is known as safener for pretilachlor in sown rice, "flurazole" (benzyl 2-chloro-4-trifluoromethyl-1,3-thiazole-5-carboxylate) (S13-3), which is known as seed dressing safener for millet against alachlor and metolachlor damage, "CL 304415" (CAS reg. no. 31541-57-8) (4-carboxy-3,4-dihydro-2H-1-benzopyran-4-acetic acid) (S13-4) from American Cyanamid, which is known as a safener for corn against damage by imidazolinones, "MG 191" (CAS reg. no. 96420-72-3) (2-dichloromethyl-2-methyl-1,3-dioxolane) (513-5) from Nitrokemia, which is known as a safener for corn, "MG-838" (CAS reg. no. 133993-74-5) (2-propenyl 1-oxa-4-azaspiro[4.5]decane-4-carbodithioate) (S13-6) from Nitrokemia, "disulfoton" (O,O-diethyl S-2-ethylthioethyl phosphorodithioate) (S13-7), "dietholate" (O,O-diethyl O-phenyl phosphorothioate) (S13-8), "mephenate" (4-chlorophenyl methylcarbamate) (S13-9).

S14) Active compounds which, in addition to herbicidal action against harmful plants, also have safener action on crop plants such as rice, for example "dimepiperate" or "MY-93" (S-1-methyl-1-phenylethylpiperidine-1-carbothioate), which is known as a safener for rice against damage by the herbicide molinate, "daimuron" or "SK 23" (1-(1-methyl-1-phenylethyl)-3-p-tolylurea), which is known as safener for rice against imazosulfuron herbicide damage, "cumyluron"="JC-940" (3-(2-chlorophenylmethyl)-1-(1-methyl-1-phenylethyl)urea, see JP-A-60087254), which is known as safener for rice against damage by some herbicides, "methoxyphenone" or "NK 049" (3,3'-dimethyl-4-methoxybenzophenone), which is known as safener for rice against damage by some herbicides, "CSB" (1-bromo-4-(chloromethylsulfonyl)benzene) from Kumiai, (CAS reg. no. 54091-06-4), which is known as a safener against damage by some herbicides in rice.

S15) Compounds of the formula (S15) or tautomers thereof

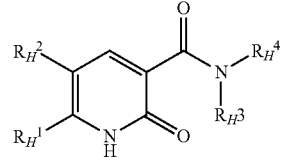

(S15)

as described in WO-A-2008/131861 and WO-A-2008/131860 in which $R_H^1$ is a $(C_1-C_6)$-haloalkyl radical and $R_H^2$ is hydrogen or halogen and $R_H^3$, $R_H^4$ are each independently hydrogen, $(C_1-C_{16})$-alkyl, $(C_2-C_{16})$-alkenyl or $(C_2-C_{16})$-alkynyl, where each of the latter 3 radicals is unsubstituted or substituted by one or more radicals from the group of halogen, hydroxyl, cyano, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]carbonyl, [$(C_1-C_4)$-haloalkoxy]carbonyl, $(C_3-C_6)$-cycloalkyl which is unsubstituted or substituted, phenyl which is unsubstituted or substituted, and heterocyclyl which is unsubstituted or substituted, or $(C_3-C_6)$-cycloalkyl, $(C_4-C_6)$-cycloalkenyl, $(C_3-C_6)$-cycloalkyl which is fused on one side of the ring to a 4 to 6-membered saturated or unsaturated carbocyclic ring, or $(C_4-C_6)$-cycloalkenyl which is fused on one side of the ring to a 4 to 6-membered saturated or unsaturated carbocyclic ring, where each of the latter 4 radicals is unsubstituted or substituted by one or more radicals from the group of halogen, hydroxyl, cyano, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]carbonyl, [$(C_1-C_4)$-haloalkoxy]carbonyl, $(C_3-C_6)$-cycloalkyl which is unsubstituted or substituted, phenyl which is unsubstituted or substituted, and heterocyclyl which is unsubstituted or substituted, or $R_H^3$ is $(C_1-C_4)$-alkoxy, $(C_2-C_4)$-alkenyloxy, $(C_2-C_6)$-alkynyloxy or $(C_2-C_4)$-haloalkoxy and $R_H^4$ is hydrogen or $(C_1-C_4)$-alkyl or $R_H^3$ and $R_H^4$ together with the directly bonded nitrogen atom are a four- to eight-membered heterocyclic ring which, as well as the nitrogen atom, may also contain further ring heteroatoms, preferably up to two further ring heteroatoms from the group of N, O and S, and which is unsubstituted or substituted by one or more radicals from the group of halogen, cyano, nitro, $(C_1-C_4)$-alkyl, $(C_1-C_4)$-haloalkyl, $(C_1-C_4)$-alkoxy, $(C_1-C_4)$-haloalkoxy and $(C_1-C_4)$-alkylthio.

S16) Active compounds which are used primarily as herbicides but also have safener action on crop plants, for example (2,4-dichlorophenoxy)acetic acid (2,4-D), (4-chlorophenoxy)acetic acid, (R,S)-2-(4-chloro-o-tolyloxy)propionic acid (mecoprop), 4-(2,4-dichlorophenoxy)butyric acid (2,4-DB), (4-chloro-o-tolyloxy) acetic acid (MCPA), 4-(4-chloro-o-tolyloxy)butyric acid, 4-(4-chlorophenoxy)butyric acid, 3,6-dichloro-2-methoxybenzoic acid (dicamba), 1-(ethoxycarbonyl)ethyl 3,6-dichloro-2-methoxybenzoate (lactidichlor-ethyl).

Most preferred as crop plant compatibility-improving compound [component (b')] are cloquintocet-mexyl, fenchlorazole-ethyl, isoxadifen-ethyl, mefenpyr-diethyl, fenclorim, cumyluron, S4-1 and S4-5, and particular emphasis is given to cloquintocet-mexyl and mefenpyr-diethyl.

Surprisingly, it has now been found that the active compound combinations defined above of compounds of the general formula (I) and safeners (antidotes) from the group (b') set out above combine very good useful plant tolerance with a particularly high herbicidal activity and can be used in various crops, in particular in cereals (especially wheat), but also in soybeans, potatoes, corn and rice, for the selective control of weeds.

In this context it is to be considered surprising that, from a multiplicity of known safeners or antidotes capable of antagonizing the damaging effect of a herbicide on the crop plants, it is specifically the compounds of group (b') set out above which are suitable for compensating—almost completely—the damaging effect of compounds of the formula (I) on the crop plants, without at the same time having any critical adverse effect on the herbicidal activity against the weeds.

Emphasis may be given here to the particularly advantageous effect of the particularly preferred and most preferred combination partners from group (b'), in particular with regard to the gentle treatment of cereal plants, such as wheat, barley and rye, for example, but also corn and rice, as crop plants.

The formula (I) provides a general definition of the compounds according to the invention. Preferred substituents or ranges of the radicals given under the formulae shown above and below are illustrated below:

W preferably represents hydrogen, halogen, $C_1$-$C_6$-alkyl, $C_2$-$C_6$-alkenyl, $C_2$-$C_6$-alkynyl, $C_3$-$C_6$-cycloalkyl which is optionally mono- to disubstituted by $C_1$-$C_2$-alkyl, $C_1$-$C_2$-alkoxy, fluorine, chlorine, trifluoromethyl or $C_3$-$C_6$-cycloalkyl, $C_1$-$C_6$-alkoxy, $C_1$-$C_4$-haloalkyl, $C_1$-$C_4$-haloalkoxy or cyano, X preferably represents halogen, $C_1$-$C_6$-alkyl, $C_2$-$C_6$-alkenyl, $C_2$-$C_6$-alkynyl, C3-C6-cycloalkyl which is optionally mono- to disubstituted by $C_1$-$C_2$-alkyl, $C_1$-$C_2$-alkoxy, fluorine, chlorine, trifluoromethyl or $C_3$-$C_6$-cycloalkyl, $C_1$-$C_6$-haloalkyl, $C_1$-$C_6$-alkoxy, $C_3$-$C_6$-alkenyloxy, $C_1$-$C_6$-alkylthio, $C_1$-$C_6$-alkylsulfinyl, $C_1$-$C_6$-alkylsulfonyl, $C_1$-$C_6$-haloalkoxy, $C_3$-$C_6$-haloalkenyloxy, nitro or cyano, Y and Z independently of one another preferably represent hydrogen, halogen, $C_1$-$C_6$-alkyl, $C_2$-$C_6$-alkenyl, $C_2$-$C_6$-alkynyl, $C_3$-$C_6$-cycloalkyl which is optionally mono- to disubstituted by $C_1$-$C_2$-alkyl, $C_1$-$C_2$-alkoxy, fluorine, chlorine, trifluoromethyl or $C_3$-$C_6$-cycloalkyl, $C_1$-$C_6$-alkoxy, $C_1$-$C_6$-haloalkyl, $C_1$-$C_6$-haloalkoxy, cyano, or represent one of the (het)aryl radicals

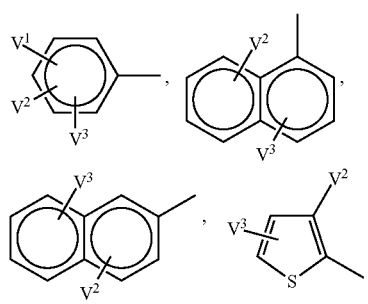

where in the case of (het)aryl only one of the radicals Y or Z may represent (het)aryl, $V^1$ preferably represents hydrogen, halogen, $C_1$-$C_{12}$-alkyl, $C_{1-6}$-alkoxy, $C_1$-$C_6$-alkylthio, $C_1$-$C_6$-alkylsulfinyl, $C_1$-$C_6$-alkylsulfonyl, $C_1$-$C_4$-haloalkyl, $C_1$-$C_4$-haloalkoxy, nitro, cyano or represents phenyl, phenoxy, phenoxy-$C_1$-$C_4$-alkyl, phenyl-$C_1$-$C_4$-alkoxy, phenylthio-$C_1$-$C_4$-alkyl or phenyl-$C_1$-$C_4$-alkylthio, each of which is optionally mono- or polysubstituted by halogen, $C_1$-$C_6$-alkyl, $C_1$-$C_6$-alkoxy, $C_1$-$C_4$-haloalkyl, $C_1$-$C_4$-haloalkoxy, nitro or cyano, $V^2$ and $V^3$ independently of one another preferably represent hydrogen, halogen, $C_1$-$C_6$-alkyl, $C_1$-$C_6$-alkoxy, $C_1$-$C_4$-haloalkyl or $C_1$-$C_4$-haloalkoxy, A preferably represents halogen, B preferably represents halogen or a bond which is attached to the same carbon atom as A, with the proviso that A and B are located in the 3'- and/or 4'-position, D preferably represents NH or oxygen, G preferably represents hydrogen (a) or represents one of the groups (b)

(c)

-continued

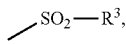  (d)

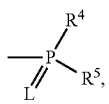  (e)

E, or  (f)

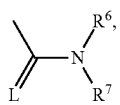  (g)

in which

E represents a metal ion or an ammonium ion,

L represents oxygen or sulfur and

M represents oxygen or sulfur, $R^1$ preferably represents in each case optionally halogen- or cyano-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl or poly-$C_1$-$C_8$-alkoxy-$C_1$-$C_8$-alkyl or represents optionally halogen-, $C_1$-$C_6$-alkyl- or $C_1$-$C_6$-alkoxy-substituted $C_3$-$C_8$-cycloalkyl in which optionally one or two not directly adjacent methylene groups are replaced by oxygen and/or sulfur, represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulfonyl-substituted phenyl, represents optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl, represents optionally halogen- or $C_1$-$C_6$-alkyl-substituted 5- or 6-membered hetaryl having one or two heteroatoms from the group consisting of oxygen, sulfur and nitrogen, represents optionally halogen- or $C_1$-$C_6$-alkyl-substituted phenoxy-$C_1$-$C_6$-alkyl or represents optionally halogen-, amino- or $C_1$-$C_6$-alkyl-substituted 5- or 6-membered hetaryloxy-$C_1$-$C_6$-alkyl having one or two heteroatoms from the group consisting of oxygen, sulfur and nitrogen, $R^2$ preferably represents in each case optionally halogen- or cyano-substituted $C_1$-$C_{20}$-alkyl, $C_2$-$C_{20}$-alkenyl, $C_1$-$C_8$-alkoxy-$C_2$-$C_8$-alkyl or poly-$C_1$-$C_8$-alkoxy-$C_2$-$C_8$-alkyl, represents optionally halogen-, $C_1$-$C_6$-alkyl- or $C_1$-$C_6$-alkoxy-substituted $C_3$-$C_8$-cycloalkyl or represents phenyl or benzyl, each of which is optionally substituted by halogen, cyano, nitro, $C_1$-$C_6$-alkyl, $C_1$-$C_6$-alkoxy, $C_1$-$C_6$-haloalkyl or $C_1$-$C_6$-haloalkoxy, $R^3$ preferably represents optionally halogen-substituted $C_1$-$C_8$-alkyl or in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl, $R^4$ and $R^5$ independently of one another preferably represent in each case optionally halogen-substituted $C_1$-$C_8$-alkyl, $C_1$-$C_8$-alkoxy, $C_1$-$C_8$-alkylamino, di-($C_1$-$C_8$-alkyl)amino, $C_1$-$C_8$-alkylthio or $C_3$-$C_8$-alkenylthio or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio, $R^6$ and $R^7$ independently of one another preferably represent hydrogen, represent in each case optionally halogen- or cyano-substituted $C_1$-$C_8$-alkyl, $C_3$-$C_8$-cycloalkyl, $C_1$-$C_8$-alkoxy, $C_3$-$C_8$-alkenyl or $C_1$-$C_8$-alkoxy-$C_2$-$C_8$-alkyl, represent in each case optionally halogen-, $C_1$-$C_8$-alkyl, $C_1$-$C_8$-haloalkyl- or $C_1$-$C_8$-alkoxy-substituted phenyl or benzyl or together represent an optionally $C_1$-$C_6$-alkyl-substituted $C_3$-$C_6$-alkylene radical in which optionally one methylene group is replaced by oxygen or sulfur.

In the radical definitions mentioned as being preferred, halogen represents fluorine, chlorine, bromine and iodine, in particular fluorine, chlorine and bromine.

W particularly preferably represents hydrogen, chlorine, bromine, $C_1$-$C_4$-alkyl, $C_2$-$C_4$-alkenyl, $C_2$-$C_4$-alkynyl, $C_3$-$C_6$-cycloalkyl which is optionally monosubstituted by methyl, ethyl, methoxy, fluorine, chlorine, trifluoromethyl or cyclopropyl, $C_1$-$C_4$-alkoxy, $C_1$-$C_2$-haloalkyl or $C_1$-$C_2$-haloalkoxy, X particularly preferably represents chlorine, bromine, iodine, $C_1$-$C_4$-alkyl, $C_2$-$C_4$-alkenyl, $C_2$-$C_4$-alkynyl, $C_3$-$C_6$-cycloalkyl which is optionally monosubstituted by methyl, ethyl, methoxy, fluorine, chlorine, trifluoromethyl or cyclopropyl, $C_1$-$C_4$-alkoxy, $C_1$-$C_4$-haloalkyl, $C_1$-$C_4$-haloalkoxy or cyano, Y and Z independently of one another particularly preferably represent hydrogen, fluorine, chlorine, bromine, iodine, $C_1$-$C_4$-alkyl, $C_2$-$C_4$-alkenyl, $C_2$-$C_4$-alkynyl, C3-C6-cycloalkyl which is optionally monosubstituted by methyl, ethyl, methoxy, fluorine, chlorine, trifluoromethyl or cyclopropyl, $C_1$-$C_6$-alkoxy, $C_1$-$C_4$-haloalkyl, $C_1$-$C_4$-haloalkoxy, cyano, or represent one of the (het)aryl radicals,

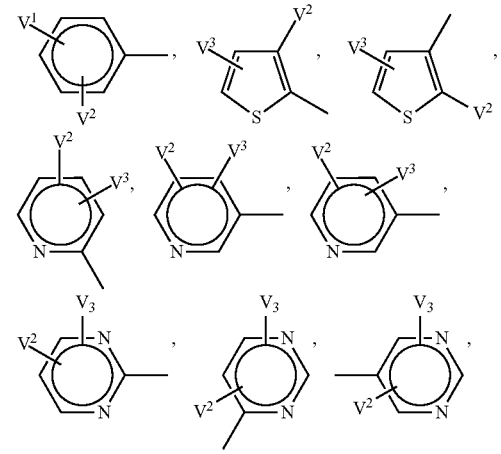

where in the case of (het)aryl only one of the radicals Y or Z may represent (het)aryl, $V^1$ particularly preferably represents hydrogen, fluorine, chlorine, bromine, $C_1$-$C_6$-alkyl, $C_1$-$C_4$-alkoxy, $C_1$-$C_2$-haloalkyl, $C_1$-$C_2$-haloalkoxy, nitro, cyano or phenyl which is optionally mono- or disubstituted by fluorine, chlorine, bromine, $C_1$-$C_4$-alkyl, $C_1$-$C_4$-alkoxy, $C_1$-$C_2$-haloalkyl, $C_1$-$C_2$-haloalkoxy, nitro or cyano, $V^2$ and $V^3$ independently of one another particularly preferably represent hydrogen, fluorine, chlorine, bromine, $C_1$-$C_4$-alkyl, $C_1$-$C_4$-alkoxy, $C_1$-$C_2$-haloalkyl or $C_1$-$C_2$-haloalkoxy, A particularly preferably represents fluorine or chlorine, B particularly preferably represents fluorine, chlorine or a bond which is attached to the same carbon atom as A, with the proviso that A and B are located in the 3'- and/or 4'-position, D particularly preferably represents NH or oxygen,
G particularly preferably represents hydrogen (a) or represents one of the groups

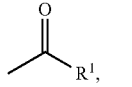 (b)

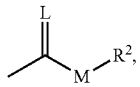 (c)

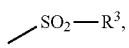 (d)

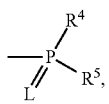 (e)

E, or (f)

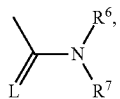 (g)

in which
E represents a metal ion or an ammonium ion,
L represents oxygen or sulfur and
M represents oxygen or sulfur,
$R^1$ particularly preferably represents $C_1$-$C_{16}$-alkyl, $C_2$-$C_{16}$-alkenyl, $C_1$-$C_6$-alkoxy-$C_1$-$C_4$-alkyl, $C_1$-$C_6$-alkylthio-$C_1$-$C_4$-alkyl or poly-$C_1$-$C_6$-alkoxy-$C_1$-$C_4$-alkyl, each of which is optionally mono- to trisubstituted by fluorine or chlorine, or represents $C_3$-$C_7$-cycloalkyl which is optionally mono- or disubstituted by fluorine, chlorine, $C_1$-$C_5$-alkyl or $C_1$-$C_5$-alkoxy and in which optionally one or two not directly adjacent methylene groups are replaced by oxygen and/or sulfur,
represents phenyl which is optionally mono- to trisubstituted by fluorine, chlorine, bromine, cyano, nitro, $C_1$-$C_4$-alkyl, $C_1$-$C_4$-alkoxy, $C_1$-$C_3$-haloalkyl, $C_1$-$C_3$-haloalkoxy, $C_1$-$C_4$-alkylthio or $C_1$-$C_4$-alkylsulfonyl,
represents phenyl-$C_1$-$C_4$-alkyl, which is optionally mono- or disubstituted by fluorine, chlorine, bromine, $C_1$-$C_4$-alkyl, $C_1$-$C_4$-alkoxy, $C_1$-$C_3$-haloalkyl or $C_1$-$C_3$-haloalkoxy,
represents pyrazolyl, thiazolyl, pyridyl, pyrimidyl, furanyl or thienyl, each of which is optionally mono- or disubstituted by fluorine, chlorine, bromine or $C_1$-$C_4$-alkyl,
represents phenoxy-$C_1$-$C_5$-alkyl which is optionally mono- or disubstituted by fluorine, chlorine, bromine or $C_1$-$C_4$-alkyl,
represents pyridyloxy-$C_1$-$C_5$-alkyl, pyrimidyloxy-$C_1$-$C_5$-alkyl or thiazolyloxy-$C_1$-$C_5$-alkyl, each of which is optionally mono- or disubstituted by fluorine, chlorine, bromine, amino or $C_1$-$C_4$-alkyl,
$R^2$ particularly preferably represents $C_1$-$C_{16}$-alkyl, $C_2$-$C_{16}$-alkenyl, $C_1$-$C_6$-alkoxy-$C_2$-$C_6$-alkyl or poly-$C_1$-$C_6$-alkoxy-$C_2$-$C_6$-alkyl, each of which is optionally mono- to trisubstituted by fluorine or chlorine,
represents $C_3$-$C_7$-cycloalkyl which is optionally mono- or disubstituted by fluorine, chlorine, $C_1$-$C_4$-alkyl or $C_1$-$C_4$-alkoxy or
represents phenyl or benzyl, each of which is optionally mono- to trisubstituted by fluorine, chlorine, bromine, cyano, nitro, $C_1$-$C_4$-alkyl, $C_1$-$C_3$-alkoxy, $C_1$-$C_3$-haloalkyl or $C_1$-$C_3$-haloalkoxy,
$R^3$ particularly preferably represents $C_1$-$C_6$-alkyl which is optionally mono- to trisubstituted by fluorine or chlorine or represents phenyl or benzyl, each of which is optionally mono- or disubstituted by fluorine, chlorine, bromine, $C_1$-$C_4$-alkyl, $C_1$-$C_4$-alkoxy, $C_1$-$C_2$-haloalkoxy, $C_1$-$C_2$-haloalkyl, cyano or nitro,
$R^4$ and $R^5$ independently of one another particularly preferably represent $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio or $C_3$-$C_4$-alkenylthio, each of which is optionally mono- to trisubstituted by fluorine or chlorine, or represent phenyl, phenoxy or phenylthio, each of which is optionally mono- or disubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or $C_1$-$C_3$-haloalkyl,
$R^6$ and $R^7$ independently of one another particularly preferably represent hydrogen, represent $C_1$-$C_6$-alkyl, $C_3$-$C_6$-cycloalkyl, $C_1$-$C_6$-alkoxy, $C_3$-$C_6$-alkenyl or $C_1$-$C_6$-alkoxy-$C_2$-$C_6$-alkyl, each of which is optionally mono- to trisubstituted by fluorine or chlorine, represent phenyl or benzyl, each of which is optionally mono- to trisubstituted by fluorine, chlorine, bromine, $C_1$-$C_5$-haloalkyl, $C_1$-$C_5$-alkyl or $C_1$-$C_5$-alkoxy, or together represent an optionally $C_1$-$C_4$-alkyl-substituted $C_3$-$C_6$-alkylene radical in which optionally one methylene group is replaced by oxygen or sulfur.

In the radical definitions mentioned as being particularly preferred, halogen represents fluorine, chlorine and bromine, in particular fluorine and chlorine.

W very particularly preferably represents hydrogen, chlorine, bromine, methyl, ethyl, vinyl, ethynyl, propynyl, cyclopropyl, methoxy, ethoxy or trifluoromethyl,
X very particularly preferably represents chlorine, bromine, methyl, ethyl, propyl, isopropyl, vinyl, ethynyl, propynyl, cyclopropyl, methoxy, ethoxy, trifluoromethyl, difluoromethoxy, trifluoromethoxy or cyano,
Y and Z independently of one another very particularly preferably represent hydrogen, fluorine, chlorine, bromine, iodine, methyl, ethyl, vinyl, ethynyl, propynyl, cyclopropyl, methoxy, trifluoromethyl, trifluoromethoxy, trifluoroethoxy, cyano or a phenyl radical,

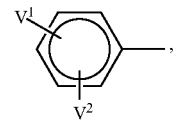

where in the case of phenyl only one of the radicals Y or Z may represent phenyl,
$V^1$ very particularly preferably represents hydrogen, fluorine or chlorine,
$V^2$ very particularly preferably represents hydrogen, fluorine, chlorine, methyl, ethyl, n-propyl, isopropyl, methoxy, ethoxy or trifluoromethyl,
A very particularly preferably represents fluorine,
B very particularly preferably represents fluorine or a bond which is attached to the same carbon atom as A,
D very particularly preferably represents NH or oxygen,
G very particularly preferably represents hydrogen (a) or represents one of the groups

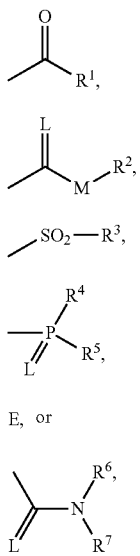

E, or (g)

in which

E represents a metal ion or an ammonium ion,

L represents oxygen or sulfur and

M represents oxygen or sulfur,

R$^1$ very particularly preferably represents $C_1$-$C_{10}$-alkyl, $C_2$-$C_{10}$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine, or represents $C_3$-$C_6$-cycloalkyl which is optionally monosubstituted by fluorine, chlorine, methyl, ethyl or methoxy, represents phenyl which is optionally mono- or disubstituted by fluorine, chlorine, bromine, cyano, nitro, methyl, ethyl, n-propyl, isopropyl, methoxy, ethoxy, trifluoromethyl or trifluoromethoxy, represents furanyl, thienyl or pyridyl, each of which is optionally monosubstituted by chlorine, bromine or methyl, R$^2$ very particularly preferably represents $C_1$-$C_{10}$-alkyl, $C_2$-$C_{10}$-alkenyl or $C_1$-$C_4$-alkoxy-$C_2$-$C_4$-alkyl, each of which is optionally mono- to trisubstituted by fluorine or chlorine, represents cyclopentyl or cyclohexyl or represents phenyl or benzyl, each of which is optionally mono- or disubstituted by fluorine, chlorine, cyano, nitro, methyl, ethyl, methoxy, trifluoromethyl or trifluoromethoxy.

R$^3$ very particularly preferably represents methyl, ethyl, propyl or isopropyl, each of which is optionally mono- to trisubstituted by fluorine or chlorine, or represents phenyl which is optionally monosubstituted by fluorine, chlorine, bromine, methyl, ethyl, isopropyl, tert-butyl, methoxy, ethoxy, isopropoxy, trifluoromethyl, trifluoromethoxy, cyano or nitro, R$^4$ and R$^5$ independently of one another very particularly preferably represent $C_1$-$C_4$-alkoxy or $C_1$-$C_4$-alkylthio or represent phenyl, phenoxy or phenylthio, each of which is optionally monosubstituted by fluorine, chlorine, bromine, nitro, cyano, methyl, methoxy, trifluoromethyl or trifluoromethoxy, R$^6$ and R$^7$ independently of one another very particularly preferably represent hydrogen, represent $C_1$-$C_4$-alkyl, $C_3$-$C_6$-cycloalkyl, $C_1$-$C_4$-alkoxy, $C_3$-$C_4$-alkenyl or $C_1$-$C_4$-alkoxy-$C_2$-$C_4$-alkyl, represent phenyl which is optionally mono- or disubstituted by fluorine, chlorine, bromine, methyl, methoxy or trifluoromethyl, or together represent a $C_5$-$C_6$-alkylene radical in which optionally one methylene group is replaced by oxygen or sulfur.

W especially preferably represents hydrogen, chlorine, bromine, methyl, ethyl or methoxy, (with emphasis hydrogen, methyl or ethyl), X especially preferably represents chlorine, bromine, methyl, ethyl, methoxy or ethoxy, (with emphasis chlorine, methyl or ethyl), Y and Z independently of one another especially preferably represent hydrogen, chlorine, bromine, methyl, trifluoroethoxy, or represent the radical

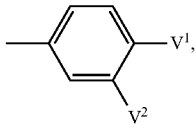

where in this case only one of the radicals Y or Z may represent

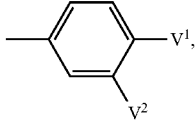

V$^1$ especially preferably represents fluorine or chlorine,

V$^2$ especially preferably represents hydrogen, fluorine or chlorine, (with emphasis hydrogen, also with emphasis fluorine), (with emphasis, Y represents hydrogen, methyl, bromine, chlorine, trifluoroethoxy,

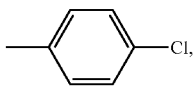

with emphasis, Z represents hydrogen, bromine,

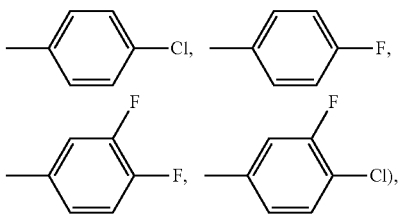

A especially preferably represents fluorine,

B especially preferably represents fluorine or a bond, where A and B are attached to the same carbon atom in the 4'-position, D especially preferably represents NH or oxygen, G especially preferably represents hydrogen (a) or one of the groups (b)

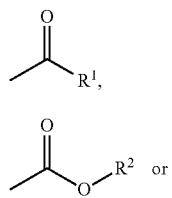

(c)

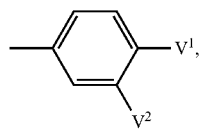

(f)

E (with emphasis, G represents groups (a), (b) or (c)),
in which
E represents a metal ion or an ammonium ion,
$R^1$ especially preferably represents $C_1$-$C_{10}$-alkyl, $C_1$-$C_4$-alkoxy-$C_1$-$C_2$-alkyl, $C_3$-$C_6$-cycloalkyl, represents phenyl which is optionally monosubstituted by chlorine or represents thienyl, (with emphasis $C_1$-$C_{10}$-alkyl),
$R^2$ especially preferably represents $C_1$-$C_{10}$-alkyl, $C_2$-$C_{10}$-alkenyl or benzyl, (with emphasis $C_1$-$C_{10}$-alkyl).

Special emphasis is given to compounds in which Z represents

![structure showing para-disubstituted phenyl with V¹ and V²]

with the especially preferred radicals W, X, Y, V¹, V², A, B, D, G, E, $R^1$ and $R^2$.

The abovementioned general or preferred radical definitions or illustrations can be combined with one another as desired, i.e. including combinations between the respective ranges and preferred ranges. They apply both to the end products and, correspondingly, to precursors and intermediates.

Preference is given in accordance with the invention to the compounds of the formula (I) in which a combination of the definitions listed above as preferred (preferably) is present.

Particular preference is given in accordance with the invention to the compounds of the formula (I) in which a combination of the definitions listed above as more preferred is present.

Very particular preference is given in accordance with the invention to the compounds of the formula (I) in which a combination of the definitions listed above as even more preferred is present.

Special preference according to the invention is given to the compounds of the formula (I) which contain a combination of the meanings listed above as being especially preferred.

Emphasis is given to compounds of the formula (I) in which G represents hydrogen.

Saturated or unsaturated hydrocarbon radicals, such as alkyl, alkanediyl or alkenyl, can in each case be straight-chain or branched as far as this is possible, including in combination with heteroatoms, such as, for example, in alkoxy.

Unless indicated otherwise, optionally substituted radicals may be mono- or polysubstituted, where in the case of polysubstitutions the substituents may be identical or different.

In addition to the compounds mentioned in the Preparation Examples, the following compounds of the formula (I-1-a) may be specifically mentioned:

TABLE 1

(I-1-a)

[Structure: spirocyclic pyrrolinone with OH, attached phenyl ring numbered 1-6 with substituents X (2'), Y (4), W (6'), Z (5), and cyclohexane with A, B at 4' position]

| A | B | X | W | Y | Z |
|---|---|---|---|---|---|
| F | F | $CH_3$ | H | H | H |
| F | F | Br | H | H | H |
| F | F | Cl | H | H | H |
| F | F | $CF_3$ | H | H | H |
| F | F | $OCH_3$ | H | H | H |
| F | F | Br | H | Cl | H |
| F | F | Cl | H | Br | H |
| F | F | Cl | H | Cl | H |
| F | F | Cl | H | $CH_3$ | H |
| F | F | $CH_3$ | H | Cl | H |
| F | F | Cl | Cl | H | H |
| F | F | Cl | $OCH_3$ | H | H |
| F | F | Cl | $CH_3$ | H | H |
| F | F | Cl | $OC_2H_5$ | H | H |
| F | F | $OCH_3$ | $OCH_3$ | H | H |
| F | F | $CH_3$ | $CH_3$ | H | H |
| F | F | $C_2H_5$ | $CH_3$ | H | H |
| F | F | $C_2H_5$ | $C_2H_5$ | H | H |
| F | F | Br | $CH_3$ | Br | H |
| F | F | Cl | $CH_3$ | Cl | H |
| F | F | $CH_3$ | Br | $CH_3$ | H |
| F | F | $CH_3$ | Cl | $CH_3$ | H |
| F | F | $OCH_3$ | $CH_3$ | $CH_3$ | H |
| F | F | $OC_2H_5$ | $CH_3$ | $CH_3$ | H |
| F | F | $OC_3H_7$ | $CH_3$ | $CH_3$ | H |
| F | F | $CH_3$ | $CH_3$ | $CH_3$ | H |
| F | F | Br | Br | $CH_3$ | H |
| F | F | Cl | Cl | $CH_3$ | H |
| F | F | $CH_3$ | $CH_3$ | Br | H |
| F | F | $OCH_3$ | $C_2H_5$ | $CH_3$ | H |
| F | F | $OC_2H_5$ | $C_2H_5$ | $CH_3$ | H |
| F | F | $CH_3$ | $CH_3$ | $OCH_3$ | H |
| F | F | Br | Cl | $CH_3$ | H |
| F | F | Br | $CH_3$ | Cl | H |
| F | F | Cl | $CH_3$ | Br | H |
| F | F | $CH_3$ | $CH_3$ | Cl | H |
| F | F | $C_2H_5$ | $CH_3$ | $CH_3$ | H |
| F | F | $C_2H_5$ | $C_2H_5$ | $CH_3$ | H |
| F | F | $C_2H_5$ | $CH_3$ | $C_2H_5$ | H |
| F | F | $C_2H_5$ | $C_2H_5$ | $C_2H_5$ | H |
| F | F | $C_2H_5$ | $CH_3$ | Cl | H |
| F | F | $C_2H_5$ | $C_2H_5$ | Cl | H |
| F | F | $C_2H_5$ | $CH_3$ | Br | H |
| F | F | $C_2H_5$ | $C_2H_5$ | Br | H |
| F | F | $C_2H_5$ | Cl | $CH_3$ | H |
| F | F | $C_2H_5$ | Br | $CH_3$ | H |
| F | F | $C_2H_5$ | Cl | Cl | H |
| F | F | $C_2H_5$ | Br | Br | H |
| F | F | $C_2H_5$ | Cl | Br | H |
| F | F | $C_2H_5$ | Br | Cl | H |
| F | F | $OCH_3$ | $CH_3$ | Cl | H |
| F | F | $OCH_3$ | $C_2H_5$ | Cl | H |
| F | F | $OC_2H_5$ | $CH_3$ | Cl | H |
| F | F | $OC_2H_5$ | $C_2H_5$ | Cl | H |
| F | F | Cl | $OCH_3$ | $CH_3$ | H |
| F | F | Cl | $OC_2H_5$ | $CH_3$ | H |
| F | F | $CH_3$ | $CH_3$ | Cl | H |
| F | F | Cl | H | Cl | Cl |
| F | F | $CH_3$ | H | $CH_3$ | $CH_3$ |
| F | F | $CH_3$ | H | Cl | $CH_3$ |
| F | F | Br | H | Cl | $CH_3$ |
| F | F | Br | H | $CH_3$ | $CH_3$ |
| F | F | Cl | H | Br | $CH_3$ |
| F | F | Cl | H | Cl | $CH_3$ |
| F | F | $CH_3$ | H | Br | $CH_3$ |
| F | F | Cl | H | $CH_3$ | Cl |
| F | F | $CH_3$ | H | H | $CH_3$ |
| F | F | Cl | H | H | $CH_3$ |

TABLE 1-continued (I-1-a)

| A | B | X | W | Y | Z |
|---|---|---|---|---|---|
| F | F | Br | H | H | CH$_3$ |
| F | F | CH$_3$ | H | H | Cl |
| F | F | CH$_3$ | H | H | Br |
| F | F | CH$_3$ | CH$_3$ | CH$_3$ | CH$_3$ |
| F | F | CH$_3$ | CH$_3$ | CH$_3$ | F |
| F | F | CH$_3$ | CH$_3$ | CH$_3$ | Cl |
| F | F | CH$_3$ | CH$_3$ | CH$_3$ | Br |
| F | F | CH$_3$ | CH$_3$ | H | Cl |
| F | F | CH$_3$ | CH$_3$ | H | Br |
| F | F | Cl | Cl | H | Br |
| F | F | CH$_3$ | CH$_3$ | 4-Cl—C$_6$H$_4$ | H |
| F | F | C$_2$H$_5$ | CH$_3$ | 4-Cl—C$_6$H$_4$ | H |
| F | F | C$_2$H$_5$ | C$_2$H$_5$ | 4-Cl—C$_6$H$_4$ | H |
| F | F | Cl | CH$_3$ | 4-Cl—C$_6$H$_4$ | H |
| F | F | Cl | C$_2$H$_5$ | 4-Cl—C$_6$H$_4$ | H |
| F | F | CH$_3$ | H | H | 4-Cl—C$_6$H$_4$ |
| F | F | CH$_3$ | H | H | 4-Cl—C$_6$H$_4$ |
| F | F | CH$_3$ | H | CH$_3$ | 4-Cl—C$_6$H$_4$ |
| F | F | CH$_3$ | CH$_3$ | CH$_3$ | 4-Cl—C$_6$H$_4$ |
| F | F | Cl | H | H | 4-Cl—C$_6$H$_4$ |
| F | F | I | H | H | H |
| F | F | I | CH$_3$ | H | H |
| F | F | I | C$_2$H$_5$ | H | H |
| F | F | CH$_3$ | H | H | I |
| F | F | CH$_3$ | H | CH$_3$ | I |
| F | F | I | CH$_3$ | CH$_3$ | H |
| F | F | I | C$_2$H$_5$ | CH$_3$ | H |
| F | F | I | CH$_3$ | Cl | H |
| F | F | I | C$_2$H$_5$ | Cl | H |
| F | F | I | Cl | CH$_3$ | H |
| F | F | I | H | CH$_3$ | CH$_3$ |
| F | F | CH$_3$ | H | I | H |
| F | F | C$_2$H$_5$ | H | I | H |
| F | F | CH$_3$ | CH$_3$ | I | H |
| F | F | C$_2$H$_5$ | CH$_3$ | I | H |
| F | F | C$_2$H$_5$ | C$_2$H$_5$ | I | H |
| F | F | Cl | CH$_3$ | I | H |
| F | F | Cl | C$_2$H$_5$ | I | H |
| F | F | CH$_3$ | H | I | CH$_3$ |
| F | F | CH$_3$ | CH$_3$ | H | I |
| F | F | I | H | H | CH$_3$ |
| F | F | C$_2$H$_5$ | H | H | H |
| F | F | cyclopropyl | H | H | H |
| F | F | cyclopropyl | CH$_3$ | H | H |
| F | F | cyclopropyl | H | CH$_3$ | H |
| F | F | cyclopropyl | C$_2$H$_5$ | H | H |
| F | F | cyclopropyl | CH$_3$ | CH$_3$ | H |
| F | F | cyclopropyl | C$_2$H$_5$ | CH$_3$ | H |
| F | F | cyclopropyl | CH$_3$ | Cl | H |
| F | F | cyclopropyl | C$_2$H$_5$ | Cl | H |
| F | F | cyclopropyl | Cl | CH$_3$ | H |
| F | F | CH$_3$ | H | cyclopropyl | H |
| F | F | C$_2$H$_5$ | H | cyclopropyl | H |
| F | F | CH$_3$ | CH$_3$ | cyclopropyl | H |
| F | F | C$_2$H$_5$ | CH$_3$ | cyclopropyl | H |
| F | F | C$_2$H$_5$ | C$_2$H$_5$ | cyclopropyl | H |
| F | F | Cl | CH$_3$ | cyclopropyl | H |
| F | F | Cl | C$_2$H$_5$ | cyclopropyl | H |

Furthermore, in addition to the compounds mentioned in the Examples, the following compounds of the formula (I-1-a) may be mentioned:

TABLE 2

(I-1-a)

| A | B | W | X | Y | V$^1$ | V$^2$ | V$^3$ |
|---|---|---|---|---|---|---|---|
| F | F | H | Cl | H | 2-F | H | H |
| F | F | H | Cl | H | 3-F | H | H |
| F | F | H | Cl | H | 4-F | H | H |
| F | F | H | Cl | H | 2-F | 4-F | H |
| F | F | H | Cl | H | 2-F | 4-Cl | H |
| F | F | H | Cl | H | 2-F | 4-CH$_3$ | H |
| F | F | H | Cl | H | 2-F | 4-OCH$_3$ | H |
| F | F | H | Cl | H | 3-F | 4-F | H |
| F | F | H | Cl | H | 3-F | 4-Cl | H |
| F | F | H | Cl | H | 3-F | 4-CH$_3$ | H |
| F | F | H | Cl | H | 3-F | 4-OCH$_3$ | H |
| F | F | H | Cl | H | 4-F | 3-Cl | H |
| F | F | H | Cl | H | 4-F | 3-CH$_3$ | H |
| F | F | H | Cl | H | 4-F | 3-OCH$_3$ | H |
| F | F | H | Cl | H | 2-F | 4-F | 5-F |
| F | F | H | Cl | H | 2-F | 4-F | 6-F |
| F | F | H | Cl | H | 2-F | 4-Cl | 5-F |

TABLE 2-continued

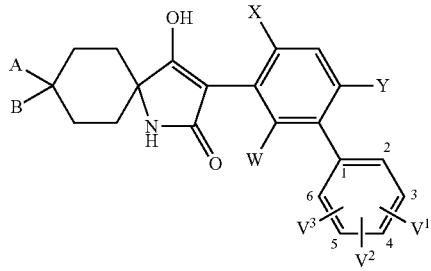

(I-1-a)

| A | B | W | X | Y | V¹ | V² | V³ |
|---|---|---|---|---|---|---|---|
| F | F | H | Cl | H | 2-F | 5-Cl | 4-F |
| F | F | H | Cl | H | 3-F | 4-F | 5-F |
| F | F | H | Cl | H | 3-Cl | 4-Cl | H |
| F | F | H | Cl | H | 4-CF$_3$ | 3-F | H |
| F | F | H | Cl | H | 4-CN | H | H |
| F | F | H | Cl | H | 3-CF$_3$ | 4-F | H |
| F | F | H | CH$_3$ | H | 2-F | H | H |
| F | F | H | CH$_3$ | H | 3-F | H | H |
| F | F | H | CH$_3$ | H | 4-F | H | H |
| F | F | H | CH$_3$ | H | 2-F | 4-F | H |
| F | F | H | CH$_3$ | H | 2-F | 4-Cl | H |
| F | F | H | CH$_3$ | H | 2-F | 4-CH$_3$ | H |
| F | F | H | CH$_3$ | H | 2-F | 4-OCH$_3$ | H |
| F | F | H | CH$_3$ | H | 3-F | 4-F | H |
| F | F | H | CH$_3$ | H | 3-F | 4-Cl | H |
| F | F | H | CH$_3$ | H | 3-F | 4-CH$_3$ | H |
| F | F | H | CH$_3$ | H | 3-F | 4-OCH$_3$ | H |
| F | F | H | CH$_3$ | H | 4-F | 3-Cl | H |
| F | F | H | CH$_3$ | H | 4-F | 3-CH$_3$ | H |
| F | F | H | CH$_3$ | H | 4-F | 3-OCH$_3$ | H |
| F | F | H | CH$_3$ | H | 2-F | 4-F | 5-F |
| F | F | H | CH$_3$ | H | 2-F | 4-F | 6-F |
| F | F | H | CH$_3$ | H | 2-F | 4-Cl | 5-F |
| F | F | H | CH$_3$ | H | 2-F | 5-Cl | 4-F |
| F | F | H | CH$_3$ | H | 3-F | 4-F | 5-F |
| F | F | H | CH$_3$ | H | 3-Cl | 4-Cl | H |
| F | F | H | CH$_3$ | H | 4-CF$_3$ | 3-F | H |
| F | F | H | CH$_3$ | H | 4-CN | H | H |
| F | F | H | CH$_3$ | H | 3-CF$_3$ | 4-F | H |
| F | F | CH$_3$ | CH$_3$ | H | 2-F | H | H |
| F | F | CH$_3$ | CH$_3$ | H | 3-F | H | H |
| F | F | CH$_3$ | CH$_3$ | H | 4-F | H | H |
| F | F | CH$_3$ | CH$_3$ | H | 2-F | 4-F | H |
| F | F | CH$_3$ | CH$_3$ | H | 2-F | 4-Cl | H |
| F | F | CH$_3$ | CH$_3$ | H | 2-F | 4-CH$_3$ | H |
| F | F | CH$_3$ | CH$_3$ | H | 2-F | 4-OCH$_3$ | H |
| F | F | CH$_3$ | CH$_3$ | H | 3-F | 4-F | H |
| F | F | CH$_3$ | CH$_3$ | H | 3-F | 4-Cl | H |
| F | F | CH$_3$ | CH$_3$ | H | 3-F | 4-CH$_3$ | H |
| F | F | CH$_3$ | CH$_3$ | H | 3-F | 4-OCH$_3$ | H |
| F | F | CH$_3$ | CH$_3$ | H | 4-F | 3-Cl | H |
| F | F | CH$_3$ | CH$_3$ | H | 4-F | 3-CH$_3$ | H |
| F | F | CH$_3$ | CH$_3$ | H | 4-F | 3-OCH$_3$ | H |
| F | F | CH$_3$ | CH$_3$ | H | 2-F | 4-F | 5-F |
| F | F | CH$_3$ | CH$_3$ | H | 2-F | 4-F | 6-F |
| F | F | CH$_3$ | CH$_3$ | H | 2-F | 4-Cl | 5-F |
| F | F | CH$_3$ | CH$_3$ | H | 2-F | 5-Cl | 4-F |
| F | F | CH$_3$ | CH$_3$ | H | 3-F | 4-F | 5-F |
| F | F | CH$_3$ | CH$_3$ | H | 3-CF$_3$ | 4-F | H |
| F | F | CH$_3$ | CH$_3$ | H | 3-Cl | 4-Cl | H |
| F | F | CH$_3$ | CH$_3$ | H | 4-CF$_3$ | 3-F | H |
| F | F | CH$_3$ | CH$_3$ | H | 4-CN | H | H |
| F | F | H | CH$_3$ | CH$_3$ | 2-F | H | H |
| F | F | H | CH$_3$ | CH$_3$ | 3-F | H | H |
| F | F | H | CH$_3$ | CH$_3$ | 4-F | H | H |
| F | F | H | CH$_3$ | CH$_3$ | 2-F | 4-F | H |
| F | F | H | CH$_3$ | CH$_3$ | 2-F | 4-Cl | H |
| F | F | H | CH$_3$ | CH$_3$ | 2-F | 4-CH$_3$ | H |
| F | F | H | CH$_3$ | CH$_3$ | 2-F | 4-OCH$_3$ | H |
| F | F | H | CH$_3$ | CH$_3$ | 3-F | 4-F | H |
| F | F | H | CH$_3$ | CH$_3$ | 3-F | 4-Cl | H |
| F | F | H | CH$_3$ | CH$_3$ | 3-F | 4-CH$_3$ | H |
| F | F | H | CH$_3$ | CH$_3$ | 3-F | 4-OCH$_3$ | H |

TABLE 2-continued

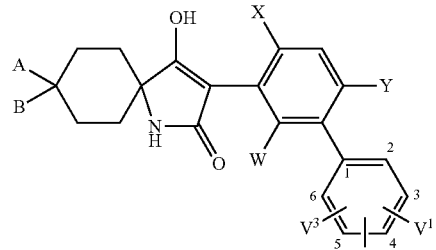

(I-1-a)

| A | B | W | X | Y | V¹ | V² | V³ |
|---|---|---|---|---|---|---|---|
| F | F | H | CH$_3$ | CH$_3$ | 4-F | 3-Cl | H |
| F | F | H | CH$_3$ | CH$_3$ | 4-F | 3-CH$_3$ | H |
| F | F | H | CH$_3$ | CH$_3$ | 4-F | 3-OCH$_3$ | H |
| F | F | H | CH$_3$ | CH$_3$ | 2-F | 4-F | 5-F |
| F | F | H | CH$_3$ | CH$_3$ | 2-F | 4-F | 6-F |
| F | F | H | CH$_3$ | CH$_3$ | 2-F | 4-Cl | 5-F |
| F | F | H | CH$_3$ | CH$_3$ | 2-F | 5-Cl | 4-F |
| F | F | H | CH$_3$ | CH$_3$ | 3-F | 4-F | 5-F |
| F | F | CH$_3$ | CH$_3$ | H | 3-Cl | 4-Cl | H |
| F | F | CH$_3$ | CH$_3$ | H | 4-CF$_3$ | 3-F | H |
| F | F | CH$_3$ | CH$_3$ | H | 4-CN | H | H |
| F | F | CH$_3$ | CH$_3$ | H | 3-CF$_3$ | 4-F | H |
| F | F | CH$_3$ | CH$_3$ | CH$_3$ | 2-F | H | H |
| F | F | CH$_3$ | CH$_3$ | CH$_3$ | 3-F | H | H |
| F | F | CH$_3$ | CH$_3$ | CH$_3$ | 4-F | H | H |
| F | F | CH$_3$ | CH$_3$ | CH$_3$ | 2-F | 4-F | H |
| F | F | CH$_3$ | CH$_3$ | CH$_3$ | 2-F | 4-Cl | H |
| F | F | CH$_3$ | CH$_3$ | CH$_3$ | 2-F | 4-CH$_3$ | H |
| F | F | CH$_3$ | CH$_3$ | CH$_3$ | 2-F | 4-OCH$_3$ | H |
| F | F | CH$_3$ | CH$_3$ | CH$_3$ | 3-F | 4-F | H |
| F | F | CH$_3$ | CH$_3$ | CH$_3$ | 3-F | 4-Cl | H |
| F | F | CH$_3$ | CH$_3$ | CH$_3$ | 3-F | 4-CH$_3$ | H |
| F | F | CH$_3$ | CH$_3$ | CH$_3$ | 3-F | 4-OCH$_3$ | H |
| F | F | CH$_3$ | CH$_3$ | CH$_3$ | 4-F | 3-Cl | H |
| F | F | CH$_3$ | CH$_3$ | CH$_3$ | 4-F | 3-CH$_3$ | H |
| F | F | CH$_3$ | CH$_3$ | CH$_3$ | 4-F | 3-OCH$_3$ | H |
| F | F | CH$_3$ | CH$_3$ | CH$_3$ | 2-F | 4-F | 5-F |
| F | F | CH$_3$ | CH$_3$ | CH$_3$ | 2-F | 4-F | 6-F |
| F | F | CH$_3$ | CH$_3$ | CH$_3$ | 2-F | 4-Cl | 5-F |
| F | F | CH$_3$ | CH$_3$ | CH$_3$ | 2-F | 5-Cl | 4-F |
| F | F | CH$_3$ | CH$_3$ | CH$_3$ | 3-F | 4-F | 5-F |
| F | F | CH$_3$ | CH$_3$ | H | 3-Cl | 4-Cl | H |
| F | F | CH$_3$ | CH$_3$ | H | 4-CF$_3$ | 3-F | H |
| F | F | CH$_3$ | CH$_3$ | H | 4-CN | H | H |
| F | F | CH$_3$ | CH$_3$ | H | 3-CF$_3$ | 4-F | H |

Table 3 X, W, Y and Z are as indicated in Tables 1 and 2

A=F; B=bond

In addition to the compounds mentioned in the Preparation Examples, the following compounds of the formula (I-2-a) may be specifically mentioned:

TABLE 4

(I-2-a)

| A | B | X | W | Y | Z |
|---|---|---|---|---|---|
| F | F | CH$_3$ | H | H | H |
| F | F | Br | H | H | H |
| F | F | Cl | H | H | H |
| F | F | CF$_3$ | H | H | H |

TABLE 4-continued

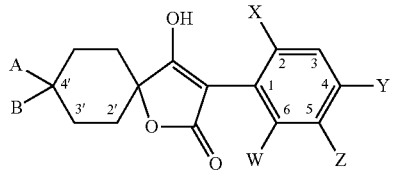

(I-2-a)

| A | B | X | W | Y | Z |
|---|---|---|---|---|---|
| F | F | OCH$_3$ | H | H | H |
| F | F | Br | H | Cl | H |
| F | F | Cl | H | Br | H |
| F | F | Cl | H | Cl | H |
| F | F | Cl | H | CH$_3$ | H |
| F | F | CH$_3$ | H | Cl | H |
| F | F | Cl | Cl | H | H |
| F | F | Cl | OCH$_3$ | H | H |
| F | F | Cl | CH$_3$ | H | H |
| F | F | Cl | OC$_2$H$_5$ | H | H |
| F | F | OCH$_3$ | OCH$_3$ | H | H |
| F | F | CH$_3$ | CH$_3$ | H | H |
| F | F | C$_2$H$_5$ | CH$_3$ | H | H |
| F | F | C$_2$H$_5$ | C$_2$H$_5$ | H | H |
| F | F | Br | CH$_3$ | Br | H |
| F | F | Cl | CH$_3$ | Cl | H |
| F | F | CH$_3$ | Br | CH$_3$ | H |
| F | F | CH$_3$ | Cl | CH$_3$ | H |
| F | F | OCH$_3$ | CH$_3$ | CH$_3$ | H |
| F | F | OC$_2$H$_5$ | CH$_3$ | CH$_3$ | H |
| F | F | OC$_3$H$_7$ | CH$_3$ | CH$_3$ | H |
| F | F | CH$_3$ | CH$_3$ | CH$_3$ | H |
| F | F | Br | Br | CH$_3$ | H |
| F | F | Cl | Cl | CH$_3$ | H |
| F | F | CH$_3$ | CH$_3$ | Br | H |
| F | F | OCH$_3$ | C$_2$H$_5$ | CH$_3$ | H |
| F | F | OC$_2$H$_5$ | C$_2$H$_5$ | CH$_3$ | H |
| F | F | CH$_3$ | CH$_3$ | OCH$_3$ | H |
| F | F | Br | Cl | CH$_3$ | H |
| F | F | Br | CH$_3$ | Cl | H |
| F | F | Cl | CH$_3$ | Br | H |
| F | F | CH$_3$ | CH$_3$ | Cl | H |
| F | F | C$_2$H$_5$ | CH$_3$ | CH$_3$ | H |
| F | F | C$_2$H$_5$ | C$_2$H$_5$ | CH$_3$ | H |
| F | F | C$_2$H$_5$ | CH$_3$ | C$_2$H$_5$ | H |
| F | F | C$_2$H$_5$ | C$_2$H$_5$ | C$_2$H$_5$ | H |
| F | F | C$_2$H$_5$ | CH$_3$ | Cl | H |
| F | F | C$_2$H$_5$ | C$_2$H$_5$ | Cl | H |
| F | F | C$_2$H$_5$ | CH$_3$ | Br | H |
| F | F | C$_2$H$_5$ | C$_2$H$_5$ | Br | H |
| F | F | C$_2$H$_5$ | Cl | CH$_3$ | H |
| F | F | C$_2$H$_5$ | Br | CH$_3$ | H |
| F | F | C$_2$H$_5$ | Cl | Cl | H |
| F | F | C$_2$H$_5$ | Br | Br | H |
| F | F | C$_2$H$_5$ | Cl | Br | H |
| F | F | C$_2$H$_5$ | Br | Cl | H |
| F | F | OCH$_3$ | CH$_3$ | Cl | H |
| F | F | OCH$_3$ | C$_2$H$_5$ | Cl | H |
| F | F | OC$_2$H$_5$ | CH$_3$ | Cl | H |
| F | F | OC$_2$H$_5$ | C$_2$H$_5$ | Cl | H |
| F | F | Cl | OCH$_3$ | CH$_3$ | H |
| F | F | Cl | OC$_2$H$_5$ | CH$_3$ | H |
| F | F | CH$_3$ | CH$_3$ | Cl | H |
| F | F | Cl | H | Cl | Cl |
| F | F | CH$_3$ | H | CH$_3$ | CH$_3$ |
| F | F | Br | H | Cl | CH$_3$ |
| F | F | Br | H | CH$_3$ | CH$_3$ |
| F | F | Cl | H | Br | CH$_3$ |
| F | F | Cl | H | Cl | CH$_3$ |
| F | F | CH$_3$ | H | Br | CH$_3$ |
| F | F | Cl | H | CH$_3$ | Cl |
| F | F | CH$_3$ | H | H | CH$_3$ |
| F | F | CH$_3$ | H | H | CH$_3$ |
| F | F | Br | H | H | CH$_3$ |
| F | F | CH$_3$ | H | H | Cl |
| F | F | CH$_3$ | H | H | Br |
| F | F | CH$_3$ | CH$_3$ | CH$_3$ | CH$_3$ |

TABLE 4-continued

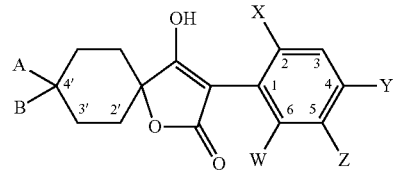

(I-2-a)

| A | B | X | W | Y | Z |
|---|---|---|---|---|---|
| F | F | CH$_3$ | CH$_3$ | CH$_3$ | F |
| F | F | CH$_3$ | CH$_3$ | CH$_3$ | Cl |
| F | F | CH$_3$ | CH$_3$ | CH$_3$ | Br |
| F | F | CH$_3$ | CH$_3$ | H | Cl |
| F | F | CH$_3$ | CH$_3$ | H | Br |
| F | F | Cl | Cl | H | Br |
| F | F | CH$_3$ | CH$_3$ | 4-Cl—C$_6$H$_4$ | H |
| F | F | C$_2$H$_5$ | CH$_3$ | 4-Cl—C$_6$H$_4$ | H |
| F | F | C$_2$H$_5$ | C$_2$H$_5$ | 4-Cl—C$_6$H$_4$ | H |
| F | F | Cl | CH$_3$ | 4-Cl—C$_6$H$_4$ | H |
| F | F | Cl | C$_2$H$_5$ | 4-Cl—C$_6$H$_4$ | H |
| F | F | CH$_3$ | H | H | 4-Cl—C$_6$H$_4$ |
| F | F | CH$_3$ | CH$_3$ | H | 4-Cl—C$_6$H$_4$ |
| F | F | CH$_3$ | H | CH$_3$ | 4-Cl—C$_6$H$_4$ |
| F | F | CH$_3$ | CH$_3$ | CH$_3$ | 4-Cl—C$_6$H$_4$ |
| F | F | Cl | H | H | 4-Cl—C$_6$H$_4$ |
| F | F | I | H | H | H |
| F | F | I | H | CH$_3$ | H |
| F | F | I | CH$_3$ | H | H |
| F | F | I | C$_2$H$_5$ | H | H |
| F | F | CH$_3$ | H | H | I |
| F | F | CH$_3$ | CH$_3$ | H | I |
| F | F | I | CH$_3$ | CH$_3$ | H |
| F | F | I | C$_2$H$_5$ | CH$_3$ | H |
| F | F | I | CH$_3$ | Cl | H |
| F | F | I | C$_2$H$_5$ | Cl | H |
| F | F | I | Cl | CH$_3$ | H |
| F | F | I | H | CH$_3$ | CH$_3$ |
| F | F | CH$_3$ | H | I | H |
| F | F | C$_2$H$_5$ | H | I | H |
| F | F | CH$_3$ | CH$_3$ | I | H |
| F | F | C$_2$H$_5$ | CH$_3$ | I | H |
| F | F | C$_2$H$_5$ | C$_2$H$_5$ | I | H |
| F | F | Cl | CH$_3$ | I | H |
| F | F | Cl | C$_2$H$_5$ | I | H |
| F | F | CH$_3$ | H | I | CH$_3$ |
| F | F | CH$_3$ | CH$_3$ | H | I |
| F | F | I | H | H | CH$_3$ |
| F | F | C$_2$H$_5$ | H | H | H |
| F | F | c-C$_3$H$_5$ | H | H | H |
| F | F | c-C$_3$H$_5$ | CH$_3$ | H | H |
| F | F | c-C$_3$H$_5$ | H | CH$_3$ | H |
| F | F | c-C$_3$H$_5$ | C$_2$H$_5$ | H | H |
| F | F | c-C$_3$H$_5$ | CH$_3$ | CH$_3$ | H |
| F | F | c-C$_3$H$_5$ | C$_2$H$_5$ | CH$_3$ | H |
| F | F | c-C$_3$H$_5$ | CH$_3$ | Cl | H |
| F | F | c-C$_3$H$_5$ | C$_2$H$_5$ | Cl | H |

TABLE 4-continued

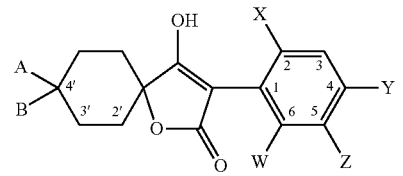

(I-2-a)

| A | B | X | W | Y | Z |
|---|---|---|---|---|---|
| F | F | △ | Cl | $CH_3$ | H |
| F | F | $CH_3$ | H | △ | H |
| F | F | $C_2H_5$ | H | △ | H |
| F | F | $CH_3$ | $CH_3$ | △ | H |
| F | F | $C_2H_5$ | $CH_3$ | △ | H |
| F | F | $C_2H_5$ | $C_2H_5$ | △ | H |
| F | F | Cl | $CH_3$ | △ | H |
| F | F | Cl | $C_2H_5$ | △ | H |

Furthermore, in addition to the compounds mentioned in the Examples, the following compounds of the formula (I-2-a) may be mentioned:

TABLE 5

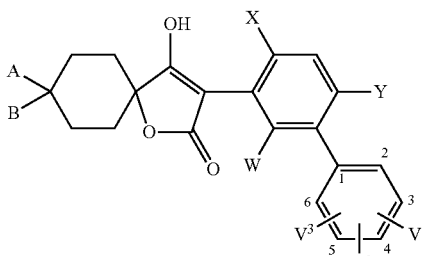

(I-2-a)

| A | B | W | X | Y | $V^1$ | $V^2$ | $V^3$ |
|---|---|---|---|---|---|---|---|
| F | F | H | Cl | H | 2-F | H | H |
| F | F | H | Cl | H | 3-F | H | H |
| F | F | H | Cl | H | 4-F | H | H |
| F | F | H | Cl | H | 2-F | 4-F | H |
| F | F | H | Cl | H | 2-F | 4-Cl | H |
| F | F | H | Cl | H | 2-F | 4-$CH_3$ | H |
| F | F | H | Cl | H | 2-F | 4-$OCH_3$ | H |
| F | F | H | Cl | H | 3-F | 4-F | H |
| F | F | H | Cl | H | 3-F | 4-Cl | H |
| F | F | H | Cl | H | 3-F | 4-$CH_3$ | H |
| F | F | H | Cl | H | 3-F | 4-$OCH_3$ | H |
| F | F | H | Cl | H | 4-F | 3-Cl | H |
| F | F | H | Cl | H | 4-F | 3-$CH_3$ | H |
| F | F | H | Cl | H | 4-F | 3-$OCH_3$ | H |
| F | F | H | Cl | H | 2-F | 4-F | 5-F |
| F | F | H | Cl | H | 2-F | 4-F | 6-F |
| F | F | H | Cl | H | 2-F | 4-Cl | 5-F |

TABLE 5-continued

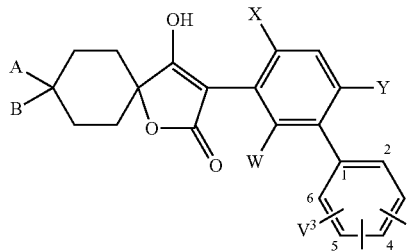

(I-2-a)

| A | B | W | X | Y | $V^1$ | $V^2$ | $V^3$ |
|---|---|---|---|---|---|---|---|
| F | F | H | Cl | H | 2-F | 5-Cl | 4-F |
| F | F | H | Cl | H | 3-F | 4-F | 5-F |
| F | F | H | Cl | H | 3-Cl | 4-Cl | H |
| F | F | H | Cl | H | 4-$CF_3$ | 3-F | H |
| F | F | H | Cl | H | 4-CN | H | H |
| F | F | H | Cl | H | 3-$CF_3$ | 4-F | H |
| F | F | H | $CH_3$ | H | 2-F | H | H |
| F | F | H | $CH_3$ | H | 3-F | H | H |
| F | F | H | $CH_3$ | H | 4-F | H | H |
| F | F | H | $CH_3$ | H | 2-F | 4-F | H |
| F | F | H | $CH_3$ | H | 2-F | 4-Cl | H |
| F | F | H | $CH_3$ | H | 2-F | 4-$CH_3$ | H |
| F | F | H | $CH_3$ | H | 2-F | 4-$OCH_3$ | H |
| F | F | H | $CH_3$ | H | 3-F | 4-F | H |
| F | F | H | $CH_3$ | H | 3-F | 4-Cl | H |
| F | F | H | $CH_3$ | H | 3-F | 4-$CH_3$ | H |
| F | F | H | $CH_3$ | H | 3-F | 4-$OCH_3$ | H |
| F | F | H | $CH_3$ | H | 4-F | 3-Cl | H |
| F | F | H | $CH_3$ | H | 4-F | 3-$CH_3$ | H |
| F | F | H | $CH_3$ | H | 4-F | 3-$OCH_3$ | H |
| F | F | H | $CH_3$ | H | 2-F | 4-F | 5-F |
| F | F | H | $CH_3$ | H | 2-F | 4-F | 6-F |
| F | F | H | $CH_3$ | H | 2-F | 4-Cl | 5-F |
| F | F | H | $CH_3$ | H | 2-F | 5-Cl | 4-F |
| F | F | H | $CH_3$ | H | 3-F | 4-F | 5-F |
| F | F | H | $CH_3$ | H | 3-Cl | 4-Cl | H |
| F | F | H | $CH_3$ | H | 4-$CF_3$ | 3-F | H |
| F | F | H | $CH_3$ | H | 4-CN | H | H |
| F | F | H | $CH_3$ | H | 3-$CF_3$ | 4-F | H |
| F | F | $CH_3$ | $CH_3$ | H | 2-F | H | H |
| F | F | $CH_3$ | $CH_3$ | H | 3-F | H | H |
| F | F | $CH_3$ | $CH_3$ | H | 4-F | H | H |
| F | F | $CH_3$ | $CH_3$ | H | 2-F | 4-F | H |
| F | F | $CH_3$ | $CH_3$ | H | 2-F | 4-Cl | H |
| F | F | $CH_3$ | $CH_3$ | H | 2-F | 4-$CH_3$ | H |
| F | F | $CH_3$ | $CH_3$ | H | 2-F | 4-$OCH_3$ | H |
| F | F | $CH_3$ | $CH_3$ | H | 3-F | 4-F | H |
| F | F | $CH_3$ | $CH_3$ | H | 3-F | 4-Cl | H |
| F | F | $CH_3$ | $CH_3$ | H | 3-F | 4-$CH_3$ | H |
| F | F | $CH_3$ | $CH_3$ | H | 3-F | 4-$OCH_3$ | H |

TABLE 5-continued (I-2-a)

[Structure diagram of compound I-2-a with labels A, B, OH, X, Y, W, O, and positions 1-6 with V¹, V², V³]

| A | B | W | X | Y | V¹ | V² | V³ |
|---|---|---|---|---|----|----|----|
| F | F | H | $CH_3$ | $CH_3$ | 4-F | 3-Cl | H |
| F | F | H | $CH_3$ | $CH_3$ | 4-F | 3-$CH_3$ | H |
| F | F | H | $CH_3$ | $CH_3$ | 4-F | 3-$OCH_3$ | H |
| F | F | H | $CH_3$ | $CH_3$ | 2-F | 4-F | 5-F |
| F | F | H | $CH_3$ | $CH_3$ | 2-F | 4-F | 6-F |
| F | F | H | $CH_3$ | $CH_3$ | 2-F | 4-Cl | 5-F |
| F | F | H | $CH_3$ | $CH_3$ | 2-F | 5-Cl | 4-F |
| F | F | H | $CH_3$ | $CH_3$ | 3-F | 4-F | 5-F |
| F | F | $CH_3$ | $CH_3$ | H | 3-Cl | 4-Cl | H |
| F | F | $CH_3$ | $CH_3$ | H | 4-$CF_3$ | 3-F | H |
| F | F | $CH_3$ | $CH_3$ | H | 4-CN | H | H |
| F | F | $CH_3$ | $CH_3$ | H | 3-$CF_3$ | 4-F | H |
| F | F | $CH_3$ | $CH_3$ | $CH_3$ | 2-F | H | H |
| F | F | $CH_3$ | $CH_3$ | $CH_3$ | 3-F | H | H |
| F | F | $CH_3$ | $CH_3$ | $CH_3$ | 4-F | H | H |
| F | F | $CH_3$ | $CH_3$ | $CH_3$ | 2-F | 4-F | H |
| F | F | $CH_3$ | $CH_3$ | $CH_3$ | 2-F | 4-Cl | H |
| F | F | $CH_3$ | $CH_3$ | $CH_3$ | 2-F | 4-$CH_3$ | H |
| F | F | $CH_3$ | $CH_3$ | $CH_3$ | 2-F | 4-$OCH_3$ | H |
| F | F | $CH_3$ | $CH_3$ | $CH_3$ | 3-F | 4-F | H |
| F | F | $CH_3$ | $CH_3$ | $CH_3$ | 3-F | 4-Cl | H |
| F | F | $CH_3$ | $CH_3$ | $CH_3$ | 3-F | 4-$CH_3$ | H |
| F | F | $CH_3$ | $CH_3$ | $CH_3$ | 3-F | 4-$OCH_3$ | H |
| F | F | $CH_3$ | $CH_3$ | $CH_3$ | 4-F | 3-Cl | H |
| F | F | $CH_3$ | $CH_3$ | $CH_3$ | 4-F | 3-$CH_3$ | H |
| F | F | $CH_3$ | $CH_3$ | $CH_3$ | 4-F | 3-$OCH_3$ | H |
| F | F | $CH_3$ | $CH_3$ | $CH_3$ | 2-F | 4-F | 5-F |
| F | F | $CH_3$ | $CH_3$ | $CH_3$ | 2-F | 4-F | 6-F |
| F | F | $CH_3$ | $CH_3$ | $CH_3$ | 2-F | 4-Cl | 5-F |
| F | F | $CH_3$ | $CH_3$ | $CH_3$ | 2-F | 5-Cl | 4-F |
| F | F | $CH_3$ | $CH_3$ | $CH_3$ | 3-F | 4-F | 5-F |
| F | F | $CH_3$ | $CH_3$ | H | 3-Cl | 4-Cl | H |
| F | F | $CH_3$ | $CH_3$ | H | 4-$CF_3$ | 3-F | H |
| F | F | $CH_3$ | $CH_3$ | H | 4-CN | H | H |
| F | F | $CH_3$ | $CH_3$ | H | 3-$CF_3$ | 4-F | H |

Table 6 X, W, Y and Z are as indicated in Tables 4 and 5 A=F; B=bond

In the literature it has already been described how the action of various active compounds can be boosted by addition of ammonium salts. However, these are salts which act as detergents (for example WO 95/017817) or salts having relatively long-chain alkyl and/or aryl substituents which act in a permeabilizing manner or increase the solubility of the active compound (for example EP-A 0 453 086, EP-A 0 664 081, FR-A 2 600 494, U.S. Pat. No. 4,844,734, U.S. Pat. No. 5,462,912, U.S. Pat. No. 5,538,937, US-A 03/0224939, US-A 05/0009880, US-A 05/0096386). Furthermore, the prior art describes the activity only for certain active compounds and/or certain applications of the corresponding compositions. In yet other cases, these are salts of sulfonic acids where the acids for their part have a paralyzing action on insects (U.S. Pat. No. 2,842,476). A boost to action by ammonium sulfate, for example, is described by way of example for the herbicides glyphosate and phosphinothricin and for phenyl-substituted cyclic ketoenols (U.S. Pat. No. 6,645,914, EP-A2 0 036 106, WO 07/068,427). A corresponding boost to action for insecticides has already been described in WO 07/068,428.

The use of ammonium sulfate as a formulating assistant has also been described for certain active compounds and applications (WO 92/16108), but its purpose therein is to stabilize the formulation, not to boost the action.

It has now been found, also surprisingly, that the action of insecticides and/or acaricides and/or nematicides and/or herbicides and/or fungicides from the class of the halogen-substituted spirocyclic ketoenols of the formula (I) can be boosted significantly through the addition of ammonium salts or phosphonium salts to the application solution or through the incorporation of these salts into a formulation comprising halogen-substituted spirocyclic ketoenols of the formula (I). The present invention therefore provides for the use of ammonium salts or phosphonium salts for boosting the action of crop protection compositions which comprise as their active compound herbicidally and/or insecticidally and/or acaricidally and/or nematicidally and/or fungicidally active halogen-substituted spirocyclic ketoenols of the formula (I). The invention likewise provides compositions which comprise herbicidally and/or acaricidally and/or insecticidally and/or nematicidally and/or fungicidally active halogen-substituted spirocyclic ketoenols of the formula (I) and action-boosting ammonium salts or phosphonium salts, including not only formulated active compounds but also ready-to-use compositions (spray liquors). The invention further provides, finally, for the use of these compositions for controlling insect pests and/or spider mites and/or nematodes and/or unwanted plant growth and/or microorganisms.

The compounds of the formula (I) possess a broad insecticidal and/or acaricidal and/or nematicidal and/or fungicidal and/or herbicidal activity, but individually the activity and/or plant tolerance leaves something to be desired.

The active compounds can be used in the compositions of the invention in a broad concentration range. The concentration of the active compounds in the formulation here is usually 0.1-50% by weight.

Formula (III') provides a definition of ammonium salts and phosphonium salts which, according to the invention, boost the activity of crop protection compositions comprising fatty acid biosynthesis inhibitors

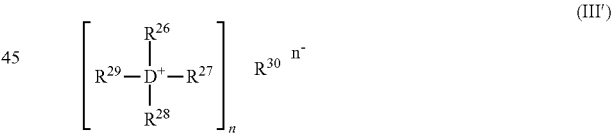

in which
D represents nitrogen or phosphorus,
D preferably represents nitrogen,
$R^{26}$, $R^{27}$, $R^{28}$ and $R^{29}$ independently of one another represent hydrogen or in each case optionally substituted $C_1$-$C_8$-alkyl or mono- or polyunsaturated, optionally substituted $C_1$-$C_8$-alkylene, where the substituents may be selected from the group consisting of halogen, nitro and cyano,
$R^{26}$, $R^{27}$, $R^{28}$ and $R^{29}$ independently of one another preferably represent hydrogen or in each case optionally substituted $C_1$-$C_4$-alkyl, where the substituents may be selected from the group consisting of halogen, nitro and cyano,
$R^{26}$, $R^{27}$, $R^{28}$ and $R^{29}$ independently of one another particularly preferably represent hydrogen, methyl, ethyl, n-propyl, isopropyl, n-butyl, isobutyl, s-butyl or t-butyl,
$R^{26}$, $R^{27}$, $R^{28}$ and $R^{29}$ very particularly preferably represent hydrogen,
n represents 1, 2, 3 or 4, n preferably represents 1 or 2,
$R^{30}$ represents an inorganic or organic anion,
$R^{30}$ preferably represents bicarbonate, tetraborate, fluoride, bromide, iodide, chloride, monohydrogenphosphate, dihydrogenphosphate, bisulfate, tartrate, sulfate, nitrate, thiosulfate, thiocyanate, formate, lactate, acetate, propionate, butyrate, pentanoate or oxalate,
$R^{30}$ particularly preferably represents lactate, sulfate, nitrate, thiosulfate, thiocyanate, oxalate or formate.
$R^{30}$ very particularly preferably represents sulfate.

The ammonium salts and phosphonium salts of the formula (III') can be used in a broad concentration range to boost the activity of crop protection compositions comprising ketoenols. In general, the ammonium salts or phosphonium salts are used in the ready-to-use crop protection composition in a concentration of from 0.5 to 80 mmol/l, preferably 0.75 to 37.5 mmol/l, particularly preferably 1.5 to 25 mmol/l. In the case of a formulated product, the concentration of ammonium salt and/or phosphonium salt in the formulation is selected such that it is within these stated general, preferred or particularly preferred ranges following dilution of the formulation to the desired active compound concentration. The concentration of the salt in the formulation here is usually 1-50% by weight.

In one preferred embodiment of the invention, it is not only an ammonium salt and/or phosphonium salt, but additionally a penetrant, that is added to the crop protection compositions to increase the activity. It is considered entirely surprising that even in these cases an even greater boost to activity is observed. Thus, the present invention also provides for the use of a combination of penetrant and ammonium salts and/or phosphonium salts to boost the activity of crop protection compositions which comprise insecticidally and/or acaricidally and/or nematicidally and/or herbicidally and/or fungicidally active halogen-substituted spirocyclic ketoenols of the formula (I) as active compound. The invention likewise provides compositions which comprise herbicidally and/or acaricidally and/or insecticidally and/or nematicidally and/or fungicidally active halogen-substituted spirocyclic ketoenols of the formula (I), penetrants and ammonium and/or phosphonium salts, including not only formulated active compounds but also ready-to-use compositions (spray liquors). The invention further provides, finally, for the use of these compositions for controlling insect pests and/or spider mites and/or nematodes and/or unwanted plant growth and/or microorganisms.

Suitable penetrants in the present context are all those substances which are usually used for improving the penetration of agrochemical active compounds into plants. Penetrants are defined in this context by their ability to penetrate from the aqueous spray liquor and/or from the spray coating into the cuticle of the plant and thereby increase the mobility of active compounds in the cuticle. The method described in the literature (Baur et al., 1997, *Pesticide Science* 51, 131-152) can be used for determining this property.

Suitable penetrants are, for example, alkanol alkoxylates. Penetrants according to the invention are alkanol alkoxylates of the formula (IV')

R—O—(-AO-)$_v$—R'  (IV')

in which
R represents straight-chain or branched alkyl having 4 to 20 carbon atoms
R' represents hydrogen, methyl, ethyl, n-propyl, isopropyl, n-butyl, isobutyl, tert-butyl, n-pentyl or n-hexyl,
AO represents an ethylene oxide radical, a propylene oxide radical, a butylene oxide radical or represents mixtures of ethylene oxide and propylene oxide radicals or butylene oxide radicals and
v represents a number from 2 to 30.

A preferred group of penetrants are alkanol alkoxylates of the formula

R—O—(-EO-)$_n$—R'  (IV'-a)

in which
R has the meaning given above,
R' has the meaning given above,
EO represents —CH$_2$—CH$_2$—O— and
n represents a number from 2 to 20.

A further preferred group of penetrants are alkanol alkoxylates of the formula

R—O—(-EO-)$_p$—(-PO—)$_q$-R'  (IV'-b)

in which
R has the meaning given above,
R' has the meaning given above,
EO represents —CH$_2$—CH$_2$—O—,
PO represents

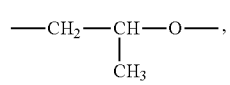
—CH$_2$—CH—O—,
       |
       CH$_3$ p represents a number from 1 to 10 and
q represents a number from 1 to 10.

A further preferred group of penetrants are alkanol alkoxylates of the formula

R—O—(-PO—)$_r$-(EO-)$_s$—R'  (IV'-c)

in which
R has the meaning given above,
R' has the meaning given above,
EO represents —CH$_2$—CH$_2$—O—,
PO represents

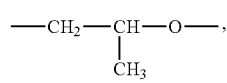
—CH$_2$—CH—O—,
       |
       CH$_3$ r represents a number from 1 to 10 and
s represents a number from 1 to 10.

A further preferred group of penetrants are alkanol alkoxylates of the formula

R—O—(-EO-)$_p$—(-BO—)$_q$-R'  (IV-d)

in which
R and R' have the meanings given above,
EO represents —CH$_2$—CH$_2$—O—,
BO represents

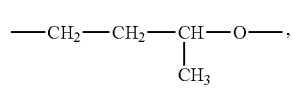
—CH$_2$—CH$_2$—CH—O—,
              |
              CH$_3$ p represents a number from 1 to 10 and
q represents a number from 1 to 10.

A further preferred group of penetrants are alkanol alkoxylates of the formula

R—O—(-BO—)$_r$—(-EO-)$_s$—R'  (IV'-e)

in which
R and R' have the meanings given above,
BO represents

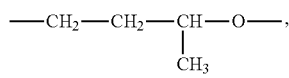

EO represents —CH$_2$—CH$_2$—O—,
r represents a number from 1 to 10 and
s represents a number from 1 to 10.

A further preferred group of penetrants are alkanol alkoxylates of the formula $$CH_3—(CH_2)_t—CH_2—O—(-CH_2—CH_2—O—)_u-R' \qquad (IV'\text{-f})$$

in which
R' has the meaning given above,
t represents a number from 8 to 13
u represents a number from 6 to 17.

In the formulae given above,
R preferably represents butyl, isobutyl, n-pentyl, isopentyl, neopentyl, n-hexyl, isohexyl, n-octyl, isooctyl, 2-ethylhexyl, nonyl, isononyl, decyl, n-dodecyl, isododecyl, lauryl, myristyl, isotridecyl, trimethylnonyl, palmityl, stearyl or eicosyl.

As an example of an alkanol alkoxylate of the formula (IV'-c), mention may be made of 2-ethylhexyl alkoxylate of the formula

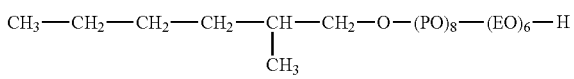

in which
EO represents —CH$_2$—CH$_2$—O—,
PO represents

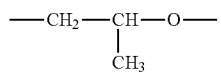

and
the numbers 8 and 6 represent average values.

As an example of an alkanol alkoxylate of the formula (IV'-d), mention may be made of the formula $$CH_3—(CH_2)_{10}—O—(-EO-)_6—(-BO—)_2—CH_3 \qquad (IV'\text{-d-1})$$

in which
EO represents —CH$_2$—CH$_2$—O—,
BO represents

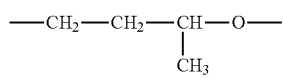

and
the numbers 10, 6 and 2 represent average values.

Particularly preferred alkanol alkoxylates of the formula (IV'-f) are compounds of this formula in which
t represents a number from 9 to 12 and
u represents a number from 7 to 9.

With very particular preference, mention may be made of alkanol alkoxylate of the formula (IV'-f-1)

$$CH_3—(CH_2)_t—CH_2—O—(-CH_2—CH_2—O—)_u\text{-}H \qquad (IV'\text{-f-1})$$

in which
t represents the average value 10.5 and
u represents the average value 8.4.

The above formulae provide general definitions of the alkanol alkoxylates. These substances are mixtures of substances of the stated type with different chain lengths. The indices are therefore average values which may also deviate from whole numbers.

The alkanol alkoxylates of the stated formulae are known, and some of them are commercially available or can be prepared by known methods (cf. WO 98/35 553, WO 00/35 278 and EP-A 0 681 865)

Suitable penetrants also include, for example, substances which promote the availability of the compounds of the formula (I) in the spray coating. These include, for example, mineral and vegetable oils. Suitable oils are all mineral or vegetable oils—modified or otherwise—which can usually be used in agrochemical compositions. By way of example, mention may be made of sunflower oil, rapeseed oil, olive oil, castor oil, colza oil, corn seed oil, cottonseed oil and soybean oil or the esters of said oils. Preference is given to rapeseed oil, sunflower oil and their methyl or ethyl esters.

The concentration of penetrant in the compositions of the invention can be varied within a wide range. In the case of a formulated crop protection composition, it is generally 1 to 95% by weight, preferably 1 to 55% by weight, particularly preferably 15-40% by weight. In the ready-to-use compositions (spray liquors), the concentrations are generally between 0.1 and 10 g/l, preferably between 0.5 and 5 g/l.

Crop protection compositions of the invention may also comprise further components, examples being surfactants and/or dispersing assistants or emulsifiers.

Suitable nonionic surfactants and/or dispersing assistants include all substances of this type that can typically be used in agrochemical compositions. Preferably mention may be made of polyethylene oxide-polypropylene oxide block copolymers, polyethylene glycol ethers of linear alcohols, reaction products of fatty acids with ethylene oxide and/or propylene oxide, and also polyvinyl alcohol, polyvinylpyrrolidone, copolymers of polyvinyl alcohol and polyvinylpyrrolidone, and copolymers of (meth)acrylic acid and (meth)acrylic esters, and additionally alkyl ethoxylates and alkylaryl ethoxylates, which optionally may be phosphated and optionally may be neutralized with bases, mention being made, by way of example, of sorbitol ethoxylates, and, as well, polyoxyalkylenamine derivatives.

Suitable anionic surfactants include all substances of this type that can typically be used in agrochemical compositions. Preference is given to alkali metal salts and alkaline earth metal salts of alkylsulfonic acids or alkylarylsulfonic acids.

A further preferred group of anionic surfactants and/or dispersing assistants are the following salts that are of low solubility in plant oil: salts of polystyrenesulfonic acids, salts of polyvinylsulfonic acids, salts of naphthalenesulfonic acid-formaldehyde condensation products, salts of condensation products of naphthalenesulfonic acid, phenolsulfonic acid and formaldehyde, and salts of lignosulfonic acid.

Suitable additives which may be included in the formulations of the invention are emulsifiers, foam inhibitors, preservatives, antioxidants, colorants and inert filling materials.

Preferred emulsifiers are ethoxylated nonylphenols, reaction products of alkylphenols with ethylene oxide and/or propylene oxide, ethoxylated arylalkylphenols, and also ethoxylated and propoxylated arylalkylphenols, and also sulfated or phosphated arylalkyl ethoxylates and/or arylalkyl ethoxypropoxylates, mention being made by way of example of sorbitan derivatives, such as polyethylene oxide-sorbitan fatty acid esters, and sorbitan fatty acid esters.

Using, in accordance with process (A), for example ethyl N-[(2,4,6-trimethyl)phenylacetyl]-1-amino-4,4'-difluorocyclohexanecarboxylate as starting material, the course of the process according to the invention can be represented by the following reaction scheme:

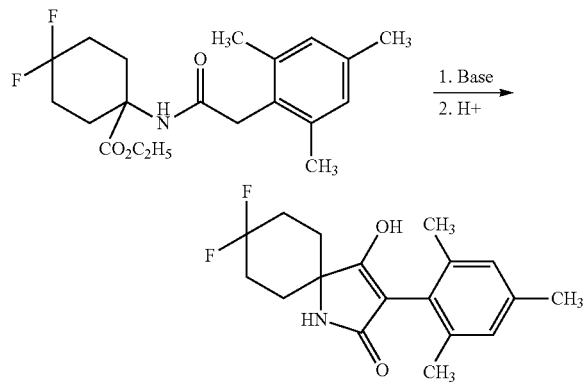

Using, in accordance with process (B), for example ethyl O-(2,6-dimethyl-4-chlorophenylacetyl)-1-hydroxy-4,4'-difluorocyclohexanecarboxylate, the course of the process according to the invention can be represented by the following reaction scheme:

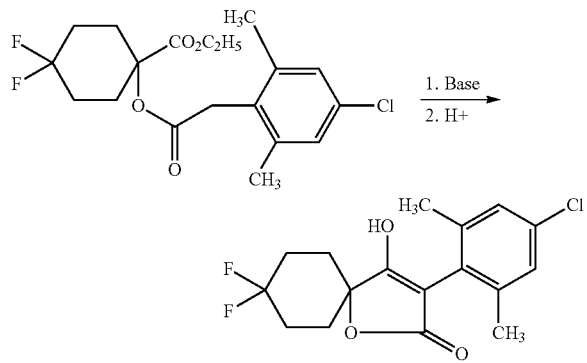

Using, in accordance with process (Cα), for example 8,8'-difluoro-3-[(4-chloro-2,6-dimethyl)phenyl]-1-azaspiro[4,5]decane-2,4-dione and pivaloyl chloride as starting materials, the course of the process according to the invention can be represented by the following reaction scheme:

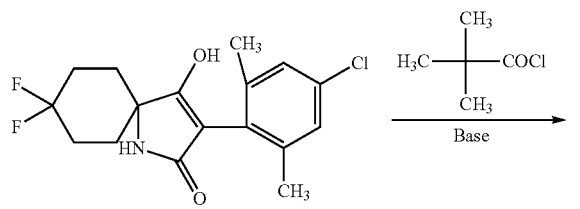

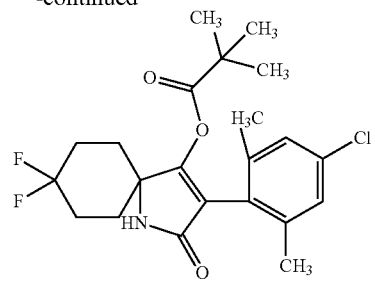

Using, in accordance with process (Cβ), for example 8,8'-difluoro-3-[(2,4-dichloro)phenyl]-1-azaspiro-[4,5]-decane-2,4-dione and acetic anhydride as starting materials, the course of the process according to the invention can be represented by the following reaction scheme:

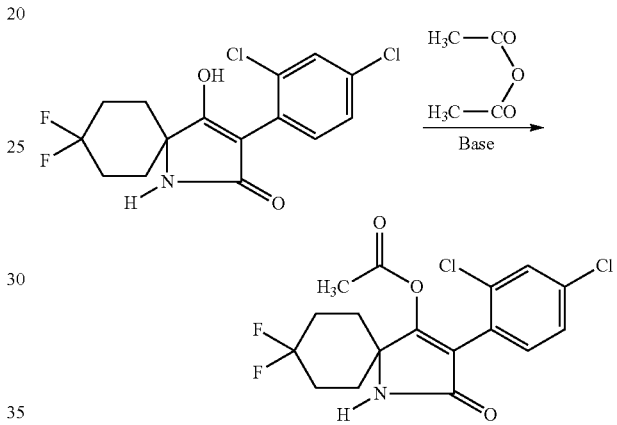

Using, in accordance with process (D), for example 8,8'-difluoro-3-[(2,4-dichloro-6-methyl)phenyl]-1-azaspiro[4,5]decane-2,4-dione and ethyl chloroformate as starting materials, the course of the process according to the invention can be represented by the following reaction scheme:

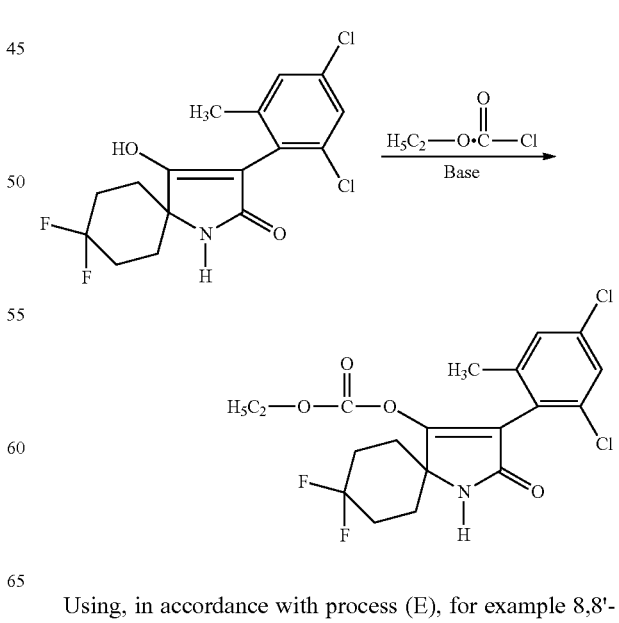

Using, in accordance with process (E), for example 8,8'-difluoro-3-[(2,4,6-trimethyl)phenyl]-1-azaspiro[4,5]decane- 2,4-dione and methyl chloromonothioformate as starting materials, the course of the reaction can be represented as follows:

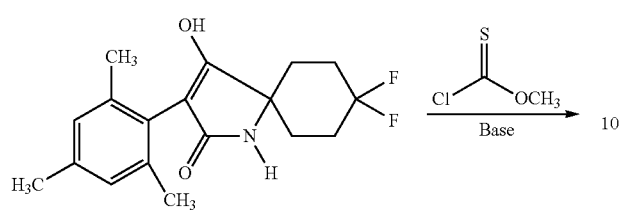

Using, in accordance with process (F), for example 8,8'-difluoro-3-[(2,4,6-trimethyl)phenyl]-1-azaspiro[4,5]decane-2,4-dione and methanesulfonyl chloride as starting materials, the course of the reaction can be represented by the following reaction scheme:

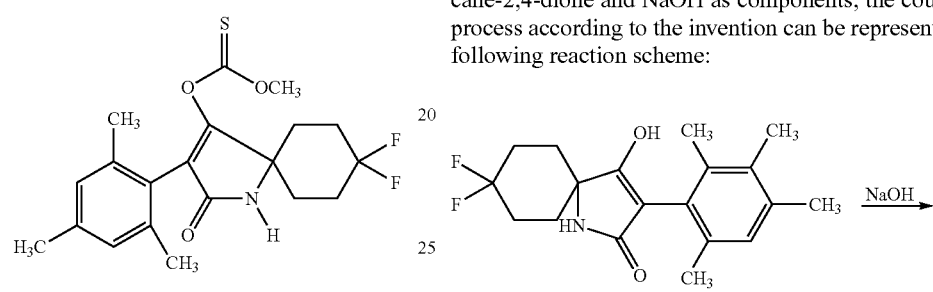

Using, in accordance with process (G), for example 8,8'-difluoro-3-[(2,4-dichloro-6-methyl)phenyl]-1-azaspiro[4,5]decane-2,4-dione and 2,2,2-trifluoroethyl methanethiophosphonyl chloride as starting materials, the course of the reaction can be represented by the following reaction scheme:

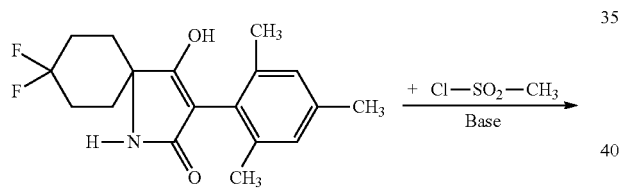

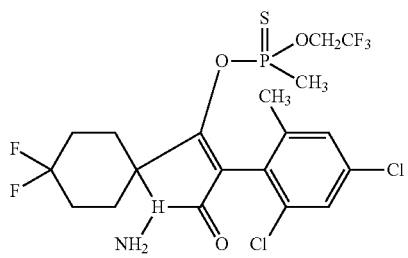

Using, in accordance with process (H), for example 8,8'-difluoro-3-[(2,3,4,6-tetramethylphenyl]-1-azaspiro[4,5]decane-2,4-dione and NaOH as components, the course of the process according to the invention can be represented by the following reaction scheme:

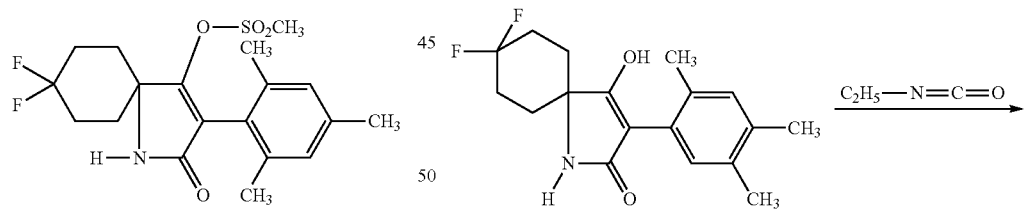

Using, in accordance with process (Iα), for example 8,8'-difluoro-3-[(2,4,5-trimethyl)phenyl]-1-azaspiro[4,5]decane-2,4-dione and ethyl isocyanate as starting materials, the course of the reaction can be represented by the following reaction scheme:

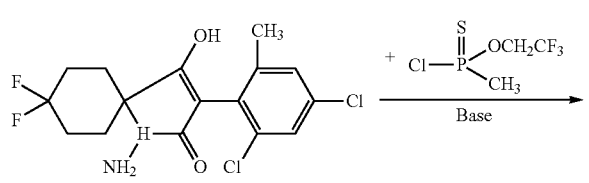

Using, in accordance with process (Iβ), for example 8,8'-difluoro-3-[(2,4,6-trimethyl)phenyl]-1-azaspiro[4,5]decane-2,4-dione and dimethylcarbamoyl chloride as starting materials, the course of the reaction can be represented by the following scheme:

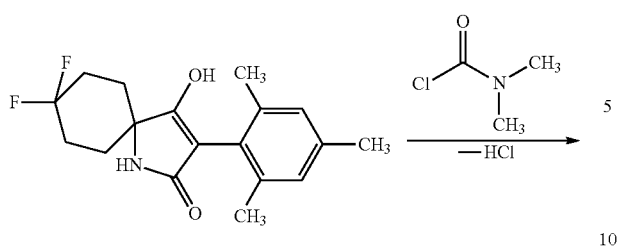
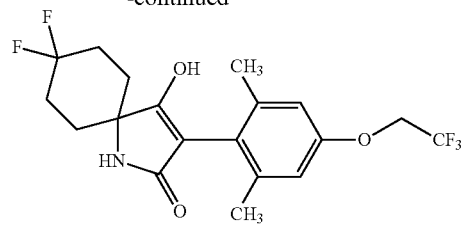

The compounds of the formula (II) which are required as starting materials in process (A) according to the invention

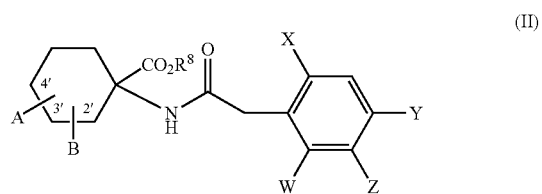

(II)

in which

A, B, W, X, Y, Z and $R^8$ have the meanings given above, are novel.

The acylamino acid esters of the formula (II) are obtained, for example, when amino acid derivatives of the formula (XVI)

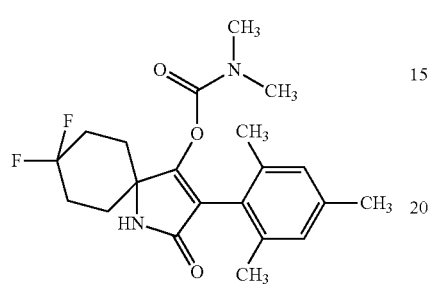

Using, in accordance with process (Jβ), for example 8,8'-difluoro-3-[(4-bromo-2,6-dimethylphenyl)]-1-azaspiro[4,5]decane-2,4-dione and 4-chlorophenylboronic acid as starting materials, the course of the reaction can be represented by the following scheme:

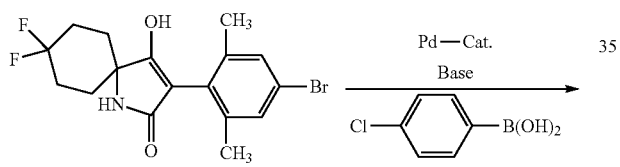
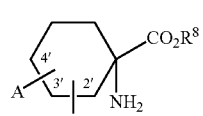

(XVI)

in which

A, B and $R^8$ have the meaning given above, are acylated with substituted phenylacetic acid derivatives of the formula (XVII)

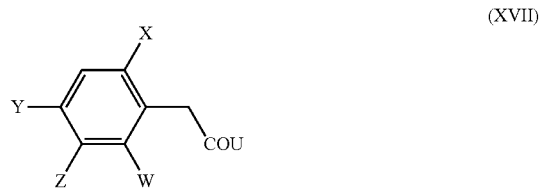

(XVII)

Using, in accordance with process (K), for example 8,8'-difluoro-3-[(4-bromo-2,6-dimethyl)phenyl]-1-azaspiro[4,5]decane-2,4-dione and trifluoroethanol as starting materials, the course of the reaction can be represented by the following scheme:

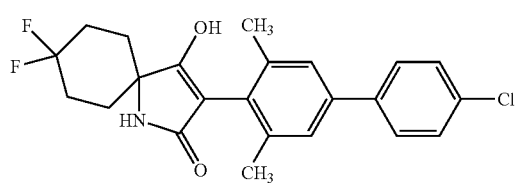

in which

W, X, Y and Z have the meanings given above and

U represents a leaving group introduced by reagents for the activation of carboxylic acids, such as carbonyldiimidazole, carbonyldiimides (such as, for example, dicyclohexylcarbodiimide), phosphorylating agents (such as, for example, POCl₃, BOP-Cl), halogenating agents, such as, for example thionyl chloride, oxalyl chloride, phosgene or chloroformic esters, (Chem. Reviews 52, 237-416 (1953); Bhattacharya, Indian J. Chem. 6, 341-5, 1968)

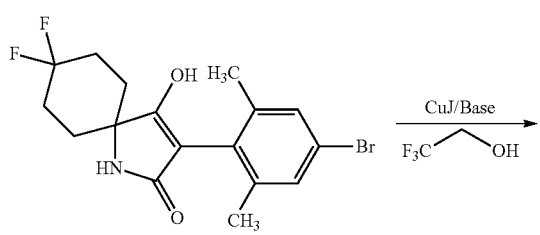

or when acylamino acids of the formula (XVIII)

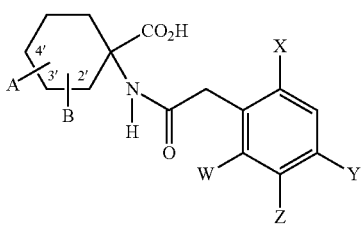
(XVIII)

in which
A, B, W, X, Y and Z have the meanings given above,
are esterified (Chem. Ind. (London) 1568 (1968)).

The compounds of the formula (XVIII)

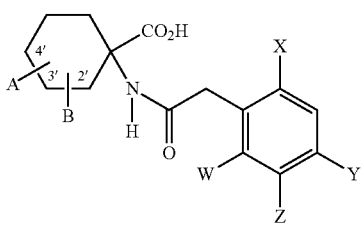
(XVIII)

in which
A, B, W, X, Y and Z have the meanings given above,
are novel.

The compounds of the formula (XVIII) are obtained, for example, when 1-aminocyclohexanecarboxylic acids of the formula (XIX)

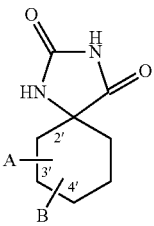
(XIX)

in which
A and B have the meanings given above,
are acylated with substituted phenylacetic acid derivatives of the formula (XVII)

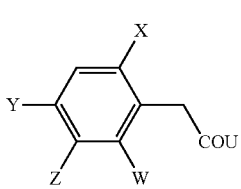
(XVII)

in which
U, W, X, Y and Z have the meanings given above,
for example following the method of Schotten-Baumann (Organikum [Organic Chemistry], VEB Deutscher Verlag der Wissenschaften, Berlin 1977, p. 505).

Some of the compounds of the formula (XVII) are known, and/or they can be prepared by the known processes of the laid-open patents cited at the outset.

The compounds of the formulae (XVI) and (XIX) are novel and can be prepared by known processes (see, for example, Compagnon, Ann. Chim. (Paris) [14] 5, pp. 11-22, 23-27 (1970), L. Munday, J. Chem. Soc. 4372 (1961); J. T. Eward, C. Jitrangeri, Can. J. Chem. 53, 3339 (1975).

The novel 1-aminocyclohexanecarboxylic acids (XIX) are generally obtainable by the Bucherer-Bergs synthesis or by the Strecker synthesis (L. Munday, J. Chem. Soc. 4372 (1961)).

The compounds of the formula (XIX) can be obtained from compounds of the formula (XX)

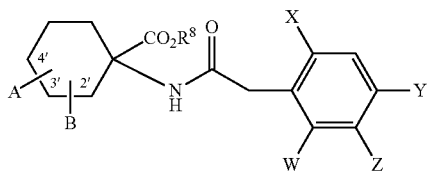
(XX)

in which A and B have the meanings given above.

The compounds of the formula (XX) are novel and can be prepared by methods known from the literature (for example Bucherer-Bergs reaction, see also the examples).

Furthermore, the starting materials, used in the above process (A), of the formula (II)

(II)

in which
A, B, W, X, Y, Z and $R^8$ have the meanings given above,
can be prepared by reacting 1-aminocyclohexanecarbonitriles of the formula (XXI)

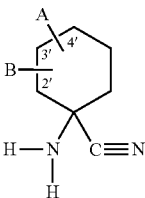
(XXI)

in which
A and B have the meanings given above,
with substituted phenylacetic acid derivatives of the formula (XVII)

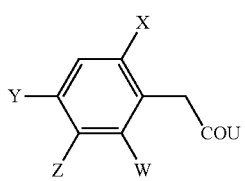
(XVII)

in which
U, W, X, Y and Z have the meanings given above,
to give compounds of the formula (XXII)

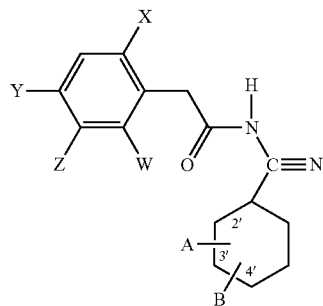

(XXII)

in which
A, B, W, X, Y and Z have the meanings given above,
and subsequently subjecting the latter to acid alcoholysis.

The compounds, required as starting materials in the process (B) according to the invention, of the formula (III)

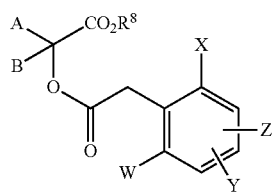

(III)

in which
A, B, W, X, Y, Z and $R^8$ have the meanings given above,
are novel.

They can be prepared by methods known in principle.

Thus, the compounds of the formula (III) are obtained, for example, when
2-hydroxycarboxylic esters of the formula (XXIII)

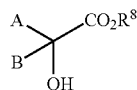

(XXIII)

in which
A, B and $R^8$ have the meanings given above,
are acylated with substituted phenylacetic acid derivatives of the formula (XVII)

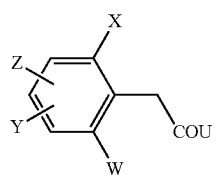

(XVII)

in which
W, X, Y, Z and U have the meanings given above,
(Chem. Reviews 52, 237-416 (1953)).

The compounds of the formulae (XXII) and (XXIII) are likewise novel and can be prepared by known processes described in the literature cited at the outset. The compounds of the formula (XXI) are likewise novel and can be prepared, for example, as described in EP-A-595 130.

The acid halides of the formula (IV), carboxylic anhydrides of the formula (V), chloroformic esters or chloroformic thioesters of the formula (VI), chloromonothioformic esters or chlorodithioformic esters of the formula (VII), sulfonyl chlorides of the formula (VIII), phosphorus compounds of the formula (IX) and metal hydroxides, metal alkoxides or amines of the formulae (X) and (XI) and isocyanates of the formula (XII) and carbamoyl chlorides of the formula (XIII) and boronic acids of the formula (XIV) and haloalcohols (XV) furthermore required as starting materials for carrying out the processes (C), (D), (E), (F), (G), (H), (I) and (J) according to the invention are generally known compounds of organic or inorganic chemistry.

The compounds of the formula (XVII) are furthermore known from the patent applications cited at the outset, and/or they can be prepared by the methods given therein.

The compounds of the formulae (I-1-a' to I-2-g') and (I-1-a" to I-2-g") can be prepared by the processes A to I described.

The process (A) is characterized in that compounds of the formula (II) in which A, B, W, X, Y, Z and $R^8$ have the meanings given above are subjected to an intramolecular condensation in the presence of a diluent and in the presence of a base.

Suitable diluents for the process (A) according to the invention are all organic solvents which are inert toward the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulfoxide, sulfolane, dimethylformamide and N-methylpyrrolidone, and also alcohols, such as methanol, ethanol, propanol, isopropanol, butanol, isobutanol and tert-butanol.

Bases (deprotonating agents) which can be employed when carrying out process (A) according to the invention are all customary proton acceptors. The following can preferably be used: the oxides, hydroxides and carbonates of alkali metals and alkaline earth metals, such as sodium hydroxide, potassium hydroxide, magnesium oxide, calcium oxide, sodium carbonate, potassium carbonate and calcium carbonate, all of which can also be employed in the presence of phase-transfer catalysts such as, for example, triethylbenzylammonium chloride, tetrabutylammonium bromide, Adogen 464 (=methyltrialkyl($C_8$-$C_{10}$)ammonium chloride) or TDA 1 (=tris-(methoxyethoxyethyl)amine). Alkali metals such as sodium or potassium can also be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can be employed.

When carrying out the process (A) according to the invention, the reaction temperature can be varied within a relatively wide range. In general, the process is carried out at temperatures between −75° C. and 200° C., preferably between −50° C. and 150° C. The process (A) according to the invention is generally carried out under atmospheric pressure.

When carrying out the process (A) according to the invention, the reaction component of the formula (II) and the deprotonating base are generally employed in equimolar to approximately double-equimolar amounts. However, it is also possible to employ one or the other component in a larger excess (of up to 3 mol).

The process (B) is characterized in that compounds of the formula (III) in which A, B, W, X, Y, Z and $R^8$ have the meanings given above are subjected to an intramolecular condensation in the presence of a diluent and in the presence of a base.

Diluents which can be employed in process (B) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulfoxide, sulfolane, dimethylformamide and N-methylpyrrolidone. It is also possible to employ alcohols, such as methanol, ethanol, propanol, isopropanol, butanol, isobutanol and tert-butanol.

Bases (deprotonating agents) which can be employed when carrying out process (B) according to the invention are all customary proton acceptors. The following can preferably be used: the oxides, hydroxides and carbonates of alkali metals and alkaline earth metals, such as sodium hydroxide, potassium hydroxide, magnesium oxide, calcium oxide, sodium carbonate, potassium carbonate and calcium carbonate, all of which can also be employed in the presence of phase-transfer catalysts such as, for example, triethylbenzylammonium chloride, tetrabutylammonium bromide, Adogen 464 (=methyltrialkyl($C_8$-$C_{10}$)ammonium chloride) or TDA 1 (=tris-(methoxyethoxyethyl)amine). Alkali metals such as sodium or potassium can also be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can be employed.

When carrying out the process (B) according to the invention, the reaction temperatures can be varied within a relatively wide range. In general, the process is carried out at temperatures between 0° C. and 250° C., preferably between 50° C. and 150° C.

Process (B) according to the invention is generally carried out under atmospheric pressure.

When carrying out process (B) according to the invention, the reactants of the formula (II) and the deprotonating bases are generally employed in approximately equimolar amounts. However, it is also possible to employ one or the other component in a larger excess (of up to 3 mol).

The process ($C_\alpha$) is characterized in that compounds of the formula (I-1-a) or (I-2-a) are in each case reacted with carbonyl halides of the formula (IV), if appropriate in the presence of a diluent and if appropriate in the presence of an acid binder.

Suitable diluents for the process ($C_\alpha$) according to the invention are all solvents which are inert to the acid halides. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethylformamide, dimethyl sulfoxide and sulfolane. If the acid halide is sufficiently stable to hydrolysis, the reaction may also be carried out in the presence of water.

Suitable acid binders when carrying out the reaction in accordance with process ($C_\alpha$) according to the invention are all customary acid acceptors. The following can preferably be used: tertiary amines such as triethylamine, pyridine, diazabicyclooctane (DABCO), diazabicycloundecene (DBU), diazabicyclononene (DBN), Hünig base and N,N-dimethylaniline, furthermore alkaline earth metal oxides such as magnesium oxide and calcium oxide, moreover alkali metal carbonates and alkaline earth metal carbonates such as sodium carbonate, potassium carbonate and calcium carbonate, and alkali metal hydroxides such as sodium hydroxide and potassium hydroxide.

In the process ($C_\alpha$) according to the invention, the reaction temperature can be varied within a relatively wide range. In general, the process is carried out at temperatures between −20° C. and +150° C., preferably between 0° C. and 100° C.

When carrying out the process ($C_\alpha$) according to the invention, the starting materials of the formula (I-1-a) or (I-2-a) and the carbonyl halide of the formula (IV) are generally in each case employed in approximately equivalent amounts. However, it is also possible to employ the carbonyl halide in a relatively large excess (of up to 5 mol). Work-up is carried out by customary methods.

The process ($C_\beta$) is characterized in that compounds of the formula (I-1-a) or (I-2-a) are in each case reacted with carboxylic anhydrides of the formula (V), if appropriate in the presence of a diluent and if appropriate in the presence of an acid binder.

Preferred diluents for the process ($C_\beta$) according to the invention are those diluents which are also preferred when acid halides are used. Besides, a carboxylic anhydride used in excess may also simultaneously act as diluent.

In the process ($C_\beta$), acid binders which are added, if appropriate, are preferably those acid binders which are also preferred when acid halides are used.

In the process ($C_\beta$) according to the invention, the reaction temperature can be varied within a relatively wide range. In general, the process is carried out at temperatures between −20° C. and +150° C., preferably between 0° C. and 100° C.

When carrying out the process ($C_\beta$) according to the invention, the starting materials of the formula (I-1-a) or (I-2-a) and the carboxylic anhydride of the formula (V) are generally in each case employed in approximately equivalent amounts. However, it is also possible to employ the carboxylic anhydride in a relatively large excess (of up to 5 mol). Work-up is carried out by customary methods.

In general, a procedure is followed in which diluent, excess carboxylic anhydride and the carboxylic acid which forms are removed by distillation or by washing with an organic solvent or with water.

Process (D) is characterized in that compounds of the formula (I-1-a) or (I-2-a) are reacted in each case with chloroformic esters or chloroformic thioesters of the formula (VI), if appropriate in the presence of a diluent and if appropriate in the presence of acid binder.

Suitable acid binders for the process (D) according to the invention are all customary acid acceptors. The following can preferably be used: tertiary amines such as triethylamine, pyridine, DABCO, DBU, DBN, Hünig base and N,N-dimethylaniline, furthermore alkaline earth metal oxides such as magnesium oxide and calcium oxide, moreover alkali metal carbonates and alkaline earth metal carbonates such as sodium carbonate, potassium carbonate and calcium carbonate, and alkali metal hydroxides such as sodium hydroxide and potassium hydroxide.

Diluents which can be employed in the process (D) according to the invention are all solvents which are inert to the chloroformic esters or chloroformic thioesters. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, moreover nitriles such as acetonitrile and also strongly polar solvents, such as dimethylformamide, dimethyl sulfoxide and sulfolane.

When carrying out the process (D) according to the invention, the reaction temperature can be varied within a relatively wide range. The reaction temperature is generally between −20° C. and +100° C., preferably between 0° C. and 50° C.

Process (D) according to the invention is generally carried out under atmospheric pressure.

When carrying out process (D) according to the invention, the starting materials of the formulae (I-1-a) or (I-2-a) and the corresponding chloroformic ester or chloroformic thioester of the formula (VI) are generally used in each case in approximately equivalent amounts. However, it is also possible to employ one or the other component in a larger excess (of up to 2 mol). Work-up is carried out by customary methods. In general, a procedure is followed in which the salts which have precipitated are removed and the reaction mixture which remains is concentrated by stripping off the diluent.

The process (E) according to the invention is characterized in that compounds of the formula (I-1-a) or (I-2-a) are in each case reacted with compounds of the formula (VI), in the presence of a diluent and if appropriate in the presence of an acid binder.

In preparation process (E), about 1 mol of chloromonothioformic ester or chlorodithioformic ester of the formula (VII) is reacted at from 0 to 120° C., preferably at from 20 to 60° C., per mole of starting material of the formula (I-1-a) or (I-2-a).

Suitable diluents which are added, if appropriate, are all inert polar organic solvents, such as ethers, amides, sulfones, sulfoxides, but also haloalkanes.

Preference is given to using dimethyl sulfoxide, tetrahydrofuran, dimethylformamide, ethyl acetate or methylene chloride.

If, in a preferred embodiment, the enolate salt of the compounds of the formula (I-1-a) or (I-2-a) is synthesized by addition of strong deprotonating agents such as, for example, sodium hydride or potassium tertiary-butoxide, the further addition of acid binders can be dispensed with.

Suitable bases for the process (E) are all customary proton acceptors. Preference is given to using alkali metal hydrides, alkali metal alkoxides, alkali metal or alkaline earth metal carbonates or bicarbonates or nitrogen bases. Examples which may be mentioned are sodium hydride, sodium methoxide, sodium hydroxide, calcium hydroxide, potassium carbonate, sodium bicarbonate, triethylamine, dibenzylamine, diisopropylamine, pyridine, quinoline, diazabicyclooctane (DABCO), diazabicyclononene (DBN) and diazabicycloundecene (DBU).

The reaction can be carried out under atmospheric pressure or under elevated pressure, preferably under atmospheric pressure. Work-up is carried out by customary methods.

The process (F) according to the invention is characterized in that compounds of the formula (I-1-a) or (I-2-a) are in each case reacted with sulfonyl chlorides of the formula (VIII), if appropriate in the presence of a diluent and if appropriate in the presence of an acid binder.

In preparation process (F), about 1 mol of sulfonyl chloride of the formula (VIII) is reacted per mole of starting material of the formula (I-1-a) or (I-2-a), at from −20 to 150° C., preferably from 0 to 70° C.

The process (F) is preferably carried out in the presence of a diluent.

Suitable diluents are all inert polar organic solvents, such as ethers, amides, ketones, carboxylic esters, nitriles, sulfones, sulfoxides or halogenated hydrocarbons, such as methylene chloride.

Preference is given to using dimethyl sulfoxide, tetrahydrofuran, dimethylformamide, ethyl acetate or methylene chloride.

If, in a preferred embodiment, the enolate salt of the compounds (I-1-a) or (I-2-a) is synthesized by addition of strong deprotonating agents (such as, for example, sodium hydride or potassium tertiary-butoxide), the further addition of acid binders can be dispensed with.

If acid binders are employed, these are customary inorganic or organic bases, for example sodium hydroxide, sodium carbonate, potassium carbonate, pyridine and triethylamine The reaction can be carried out under atmospheric pressure or under elevated pressure, preferably under atmospheric pressure. Work-up is carried out by customary methods.

The process (G) according to the invention is characterized in that compounds of the formula (I-1-a) or (I-2-a) are in each case reacted with phosphorus compounds of the formula (IX), if appropriate in the presence of a diluent and if appropriate in the presence of an acid binder.

In preparation process (G), 1 to 2, preferably 1 to 1.3, mol of the phosphorus compound of the formula (IX) are reacted at temperatures of between −40° C. and 150° C., preferably between −10 and 110° C., per mole of the compounds of the formula (I-1-a) or (I-2-a) in order to obtain compounds of the formula (I-e).

The process (G) is preferably carried out in the presence of a diluent.

Suitable diluents are all inert polar organic solvents, such as ethers, carboxylic esters, halogenated hydrocarbons, ketones, amides, nitriles, sulfones, sulfoxides, etc.

Substances which are preferably employed are acetonitrile, dimethyl sulfoxide, tetrahydrofuran, dimethylformamide, methylene chloride.

Suitable acid binders which are optionally added are customary inorganic or organic bases such as hydroxides, carbonates or amines. Examples include sodium hydroxide, sodium carbonate, potassium carbonate, pyridine and triethylamine.

The reaction can be carried out under atmospheric pressure or under elevated pressure, preferably under atmospheric pressure. Work-up is carried out by customary methods of organic chemistry. The end products are preferably purified by crystallization, chromatographic purification or "incipient distillation", i.e. removal of the volatile components under reduced pressure.

The process (H) is characterized in that compounds of the formula (I-1-a) or (I-2-a) are in each case reacted with metal hydroxides or metal alkoxides of the formula (X) or amines of the formula (XI), if appropriate in the presence of a diluent.

Preferred diluents for the process (H) according to the invention are ethers, such as tetrahydrofuran, dioxane, diethyl ether, or else alcohols, such as methanol, ethanol, isopropanol, but also water. Process (H) according to the invention is generally carried out under atmospheric pressure. The reaction temperature is generally between −20° C. and 100° C., preferably between 0° C. and 50° C.

The process (I) according to the invention is characterized in that compounds of the formula (I-1-a) or (I-2-a) are in each case reacted with (Iα) compounds of the formula (XII), if appropriate in the presence of a diluent and if appropriate in the presence of a catalyst, or (Iβ) with compounds of the formula (XIII), if appropriate in the presence of a diluent and if appropriate in the presence of an acid binder.

In the preparation process (Iα), approximately 1 mol of isocyanate of the formula (XII) is reacted per mole of starting material of the formula (I-1-a) or (I-2-a), at from 0 to 100° C., preferably at from 20 to 50° C.

The process (Iα) is preferably carried out in the presence of a diluent.

Suitable diluents are all inert organic solvents, such as aromatic hydrocarbons, halogenated hydrocarbons, ethers, amides, nitriles, sulfones or sulfoxides.

If appropriate, catalysts may be added to accelerate the reaction. Catalysts which can be employed very advantageously are organotin compounds such as, for example, dibutyltin dilaurate.

The process is preferably carried out under atmospheric pressure.

In preparation process (Iβ), about 1 mol of carbamoyl chloride of the formula (XIII) is reacted per mole of starting material of the formula (I-1-a) or (I-2-a), at from 0 to 150° C., preferably from 20 to 70° C.

Suitable diluents which are added, if appropriate, are all inert polar organic solvents, such as ethers, carboxylic esters, nitriles, ketones, amides, sulfones, sulfoxides or halogenated hydrocarbons.

Preference is given to using dimethyl sulfoxide, tetrahydrofuran, dimethylformamide or methylene chloride.

If, in a preferred embodiment, the enolate salt of the compounds (I-1-a) or (I-2-a) is synthesized by addition of strong deprotonating agents (such as, for example, sodium hydride or potassium tertiary-butoxide), the further addition of acid binders can be dispensed with.

If acid binders are employed, these are customary inorganic or organic bases, for example sodium hydroxide, sodium carbonate, potassium carbonate, triethylamine or pyridine.

The reaction can be carried out under atmospheric pressure or under elevated pressure, preferably under atmospheric pressure. Work-up is carried out by customary methods.

Suitable catalysts for carrying out the process (Jα) and (Jβ) according to the invention are palladium(0) complexes. Preference is given, for example, to tetrakis(triphenylphosphine) palladium. If appropriate, it is also possible to use palladium (II) compounds, for example PdCl$_2$, Pd(OAc)$_2$. When palladium(II) compounds are employed, phosphines such as tricyclohexylphosphine are generally used as complex formers, for example.

Suitable acid acceptors for carrying out the process (Jα) and (Jβ) according to the invention are inorganic or organic bases. These preferably include alkaline earth metal or alkali metal hydroxides, acetates, carbonates or bicarbonates, such as, for example, sodium hydroxide, potassium hydroxide, barium hydroxide or ammonium hydroxide, sodium acetate, potassium acetate, calcium acetate or ammonium acetate, sodium carbonate, potassium carbonate, cesium carbonate or ammonium carbonate, sodium bicarbonate or potassium bicarbonate, alkali metal fluorides, such as, for example, cesium fluoride, alkali metal phosphates, such as, for example, potassium dihydrogen phosphate, potassium phosphate and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Suitable diluents for carrying out the process (Jα) and (Jβ) according to the invention are water, organic solvents and any mixtures thereof. Examples which may be mentioned are: aliphatic, alicyclic or aromatic hydrocarbons, such as, for example, petroleum ether, hexane, heptane, cyclohexane, methylcyclohexane, benzene, toluene, xylene or deicalin; halogenated hydrocarbons, such as, for example, chlorobenzene, dichlorobenzene, methylene chloride, chloroform, carbon tetrachloride, dichloroethane, trichloroethane or tetrachloroethylene; ethers, such as diethyl ether, diisoproypl ether, methyl t-butyl ether, methyl t-amyl ether, dioxane, tetrahydrofuran, 1,2-dimethoxyethane, 1,2-diethoxyethane, diethylene glycol dimethyl ether or anisole; alcohols, such as methanol, ethanol, n- or isopropanol, n-, iso-, sec- or tert-butanol, ethanediol, propane-1,2-diol, ethoxyethanol, methoxyethanol, diethylene glycol monomethyl ether, diethylene glycol monomethyl ether; water.

In the process (Jα) and (Jβ) according to the invention, the reaction temperature can be varied within a relatively wide range. In general, the process is carried out at temperatures between 0° C. and +140° C., preferably between 50° C. and +100° C.

When carrying out the process (Jα) and (Jβ) according to the invention, the boronic acids of the formulae (XIVα) and (XIVβ) in which Y and Z have the meaning given above and compounds of the formulae (I-1') to (I-2') or (I-1") to (I-2") in which A, B, D, G, W, X, Y, Z, Y', Z' have the meaning given above are employed in a molar ratio of from 1:1 to 3:1, preferably from 1:1 to 2:1. In general, from 0.005 to 0.5 mol, preferably from 0.01 mol to 0.1 mol, of catalyst are employed per mole of the compounds of the formulae (I-1') to (I-2') or (I-1") to (I-2"). The base is generally employed in excess. Work-up is carried out by customary methods.

The process (K) is characterized in that compounds of the formulae (I-1") to (I-2") in which A, B, G, W, X and Z have the meanings given above and Y' preferably represents bromine or iodine are reacted with alcohols of the formula YOH in which Y has the meaning given above, in the presence of a base and a Cu(I) salt (for example CuBr or CuI).

Suitable diluents for the process (K) according to the invention are all organic solvents which are inert toward the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as collidine, dimethyl sulfoxide, sulfolane, dimethylformamide, dimethylacetamide and N-methylpyrrolidone, esters such as methyl acetate, ethyl acetate, propyl acetate and also alcohols of the formula WOH, such as methanol, ethanol, propanol, isopropanol, butanol and isobutanol.

Bases (deprotonating agents) which can be employed when carrying out process (K) according to the invention are all customary proton acceptors. Preference is given to using alkali metals such as sodium or potassium. Furthermore, alkali metal and alkaline earth metal amides and hydrides, such as sodium amide, sodium hydride and calcium hydride, and preferably also alkali metal alkoxides, such as sodium methoxide, sodium ethoxide, sodium isopropoxide, sodium tert-butoxide and potassium tert-butoxide can be employed.

When carrying out the process (K) according to the invention, the reaction temperature can be varied within a relatively wide range. In general, the process is carried out at temperatures between 0° C. and 250° C., preferably between 50° C. and 150° C.

Process (K) according to the invention is generally carried out under atmospheric pressure.

When carrying out the process (K) according to the invention, the reaction component of the formula (I-1") to (I-2") is generally reacted with an excess of the alcohols YOH and the bases of up to 20 mol, preferably from 3 to 5 mol. The copper(I) salts are generally employed in catalytic amounts of from 0.001 to 0.5 mol, preferably from 0.01 to 0.2 mol. However, they can also be employed in equimolar amounts.

The active compounds according to the invention, in combination with good plant tolerance and favorable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They can preferably be used as crop protection compositions. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus* spp., *Aceria sheldoni*, *Aculops* spp., *Aculus* spp., *Amblyomma* spp., *Amphitetranychus viennensis*, *Argas* spp., *Boophilus* spp., *Brevipalpus* spp., *Bryobia praetiosa*, *Chorioptes* spp., *Dermanyssus gallinae*, *Eotetranychus* spp., *Epitrimerus pyri*, *Eutetranychus* spp., *Eriophyes* spp., *Halotydeus destructor*, *Hemitarsonemus* spp., *Hyalomma* spp., *Ixodes* spp., *Latrodectus mactans*, *Metatetranychus* spp., *Nuphersa* spp., *Oligonychus* spp., *Ornithodoros* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acalymma vittatum*, *Acanthoscelides obtectus*, *Adoretus* spp., *Agelastica alni*, *Agriotes* spp., *Amphimallon solstitialis*, *Anobium punctatum*, *Anoplophora* spp., *Anthonomus* spp., *Anthrenus* spp., *Apion* spp., *Apogonia* spp., *Atomaria* spp., *Attagenus* spp., *Bruchidius obtectus*, *Bruchus* spp., *Cassida* spp., *Cerotoma trifurcata*, *Ceutorrhynchus* spp., *Chaetocnema* spp., *Cleonus mendicus*, *Conoderus* spp., *Cosmopolites* spp., *Costelytra zealandica*, *Ctenicera* spp., *Curculio* spp., *Cryptorhynchus lapathi*, *Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides*, *Hellula undalis*, *Heteronychus arator*, *Heteronyx* spp., *Hylamorpha elegans*, *Hylotrupes bajulus*, *Hypera postica*, *Hypothenemus* spp., *Lachnosterna consanguinea*, *Lema* spp., *Leptinotarsa decemlineata*, *Leucoptera* spp., *Lissorhoptrus oryzophilus*, *Lixus* spp., *Luperodes* spp., *Lyctus* spp., *Megascelis* spp., *Melanotus* spp., *Meligethes aeneus*, *Melolontha* spp., *Migdolus* spp., *Monochamus* spp., *Naupactus xanthographus*, *Niptus hololeucus*, *Oryctes rhinoceros*, *Oryzaephilus surinamensis*, *Oryzaphagus oryzae*, *Otiorrhynchus* spp., *Oxycetonia jucunda*, *Phaedon cochleariae*, *Phyllophaga* spp., *Phyllotreta* spp., *Popillia japonica*, *Premnotrypes* spp., *Psylliodes* spp., *Ptinus* spp., *Rhizobius ventralis*, *Rhizopertha dominica*, *Sitophilus* spp., *Sphenophorus* spp., *Sternechus* spp., *Symphyletes* spp., *Tanymecus* spp., *Tenebrio molitor*, *Tribolium* spp., *Trogoderma* spp., *Tychius* spp., *Xylotrechus* spp., *Zabrus* spp.

From the order of the Collembola, for example, *Onychiurus armatus*.

From the order of the Diplopoda, for example, *Blaniulus guttulatus*.

From the order of the Diptera, for example, *Aedes* spp., *Agromyza* spp., *Anastrepha* spp., *Anopheles* spp., *Asphondylia* spp., *Bactrocera* spp., *Bibio hortulanus*, *Calliphora erythrocephala*, *Ceratitis capitata*, *Chironomus* spp., *Chrysomyia* spp., *Cochliomyia* spp., *Contarinia* spp., *Cordylobia anthropophaga*, *Culex* spp., *Cuterebra* spp., *Dacus oleae*, *Dasyneura* spp., *Delia* spp., *Dermatobia hominis*, *Drosophila* spp., *Echinocnemus* spp., *Fannia* spp., *Gastrophilus* spp., *Hydrellia* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit*, *Pegomyia* spp., *Phorbia* spp., *Prodiplosis* spp., *Psila rosae*, *Rhagoletis* spp., *Stomoxys* spp., *Tabanus* spp., *Tannia* spp., *Tetanops* spp., *Tipula* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Pomacea* spp., *Succinea* spp.

From the class of the helminths, for example, *Ancylostoma duodenale*, *Ancylostoma ceylanicum*, *Acylostoma braziliensis*, *Ancylostoma* spp., *Ascaris lubricoides*, *Ascaris* spp., *Brugia malayi*, *Brugia timori*, *Bunostomum* spp., *Chabertia* spp., *Clonorchis* spp., *Cooperia* spp., *Dicrocoelium* spp., *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*.

It is furthermore possible to control protozoa, such as *Eimeria*.

From the order of the Heteroptera, for example, *Anasa tristis*, *Antestiopsis* spp., *Blissus* spp., *Calocoris* spp., *Campylomma livida*, *Cavelerius* spp., *Cimex* spp., *Collaria* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Monalonion atratum*, *Nezara* spp., *Oebalus* spp., *Pentomidae*, *Piesma quadrata*, *Piezodorus* spp., *Psallus* spp., *Pseudacysta persea*, *Rhodnius* spp., *Sahlbergella singularis*, *Scaptocoris castanea*, *Scotinophora* spp., *Stephanitis nashi*, *Tibraca* spp., *Triatoma* spp.

From the order of the Homoptera, for example, *Acyrthosipon* spp., *Acrogonia* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*,

*Cicadulina mbila, Coccomytilus halli, Coccus* spp., *Cryptomyzus ribis, Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus, Ferrisia* spp., *Geococcus coffeae, Hieroglyphus* spp., *Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva* spp., *Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes* spp., *Trioza* spp., *Typhlocyba* spp., *Unaspis* spp., *Viteus vitifolii, Zygina* spp.

From the order of the Hymenoptera, for example, *Athalia* spp., *Diprion* spp., *Hoplocampa* spp., *Lasius* spp., *Monomorium pharaonis, Vespa* spp.

From the order of the Isopoda, for example, *Armadillidium vulgare, Oniscus asellus, Porcellio scaber.*

From the order of the Isoptera, for example, *Acromyrmex* spp., *Atta* spp., *Cornitermes cumulans, Microtermes obesi, Odontotermes* spp., *Reticulitermes* spp, From the order of the Lepidoptera, for example, *Acronicta major, Adoxophyes* spp., *Aedia leucomelas, Agrotis* spp., *Alabama* spp., *Amyelois transitella, Anarsia* spp., *Anticarsia* spp., *Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Chematobia brumata, Chilo* spp., *Choristoneura* spp., *Clysia ambiguella, Cnaphalocerus* spp., *Cnephasia* spp., *Conopomorpha* spp., *Conotrachelus* spp., *Copitarsia* spp., *Cydia* spp., *Dalaca noctuides, Diaphania* spp., *Diatraea saccharalis, Earias* spp., *Ecdytolopha aurantium, Elasmopalpus lignosellus, Eldana saccharina, Ephestia kuehniella, Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Heliothis* spp., *Hofinannophila pseudospretella, Homoeosoma* spp., *Homona* spp., *Hyponomeuta padella, Kakivoria flavofasciata, Laphygma* spp., *Laspeyresia molesta, Leucinodes orbonalis, Leucoptera* spp., *Lithocolletis* spp., *Lithophane antennata, Lobesia* spp., *Loxagrotis albicosta, Lymantria* spp., *Lyonetia* spp., *Malacosoma neustria, Maruca testulalis, Mamestra brassicae, Mocis* spp., *Mythimna separata, Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., *Pieris* spp., *Platynota stultana, Plusia* spp., *Plutella xylostella, Prays* spp., *Prodenia* spp., *Protoparce* spp., *Pseudaletia* spp., *Pseudoplusia includens, Pyrausta nubilalis, Rachiplusia nu, Schoenobius* spp., *Scirpophaga* spp., *Scotia segetum, Sesamia* spp., *Sparganothis* spp., *Spodoptera* spp., *Stathmopoda* spp., *Stomopteryx subsecivella, Synanthedon* spp., *Tecia solanivora, Thermesia gemmatalis, Tinea pellionella, Tineola bisselliella, Tortrix* spp., *Trichoplusia* spp., *Tuta absoluta, Virachola* spp.

From the order of the Orthoptera, for example, *Acheta domesticus, Blatta orientalis, Blattella germanica, Dichroplus* spp., *Gryllotalpa* spp., *Leucophaea maderae, Locusta* spp., *Melanoplus* spp., *Periplaneta americana, Schistocerca gregaria.*

From the order of the Siphonaptera, for example, *Ceratophyllus* spp., *Xenopsylla cheopis.*

From the order of the Symphyla, for example, *Scutigerella* spp.

From the order of the Thysanoptera, for example, *Anaphothrips obscurus, Baliothrips biformis, Drepanothris reuteri, Enneothrips flavens, Frankliniella* spp., *Heliothrips* spp., *Hercinothrips femoralis, Rhipiphorothrips cruentatus, Scirtothrips* spp., *Taeniothrips cardamoni, Thrips* spp.

From the order of the Thysanura, for example, *Lepisma saccharina.*

The phytoparasitic nematodes include, for example, *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis, Trichodorus* spp., *Tylenchulus semipenetrans, Xiphinema* spp.

The compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). They can also be used as intermediates or precursors for the synthesis of further active compounds.

The active compounds can be converted into the customary formulations, such as solutions, emulsions, wettable powders, water- and oil-based suspensions, powders, dusts, pastes, soluble powders, soluble granules, granules for broadcasting, suspoemulsion concentrates, natural compounds impregnated with active compound, synthetic substances impregnated with active compound, fertilizers and also microencapsulations in polymeric substances.

These formulations are produced in a known manner, for example by mixing the active compounds with extenders, i.e. liquid solvents, and/or solid carriers, optionally with the use of surfactants, i.e. emulsifiers and/or dispersants, and/or foam formers. The formulations are produced either in suitable production plants or else before or during application.

Suitable for use as auxiliaries are substances which are suitable for imparting to the composition itself and/or to preparations derived therefrom (for example spray liquors, seed dressings) particular properties such as certain technical properties and/or also particular biological properties. Typical auxiliaries include: extenders, solvents and carriers.

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulfones and sulfoxides (such as dimethyl sulfoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulfoxide, and also water.

According to the invention, a carrier is a natural or synthetic, organic or inorganic substance which may be solid or liquid and with which the active compounds are mixed or bonded for better applicability, in particular for application to plants or plant parts. The solid or liquid carrier is generally inert and should be suitable for use in agriculture.

Suitable solid carriers are:
for example ammonium salts and natural rock flours, such as kaolins, clays, talc, chalk, quartz, attapulgite, montmorillonite or diatomaceous earth, and synthetic rock flours, such as finely divided silica, alumina and silicates; useful solid carriers for granules include: for example, crushed and fractionated natural rocks such as calcite, marble, pumice, sepiolite and dolomite, and also synthetic granules of inorganic and organic flours, and granules of organic material such as paper, sawdust, coconut shells, corn cobs and tobacco stalks; useful emulsifiers and/or foam-formers include: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and also protein hydrolysates; suitable dispersants are nonionic and/or ionic substances, for example from the classes of the alcohol-POE and/or -POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulfates, alkyl- or arylsulfonates and alkyl or aryl phosphates or the corresponding PO-ether adducts. Furthermore, suitable oligomers or polymers, for example those derived from vinylic monomers, from acrylic acid, from EO and/or PO alone or in combination with, for example, (poly)alcohols or (poly)amines. It is also possible to use lignin and its sulfonic acid derivatives, unmodified and modified celluloses, aromatic and/or aliphatic sulfonic acids and also their adducts with formaldehyde.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

Other possible additives are perfumes, mineral or vegetable oils which are optionally modified, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability, may also be present.

The formulations generally comprise between 0.01 and 98% by weight of active compound, preferably between 0.5 and 90%.

The active compounds according to the invention may be used as such or in formulations thereof, including in a mixture with one or more suitable fungicides, bactericides, acaricides, nematicides, insecticides, microbicides, fertilizers, attractants, sterilants, synergists, safeners, semiochemicals and/or plant growth regulators, in order thus, for example, to broaden the spectrum of action, to prolong the duration of action, to increase the rate of action, to prevent repulsion or prevent evolution of resistance. Furthermore, active compound combinations of this kind can improve plant growth, increase tolerance to high or low temperatures, to drought or to increased levels of water and/or soil salinity, improve flowering performance, facilitate harvesting and increase yields, accelerate ripening, increase the quality and/or nutritional value of the harvested products, prolong storage life and/or improve the processibility of the harvested products. By combining the active compounds according to the invention with mixing partners, synergistic effects are obtained, i.e. the efficacy of the particular mixture is greater than expected on the basis of the efficacies of the individual components. In general, the combinations can be used either as seed treatments or else in premixes, tankmixes or readymixes.

Any additional active compound can be mixed with the active compounds according to the invention within a wide range, preferably in a ratio of 100:1 to 1:100, more preferably of 5:1 to 1:5.

Particularly favorable mixing partners are, for example, the following:
Insecticides/Acaricides/Nematicides:

The active compounds identified here by their common name are known and are described, for example, in the pesticide handbook ("The Pesticide Manual" 14th Ed., British Crop Protection Council 2006) or can be found on the Internet (e.g. http://www.alanwood.net/pesticides).
(1) Acetylcholinesterase (AChE) inhibitors such as, for example,
carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or
organophosphates, for example acephate, azamethiphos, azinphos-ethyl, azinphos-methyl, cadusafos, chlorethoxyfos, chlorfenvinphos, chlormephos, chloropyrifos, chloropyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl)salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion.
(2) GABA-gated chloride channel antagonists such as, for example,
cyclodiene organochlorines, for example chlordane and endosulfan; or
phenylpyrazoles (fiproles), for example ethiprole and fipronil.

(3) Sodium channel modulators/voltage-dependent sodium channel blockers such as, for example,
pyrethroids, for example acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomers], deltamethrin, empenthrin [(EZ)-(1R) isomers), esfenvalerate, etofenprox, fenpropathrin, fenvalerate, flucythrinate, flumethrin, tau-fluvalinate, halfenprox, imiprothrin, kadethrin, permethrin, phenothrin [(1R)-trans isomer), prallethrin, pyrethrine (pyrethrum), resmethrin, silafluofen, tefluthrin, tetramethrin, tetramethrin [(1R) isomers)], tralomethrin and transfluthrin; or
DDT; or methoxychlor.
(4) Nicotinergic acetylcholine receptor (nAChR) agonists such as, for example,
neonicotinoids, for example acetamiprid, clothianidin, dinotefuran, imidacloprid, nitenpyram, thiacloprid and thiamethoxam; or
nicotine.
(5) Nicotinergic acetylcholine receptor (nAChR) allosteric activators such as, for example,
spinosyns, for example spinetoram and spinosad.
(6) Chloride channel activators such as, for example,
avermectins/milbemycins, for example abamectin, emamectin benzoate, lepimectin and milbemectin.
(7) Juvenile hormone imitators such as, for example,
juvenile hormone analogues, for example hydroprene, kinoprene and methoprene; or
fenoxycarb; or pyriproxyfen.
(8) Active compounds with unknown or nonspecific mechanisms of action such as, for example,
alkyl halides, for example methyl bromide and other alkyl halides; or
chloropicrin; or sulfuryl fluoride; or borax; or tartar emetic.
(9) selective antifeedants, for example pymetrozine; or flonicamid;
(10) Mite growth inhibitors, for example clofentezine, hexythiazox and diflovidazin; or
etoxazole.
(11) Microbial disruptors of the insect gut membrane, for example *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT plant proteins: Cry1Ab, Cry1Ac, Cry1Fa, Cry2Ab, mCry3A, Cry3Ab, Cry3Bb, Cry34/35Ab1.
(12) Oxidative phosphorylation inhibitors, ATP disruptors such as, for example, diafenthiuron; or
organotin compounds, for example azocyclotin, cyhexatin and fenbutatin oxide; or
propargite; or tetradifon.
(13) Oxidative phosphorylation decouplers acting by interrupting the H proton gradient such as, for example, chlorfenapyr, DNOC and sulfluramid.
(14) Nicotinergic acetylcholine receptor antagonists such as, for example, bensultap, cartap hydrochloride, thiocylam, and thiosultap-sodium.
(15) Chitin biosynthesis inhibitors, type 0, such as, for example, bistrifluoron, chlorfluazuron, diflubenzuron, flucycloxuron, flufenoxuron, hexaflumuron, lufenuron, novaluron, noviflumuron, teflubenzuron and triflumuron.
(16) Chitin biosynthesis inhibitors, type 1, such as, for example, buprofezin.
(17) Molting disruptors, dipteran such as, for example, cyromazine.
(18) Ecdysone receptor agonists such as, for example, chromafenozide, halofenozide, methoxyfenozide and tebufenozide.
(19) Octopaminergic agonists such as, for example, amitraz.
(20) Complex-III electron transport inhibitors such as, for example, hydramethylnone; or acequinocyl; or fluacrypyrim.
(21) Complex-I electron transport inhibitors, for example METI acaricides, for example fenazaquin, fenpyroximate, pyrimidifen, pyridaben, tebufenpyrad and tolfenpyrad; or rotenone (Denis).
(22) Voltage-dependent sodium channel blockers, for example indoxacarb; or metaflumizone.
(23) Inhibitors of acetyl-CoA carboxylase such as, for example,
tetronic and tetramic acid derivatives, for example spirodiclofen, spiromesifen and spirotetramat.
(24) Complex-IV electron transport inhibitors such as, for example,
phosphines, for example aluminum phosphide, calcium phosphide, phosphine and zinc phosphide; or
cyanide.
(25) Complex-II electron transport inhibitors such as, for example, cyenopyrafen.
(28) Ryanodine receptor effectors such as, for example,
diamides, for example chlorantraniliprole and flubendiamide.

Further active compounds with unknown mechanism of action, for example amidoflumet, azadirachtin, benclothiaz, benzoximate, bifenazate, bromopropylate, chinomethionat, cryolite, cyantraniliprole (Cyazypyr), cyflumetofen, dicofol, diflovidazin, fluensulfone, flufenerim, flufiprole, fluopyram, fufenozide, imidaclothiz, iprodione, pyridalyl, pyrifluquinazon and iodomethane; and additionally preparations based on *Bacillus* firmus (I-1582, BioNeem, Votivo), and the following known active compounds:

3-bromo-N-{2-bromo-4-chloro-6-[(1-cyclopropylethyl) carbamoyl]phenyl}-1-(3-chloropyridin-2-yl)-1H-pyrazole-5-carboxamide (known from WO2005/077934), 4-{[(6-bromopyrid-3-yl)methyl](2-fluoroethyl)amino}furan-2(5H)-one (known from WO2007/115644), 4-{[(6-fluoropyrid-3-yl)methyl](2,2-difluoroethyl)amino}furan-2(5H)-one (known from WO2007/115644), 4-{[(2-chloro-1,3-thiazol-5-yl)methyl](2-fluoroethyl)amino}furan-2(5H)-one (known from WO2007/115644), 4-{[(6-chloropyrid-3-yl)methyl](2-fluoroethyl)amino}furan-2(5H)-one (known from WO2007/115644), 4-{[(6-chloropyrid-3-yl)methyl](2,2-difluoroethyl)amino}furan-2(5H)-one (known from WO2007/115644), 4-{[(6-chloro-5-fluoropyrid-3-yl)methyl](methyl)amino}furan-2(5H)-one (known from WO2007/115643), 4-{[(5,6-dichloropyrid-3-yl)methyl](2-fluoroethyl) amino}furan-2(5H)-one (known from WO2007/115646), 4-{[(6-chloro-5-fluoropyrid-3-yl)methyl](cyclopropyl) amino}furan-2(5H)-one (known from WO2007/115643), 4-{[(6-chloropyrid-3-yl)methyl](cyclopropyl)amino}furan-2(5H)-one (known from EP-A-0 539 588), 4-{[(6-chloropyrid-3-yl)methyl](methyl)amino}furan-2(5H)-one (known from EP-A-0 539 588), {[1-(6-chloropyridin-3-yl)ethyl](methyl)oxido-$\lambda^4$-sulfanylidene}cyanamide (known from WO2007/149134) and diastereomers thereof {[(1R)-1-(6-chloropyridin-3-yl)ethyl](methyl)oxido-$\lambda^4$-sulfanylidene}cyanamide (A) and {[(1S)-1-(6-chloropyridin-3-yl)ethyl](methyl)oxido-$\lambda^4$-sulfanylidene}cyanamide (B) (likewise known from WO2007/149134) and sulfoxaflor (also known from WO2007/149134) and diastereomers thereof [(R)-methyl(oxido){(1R)-1-[6-(trifluoromethyl)pyridin-3-yl]ethyl}-λ⁴-sulfanylidene]cyanamide (A1) and [(S)-methyl(oxido){(1S)-1-[6-(trifluoromethyl)pyridin-3-yl]ethyl}-λ⁴-sulfanylidene]cyanamide (A2), designated as diastereomer group A (known from WO 2010/074747, WO 2010/074751), [(R)-methyl(oxido){(1S)-1-[6-(trifluoromethyl)pyridin-3-yl]ethyl}-λ⁴-sulfanylidene]cyanamide (B1) and [(S)-methyl(oxido){(1R)-1-[6-(trifluoromethyl)pyridin-3-yl]ethyl}-λ⁴-sulfanylidene]cyanamide (B2), designated as diastereomer group B (likewise known from WO 2010/074747, WO 2010/074751) and 11-(4-chloro-2,6-dimethylphenyl)-12-hydroxy-1,4-dioxa-9-azadispiro[4.2.4.2]tetradec-11-en-10-one (known from WO2006/089633), 3-(4'-fluoro-2,4-dimethylbiphenyl-3-yl)-4-hydroxy-8-oxa-1-azaspiro[4.5]dec-3-en-2-one (known from WO2008/067911), 1-{2-fluoro-4-methyl-5-[(2,2,2-trifluoroethyl)sulfinyl]phenyl}-3-(trifluoromethyl)-1H-1,2,4-triazol-5-amine (known from WO2006/043635), [(3S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H,11H-benzo[f]pyrano[4,3-b]chromen-4-yl]methyl cyclopropanecarboxylate (known from WO2008/066153), 2-cyano-3-(difluoromethoxy)-N,N-dimethylbenzenesulfonamide (known from WO2006/056433), 2-cyano-3-(difluoromethoxy)-N-methylbenzenesulfonamide (known from WO2006/100288), 2-cyano-3-(difluoromethoxy)-N-ethylbenzenesulfonamide (known from WO2005/035486), 4-(difluoromethoxy)-N-ethyl-N-methyl-1,2-benzothiazol-3-amine 1,1-dioxide (known from WO2007/057407), N-[1-(2,3-dimethylphenyl)-2-(3,5-dimethylphenyl)ethyl]-4,5-dihydro-1,3-thiazol-2-amine (known from WO2008/104503), {1'-[(2E)-3-(4-chlorophenyl)prop-2-en-1-yl]-5-fluorospiro[indole-3,4'-piperidin]-1(2H)-yl}(2-chloropyridin-4-yl)methanone (known from WO2003/106457), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-yl ethyl carbonate (known from WO2009/049851), 4-(but-2-yn-1-yloxy)-6-(3,5-dimethylpiperidin-1-yl)-5-fluoropyrimidine (known from WO2004/099160), (2,2,3,3,4,4,5,5-octafluoropentyl)(3,3,3-trifluoropropyl)malononitrile (known from WO2005/063094), (2,2,3,3,4,4,5,5-octafluoropentyl)(3,3,4,4,4-pentafluorobutyl)malononitrile (known from WO2005/063094), 8-[2-(cyclopropylmethoxy)-4-(trifluoromethyl)phenoxy]-3-[6-(trifluoromethyl)pyridazin-3-yl]-3-azabicyclo[3.2.1]octane (known from WO2007/040280), 2-ethyl-7-methoxy-3-methyl-6-[(2,2,3,3-tetrafluoro-2,3-dihydro-1,4-benzodioxin-6-yl)oxy]quinolin-4-yl methylcarbonate (known from JP2008/110953), 2-ethyl-7-methoxy-3-methyl-6-[(2,2,3,3-tetrafluoro-2,3-dihydro-1,4-benzodioxin-6-yl)oxy]quinolin-4-yl acetate (known from JP2008/110953), PF1364 (CAS Reg. No. 1204776-60-2) (known from JP2010/018586), 5-[5-(3,5-dichlorophenyl)-5-(trifluoromethyl)-4,5-dihydro-1,2-oxazol-3-yl]-2-(1H-1,2,4-triazol-1-yl)benzonitrile (known from WO2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (known from WO2007/075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO2005/085216), 4-{[(6-chloropyridin-3-yl)methyl](cyclopropyl)amino}-1,3-oxazol-2(5H)-one, 4-{[(6-chloropyridin-3-yl)methyl](2,2-difluoroethyl)amino}-1,3-oxazol-2(5H)-one, 4-{[(6-chloropyridin-3-yl)methyl](ethyl)amino}-1,3-oxazol-2(5H)-one, 4-{[(6-chloropyridin-3-yl)methyl](methyl)amino}-1,3-oxazol-2(5H)-one (all known from WO2010/005692), NNI-0711 (known from WO2002/096882), 1-acetyl-N-[4-(1,1,1,3,3,3-hexafluoro-2-methoxypropan-2-yl)-3-isobutylphenyl]-N-isobutyryl-3,5-dimethyl-1H-pyrazole-4-carboxamide (known from WO2002/096882), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-1,2-diethylhydrazinecarboxylate (known from WO2005/085216), methyl 2-[3,5-d]bromo-2-({[3-bromo-1-(3-chloropyridin-2-yl)-1H-pyrazol-5-yl]carbonyl}amino)benzoyl]-2-ethylhydrazinecarboxylate (known from WO2005/085216), (5RS,7RS;5RS,7SR)-1-(6-chloro-3-pyridylmethyl)-1,2,3,5,6,7-hexahydro-7-methyl-8-nitro-5-propoxyimidazo[1,2-a]pyridine (known from WO2007/101369), 2-{6-[2-(5-fluoropyridin-3-yl)-1,3-thiazol-5-yl]pyridin-2-yl}pyrimidine (known from WO2010/006713), 2-{6-[2-(pyridin-3-yl)-1,3-thiazol-5-yl]pyridin-2-yl}pyrimidine (known from WO2010/006713), 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide (known from WO2010/069502), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO2010/069502), N-[2-(tert-butylcarbamoyl)-4-cyano-6-methylphenyl]-1-(3-chloropyridin-2-yl)-3-{[5-(trifluoromethyl)-1H-tetrazol-1-yl]methyl}-1H-pyrazole-5-carboxamide (known from WO2010/069502), N-[2-(tert-butylcarbamoyl)-4-cyano-6-methylphenyl]-1-(3-chloropyridin-2-yl)-3-{[5-(trifluoromethyl)-2H-tetrazol-2-yl]methyl}-1H-pyrazole-5-carboxamide (known from WO2010/069502) and (1E)-N-[(6-chloropyridin-3-yl)methyl]-N'-cyano-N-(2,2-difluoroethyl)ethanimidamide (known from WO2008/009360).

In a preferred embodiment of the invention, a penetrant is additionally added to the crop protection compositions to enhance the action. Suitable penetrants also include, for example, substances which promote the availability of the compounds of the formula (I) in the spray coating. These include, for example, mineral and vegetable oils. Suitable oils are all mineral or vegetable oils—modified or otherwise—which can usually be used in agrochemical compositions. By way of example, mention may be made of sunflower oil, rapeseed oil, olive oil, castor oil, colza oil, corn seed oil, cottonseed oil and soybean oil or the esters of said oils. Preference is given to rapeseed oil, sunflower oil and their methyl or ethyl esters, especially rapeseed oil methyl ester.

The concentration of penetrant in the compositions of the invention can be varied within a wide range. In the case of a formulated crop protection composition, it is generally 1 to 95% by weight, preferably 1 to 55% by weight, particularly preferably 15-40% by weight. In the ready-to-use compositions (spray liquors), the concentrations are generally between 0.1 and 10 g/l, preferably between 0.5 and 5 g/l.

When used as insecticides, the active compounds according to the invention may also be present in their commercially available formulations and in the use forms, prepared from these formulations, as a mixture with synergists. Synergists are compounds which enhance the action of the active compounds, without any need for the synergist added to be active itself.

When used as insecticides, the active compounds according to the invention can furthermore be present in their commercially available formulations and in the use forms, prepared from these formulations, as a mixture with inhibitors which reduce degradation of the active compound after use in the environment of the plant, on the surface of parts of plants or in plant tissues.

The active compound content of the use forms prepared from the commercially available formulations may vary within wide limits. The active compound concentration of the application forms may be from 0.00000001 to 95% by weight of active compound, preferably between 0.00001 and 1% by weight.

The compounds are employed in a customary manner appropriate for the use forms.

All plants and plant parts can be treated in accordance with the invention. Plants are understood here to mean all plants and plant populations, such as wanted and unwanted wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Examples which may be mentioned are the important crop plants, such as cereals (wheat, rice), corn, soybeans, potatoes, sugar beet, tomatoes, peas and other vegetable species, cotton, tobacco, oilseed rape and also fruit plants (with the fruits apples, pears, citrus fruits and grapes). Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. The plant parts also include harvested material and vegetative and generative propagation material, for example cuttings, tubers, rhizomes, slips and seeds.

Treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on, injection and, in the case of propagation material, in particular in the case of seeds, also by applying one or more coats.

As already mentioned above, it is possible to treat all plants and their parts in accordance with the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering, if appropriate in combination with conventional methods (Genetically Modified Organisms), and parts thereof are treated. The terms "parts" or "parts of plants" or "plant parts" have been explained above.

More preferably, plants of the plant cultivars which are commercially available or are in use are treated in accordance with the invention. Plant cultivars are understood to mean plants having new properties ("traits") and which have been obtained by conventional breeding, by mutagenesis or by recombinant DNA techniques. They may be cultivars, biotypes and genotypes.

Depending on the plant species or plant cultivars, and the location and growth conditions (soils, climate, vegetation period, diet) thereof, the treatment according to the invention may also result in superadditive ("synergistic") effects. For example, possibilities include reduced application rates and/or broadening of the activity spectrum and/or an increase in the activity of the compounds and compositions usable in accordance with the invention, better plant growth, increased tolerance to high or low temperatures, increased tolerance to drought or to levels of water or soil salinity, enhanced flowering performance, easier harvesting, accelerated ripening, higher yields, higher quality and/or higher nutritional value of the harvested products, increased storage life and/or processibility of the harvested products, which exceed the effects normally to be expected.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp. (*Ctenocephalides canis*, *Ctenocephalides felis*), *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example *Blatta orientalis*, *Periplaneta americana*, *Blattella germanica* and *Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds of the formula (I) according to the invention are also suitable for controlling arthropods which attack agricultural livestock, for example cattle, sheep, goats, horses, pigs, donkeys, camels, buffaloes, rabbits, chickens, turkeys, ducks, geese, honey-bees, other domestic animals such as, for example, dogs, cats, caged birds, aquarium fish, and experimental animals, for example hamsters, guinea pigs, rats and mice. The control of these arthropods is intended to reduce cases of death and reduced productivity (of meat, milk, wool, hides, eggs, honey etc.), and so more economic and easier animal husbandry is possible by use of the active compounds according to the invention.

The active compounds according to the invention are used in the veterinary sector and in animal husbandry in a known manner by enteral administration in the form of, for example, tablets, capsules, portions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of molded articles containing the active compound, such as collars, ear marks, tail marks, limb bands, halters, marking devices and the like.

When used for livestock, poultry, domestic animals and the like, the active compounds of the formula (I) can be used as formulations (for example powders, emulsions, flowables) comprising the active compounds in an amount of 1 to 80% by weight, either directly or after 100 to 10 000-fold dilution, or they may be used as a chemical bath.

It has also been found that the compounds according to the invention have strong insecticidal action against insects which destroy industrial materials.

Preferred but nonlimiting examples include the following insects:

beetles, such as *Hylotrupes bajulus, Chlorophorus pilosis, Anobium punctatum, Xestobium rufovillosum, Ptilinus pectinicornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;*

Dermapterans, such as *Sirex juvencus, Urocerus gigas, Urocerus gigas taignus, Urocerus augur;* termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;* bristletails, such as *Lepisma saccarina.*

Industrial materials in the present connection are understood to mean inanimate materials, such as preferably plastics, adhesives, sizes, papers and cards, leather, wood, processed wood products and coating compositions.

The ready-to-use compositions may optionally also comprise other insecticides, and optionally one or more fungicides.

With respect to possible additional partners for mixing, reference is made to the insecticides and fungicides mentioned above.

Moreover, the compounds according to the invention can be employed for protecting objects which come into contact with saltwater or brackish water, in particular hulls, screens, nets, buildings, moorings and signaling systems, against fouling.

Furthermore, the compounds according to the invention can be used alone or in combinations with other active compounds as antifouling compositions.

The active compounds are also suitable for controlling animal pests in the domestic sector, in the hygiene sector and in the protection of stored products, especially insects, arachnids and mites, which are found in enclosed spaces, for example homes, factory halls, offices, vehicle cabins and the like. They can be used to control these pests alone or in combination with other active compounds and auxiliaries in domestic insecticide products. They are effective against sensitive and resistant species, and against all developmental stages. These pests include:

From the order of the Scorpionidea, for example, *Buthus occitanus.*

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, *Aviculariidae, Araneidae.*

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Pemphigus* spp., *Phylloera vastatrix, Phthirus pubis.*

From the order of the Heteroptera, for example, *Cimex hemipterus, Cimex lectularius, Rhodinus prolixus, Triatoma infestans*.

In the field of household insecticides, they are used alone or in combination with other suitable active compounds, such as phosphoric acid esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

The compounds of the formula (I) according to the invention (active compounds) have excellent herbicidal activity against a broad spectrum of economically important mono- and dicotyledonous annual harmful plants. The active compounds act efficiently even on perennial harmful plants which produce shoots from rhizomes, root stocks and other perennial organs and which are difficult to control.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The advantageous effect of the compatibility with crop plants of the active compound combinations according to the invention is particularly pronounced at certain concentration ratios. However, the weight ratios of the active compounds in the active compound combinations can be varied within relatively wide ranges. In general, amounts of 0.001 to 1000 parts by weight, preferably from 0.01 to 100 parts by weight, particularly preferably 0.05 to 20 parts by weight, of one of the compounds which improves crop plant compatibility (antidotes/safeners) mentioned above under (b') are present per part by weight of active compound of the formula (I).

The active compound combinations according to the invention are generally applied in the form of finished formulations. However, the active compounds contained in the active compound combinations can, as individual formulations, also be mixed during use, i.e. be applied in the form of tank mixes.

For certain applications, in particular by the post-emergence method, it may furthermore be advantageous to include, as further additives in the formulations, mineral or vegetable oils which are tolerated by plants (for example the commercial preparation "Rako Binol"), or ammonium salts, such as, for example, ammonium sulfate or ammonium thiocyanate.

The novel active compound combinations can be used as such, in the form of their formulations or in the use forms prepared therefrom by further dilution, such as ready-to-use solutions, suspensions, emulsions, powders, pastes and granules. They are used in a customary manner, for example by watering, spraying, atomizing, dusting or broadcasting.

The application rates of the active compound combinations according to the invention can be varied within a certain range; they depend, inter alia, on the weather and on soil factors. In general, the application rates are between 0.001 and 5 kg per ha, preferably between 0.005 and 2 kg per ha, particularly preferably between 0.01 and 0.5 kg per ha.

Depending on their properties, the safeners to be used according to the invention can be used for pretreating the seed of the crop plant (seed dressing) or can be introduced into the seed furrows prior to sowing or be used separately prior to the herbicide or together with the herbicide, before or after emergence of the plants.

Examples of plants which may be mentioned are the important crop plants, such as cereals (wheat, barley, rice), corn, soybeans, potatoes, cotton, oilseed rape, beet, sugar cane and also fruit plants (with the fruits apples, pears, citrus fruits and grapevines), greater emphasis being given to cereals, corn, soybeans, potatoes, cotton and oilseed rape.

The active compounds according to the invention can be used to treat all plants and parts of plants. Plants are understood here to mean all plants and plant populations, such as wanted and unwanted wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. The plant parts also include harvested material and vegetative and generative propagation material, for example cuttings, tubers, rhizomes, slips and seeds.

Treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on, injection and, in the case of propagation material, in particular in the case of seeds, also by applying one or more coats.

The present invention therefore also relates to a method for controlling unwanted plants or for regulating the growth of plants, preferably in crops of plants, where one or more compound(s) according to the invention is/are applied to the plants (for example harmful plants such as monocotyledonous or dicotyledonous weeds or undesired crop plants), to the seeds (for example grains, seeds or vegetative propagules such as tubers or shoot parts with buds) or to the area on which the plants grow (for example the area under cultivation). The compounds according to the invention can be applied, for example, prior to sowing (if appropriate also by incorporation into the soil), prior to emergence or after emergence. Specific examples may be mentioned of some representatives of the monocotyledonous and dicotyledonous weed flora which can be controlled by the compounds according to the invention, without the enumeration being restricted to certain species.

Monocotyledonous Harmful Plants of the Genera:

*Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous Weeds of the Genera:

*Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum,*

*Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

The plants listed can be treated in accordance with the invention in a particularly advantageous manner with the compounds of the general formula I and/or the active compound mixtures according to the invention. The preferred ranges stated above for the active compounds or mixtures also apply to the treatment of these plants. Particular emphasis is given to the treatment of plants with the compounds or mixtures specifically mentioned in the present text.

If the compounds according to the invention are applied to the soil surface before germination, the weed seedlings are either prevented completely from emerging or else the weeds grow until they have reached the cotyledon stage, but then their growth stops, and, eventually, after three to four weeks have elapsed, they die completely.

If the active compounds are applied post-emergence to the green parts of the plants, growth stops after the treatment, and the harmful plants remain at the growth stage of the point of time of application, or they die completely after a certain time, so that in this manner competition by the weeds, which is harmful to the crop plants, is eliminated very early and in a sustained manner.

Although the compounds according to the invention display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Miscanthus, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, are damaged only to an insignificant extent, or not at all, depending on the structure of the respective compound according to the invention and its application rate. This is why the present compounds are highly suitable for the selective control of unwanted plant growth in plant crops such as agriculturally useful plants or ornamentals.

Moreover, the compounds according to the invention (depending on their respective structure and the application rate applied) have outstanding growth-regulatory properties in crop plants. They engage in the plant's metabolism in a regulatory fashion and can therefore be employed for the influencing, in a targeted manner, of plant constituents and for facilitating harvesting, such as, for example, by triggering desiccation and stunted growth. Moreover, they are also suitable for generally controlling and inhibiting unwanted vegetative growth without destroying the plants in the process Inhibiting vegetative growth plays a major role for many monocotyledonous and dicotyledonous crops, since, for example, this can reduce or completely prevent lodging.

As already mentioned above, it is possible to treat all plants and their parts in accordance with the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering, if appropriate in combination with conventional methods (Genetically Modified Organisms), and parts thereof are treated. The terms "parts" or "parts of plants" or "plant parts" have been explained above.

More preferably, plants of the plant cultivars which are commercially available or are in use are treated in accordance with the invention. Plant cultivars are understood to mean plants having new properties ("traits") and which have been obtained by conventional breeding, by mutagenesis or by recombinant DNA techniques. They may be cultivars, biotypes and genotypes.

Depending on the plant species or plant cultivars, and the location and growth conditions (soils, climate, vegetation period, diet) thereof, the treatment according to the invention may also result in superadditive ("synergistic") effects. For example, possibilities include reduced application rates and/or broadening of the activity spectrum and/or an increase in the activity of the compounds and compositions usable in accordance with the invention, better plant growth, increased tolerance to high or low temperatures, increased tolerance to drought or to levels of water or soil salinity, enhanced flowering performance, easier harvesting, accelerated ripening, higher yields, higher quality and/or higher nutritional value of the harvested products, increased storage life and/or processibility of the harvested products, which exceed the effects normally to be expected.

Owing to their herbicidal and plant growth-regulating properties, the active compounds can also be used to control harmful plants in crops of known genetically modified plants or of those yet to be developed. In general, the transgenic plants are notable for special advantageous properties, for example for resistances to certain pesticides, in particular certain herbicides, resistances to plant diseases or organisms that cause plant diseases, such as certain insects or microorganisms such as fungi, bacteria or viruses. Other special properties relate, for example, to the harvested material with regard to quantity, quality, storability, composition and specific constituents. For instance, there are known transgenic plants with an elevated starch content or altered starch quality, or with a different fatty acid composition in the harvested material. Further special properties may be tolerance or resistance to abiotic stress factors, for example heat, cold, drought, salinity and ultraviolet radiation. The active compounds can also be used in transgenic plants distinguished by higher yields, for example an improved photosynthesis performance or an improved nutrient uptake.

Preference is given to the use of the compounds of the formula (I) according to the invention or salts thereof in economically important transgenic crops of useful plants and ornamental plants, for example of cereals such as wheat, barley, rye, oats, sorghum and millet, rice, cassaya and corn, or else crops of sugar beet, cotton, soybean, oilseed rape, potatoes, tomatoes, peas and other vegetables.

The compounds of the formula (I) can preferably be used as herbicides in crops of useful plants which are resistant, or have been made resistant by recombinant means, to the phytotoxic effects of the herbicides.

Conventional ways of producing novel plants which have modified properties in comparison to plants which have occurred to date consist, for example, in traditional breeding methods and the generation of mutants. Alternatively, novel plants with altered properties can be generated with the aid of recombinant methods (see, for example, EP 0221044, EP 0131624). For example, there have been many descriptions of:

genetic modifications of crop plants for the purpose of modifying the starch synthesized in the plants (for example WO 92/011376 A, WO 92/014827 A, WO 91/019806 A), transgenic crop plants which are resistant to certain herbicides of the glufosinate type (cf., for example, EP 0242236 A, EP 0242246 A) or of the glyphosate type (WO 92/000377A) or of the sulfonylurea type (EP 0257993 A, U.S. Pat. No. 5,013,659) or to combinations or mixtures of these herbicides through "gene stacking", such as transgenic crop plants, for example corn or soybean with the tradename or the designation Optimum™ GAT™ (glyphosate ALS tolerant). Also described were transgenic plants resistant to synthetic auxins (e.g. 2,4 D) HRAC mode of action Class O and aryloxyphenoxy propionate (fops, HRAC, Class A) (DHT, Dow Agroscience Herbicide Tolerance Trait)

transgenic crop plants, for example cotton, which are capable of producing *Bacillus thuringiensis* toxins (Bt toxins), which make the plants resistant to certain pests (EP 0142924 A, EP 0193259 A), transgenic crop plants having a modified fatty acid composition (WO 91/013972 A), genetically modified plants having novel insect resistances based, for example, on the expression of toxins from *Photorhabdus, Xenorhabdus* symbionts from entomopathogenic nematodes and toxins from spiders, scorpions, ants, parasitic wasps.

genetically modified crop plants with novel constituents or secondary metabolites, for example novel phytoalexins, which bring about an increased disease resistance (EP 0309862 A, EP 0464461 A)

genetically modified plants with reduced photorespiration which feature higher yields and higher stress tolerance (EP 0305398 A), transgenic crop plants which produce pharmaceutically or diagnostically important proteins ("molecular pharming"), transgenic crop plants which are notable for higher yields or better quality, transgenic crop plants distinguished by increased tolerances to abiotic and biotic stress factors transgenic crop plants which are notable for a combination, for example, of the abovementioned novel properties ("gene stacking").

Numerous molecular biology techniques which can be used to produce novel transgenic plants with modified properties are known in principle; see, for example, I. Potrykus and G. Spangenberg (eds.) Gene Transfer to Plants, Springer Lab Manual (1995), Springer Verlag Berlin, Heidelberg, or Christou, "Trends in Plant Science" 1 (1996) 423-431.

To carry out such recombinant manipulations, nucleic acid molecules which allow mutagenesis or a sequence change by recombination of DNA sequences can be introduced into plasmids. With the aid of standard methods, it it possible, for example, to undertake base exchanges, remove parts of sequences or add natural or synthetic sequences. For the joining of the DNA fragments to one another, adaptors or linkers can be attached to the fragments; see, for example, Sambrook et al., 1989, Molecular Cloning, A Laboratory Manual, 2nd ed. Cold Spring Harbor Laboratory Press, Cold Spring Harbor, N.Y.; or Winnacker "Gene and Klone", VCH Weinheim 2nd edition 1996.

For example, the generation of plant cells with a reduced activity of a gene product can be achieved by expressing at least one corresponding antisense RNA, a sense RNA for achieving a cosuppression effect or by expressing at least one suitably constructed ribozyme which specifically cleaves transcripts of the abovementioned gene product.

To this end, it is possible to use DNA molecules which encompass the entire coding sequence of a gene product inclusive of any flanking sequences which may be present, and also DNA molecules which only encompass portions of the coding sequence, it being necessary for these portions to be long enough to have an antisense effect in the cells. The use of DNA sequences which have a high degree of homology to the coding sequences of a gene product, but are not completely identical to them, is also possible.

When expressing nucleic acid molecules in plants, the protein synthesized can be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants can be plants of any desired plant species, i.e. not only monocotyledonous, but also dicotyledonous, plants.

Thus, transgenic plants can be obtained whose properties are altered by overexpression, suppression or inhibition of homologous (=natural) genes or gene sequences or the expression of heterologous (=foreign) genes or gene sequences.

It is preferred to employ the compounds (I) according to the invention in transgenic crops which are resistant to growth regulators such as, for example, 2,4 D, dicamba, or against herbicides which inhibit essential plant enzymes, for example acetyl CoA carboxylases, acetolactate synthases (ALS), EPSP synthases, glutamine synthases (GS) or hydroxyphenylpyruvate dioxygenases (HPPD), or against herbicides from the group of the FOPs, sulfonylureas, glyphosates, glufosinates or benzoylisoxazoles and analogous active compounds, or against any combinations of these active compounds.

Particularly preferably, the compounds according to the invention can be used in transgenic crop plants which are resistant to a combination of glyphosates and glufosinates, glyphosates and sulfonylureas or imidazolinones. The compounds according to the invention can be used with very particular preference in transgenic crop plants, for example corn or soybeans with the trade name or the designation Optimum™ GAT™ (glyphosate ALS tolerant). Furthermore and particularly preferably, the compounds according to the invention can be employed in transgenic plants resistant to synthetic auxins (for example 2,4 D) having "HRAC mode of action Class O" and aryloxyphenoxy propionate (fops) having "HRAC mode of action Class A" (for example DHT, Dow Agroscience Herbicide Tolerance Trait).

When the active compounds according to the invention are used in transgenic crops, effects are frequently observed—in addition to the effects on harmful plants which can be observed in other crops—which are specific for the application in the transgenic crop in question, for example a modified or specifically widened spectrum of weeds which can be controlled, modified application rates which may be employed for application, preferably good combinability with the herbicides to which the transgenic crop is resistant, and an effect on growth and yield of the transgenic crop plants.

The invention therefore also relates to the use of the compounds of the formula (I) according to the invention as herbicides for controlling harmful plants in transgenic crop plants.

The compounds according to the invention can be used in the form of wettable powders, emulsifiable concentrates, sprayable solutions, dusting products or granules in the customary formulations. The invention therefore also provides herbicidal and plant-growth-regulating compositions which comprise the compounds according to the invention.

The compounds according to the invention can be formulated in various ways, according to the biological and/or physicochemical parameters required. Examples of possible formulations include: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie" [Chemical Technology], Volume 7, C. Hanser Verlag Munich, 4. ed. 1986; Wade van Valkenburg, "Pesticide Formulations", Marcel Dekker, N.Y., 1973; K. Martens, "Spray Drying" Handbook, 3rd ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd ed., Darland Books, Caldwell N.J., H. v. Olphen, "Introduction to Clay Colloid Chemistry"; 2nd ed., J. Wiley & Sons, N.Y.; C. Marsden, "Solvents Guide"; 2nd ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active Ethylene Oxide Adducts], Wiss. Verlagsgesell., Stuttgart 1976; Winnacker-Küchler, "Chemische Technologie", volume 7, C. Hanser Verlag Munich, 4th ed. 1986.

Based on these formulations, it is also possible to produce combinations with other pesticidally active compounds, such as, for example, insecticides, acaricides, herbicides, fungicides, and also with safeners, fertilizers and/or growth regulators, for example in the form of a finished formulation or as a tank mix.

Active compounds which can be employed in combination with the compounds according to the invention in mixed formulations or in the tank mix are, for example, known active compounds which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoen desaturase, photosystem I, photosystem II, protoporphyrinogen oxidase, as are described in, for example, Weed Research 26 (1986) 441-445 or "The Pesticide Manual", 13th edition, The British Crop Protection Council and the Royal Soc. of Chemistry, 2003 and the literature cited therein.

Known herbicides or plant growth regulators which may be mentioned as being suitable for being combined with the compounds according to the invention are, for example, the following active compounds:
acetochlor, acibenzolar, acibenzolar-S-methyl, acifluorfen, acifluorfen-sodium, aclonifen, alachlor, allidochlor, alloxydim, alloxydim-sodium, ametryn, amicarbazone, amidochlor, amidosulfuron, aminopyralid, amitrole, ammonium sulfamate, ancymidol, anilofos, asulam, atrazine, azafenidin, azimsulfuron, aziprotryn, BAH-043, BAS-140H, BAS-693H, BAS-714H, BAS-762H, BAS-776H, BAS-800H, beflubutamid, benazolin, benazolin-ethyl, bencarbazone, benfluralin, benfuresate, bensulide, bensulfuron-methyl, bentazone, benzfendizone, benzobicyclon, benzofenap, benzofluor, benzoylprop, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat chloride, chlornitrofen, chlorophthalim, chlorthal-dimethyl, chlorotoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat dibromide, dithiopyr, diuron, DNOC, eglinazine-ethyl, endothal, EPTC, esprocarb, ethalfluralin, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl]ethanesulfonamide, fenoprop, fenoxaprop, fenoxaprop-P, fenoxaprop-ethyl, fenoxaprop-P-ethyl, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, fluorochloridone, fluoroxypyr, fluoroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, L-glufosinate, L-glufosinate-ammonium, glufosinate-ammonium, glyphosate, glyphosate-isopropylammonium, H-9201, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HNPC-9908, HOK-201, HW-02, imazamethabenz, imazamethabenz-methyl, imazamox, imazapic, imazapyr, imazaquin, imazethapyr, imazosulfuron, inabenfide, indanofan, indoleacetic acid (IAA), 4-indol-3-ylbutyric acid (IBA), iodosulfuron, iodosulfuron-methyl-sodium, ioxynil, isocarbamid, isopropalin, isoproturon, isouron, isoxaben, isoxachlortole, isoxaflutole, isoxapyrifop, IDH-100, KUH-043, KUH-071, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat chloride, mesosulfuron, mesosulfuron-methyl, mesotrione, methabenzthiazuron, metam, metamifop, metamitron, metazachlor, methazole, methoxyphenone, methyldymron, 1-methylcyclopropene, methyl isothiocyanate, metobenzuron, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monuron, MT 128, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolate-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazole, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron-ethyl, pyrazoxyfen, pyribambenz, pyribambenz-isopropyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, secbumeton, sethoxydim, siduron, simazine, simetryn, SN-106279, sulcotrione, sulfallate (CDEC), sulfentrazone, sulfometuron, sulfometuron-methyl, sulfosate (glyphosate-trimesium), sulfosulfuron, SYN-523, SYP-249, SYP-298, SYP-300, tebutam, tebuthiuron, tecnazene, tefuryltrione, tembotrione, tepraloxydim, terbacil, terbucarb, terbuchlor, terbumeton, terbuthylazine, terbutryn, TH-547, thenylchlor, thiafluamide, thiazafluoron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0166, ZJ-0270, ZJ-0543, or ZJ-0862 and also the following compounds

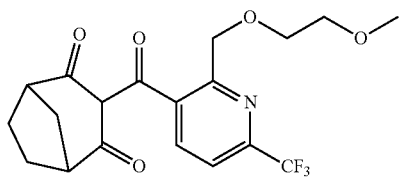

-continued

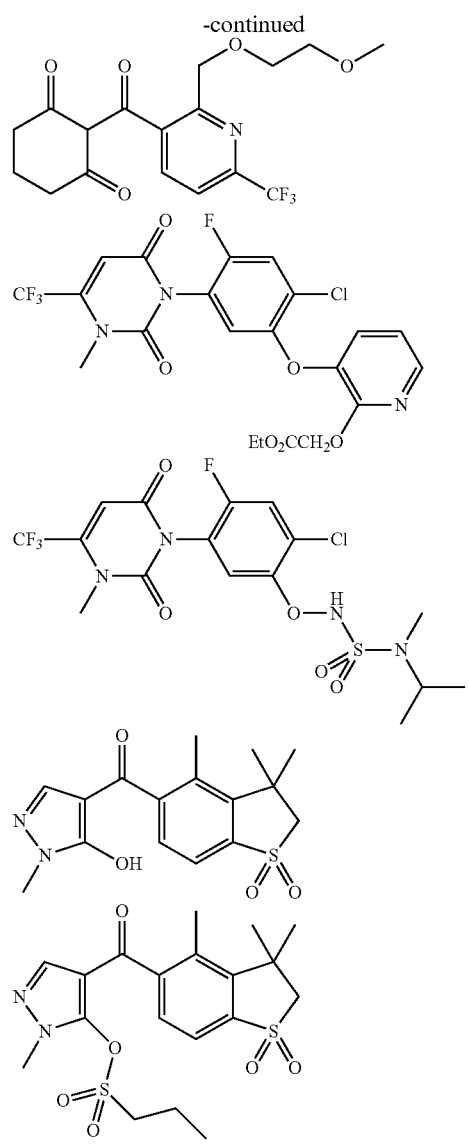

Compounds are referred to either by the "common name" in accordance with the International Organization for Standardization (ISO) or by their chemical name or code number, and in each case include all use forms, such as acids, salts, esters or modifications, such as isomers, stereoisomers and optical isomers. One or else more use forms or modifications are mentioned by way of example.

Wettable powders are preparations which can be dispersed uniformly in water and, as well as the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2' dinaphthylmethane-6,6'-disulfonate, sodium dibutylnaphthalenesulfonate or else sodium oleoylmethyltaurinate. To produce the wettable powders, the herbicidally active compounds are ground finely, for example in customary apparatus such as hammer mills, blower mills and air jet mills, and simultaneously or subsequently mixed with the formulation assistants.

Emulsifiable concentrates are prepared by dissolving the active compound in an organic solvent, for example butanol, cyclohexanone, dimethylformamide, xylene or else relatively high-boiling aromatics or hydrocarbons or mixtures of the organic solvents with addition of one or more surfactants of the ionic and/or nonionic type (emulsifiers). The emulsifiers used may be, for example: calcium alkylarylsulfonates salts such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusts are obtained by grinding the active compound with finely distributed solid substances, for example talc, natural clays, such as kaolin, bentonite and pyrophyllite, or diatomaceous earth.

Suspension concentrates may be water- or oil-based. They may be prepared, for example, by wet grinding by means of commercial bead mills and optional addition of surfactants as have, for example, already been listed above for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be prepared either by spraying the active compound onto granulated inert material capable of adsorption or by applying active compound concentrates to the surface of carrier substances, such as sand, kaolinites or granulated inert material, by means of adhesives, for example polyvinyl alcohol, sodium polyacrylate or mineral oils. Suitable active compounds can also be granulated in the manner customary for the production of fertilizer granules—if desired as a mixture with fertilizers.

Water-dispersible granules are prepared generally by the customary processes such as spray-drying, fluidized bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th Ed., McGraw-Hill, New York 1973, pp. 8-57.

For further details regarding the formulation of crop protection agents, see, for example, G. C. Klingman, "Weed Control as a Science", John Wiley and Sons, Inc., New York, 1961, pages 81-96 and J. D. Freyer, S. A. Evans, "Weed Control Handbook", 5th ed., Blackwell Scientific Publications, Oxford, 1968, pages 101-103.

The agrochemical formulations contain generally 0.1 to 99% by weight, especially 0.1 to 95% by weight, of compounds according to the invention.

In wettable powders, the active compound concentration is, for example, from about 10 to 90% by weight, the remainder to 100% by weight consisting of customary formulation components. In the case of emulsifiable concentrates, the active compound concentration can be from about 1 to 90, preferably from 5 to 80, % by weight. Dust-type formulations contain from 1 to 30% by weight of active compound, preferably usually from 5 to 20% by weight of active compound; sprayable solutions contain from about 0.05 to 80% by weight, preferably from 2 to 50% by weight of active compound. In the case of water-dispersible granules, the active compound content depends partially on whether the active compound is present in liquid or solid form and on which granulation auxiliaries, fillers, etc., are used. In the water-dispersible granules, the content of active compound is, for example, between 1 and 95% by weight, preferably between 10 and 80% by weight.

In addition, the active compound formulations mentioned optionally comprise the respective customary adhesives, wetting agents, dispersants, emulsifiers, penetrants, preservatives, antifreeze agents and solvents, fillers, carriers and dyes, defoamers, evaporation inhibitors and agents which influence the pH and the viscosity.

The compounds according to the invention have a potent microbicidal activity and can be employed for controlling undesirable microorganisms, such as fungi and bacteria, in crop protection and in the protection of materials.

Fungicides can be used in crop protection for control of Plasmodiophoromycetes, Oomycetes, Chytridiomycetes, Zygomycetes, Ascomycetes, Basidiomycetes and Deuteromycetes.

Bactericides can be used in crop protection for control of Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation: diseases caused by powdery mildew pathogens, such as, for example, *Blumeria* species such as, for example, *Blumeria graminis;*
*Podosphaera* species such as, for example, *Podosphaera leucotricha;*
*Sphaerotheca* species such as, for example, *Sphaerotheca fuliginea;*
*Uncinula* species such as, for example, *Uncinula necator;*
diseases caused by rust disease pathogens such as, for example,
*Gymnosporangium* species such as, for example, *Gymnosporangium sabinae*
*Hemileia* species such as, for example, *Hemileia vastatrix;*
*Phakopsora* species such as, for example, *Phakopsora pachyrhizi* and *Phakopsora meibomiae;*
*Puccinia* species such as, for example, *Puccinia recondita;*
*Uromyces* species such as, for example, *Uromyces appendiculatus;*
diseases caused by pathogens from the group of the Oomycetes such as, for example,
*Bremia* species such as, for example, *Bremia lactucae;*
*Peronospora* species such as, for example, *Peronospora pisi* or *P. brassicae;*
*Phytophthora* species such as, for example, *Phytophthora infestans;*
*Plasmopara* species such as, for example, *Plasmopara viticola;*
*Pseudoperonospora* species such as, for example, *Pseudoperonospora humuli* or *Pseudoperonospora cubensis;*
*Pythium* species such as, for example, *Pythium ultimum;*
leaf blotch diseases and leaf wilt diseases caused, for example, by
*Alternaria* species such as, for example, *Alternaria solani;*
*Cercospora* species such as, for example, *Cercospora beticola;*
*Cladosporium* species such as, for example, *Cladosporium cucumerinum;*
*Cochliobolus* species such as, for example, *Cochliobolus sativus*
(conidia form: *Drechslera*, syn: *Helminthosporium*);

*Colletotrichum* species such as, for example, *Colletotrichum lindemuthanium;*
*Cycloconium* species such as, for example, *Cycloconium oleaginum;*
*Diaporthe* species such as, for example, *Diaporthe citri;*
*Elsinoe* species such as, for example, *Elsinoe fawcettii;*
*Gloeosporium* species such as, for example, *Gloeosporium laeticolor;*
*Glomerella* species such as, for example, *Glomerella cingulata;*
*Guignardia* species such as, for example, *Guignardia bidwelli;*
*Leptosphaeria* species such as, for example, *Leptosphaeria maculans;*
*Magnaporthe* species such as, for example, *Magnaporthe grisea;*
*Mycosphaerella* species such as, for example, *Mycosphaerella graminicola* and *Mycosphaerella fijiensis;*
*Phaeosphaeria* species such as, for example, *Phaeosphaeria nodorum;*
*Pyrenophora* species such as, for example, *Pyrenophora teres;*
*Ramularia* species such as, for example, *Ramularia collocygni;*
*Rhynchosporium* species such as, for example, *Rhynchosporium secalis;*
*Septoria* species such as, for example, *Septoria apii;*
*Typhula* species such as, for example, *Typhula incarnata;*
*Venturia* species such as, for example, *Venturia inaequalis;*
root and stem diseases caused, for example, by
*Corticium* species such as, for example, *Corticium graminearum;*
*Fusarium* species such as, for example, *Fusarium oxysporum;*
*Gaeumannomyces* species such as, for example, *Gaeumannomyces graminis;*
*Rhizoctonia* species such as, for example, *Rhizoctonia solani;*
*Tapesia* species such as, for example, *Tapesia acuformis;*
*Thielaviopsis* species such as, for example, *Thielaviopsis basicola;*
ear and panicle diseases (including corn cobs) caused, for example, by
*Alternaria* species such as, for example, *Alternaria* spp.;
*Aspergillus* species such as, for example, *Aspergillus flavus;*
*Cladosporium* species such as, for example, *Cladosporium cladosporioides;*
*Claviceps* species such as, for example, *Claviceps purpurea;*
*Fusarium* species such as, for example, *Fusarium culmorum;*
*Gibberella* species such as, for example, *Gibberella zeae;*
*Monographella* species such as, for example, *Monographella nivalis;*
diseases caused by smut fungi such as, for example,
*Sphacelotheca* species such as, for example, *Sphacelotheca reiliana;*
*Tilletia* species such as, for example, *Tilletia caries;*
*Urocystis* species such as, for example, *Urocystis occulta;*
*Ustilago* species such as, for example, *Ustilago nuda;*
fruit rot caused, for example, by
*Aspergillus* species such as, for example, *Aspergillus flavus;*
*Botrytis* species such as, for example, *Botrytis cinerea;*
*Penicillium* species such as, for example, *Penicillium expansum* and *Penicillium purpurogenum;*
*Sclerotinia* species such as, for example, *Sclerotinia sclerotiorum;*
*Verticilium* species such as, for example, *Verticilium alboatrum;*
seed- and soil-borne rot and wilt diseases, and also diseases of seedlings, caused, for example, by
*Alternaria* species such as, for example, *Alternaria brassicicola;*
*Aphanomyces* species such as, for example, *Aphanomyces euteiches;*
*Ascochyta* species such as, for example, *Ascochyta lentis;*
*Aspergillus* species such as, for example, *Aspergillus flavus;*
*Cladosporium* species such as, for example, *Cladosporium herbarum;*
*Cochliobolus* species such as, for example, *Cochliobolus sativus*
(conidia form: *Drechslera, Bipolaris* Syn: *Helminthosporium*);
*Colletotrichum* species such as, for example, *Colletotrichum coccodes;*
*Fusarium* species such as, for example, *Fusarium culmorum;*
*Gibberella* species such as, for example, *Gibberella zeae;*
*Macrophomina* species such as, for example, *Macrophomina phaseolina;*
*Monographella* species such as, for example, *Monographella nivalis;*
*Penicillium* species such as, for example, *Penicillium expansum;*
*Phoma* species such as, for example, *Phoma lingam;*
*Phomopsis* species such as, for example, *Phomopsis sojae;*
*Phytophthora* species such as, for example, *Phytophthora cactorum;*
*Pyrenophora* species such as, for example, *Pyrenophora graminea;*
*Pyricularia* species such as, for example, *Pyricularia oryzae;*
*Pythium* species such as, for example, *Pythium ultimum;*
*Rhizoctonia* species such as, for example, *Rhizoctonia solani;*
*Rhizopus* species such as, for example, *Rhizopus oryzae*
*Sclerotium* species such as, for example, *Sclerotium rolfsii;*
*Septoria* species such as, for example, *Septoria nodorum;*
*Typhula* species such as, for example, *Typhula incarnata;*
*Verticillium* species such as, for example, *Verticillium dahliae*
cancerous diseases, galls and witches' broom caused, for example, by
*Nectria* species such as, for example, *Nectria galligena;*
wilt diseases caused, for example, by
*Monilinia* species such as, for example, *Monilinia laxa;*
deformations of leaves, flowers and fruits caused, for example, by
*Taphrina* species such as, for example, *Taphrina deformans;*
degenerative diseases of woody plants caused, for example, by
*Esca* species such as, for example, *Phaeomoniella chlamydospora* and *Phaeoacremonium aleophilum* and *Fomitiporia mediterranea;*
diseases of flowers and seeds caused, for example, by
*Botrytis* species such as, for example, *Botrytis cinerea;*
diseases of plant tubers caused, for example, by
*Rhizoctonia* species such as, for example, *Rhizoctonia solani;*
*Helminthosporium* species such as, for example, *Helminthosporium solani;*
diseases caused by bacterial pathogens such as, for example,
*Xanthomonas* species such as, for example, *Xanthomonas campestris* pv. *oryzae;*
*Pseudomonas* species such as, for example, *Pseudomonas syringae* pv. *lachrymans;*
*Erwinia* species such as, for example, *Erwinia amylovora;*
Preference is given to controlling the following diseases of soya beans:
fungal diseases on leaves, stems, pods and seeds caused, for example, by *alternaria* leaf spot (*Alternaria* spec. *atrans*

*tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi*), scab (*Sphaceloma glycines*), stemphylium leaf blight (*Stemphylium botryosum*), target spot (*Corynespora cassiicola*).

Fungal diseases on roots and the stem base caused, for example, by
black root rot (*Calonectria crotalariae*), charcoal rot (*Macrophomina phaseolina*), *fusarium* blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The active compounds according to the invention also exhibit a strengthening effect in plants. They can therefore be used to mobilize the plant's own defences against attack by unwanted microorganisms.

Plant-strengthening (resistance-inducing) substances are to be understood as meaning, in the present context, those substances which are capable of stimulating the defence system of plants in such a way that the treated plants, when subsequently inoculated with unwanted microorganisms, develop a high degree of resistance to these microorganisms.

In the present case, unwanted microorganisms are to be understood as meaning phytopathogenic fungi, bacteria and viruses. Accordingly, the substances according to the invention can be used to protect plants for a certain period after the treatment against attack by the pathogens mentioned. The period for which protection is provided generally extends over 1 to 10 days, preferably 1 to 7 days, after the treatment of the plants with the active compounds.

The fact that the active compounds are well tolerated by plants at the concentrations required for controlling plant diseases allows the treatment of above-ground parts of plants, of propagation stock and seeds, and of the soil.

The active compounds according to the invention can be employed particularly successfully for controlling cereal diseases such as, for example, against *Puccinia* species and diseases in viticulture and fruit and vegetable growing such as, for example, against *Botrytis, Venturia* or *Alternaria* species.

The active compounds according to the invention are also suitable for enhancing the yield of crops. In addition, they have low toxicity and are well tolerated by plants.

In addition, by the treatment according to the invention it is possible to reduce the mycotoxin content in the harvested material and the foodstuffs and feedstuffs prepared therefrom. Particular, but not exclusive, mention may be made here of the following mycotoxins: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins produced, for example, by the following fungi: *Fusarium* spec., such as *Fusarium acuminatum, F. avenaceum, F. crookwellense, F. culmorum, F. graminearum* (*Gibberella zeae*)*, F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides*, inter alia, and also by *Aspergillus* spec., *Penicillium* spec., *Claviceps purpurea, Stachybotrys* spec., inter alia.

In the protection of materials, the compounds according to the invention can be employed for protecting industrial materials against infection with, and destruction by, unwanted microorganisms.

Industrial materials in the present context are understood as meaning non-living materials which have been prepared for use in industry. For example, industrial materials which are to be protected by active compounds according to the invention from microbial alteration or destruction may be adhesives, sizes, paper and cardboard, textiles, leather, wood, paints and plastic articles, cooling lubricants and other materials which can be infected with or destroyed by microorganisms. The range of materials to be protected also includes parts of production plants, for example cooling water circuits, which may be impaired by the proliferation of microorganisms. Industrial materials within the scope of the present invention preferably include adhesives, sizes, paper and card, leather, wood, paints, cooling lubricants and heat transfer fluids, more preferably wood.

Microorganisms capable of degrading or altering the industrial materials include, for example, bacteria, fungi, yeasts, algae and slime organisms. The active compounds according to the invention preferably act against fungi, in particular molds, wood-discolouring and wood-destroying fungi (Basidiomycetes), and against slime organisms and algae.

Examples include microorganisms of the following genera:
*Alternaria* such as *Alternaria tenuis*,
*Aspergillus* such as *Aspergillus niger*,
*Chaetomium* such as *Chaetomium globosum*,
*Coniophora* such as *Coniophora puetana*,
*Lentinus* such as *Lentinus tigrinus*,
*Penicillium* such as *Penicillium glaucum*,
*Polyporus* such as *Polyporus versicolor*,
*Aureobasidium* such as *Aureobasidium pullulans*,
*Sclerophoma* such as *Sclerophoma pityophila*,
*Trichoderma* such as *Trichoderma viride*,
*Escherichia* such as *Escherichia coli*,
*Pseudomonas* such as *Pseudomonas aeruginosa*, and
*Staphylococcus* such as *Staphylococcus aureus*.

The present invention relates to a composition for controlling unwanted microorganisms which comprises at least one of the compounds according to the invention.

To this end, depending on their particular physical and/or chemical properties, the compounds according to the invention can be converted into the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulfoxide, or else water. Liquefied gaseous extenders or carriers are understood to mean liquids which are gaseous at standard temperature and under standard pressure, for example aerosol propellants such as halohydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Useful solid carriers for granules include: for example crushed and fractionated natural rocks such as calcite, pumice, marble, sepiolite, dolomite, and synthetic granules of inorganic and organic meals, and also granules of organic material such as sawdust, coconut shells, corn cobs and tobacco stalks. Suitable emulsifiers and/or foam formers are: for example, nonionic and anionic emulsifiers, such as polyoxyethylene fatty acid esters, polyoxyethylene fatty alcohol ethers, for example alkylaryl polyglycol ethers, alkylsulfonates, alkylsulfates, arylsulfonates and protein hydrolyzates. Suitable dispersants are: for example lignosulfite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Further additives may be mineral and vegetable oils.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

The formulations described above can be used in a method according to the invention for controlling unwanted microorganisms, where the compounds according to the invention are applied to the microorganisms and/or to their habitat.

The control of phytopathogenic fungi by treating the seed of plants has been known for a long time and is the subject of continuous improvements. However, the treatment of seed entails a series of problems which cannot always be solved in a satisfactory manner. For instance, it is desirable to develop methods for protecting the seed and the germinating plant, which dispense with, or at least significantly reduce, the additional deployment of crop protection compositions after planting or after emergence of the plants. It is furthermore desirable to optimize the amount of active compound employed in such a way as to provide optimum protection for the seed and the germinating plant from attack by phytopathogenic fungi, but without damaging the plant itself by the active compound employed. In particular, methods for the treatment of seed should also take into consideration the intrinsic fungicidal properties of transgenic plants in order to achieve optimum protection of the seed and the germinating plant with a minimum of crop protection compositions being employed.

The present invention therefore in particular also relates to a method for the protection of seed and germinating plants from attack by phytopathogenic fungi, by treating the seed with a composition according to the invention.

The invention also relates to the use of the compositions according to the invention for treatment of seed for protection of the seed and the germinating plant against phytopathogenic fungi.

Furthermore, the invention relates to seed treated with a composition according to the invention for protection against phytopathogenic fungi.

One of the advantages of the present invention is that the particular systemic properties of the compositions according to the invention mean that treatment of the seed with these compositions not only protects the seed itself, but also the resulting plants after emergence, from phytopathogenic fungi. In this manner, the immediate treatment of the crop at the time of sowing or shortly thereafter can be dispensed with.

It is likewise to be considered advantageous that the mixtures according to the invention can be used in particular also for transgenic seed.

The compositions according to the invention are suitable for protecting seed of any plant variety which is employed in agriculture, in the greenhouse, in forests or in horticulture. In particular, this takes the form of seed of cereals (such as wheat, barley, rye, millet and oats), corn, cotton, soybeans, rice, potatoes, sunflowers, beans, coffee, beets (for example sugarbeets and fodder beets), peanuts, vegetables (such as tomatoes, cucumbers, onions and lettuce), lawns and ornamental plants. The treatment of the seed of cereals (such as wheat, barley, rye and oats), corn and rice is of particular importance.

In the context of the present invention, the composition according to the invention is applied to the seed either alone or in a suitable formulation. Preferably, the seed is treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. Thus, it is possible to use, for example, seed which has been harvested, cleaned and dried to a moisture content of less than 15% by weight. Alternatively, it is also possible to use seed which, after drying, has been treated, for example, with water and then dried again.

When treating the seed, care must generally be taken that the amount of the composition according to the invention applied to the seed and/or the amount of further additives is chosen in such a way that the germination of the seed is not adversely affected, or that the resulting plant is not damaged. This must be ensured particularly in the case of active compounds which can exhibit phytotoxic effects at certain application rates.

The compositions according to the invention can be applied directly, i.e. without containing any other components and undiluted. In general, it is preferred to apply the compositions to the seed in the form of a suitable formulation. Suitable formulations and methods for treating seed are known to the person skilled in the art and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active compound combinations which can be used in accordance with the invention can be converted into the customary seed-dressing formulations, such as solutions, emulsions, suspensions, powders, foams, slurries or other coating compositions for seed, and also ULV formulations.

These formulations are prepared in a known manner, by mixing the active compounds or active compound combinations with customary additives, for example customary extenders and solvents or diluents, dyes, wetting agents, dispersants, emulsifiers, antifoams, preservatives, secondary thickeners, tackifiers, gibberellins, and also water.

Colorants which may be present in the seed-dressing formulations which can be used in accordance with the invention are all colorants which are customary for such purposes. In this context, not only pigments, which are sparingly soluble in water, but also dyes, which are soluble in water, may be used. Examples include the dyes known by the names Rhodamine B, C.I. Pigment Red 112 and C.I. Solvent Red 1.

Suitable wetting agents which may be present in the seed-dressing formulations which can be used in accordance with the invention are all substances which promote wetting and which are conventionally used for the formulation of agrochemical active compounds. Usable with preference are alkylnaphthalenesulfonates, such as diisopropyl- or diisobutyl-naphthalenesulfonates.

Suitable dispersants and/or emulsifiers which may be present in the seed-dressing formulations which can be used in accordance with the invention are all nonionic, anionic and cationic dispersants conventionally used for the formulation of agrochemical active compounds. Preference is given to using nonionic or anionic dispersants or mixtures of nonionic or anionic dispersants. Suitable nonionic dispersants include especially ethylene oxide/propylene oxide block polymers, alkylphenol polyglycol ethers and tristryrylphenol polyglycol ether, and the phosphated or sulfated derivatives thereof. Suitable anionic dispersants are, in particular, lignosulfonates, polyacrylic acid salts and arylsulfonate/formaldehyde condensates.

Antifoams which may be present in the seed-dressing formulations which can be used in accordance with the invention are all foam-inhibiting substances conventionally used for the formulation of agrochemically active compounds. Silicone antifoams and magnesium stearate can preferably be used.

Preservatives which may be present in the seed-dressing formulations which can be used in accordance with the invention are all substances which can be employed for such purposes in agrochemical compositions. Dichlorophene and benzyl alcohol hemiformal may be mentioned by way of example.

Secondary thickeners which may be present in the seed dressing formulations usable in accordance with the invention are all substances usable for such purposes in agrochemical compositions. Cellulose derivatives, acrylic acid derivatives, xanthan, modified clays and finely divided silica are preferred.

Adhesives which may be present in the seed-dressing formulations which can be used in accordance with the invention are all customary binders which can be employed in seed-dressing products. Polyvinylpyrrolidone, polyvinyl acetate, polyvinyl alcohol and tylose may be mentioned as being preferred.

Gibberellins which can be present in the seed-dressing formulations which can be used in accordance with the invention are preferably the gibberellins A1, A3 (=gibberellic acid), A4 and A7; gibberellic acid is especially preferably used. The gibberellins are known (cf. R. Wegler "Chemie der Pflanzenschutz- and Schädlingsbekämpfungsmittel" [Chemistry of the Crop Protection Compositions and Pesticides], vol. 2, Springer Verlag, 1970, pp. 401-412).

The seed-dressing formulations which can be used in accordance with the invention can be employed for the treatment of a wide range of seed, either directly or after previously having been diluted with water. Thus, the concentrates or the preparations obtainable therefrom by dilution with water may be used to dress the seed of cereals, such as wheat, barley, rye, oats, and triticale, and also the seed of corn, rice, oilseed rape, peas, beans, cotton, sunflowers, and beets, or else vegetable seed of any of a very wide variety of kinds. The seed-dressing formulations which can be used according to the invention or their dilute preparations may also be used to dress seed of transgenic plants. In this context, additional synergistic effects may also occur in cooperation with the substances formed by expression.

All mixers which can conventionally be employed for the seed-dressing operation are suitable for treating seed with the seed-dressing formulations which can be used in accordance with the invention or with the preparations prepared therefrom by addition of water. Specifically, the procedure in the seed dressing is to place the seed into a mixer, to add the particular desired amount of seed dressing formulations, either as such or after prior dilution with water, and to mix everything until the formulation is distributed homogeneously on the seed. If appropriate, this is followed by a drying process.

The application rate of the seed-dressing formulations which can be used according to the invention may be varied within a relatively wide range. It depends on the respective content of the active compounds in the formulations and on the seed. The active compound combination application rates are generally between 0.001 and 50 g per kilogram of seed, preferably between 0.01 and 15 g per kilogram of seed.

The compounds according to the invention can be used as such or in their formulations, also in a mixture with known fungicides, bactericides, acaricides, nematicides or insecticides, to broaden, for example, the activity spectrum or to prevent development of resistances.

A mixture with other known active compounds, such as herbicides, or with fertilizers and growth regulators, safeners and/or semiochemicals is also possible.

In addition, the compounds of the formula (I) according to the invention also have very good antimycotic activity. They have a very broad antimycotic activity spectrum, especially against dermatophytes and yeasts, molds and diphasic fungi (for example against *Candida* species, such as *Candida albicans, Candida glabrata*), and *Epidermophyton floccosum, Aspergillus* species, such as *Aspergillus niger* and *Aspergillus fumigatus, Trichophyton* species, such as *Trichophyton mentagrophytes, Microsporon* species such as *Microsporon canis* and *audouinii*. The list of these fungi by no means constitutes a restriction of the mycotic spectrum covered, and is merely of illustrative character.

Accordingly, the compounds according to the invention can be used both in medical and in non-medical applications.

The active compounds can be used as such, in the form of their formulations or the use forms prepared therefrom, such as ready-to-use solutions, suspensions, wettable powders, pastes, soluble powders, dusts and granules. Application is accomplished in a customary manner, for example by watering, spraying, atomizing, broadcasting, dusting, foaming, spreading, etc. It is also possible to apply the active compounds by the ultra-low volume method, or to inject the active compound preparation or the active compound itself into the soil.

It is also possible to treat the seed of the plants.

When using the compounds according to the invention as fungicides, the application rates can be varied within a relatively wide range, depending on the kind of application. For the treatment of parts of plants, the active compound application rates are generally between 0.1 and 10 000 g/ha, preferably between 10 and 1000 g/ha. For seed treatment, the active compound application rates are generally between 0.001 and 50 g per kilogram of seed, preferably between 0.01 and 10 g per kilogram of seed. For the treatment of the soil, the active compound application rates are generally between 0.1 and 10 000 g/ha, preferably between 1 and 5000 g/ha.

The treatment method according to the invention is preferably employed for genetically modified organisms such as, for example, plants or plant parts.

Genetically modified plants, so-called transgenic plants, are plants in which a heterologous gene has been stably integrated into the genome.

The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example antisense technology, cosuppression technology or RNAi technology [RNA interference]). A heterologous gene that is present in the genome is also called a transgene. A transgene that is defined by its particular location in the plant genome is called a transformation or transgenic event.

Depending on the plant species or plant varieties, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are suitable for mobilizing the defence system of the plant against attack by unwanted phytopathogenic fungi and/or microorganisms and/or viruses. This may, if appropriate, be one of the reasons for the enhanced activity of the combinations according to the invention, for example against fungi. Plant-strengthening (resistance-inducing) substances are to be understood as meaning, in the present context, also those substances or combinations of substances which are capable of stimulating the defence system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are understood as meaning phytopathogenic fungi, bacteria and viruses. Thus, the substances according to the invention can be employed for protecting plants against attack by the abovementioned pathogens within a certain period of time after the treatment. The period within which protection is achieved generally extends for from 1 to 10 days, preferably 1 to 7 days, after the treatment of the plants with the active compounds.

Plants and plant varieties which are preferably treated according to the invention include all plants which have genetic material which imparts particularly advantageous, useful traits to these plants (whether obtained by breeding and/or biotechnological means).

Plants which are furthermore preferably treated according to the invention are resistant against one or more biotic stress factors, i.e. said plants have a better defence against animal and microbial pests, such as against nematodes, insects, mites, phytopathogenic fungi, bacteria, viruses and/or viroids.

In addition to the plants and plant cultivars mentioned above, is also possible to treat those according to the invention which are resistant to one or more abiotic stress factors.

The abiotic stress conditions may include, for example, drought, cold and hot conditions, osmotic stress, waterlogging, elevated soil salinity, elevated exposure to minerals, ozone conditions, strong light conditions, limited availability of nitrogen nutrients, limited availability of phosphorus nutrients or avoidance of shade.

Plants and plant cultivars which can likewise be treated in accordance with the invention are those plants which are characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristics of heterosis, or hybrid vigor, which results in generally higher yield, increased vigor, better health and better resistance towards biotic and abiotic stress factors. Such plants are typically made by crossing an inbred male-sterile parent line (the female parent) with another inbred male-fertile parent line (the male parent). Hybrid seed is typically harvested from the male-sterile plants and sold to growers. Male-sterile plants can sometimes (e.g. in corn) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species. However, genetic determinants for male sterility can also be located in the nuclear genome. Male-sterile plants can also be obtained by plant biotechnology methods such as genetic engineering. A particularly useful means for obtaining male-sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar.

Plants or plant varieties (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp., the genes encoding a petunia EPSPS, a tomato EPSPS, or an eleusine EPSPS. It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyl transferase enzyme. Glyphosate-tolerant plants can also be obtained by selecting plants naturally-occurring mutations of the above-mentioned genes.

Other herbicide-resistant plants are for example plants which have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species for example). Plants expressing an exogenous phosphinothricin acetyltransferase have been described.

Further herbicide-tolerant plants are also plants that have been made tolerant to the herbicides inhibiting the enzyme hydroxyphenylpyruvatedioxygenase (HPPD). Hydroxyphenylpyruvate dioxygenases are enzymes that catalyze the reaction in which para-hydroxyphenylpyruvate (HPP) is transformed into homogentisate. Plants tolerant to HPPD inhibitors can be transformed with a gene encoding a naturally occurring resistant HPPD enzyme, or a gene encoding a mutated HPPD enzyme. Tolerance to HPPD inhibitors can also be obtained by transforming plants with genes encoding certain enzymes enabling the formation of homogentisate despite the inhibition of the native HPPD enzyme by the HPPD inhibitor. Tolerance of plants to HPPD inhibitors can also be improved by transforming plants with a gene encoding an enzyme prephenate dehydrogenase in addition to a gene encoding an HPPD-tolerant enzyme.

Further herbicide-resistant plants are plants that have been made tolerant to acetolactate synthase (ALS) inhibitors. Known ALS inhibitors include, for example, sulfonylurea, imidazolinone, triazolopyrimidines, pyrimidinyl oxy(thio) benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides. The production of sulfonylurea-tolerant plants and imidazolinone-tolerant plants is described in international publication WO 1996/033270. Further sulfonylurea- and imidazolinone-tolerant plants are also described, for example in WO 2007/024782.

Further herbicide-resistant plants are plants that have been made tolerant to ACCase inhibitors.

Other plants tolerant to imidazolinone and/or sulfonylurea can be obtained by induced mutagenesis, by selection in cell cultures in the presence of the herbicide or by mutation breeding.

Plants or plant varieties (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

In the present context, the term "insect-resistant transgenic plant" includes any plant containing at least one transgene comprising a coding sequence encoding the following:

1) an insecticidal crystal protein from *Bacillus thuringiensis* or an insecticidal portion thereof, such as the insecticidal crystal proteins described compiled online at: http://www.lifesci.sussex.ac.uk/Home/Neil_Crickmore/Bt/, or insecticidal portions thereof, e.g., proteins of the Cry protein classes Cry1Ab, Cry1Ac, Cry1F, Cry2Ab, Cry3Ae, or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins; or 3) a hybrid insecticidal protein comprising portions of two different insecticidal crystal proteins from *Bacillus thuringiensis*, such as a hybrid of the proteins of 1) above or a hybrid of the proteins of 2) above, for example the Cry1A.105 protein produced by corn event MON98034 (WO 2007/027777); or 4) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in corn events MON863 or MON88017, or the Cry3A protein in corn event MIR604; or 5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/Home/Neil_Crickmore/Bt/vip.html, for example proteins from the VIP3Aa protein class; or 6) a secreted protein from *Bacillus thuringiensis* or *Bacillus cereus* which is insecticidal in the presence of a second secreted protein from *Bacillus thuringiensis* oder *B. cereus*, such as the binary toxin made up of the VIP1A and VIP2A proteins.

7) a hybrid insecticidal protein comprising portions from different secreted proteins from *Bacillus thuringiensis* or *Bacillus cereus*, such as a hybrid of the proteins in 1) above or a hybrid of the proteins in 2) above; or 8) a protein of any one of points 1) to 3) above wherein some, particularly 1 to 10, amino acids have been replaced by another amino acid to obtain a higher insecticidal activity to a target insect species, and/or to expand the range of the target insect species affected, and/or because of changes induced in the encoding DNA during cloning or transformation (while still encoding an insecticidal protein), such as the VIP3Aa protein in cotton event COT 102.

Of course, insect-resistant transgenic plants, as used herein, also include any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected or to delay insect resistance development to the plants, by using different proteins insecticidal to the same target insect species but having a different mode of action, such as binding to different receptor binding sites in the insect.

Plants or plant varieties (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress-tolerance plants include the following:

a. plants which contain a transgene capable of reducing the expression and/or the activity of the poly(ADP-ribose) polymerase (PARP) gene in the plant cells or plants;
b. plants which contain a stress tolerance enhancing transgene capable of reducing the expression and/or the activity of the PARG encoding genes of the plants or plants cells;
c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant varieties (obtained by plant biotechnology methods such as genetic engineering) which may also be treated according to the invention show altered quantity, quality and/or storage stability in the harvested product and/or altered properties of specific compounds of the harvested product such as, for example:

1) Transgenic plants which synthesize a modified starch, which in its physical-chemical characteristics, in particular the amylose content or the amylose/amylopectin ratio, the degree of branching, the average chain length, the side chain distribution, the viscosity behavior, the gelling strength, the starch grain size and/or the starch grain morphology, is changed in comparison with the synthesised starch in wild-type plant cells or plants, so that this is better suited for special applications.
2) Transgenic plants which synthesize non-starch carbohydrate polymers or which synthesize non-starch carbohydrate polymers with altered properties in comparison to wild-type plants without genetic modification. Examples are plants which produce polyfructose, especially of the inulin and levan type, plants which produce alpha-1,4-glucans, plants which produce alpha-1,6-branched alpha-1,4-glucans, and plants producing alternan.
3) Transgenic plants which produce hyaluronan.

Plants or plant varieties (obtained by plant biotechnology methods such as genetic engineering) which may also be treated according to the invention are plants, such as cotton plants, with altered fiber characteristics. Such plants can be obtained by genetic transformation, or by selection of plants containing a mutation imparting such altered fiber characteristics and include:

a) plants, such as cotton plants, containing an altered form of cellulose synthase genes;
b) plants, such as cotton plants, containing an altered form of rsw2 or rsw3 homologous nucleic acids;
c) plants, such as cotton plants, with increased expression of sucrose phosphate synthase;
d) plants, such as cotton plants, with increased expression of sucrose synthase;
e) plants, such as cotton plants, wherein the timing of the plasmodesmatal gating at the basis of the fiber cell is altered, e.g. through downregulation of fiber-selective β-1,3-glucanase;
f) plants, such as cotton plants, having fibers with altered reactivity, e.g. through the expression of N-acetylglucosaminetransferase gene including nodC and chitin synthase genes.

Plants or plant varieties (obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants containing a mutation imparting such altered oil characteristics, and include:

a) plants, such as oilseed rape plants, producing oil having a high oleic acid content;
b) plants, such as oilseed rape plants, which produce oil having a low linolenic acid content;
c) plants, such as oilseed rape plants, producing oil having a low level of saturated fatty acids.

Particularly useful transgenic plants which may be treated according to the invention are plants which comprise one or more genes which encode one or more toxins and are the transgenic plants available under the following trade names: YIELD GARD® (for example corn, cotton, soybeans), KnockOut® (for example corn), BiteGard® (for example corn), BT-Xtra® (for example corn), StarLink® (for example corn), Bollgard® (cotton), Nucotn® (cotton), Nucotn 33B® (cotton), NatureGard® (for example corn), Protecta® and NewLeaf® (potatoes). Examples of herbicide-tolerant plants which may be mentioned are corn varieties, cotton varieties and soybean varieties which are available under the following trade names: Roundup Ready® (glyphosate tolerance, for example corn, cotton, soybean), Liberty Link® (phosphinotricin tolerance, for example oilseed rape), IMI® (imidazolinone tolerance) and SCS® (sulfonylurea tolerance), for example corn. Herbicide-resistant plants (plants bred in a conventional manner for herbicide tolerance) which should be mentioned include the varieties sold under the Clearfield® name (for example corn).

Particularly useful transgenic plants which may be treated according to the invention are plants containing transformation events, or a combination of transformation events, and that are listed for example in the databases for various national or regional regulatory agencies (see for example http://gmoinfo.jrc.it/gmp_browse.aspx and http://www.agbios.com/dbase.php).

The term "active compounds" or "compounds" always also includes the active compound combinations mentioned here.

PREPARATION EXAMPLES

Example (I-1-a-1)

Process A

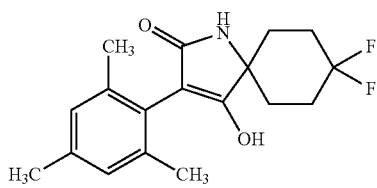 [SMILES: Cc1cc(C)c(C2=C(O)C3(CCC(F)(F)CC3)NC2=O)c(C)c1]

1.52 g (4 2 mmol) of the compound according to Example II-1-a-1 are initially charged in a solution of 5 ml of DMA (N,N-dimethylacetamide), a solution of 5 ml of DMA and 1.1 g (2.2 eq) of potassium t-butoxide is added dropwise at 0° C. and the mixture is stirred at room temperature for 24 h. The mixture is poured into 200 ml of water and the reaction is adjusted to pH=2 using concentrated hydrochloric acid, and the resulting residue is filtered off with suction. Purification by column chromatography (RP silica gel gradient acetonitrile/water) gives the product (I-1-a-1) according to the invention=600 mg (43% of theory) of melting point m.p. 257° C.

$^1$H NMR (400 MHz, $d_6$-DMSO): δ=1.51-1.54 (d, br, 2H), 2.04 (s, 6H, ArCH$_3$), 2.07-2.32 (m, 6H), 2.23 (s, 3H, ArCH$_3$), 6.84 (s, 2H, ArH), 8.19 (s, br, 1H, NH), 10.8 (s, br, 1H, OH) ppm.

Example I-1-a-9

Process J

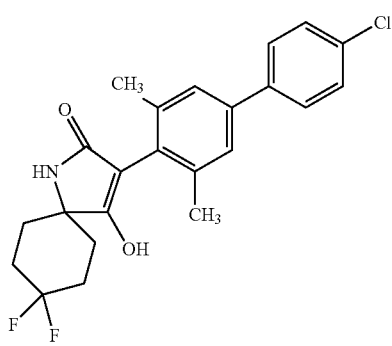 [SMILES: Cc1cc(-c2ccc(Cl)cc2)cc(C)c1C1=C(O)C2(CCC(F)(F)CC2)NC1=O]

0.424 g (1 mmol) of the compound from Ex. I-1-5-a is initially charged in 4.3 ml of ethylene glycol dimethyl ether, 7.2 ml of 2M sodium carbonate solution are added dropwise and 6 mg of bis(trisphenylphosphine)palladium(II) chloride are added. 0.25 g (1 6 mmol) of 4-chlorophenylboronic acid is then added, and the mixture is stirred under reflux overnight. After cooling, the mixture was acidified with 2N hydrochloric acid and extracted with ethyl acetate, and the extract is dried and concentrated. Purification is carried out by MPLC separation on silica gel using the mobile phase hexane+ethyl acetate 1:1.

Yield: 0.24 g (=48% of theory), m.p. 243° C.

Example I-1-a-8

Process K

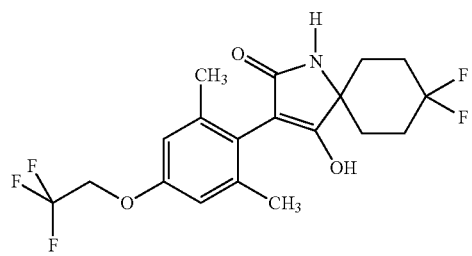 [SMILES: Cc1cc(OCC(F)(F)F)cc(C)c1C1=C(O)C2(CCC(F)(F)CC2)NC1=O]

0.424 g (1.0 mmol) of the compound according to Example (I-1-a-5) are dissolved in 3.5 ml of DMA, and 0.236 g (2 eq) of potassium t-butoxide is added (solution 1). Furthermore, under inert gas, 0.19 g (1 eq) of copper(I) iodide and 0.8 g (8 eq) of 2,2,2-trifluoroethanol are suspended in 6 ml of DMA, and 0.65 g (5.5 eq) of potassium t-butoxide is added. Solution 1 is added dropwise at 70° C. and the mixture is stirred under reflux (125° C.) overnight. Under reduced pressure, the reaction mixture is freed from the solvent, water is added and the residue that remains is separated off and discarded. Using 1N hydrochloric acid, the aqueous phase is adjusted to pH 1, and the residue formed is filtered off. Purification by column chromatography (RP silica gel, gradient water/methanol) gives 0.276 g=64% of theory of the compound I-1-a-8 according to the invention of m.p. 253° C.

The following compounds of the formula (I-1-a) are obtained analogously to Example (I-1-a-1), (I-1-a-8), (I-1-a-9) and following the general preparation instructions:

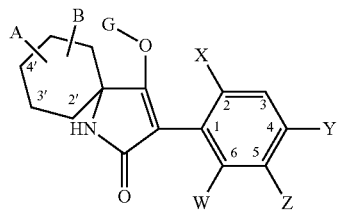

(I-1-a)

| Ex. No. | W | X | Y | Z | A | B | m.p. ° C. | Process |
|---|---|---|---|---|---|---|---|---|
| I-1-a-2 | CH$_3$ | CH$_3$ | H | 4-F—Ph | 4'-F | 4'-F | 296 | A |
| I-1-a-3 | H | CH$_3$ | H | 4-F—Ph | 4'-F | 4'-F |  | A |
| I-1-a-4 | H | Cl | H | 4-Cl—Ph | 4'-F | 4'-F | 160 | A |
| I-1-a-5 | CH$_3$ | CH$_3$ | Br | H | 4'-F | 4'-F | 272-274 | A |
| I-1-a-6 | H | CH$_3$ | H | 4-Cl—Ph | 4'-F | 4'-F | 105 | A |

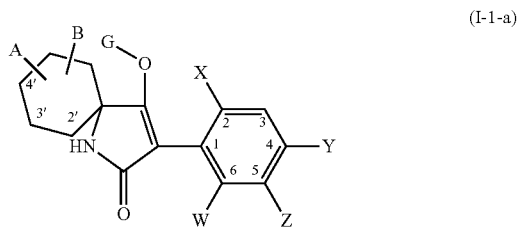

(I-1-a)

| Ex. No. | W | X | Y | Z | A | B | m.p. °C | Process |
|---|---|---|---|---|---|---|---|---|
| I-1-a-7 | CH₃ | CH₃ | Cl | H | 4'-F | 4'-F | 269-271 | A |
| I-1-a-8 | CH₃ | CH₃ | OCH₂CF₃ | H | 4'-F | 4'-F | 249-253 | K |
| I-1-a-9 | CH₃ | CH₃ | 4-Cl-Ph | H | 4'-F | 4'-F | 243-244 | I |
| I-1-a-10 | CH₃ | CH₃ | H | 4-Cl—Ph | 4'-F | 4'-F | 141-145 | A |
| I-1-a-11 | CH₃ | C2H5 | CH₃ | H | 4'-F | 4'-F | 88 | A |
| I-1-a-12*¹ | CH₃ | CH₃ | H | 4-F—Ph | 4'-F | bond | 263 | A |
| I-1-a-13*² | CH₃ | CH₃ | Cl | H | 4'-F | bond | | A |
| I-1-a-14 | H | CH₃ | H | Br | 4'-F | 4'-F | | A |
| I-1-a-15 | H | CH₃ | H | 3,4-F₂—Ph | 4'-F | 4'-F | 223 | I |
| I-1-a-16 | H | CH₃ | H | 3-F,4-Cl—Ph | 4'-F | 4'-F | | I |

*¹This compound was obtained as a byproduct in the preparation of Example (I-1-a-2) in a yield of 4%.
*²This compound was obtained as a byproduct in the preparation of Example (I-1-a-7) in a yield of 1%.

Analysis:

I-1-a-2

$^1$H NMR (400 MHz, $d_6$-DMSO): δ=1.55-1.59 (cm, 2H), 1.98 (s, 3H, ArCH₃), 2.10-2.28 (m, 6H) 2.13 (s, 3H, ArCH₃), 7.02-7.04 (d, 1H, ArH), 7.09-7.11 (d, 1H, ArH), 7.19-7.25 (m, 2H, ArH), 7.27-731 (m, 2H, ArH), 8.10 (s, br, 1H, NH), 10.74 (s, br, 1H, OH) ppm.

I-1-a-3

$^1$H NMR (400 MHz, $d_6$-DMSO): δ=1.55-1.57 (m, br, 2H), 2.07-2.30 (m, 6H), 2.19 (s, 3H, ArCH₃), 7.24-7.34 (m, 4H), 7.45-7.47 (dd, 1H, ArH), 7.63-7.67 (m, 2H, ArH), 8.28 (s, br, 1H, NH), 11.05 (s, br, 1H, OH) ppm.

I-1-a-4

$^1$H NMR (600 MHz, $d_6$-DMSO): δ=1.50-1.52 (d, br, 2H), 2.03-2.18 (m, 6H), 7.46-7.50 (m, 3H, ArH), 7.56-7.57 (dd, 1H, ArH), 7.62-7.64 (m, 2H, ArH), 8.35 (s, br, 1H, NH), 11.3 (s, br, 1H, OH) ppm.

I-1-a-5

$^1$H NMR (400 MHz, $d_6$-DMSO): δ=1.53-1.55 (d, br, 2H), 2.08 (s, 6H, ArCH₃), 2.10-2.26 (m, 6H) 7.26 (s, 2H, ArH), 8.28 (s, br, 1H, NH), 11.0 (s, br, 1H, OH) ppm.

I-1-a-6

$^1$H NMR (400 MHz, $d_6$-DMSO): δ=1.54-1.56 (d, br, 2H), 2.07-2.33 (m, 6H), 2.19 (s, 3H, ArCH₃), 7.29-7.31 (d, 1H, ArH), 7.36 (d, 1H, ArH), 7.48-7.53 (m, 3H, ArH), 7.64-7.71 (m, 2H, ArH), 8.28 (s, br, 1H, NH), 11.5 (s, br, 1H, OH) ppm.

I-1-a-7

$^1$H NMR (400 MHz, $d_6$-DMSO): δ=1.53-1.55 (d, br, 2H), 2.09 (s, 6H, ArCH₃), 2.11-2.27 (m, 6H), 7.12 (s, 2H, ArH), 8.28 (s, br, 1H, NH), 10.99 (s, br, 1H, OH) ppm.

I-1-a-8

$^1$H NMR (601 MHz, $d_6$-DMSO): δ=1.51-1.53 (d, br, 2H), 2.07 (s, 6H, ArCH₃), 2.05-2.27 (m, 6H), 3.29-3.35 (q, 2H, O—CH₂CF₃), 6.76 (s, 2H, ArH), 8.27 (s, br, 1H, NH), 10.88 (s, br, 1H, OH) ppm.

I-1-a-9

$^1$H NMR (400 MHz, $d_6$-DMSO): δ=1.54-1.57 (d, br, 2H), 2.09-2.33 (m, 6H), 2.16 (s, 6H, ArCH₃), 7.34 (s, 2H, ArH), 7.49-7.51 ("d", 2H, ArH), 7.67-7.69 ("d", 2H, ArH), 8.26 (s, br, 1H, NH), 10.96 (s, br, 1H, OH) ppm.

I-1-a-10

$^1$H NMR (400 MHz, $d_6$-DMSO): δ=1.55 (cm, br, 2H), 2.07-2.33 (m, 6H), 1.98 (d, 3H, ArCH₃), 2.13 (s, 3H, ArCH₃), 7.03-7.05 (d, 1H, ArH), 7.11-7.13 (d, 1H, ArH), 7.28-7.31 (m, 2H, ArH), 7.46-7.49 (m, 2H, ArH), 8.22 (s, br, 1H, NH), 10.95 (s, br, 1H, OH) ppm.

I-1-a-11

$^1$H NMR (400 MHz, $d_6$-DMSO): δ=1.01 (t, 3H, CH₂$\underline{CH_3}$), 1.48-1.54 (t, br, 2H), 2.03 (s, 3H, ArCH₃), 2.07-2.28 (m, 6H), 2.25 (s, 3H, ArCH₃), 2.34-2.40 (q, 2H, $\underline{CH_2}$—CH₃), 6.85 (s, 2H, ArH), 8.21 (s, br, 1H, NH), 10.77 (s, br, 1H, OH) ppm.

I-1-a-12

$^1$H NMR (400 MHz, $d_6$-DMSO): δ=1.57-1.68 (m, 1H), 1.87-1.96 (m, 1H), 1.98, 1.99 (2s, 3H, ArCH₃), 2.12-2.21 (m, 2H), 2.15, 2.16 (2s, in each case 3H, ArCH₃), 2.25-2.33 (m, 1H), 2.68-2.78 (m, 1H), 5.22-5.27 (d, m, 1H —CF═$\underline{CH}$—), 7.02-7.04 (d, 1H, ArH), 7.09-7.11 (d, 1H, ArH), 7.19-7.25 (m, 2H, ArH), 7.28-7.31 (m, 2H, ArH), 7.74 (s, br, 1H, NH), 10.65 (s, br, 1H, OH) ppm.

I-1-a-13

$^1$H NMR (400 MHz, $d_6$-DMSO): δ=1.55-1.63 (m, 1H), 1.87-1.91 (d, m, 1H), 2.07-2.17 (m, 2H), 2.09, 2.10 (2s, 6H, ArCH₃), 2.25-2.33 (m, 1H), 2.67-2.73 (m, 1H), 5.23-5.28 (d m, 1H, —CF═$\underline{CH}$—), 7.12 (s, 2H, ArH), 8.01 (s, br, 1H, NH), 10.88 (s, br, 1H, OH) ppm.

I-1-a-14

$^1$H NMR (400 MHz, $d_6$-DMSO): δ=1.53-1.56 (m, 2H), 1.92-2.23 (m, 6H), 2.11 (s, 3H), 7.17-7.19 (d, 1H), 7.24 (d, 1H), 7.36-7.40 (dd, 1H), 8.80 (s, 1H), 11.2 (s, 1H) ppm.

I-1-a-15

$^1$H NMR (600 MHz, $d_6$-DMSO): δ=1.56-1.58 (d, br, 2H), 2.07-2.26 (m, 6H), 2.19 (s, 3H, ArCH₃), 7.30-7.2 (d, 1H, ArH), 7.37 (d, 1H, ArH), 7.48-7.53 (m, 4H, ArH), 7.68-7.73 (m, 1H, ArH), 8.36 (s, br, 1H, NH), 11.8 (s, br, 1H, OH) ppm.

I-1-a-16

$^1$H NMR (400 MHz, $d_6$-DMSO): δ=1.50-1.62 (m, 2H), 2.05-2.31 (m, 6H), 2.20 (s, 3H), 7.32 (d, 1H), 7.41 (d, 1H), 7.49-7.57 (m, 2H), 7.64 (t, 1H), 7.69 (dd, 1H), 8.32 (s, 1H), 11.08 (s, 1H) ppm.

Example (I-1-b-1)

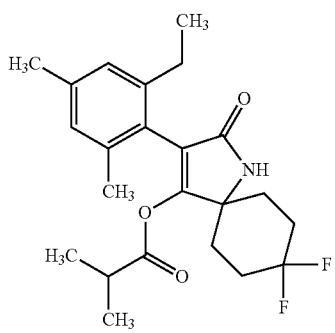

(I-1-b-1)

0.2 g (0 6 mmol) of the compound according to Example (I-1-a-11) is initially charged in 8 ml of ethyl acetate, and 0.116 g of triethylamine (1.5 eq) and 0.01 g of DMAP (0.15 eq) are added. At 60° C., a solution of 0.076 g (1.2 eq) of isobutyryl chloride in 2 ml of ethyl acetate is then added dropwise over a period of 60 min. The mixture is stirred at 60° C. for 5 h and then allowed to stir at room temperature overnight. After addition of 3 ml of water, the organic phase is separated off, dried and concentrated. The residue obtained is purified by column chromatography (silica gel, mobile phase: n-heptane/ethyl acetate, gradient:10:1 to 0:100). This gives 0.15 g (59% of theory) of the target compound (I-1-b-1)

$^1$H NMR (400 MHz, CDCl$_3$): δ=7.52 (s (broad), 1H, NH), 6.86 (d, 2H, Ar—H), 2.50 (m, 3H, C$\underline{H}_2$—Ar, C$\underline{H}$—(CH$_3$)$_2$), 2.23 (s, 3H, Ar—CH$_3$), 2.16 (s, 3H, Ar—CH$_3$), 2.30-1.90 (plurality of signals, 6H), 1.79 (m, 2H), 1.12 (t, 3H, CH$_2$—C$\underline{H}_3$), 0.99 (m, 6H, CH—(C$\underline{H}_3$)$_2$)ppm.

Example (I-1-c-1)

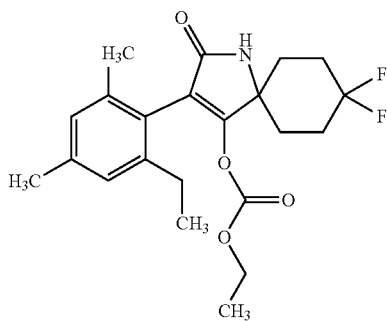

(I-1-c-1)

0.2 g (0.6 mmol) of the compound according to Example (I-1-a-11) is initially charged in 10 ml of dichloromethane, and 0.078 g (1.3 eq) of triethylamine is added. 0.071 g (1.1 eq) of ethyl chloroformate is then added dropwise, and the mixture is stirred at room temperature for 24 h. 5 ml of five percent strength sodium bicarbonate solution are added, the mixture is allowed to stir for 30 min, the organic phase is separated off and dried and the solvent is removed under reduced pressure. The residue obtained in this manner is purified by column chromatography (silica gel, mobile phase: n-heptane/ethyl acetate, gradient:10:1 to 0:100). This gives 0.10 g (39% of theory) of the target compound (I-1-c-1).

$^1$H NMR (400 MHz, CDCl$_3$): δ=7.69 (s, (broad), 1H, NH), 6.89 (d, 2H, Ar—H), 4.02 (m, 2H, O—CH$_2$), 2.50 (m, 2H, C$\underline{H}_2$—Ar), 2.24 (s, 3H, Ar—CH$_3$), 2.16 (s, 3H, Ar—CH$_3$), 2.20-1.90 (plurality of signals, 6H), 1.77 (m, 2H), 1.17 (t, 3H, O—CH$_2$—C$\underline{H}_3$), 1.10 (m, 3H, Ar—CH$_2$—C$\underline{H}_3$) ppm.

Example II-1

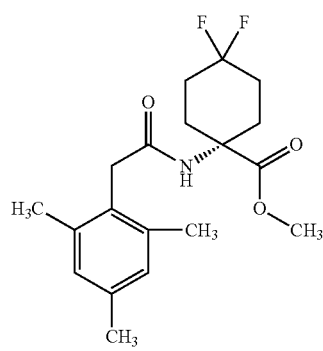

1.26 g (5.5 mmol) of methyl 4,4-difluoro-1-aminocyclohexanecarboxylate (XVI-1) and 1.24 g (11 mmol) of triethylamine are initially charged in 50 ml of tetrahydrofuron, and a solution of 1 g (5 mmol) of mesitylacetyl chloride in 5 ml of tetrahydrofuron is added dropwise at 20° C. over a period of 1 h. After 4 h of stirring at 40° C., the mixture is concentrated and purified by column chromatography on silica gel using a methylene chloride/ethyl acetate gradient. This gives 1.6 g (75% of theory) of Example II-1 of melting point m.p. 160° C.

$^1$H NMR (400 MHz, CD$_3$CN): δ=1.82-2.16 (m, 8H), 2.22 (s, 3H, ArCH$_3$) 2.24 (s, 6H, ArCH$_3$), 3.55 (s, 2H, COCH$_2$), 3.60 (s, 3H, OCH$_3$), 6.41 (s, br, 1H, NH), 6.85 (s, 2H, ArH) ppm.

The following compounds of the formula (II) are obtained analogously to Example (II-1) and following the general preparation instructions:

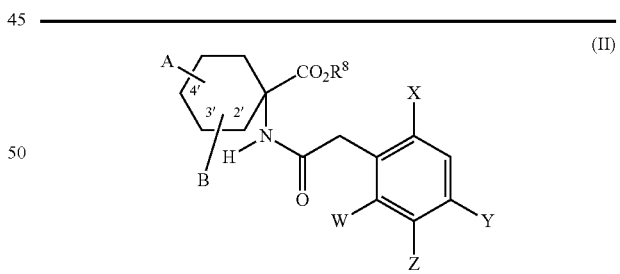

(II)

| Ex. No. | W | X | Y | Z | A | B | R$^8$ | m.p. °C. |
|---|---|---|---|---|---|---|---|---|
| II-2 | CH$_3$ | CH$_3$ | H | 4-F—Ph | 4'-F | 4'-F | CH$_3$ | 168 |
| II-3 | H | CH$_3$ | H | 4-F—Ph | 4'-F | 4'-F | CH$_3$ | 187 |
| II-4 | H | Cl | H | 4-Cl—Ph | 4'-F | 4'-F | CH$_3$ | 146-147 |
| II-5 | CH$_3$ | CH$_3$ | Br | H | 4'-F | 4'-F | CH$_3$ | 171-172 |
| II-6 | CH$_3$ | CH$_3$ | H | 4-Cl—Ph | 4'-F | 4'-F | CH$_3$ | 179-183 |
| II-7 | H | CH$_3$ | H | 4-Cl—Ph | 4'-F | 4'-F | CH$_3$ | 185-186 |
| II-8 | CH$_3$ | CH$_3$ | Cl | CH$_3$ | 4'-F | 4'-F | CH$_3$ | 172-175 |
| II-9 | CH$_3$ | C$_2$H$_5$ | CH$_3$ | H | 4'-F | 4'-F | CH$_3$ | 135 |
| II-10 | H | CH$_3$ | Br | H | 4'-F | 4'-F | CH$_3$ | |

3.58 (s, 3H, CO₂CH₃), 7.11-7.13 (d, 1H, ArH), 7.31-7.33 (dd, 1H, ArH), 7.39-7.40 (d, 1H, ArH), 8.54 (s, br, 1H, NH) ppm.

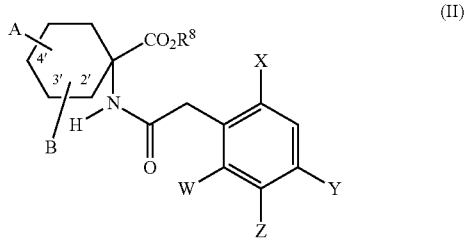

| Ex. No. | W | X | Y | Z | A | B | R⁸ | m.p. °C. |
|---|---|---|---|---|---|---|---|---|

Ph = phenyl

Analysis:

II-2

¹H NMR (400 MHz, CD₃CN): δ=1.83-2.17 (m, 8H), 2.14 (s, 3H, ArCH₃), 2.33 (s, 3H, ArCH₃), 3.61 (s, 3H, CO₂CH₃), 3.69 (s, 2H, COC$\underline{H_2}$), 6.55 (s, br, 1H, NH), 6.99-7.01 (d, 1H, ArH), 7.07-7.09 (d, 1H, ArH), 7.11-7.15 (m, 2H, ArH), 7.25-7.28 (m, 2H, ArH) ppm.

II-3

¹H NMR (400 MHz, d₆-DMSO): δ=1.88-2.14 (m, 8H), 2.27 (s, 3H, ArCH₃), 3.54 (s, 3H, CO₂CH₃), 3.59 (s, 2H, COC$\underline{H_2}$), 7.22-7.29 (m, 3H, ArH), 7.40-7.42 (m, 1H, ArH), 7.48-7.49 (m, 1H, ArH), 7.63-7.66 (m, 2H, ArH), 8.48 (s, br, 1H, NH) ppm.

II-4

¹H NMR (400 MHz, d₆-DMSO): δ=1.89-2.17 (m, 8H), 3.56 (s, 3H, CO₂CH₃), 3.74 (s, 2H, COC$\underline{H_2}$), 7.49-7.59 (m, 4H, ArH), 7.67-7.71 (m, 3H, ArH), 8.56 (s, br, 1H, NH) ppm.

II-5

¹H NMR (400 MHz, d₆-DMSO): δ=1.88-1.92 (m, 2H), 1.99-2.02 (m, 4H), 2.10-2.13 (dm, 2H), 2.23 (s, 6H, ArCH₃), 3.55 (s, 3H, CO₂CH₃), 3.56 (s, 2H, COC$\underline{H_2}$), 7.12 (s, 2H, ArH), 8.49 (s, br, 1H, NH) ppm.

II-6

¹H-NMR (400 MHz, d₆-DMSO): δ=1.89-2.15 (m, 8H), 2.11 (s, 3H, ArCH₃), 2.28 (s, 3H, ArCH₃), 3.55 (s, 3H, COCH₃) 3.68 (s, 2H, COCH₂), 6.94-6.96 (d, 1H, ArH), 7.05-7.07 (d, 1H, ArH), 7.26-7.28 ("d", 2H, ArH), 7.46-7.48 ("d", 2H, ArH), 8.46 (s, br, 1H, NH) ppm.

II-7

¹H NMR (400 MHz, d₆-DMSO): δ=1.87-2.07 (m, 6H), 2.11-2.15 (dm, 2H), 2.28 (s, 3H, ArCH₃), 3.55 (s, 3H, CO₂CH₃), 3.60 (s, 2H, COC$\underline{H_2}$), 7.23-7.25 (d, 1H, ArH), 7.43-7.45 (dd, 1H, ArH), 7.49-7.52 (m, 3H, ArH), 7.63-7.66 (m, 2H, ArH), 8.49 (s, br, 1H, NH) ppm.

II-8

¹H NMR (400 MHz, d₆-DMSO): δ=1.87-2.07 (m, 6H), 2.10-2.14 (dm, 2H), 2.23 (s, 6H, ArCH₃), 3.55 (s, 3H, CO₂CH₃), 3.57 (s, 2H, COC$\underline{H_2}$), 7.06 (s, 2H, ArH), 8.44 (s, br, 1H, NH) ppm.

II-9

¹H NMR (400 MHz, d₆-DMSO): δ=1.09 (t, 3H, CH₂C$\underline{H_3}$), 1.86-2.04 (m, 6H), 2.09-2.13 (dm, 2H), 2.18 (s, 3H, ArCH₃), 2.20 (s, 3H, ArCH₃), 2.51-2.57 (qm, 2H, C$\underline{H_2}$CH₃), 3.54 (s, 5H, CO₂CH₃, CO₂C$\underline{H_2}$), 6.79 (s, 2H, ArH), 8.36 (s, br, 1H, NH) ppm.

II-10

¹H NMR (400 MHz, d₆-DMSO): δ=1.91-2.02 (m, 6H), 2.09-2.13 (m, 2H), 2.19 (s, 3H, ArCH₃), 3.54 (s, 2H, COCH₂),

Example (I-2-a-1)

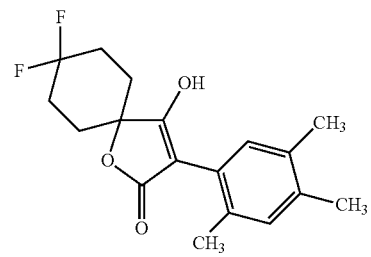 [SMILES: Cc1cc(C)c(C2=C(O)C3(CCC(F)(F)CC3)OC2=O)cc1C]

183 mg (1.63 mmol) of potassium tert-butoxide are initially charged in 5 ml of dimethylformamide, a solution of 400 mg (1.01 mmol) of the compound according to Example (III-1) in 5 ml of dimethylformamide is added dropwise at room temperature and the mixture is stirred for 16 h. For work-up, the solvent is removed under reduced pressure, the residue is partitioned between water and methyl tert-butyl ether and the aqueous phase is acidified with hydrochloric acid and extracted with dichloromethane. The organic phase is dried and concentrated.

The crude product is purified by means of column chromatography on RP-18 silica gel (mobile phase gradient acetonitrile/water/formic acid).

Yield: 84 mg (24% of theory)

¹H NMR (400 MHz, CDCl₃): δ=2.15-2.38 (m, 8H), 2.18 (s, 3H), 2.23 (s, 3H), 2.24 (s, 3H), 6.95 (s, 1H), 7.08 (s, 1H) ppm.

The following compounds of the formula (I-2-a) are obtained analogously to Example (I-2-a-1) and following the general preparation instructions:

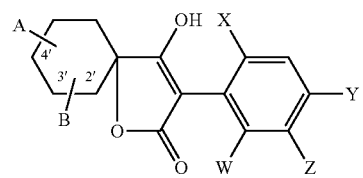

| Ex. No. | W | X | Y | Z | A | B |
|---|---|---|---|---|---|---|
| I-2-a-2 | CH₃ | CH₃ | H | 4-F—Ph | 4'-F | 4'-F |
| I-2-a-3 | H | CH₃ | H | 4-Cl—Ph | 4'-F | 4'-F |
| I-2-a-4 | CH₃ | CH₃ | CH₃ | H | 4'-F | 4'-F |

Analysis:

I-2-a-2

¹H NMR (400 MHz, d₆-DMSO): δ=1.7-2.3 (m, 8H), 2.0 (s, 3H), 2.18 (s, 3H), 7.07-7.34 (m, 6H) ppm.

I-2-a-3

¹H NMR (400 MHz, d₇-DMF): δ=1.9-2.3 (m, 8H), 2.38 (s, 3H), 7.38 (m, 1H), 7.56 (m, 3H), 7.61 (m, 1H), 7.73 (m, 2H) ppm.

I-2-a-4

$^1$H NMR (400 MHz, $d_6$-DMSO): δ=1.78-2.28 (m, 8H), 2.07 (s, 6H), 2.22 (s, 3H), 6.89 (s, 2H) ppm.

Example (I-2-b-1)

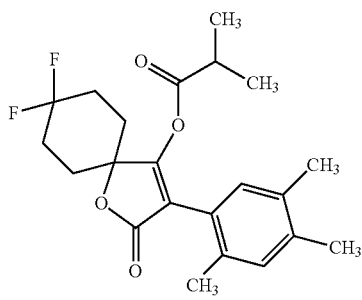

(I-2-b-1)

100 mg (0.31 mmol) of the compound according to Example (I-2-a-1) and 38 mg (0.37 mmol) of triethylamine are initially charged in 5 ml of dichloromethane, 40 mg (0.37 mmol) of 2-methylpropionyl chloride are added and the mixture is stirred at room temperature for 16 h. For work-up, the solvent is removed under reduced pressure and the crude mixture is purified by means of column chromatography on RP-18 silica gel (mobile phase gradient acetonitrile/water/formic acid).

Yield: 60 mg (49% of theory)

$^1$H NMR (400 MHz, $d_6$-DMSO): δ=1.0 (d, 6H), 1.9-2.2 (m, 8H), 2.10 (s, 3H), 2.18 (s, 3H), 2.2 (s, 3H), 2.72 (m, 1H), 6.82 (s, 1H), 7.02 (s, 1H) ppm.

Example (III-1)

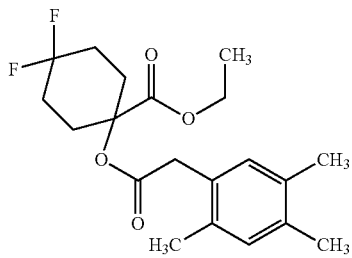

(III-1)

833 mg (4 mmol) of ethyl 1-hydroxy 4,4'-difluorocyclohexanecarboxylate and 787 mg (4 mmol) of the 2,4,5-trimethylphenylacetyl chloride in 30 ml of toluene are heated at reflux for 16 h. For work-up, the solvent is removed under reduced pressure, the residue is partitioned between 5% strength aqueous sodium hydroxide solution and methyl tert-butyl ether and the organic phase is dried and concentrated.

The crude product is purified by means of column chromatography on silica gel (mobile phase cyclohexane/ethyl acetate 100:15).

Yield: 400 mg (27% of theory)

$^1$H NMR (400 MHz, $d_6$-DMSO): δ=1.12 (t, 3H), 1.7-2.0 (m, 8H), 2.15 (s, 6H), 2.18 (s, 3H), 3.65 (s, 2H), 4.1 (q, 2H), 6.93 (s, 1H), 6.97 (s, 1H) ppm.

Example XVI-1

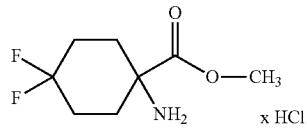

Under argon, 4.3 g of the compound according to Example XVII-1 are initially charged in 100 ml of methanol at 0 to 5° C. 10 ml of thionyl chloride are added dropwise, and the mixture is stirred at 0° C. for 30 minutes and at 70° C. for 24 h. The mixture is then cooled to 5° C. and the precipitate is filtered off with suction. The solution is concentrated using a rotary evaporator and the residue is crystallized using methyl tert-butyl ether.

Yield: 5.2 g quantitative, still contains salts $^1$H NMR (400 MHz, $d_6$-DMSO): δ=1.97-2.33 (m, 6H), 2.14-2.17 (dm, 2H), 3.78 (s, 3H, $CO_2CH_3$), 9.00 (br, 3H, $NH_3^+$) ppm.

Example XVII-1

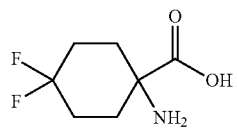

Under nitrogen gas, 4.1 g of the compound according to Example XVIII-1 are suspended in 100 ml of 30% strength KOH, and the mixture is stirred at reflux overnight.

The mixture is concentrated to about 25% of its original volume using a rotary evaporator and, at 0-10° C., adjusted to pH 5.5 with conc. HCl. The solution is concentrated using a rotary evaporator and dried. The residue (4.3 g) is directly esterified to XVI-1.

Example XVIII-1

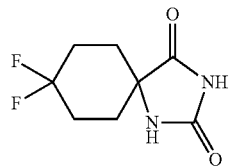

Ammonium carbonate (33 g) and sodium cyanide (3.5 g) are initially charged in 100 ml of water. Starting at room temperature, 7.7 g of 4,4'-difluorocyclohexanone are added dropwise and the reaction mixture is stirred at 55° C. to 60° C. for 24 hours and then at 0 to 5° C. for two hours, and the precipitate is filtered off with suction, washed with a little ice-water and dried.

Yield: 10.1 g (88% of theory)

$^1$H NMR (400 MHz, $CD_3OD$): δ=1.77-1.84 (m, 2H), 1.93-2.09 (m, 4H), 2.17-2.28 (m, 2H) ppm.

USE EXAMPLES

Example 1

Phaedon Test (PHAECO Spray Treatment)

Solvents: 78.0 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration. Disks of Chinese cabbage (*Brassica pekinensis*) are sprayed with an active compound preparation of the desired concentration and, after drying, populated with larvae of the mustard beetle (*Phaedon cochleariae*).

After 7 days, the effect in % is determined 100% means that all beetle larvae have been killed; 0% means that none of the beetle larvae have been killed.

In this test, for example, the following compounds of the Preparation Examples show, at an application rate of 500 g/ha, an effect of 100%: I-1-a-2, I-1-a-3, I-1-a-4, I-1-a-5, I-1-a-6, I-1-a-7, I-1-a-8, I-1-a-9, I-1-a-12, I-1-a-13, I-1-a-15, I-1-a-16, I-2-a-2, I-2-a-3, I-2-a-4.

Example 2

*Spodoptera frugiperda* Test (SPODFR Spray Treatment)

Solvents: 78.0 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration. Disks of corn leaves (*Zea mays*) are sprayed with an active compound preparation of the desired concentration and, after drying, populated with caterpillars of the armyworm (*Spodoptera frugiperda*).

After 7 days, the effect in % is determined. 100% means that all caterpillars have been killed; 0% means that none of the caterpillars have been killed.

In this test, for example, the following compounds of the Preparation Examples show, at an application rate of 500 g/ha, an effect of 83%: I-1-a-1, I-2-b-1

In this test, for example, the following compounds of the Preparation Examples show, at an application rate of 500 g/ha, an effect of 100%: I-1-a-2, I-1-a-3, I-1-a-4, I-1-a-6, I-1-a-12, I-1-a-16, I-2-a-2, I-2-a-3.

Example 3

*Myzus* Test (MYZUPE Spray Treatment)

Solvents: 78 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration. Disks of Chinese cabbage (*Brassica pekinensis*) infested by all stages of the green peach aphid (*Myzus persicae*) are sprayed with an active compound formulation of the desired concentration.

After 6 days, the effect in % is determined. 100% means that all of the aphids have been killed; 0% means that none of the aphids have been killed.

In this test, for example, the following compounds of the Preparation Examples show, at an application rate of 500 g/ha, an effect of 90%: I-1-a-3, I-1-a-4, I-1-a-16, I-1-c-1, I-2-a-3.

In this test, for example, the following compounds of the Preparation Examples show, at an application rate of 500 g/ha, an effect of 100%: I-1-a-1, I-1-a-2, I-1-a-5, I-1-a-6, I-1-a-7, I-1-a-8, I-1-a-9, I-1-a-10, I-1-a-12, I-1-a-13, I-1-a-14, I-1-a-15, I-1-b-1, I-2-a-1, I-2-a-2, I-2-a-4, I-2-b-1.

Example 4

*Tetranychus* Test, OP-Resistant (TETRUR Spray Treatment)

Solvents: 78.0 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration. Disks of bean leaves (*Phaseolus vulgaris*) which are infested by all stages of the greenhouse red spider mite (*Tetranychus urticae*) are sprayed with an active compound preparation of the desired concentration.

After 6 days, the effect in % is determined. 100% means that all of the spider mites have been killed; 0% means that none of the spider mites have been killed.

In this test, for example, the following compounds of the Preparation Examples show, at an application rate of 500 g/ha, an effect of 100%: I-1-a-2, I-1-a-12, I-2-a-2.

In this test, for example, the following compounds of the Preparation Examples show, at an application rate of 100 g/ha, an effect of 90%: I-1-a-4, I-1-a-10, I-1-a-13, I-1-a-15, I-1-a-16.

In this test, for example, the following compounds of the Preparation Examples show, at an application rate of 100 g/ha, an effect of 100%: I-1-a-1, I-1-a-3, I-1-a-5, I-1-a-6, I-1-a-7, I-1-a-8, I-1-a-9, I-1-a-11, I-1-b-1, I-1-c-1.

Example 5

*Meloidogyne incognita* Test (MELGIN)

Solvent: 125 parts by weight of acetone

To produce a suitable preparation of active compound, 1 part by weight of active compound is mixed with the stated amounts of solvent and emulsifier, and the concentrate is diluted with water to the desired concentration. Containers are filled with sand, solution of active compound, *Meloidogyne incognita* egg/larvae suspension and lettuce seeds. The lettuce seeds germinate and the plants develop. On the roots, galls are formed. After 14 days, the nematicidal effect in % is determined by the formation of galls. 100% means that no galls have been found; 0% means that the number of galls on the treated plants corresponds to the untreated control.

In this test, for example, the following compounds of the Preparation Examples show, at an application rate of 20 ppm, an effect of 100%: I-1-a-2, I-1-a-10.

Example 6

*Lucilia cuprina* Test (LUCICU)

Solvent: dimethyl sulfoxide

To prepare an appropriate active compound formulation, 10 mg of active compound are mixed with 0.5 ml of dimethyl sulfoxide and the concentrate is diluted with water to the desired concentration. Vessels containing horse meat treated with the active compound preparation of the desired concentration are populated with about 20 *Lucilia cuprina* larvae.

After 2 days, the kill in % is determined. 100% means that all of the larvae have been killed; 0% means that none of the larvae have been killed.

In this test, for example, the following compounds of the Preparation Examples show an effect of 100% at an application rate of 100 ppm: I-1-a-2

Example 7

*Boophilus microplus* Test (BOOPMI Injection)

Solvent: dimethyl sulfoxide

To prepare an appropriate active compound formulation, 10 mg of active compound are mixed with 0.5 ml of solvent and the concentrate is diluted with solvent to the desired concentration. The solution of active compound is injected into the abdomen (*Boophilus microplus*), and the animals are transferred into dishes and kept in a climatized room. The activity is assessed by position of fertile eggs.

After 7 days, the effect in % is determined. 100% means that none of the ticks has laid any fertile eggs.

In this test, for example, the following compounds of the Preparation Examples show an effect of 80% at an application rate of 20 µg/animal: I-1-a-2

Example 8

1. Herbicidal Pre-Emergence Action

Seeds of monocotyledonous and dicotyledonous weed plants and crop plants are placed in wood-fiber pots in sandy loam and covered with soil. The test compounds, formulated in the form of wettable powders (WP), are then, as an aqueous suspension with a water application rate of 600 l/ha (converted), with 0.2% of wetting agent added, applied at various dosages to the surface of the covering soil.

After the treatment, the pots are placed in a greenhouse and kept under good growth conditions for the test plants. The visual assessment of the damage to the test plants is carried out after a trial period of about 3 weeks by comparison with untreated controls (herbicidal activity in percent: 100% activity=the plants have died, 0% activity=like control plants).

In addition to the compounds mentioned above, the following compounds show an activity of 90-100% against *Alopecurus myosuroides, Echinocloa crus-galli, Lolium multiflorum* and *Setaria viridis* when applied by the pre-emergence method at 320 g/ha of a.i.: I-1-a-8, I-1-b-1, I-1-c-1.

2. Herbicidal Post-Emergence Action

Seeds of monocotyledonous and dicotyledonous weed and crop plants are placed in sandy loam in wood-fiber pots, covered with soil and cultivated in a greenhouse under good growth conditions. 2 to 3 weeks after sowing, the test plants are treated at the one-leaf stage. The test compounds, formulated as wettable powders (WP), are then, with a water application rate of 600 l/ha (converted), with 0.2% of wetting agent added, sprayed at various dosages onto the green parts of the plants. After the test plants have been kept in the greenhouse under optimum growth conditions for about 3 weeks, the activity of the preparations is rated visually in comparison to untreated controls (herbicidal activity in percent: 100% activity=the plants have died, 0% activity=like control plants).

In addition to the compounds mentioned above, the following compounds show an activity of 90-100% against *Alopecurus myosuroides, Echinocloa crus-galli, Lolium multiflorum* and *Setaria viridis* when applied by the post-emergence method at 80 g/ha: I-1-a-1, I-1-a-8, I-1-a-11, I-1-c-1.

In addition to the compounds mentioned above, the following compounds show an activity of 90-100% against Echinocloa crus-galli, *Lolium multiflorum* and *Setaria viridis* when applied by the post-emergence method at 80 g/ha: I-1-a-3, I-1-a-4, I-1-a-9.

Example 9

Comparative Test

Phaedon Test (PHAECO Spray Treatment)

Solvents: 78.0 parts by weight of acetone 1.5 parts by weight of dimethylformamide Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Disks of Chinese cabbage (*Brassica pekinensis*) are sprayed with an active compound preparation of the desired concentration and, after drying, populated with larvae of the mustard beetle (*Phaedon cochleariae*).

After the desired period of time, the activity in % is determined. 100% means that all beetle larvae have been killed; 0% means that none of the beetle larvae have been killed.

In this test, for example, the following compounds of the Preparation Examples show superior efficacy to the prior art: see table Myzus Test (MYZUPE Spray Treatment)

Solvents: 78.0 parts by weight of acetone 1.5 parts by weight of dimethylformamide Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Disks of Chinese cabbage (*Brassica pekinensis*) infected by all stages of the green peach aphid (*Myzus persicae*) are sprayed with an active compound preparation of the desired concentration. After the desired period of time, the activity in % is determined. 100% means that all of the aphids have been killed; 0% means that none of the aphids have been killed.

In this test, for example, the following compounds of the Preparation Examples show superior efficacy to the prior art: see table

*Tetranychus* Test, OP-Resistant (TETRUR Spray Treatment)
Solvents: 78.0 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Disks of bean leaves (*Phaseolus vulgaris*) which are infested by all stages of the greenhouse red spider mite (*Tetranychus urticae*) are sprayed with an active compound preparation of the desired concentration.

After the desired period of time, the activity in % is determined. 100% means that all of the spider mites have been killed; 0% means that none of the spider mites have been killed.

In this test, for example, the following compounds of the Preparation Examples show superior efficacy to the prior art: see table

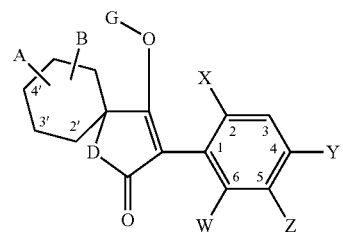

(I)

in which

W represents hydrogen, halogen, alkyl, alkenyl, alkynyl, optionally substituted cycloalkyl, alkoxy, alkenyloxy, haloalkyl, haloalkoxy or cyano, X represents halogen, alkyl, alkenyl, alkynyl, optionally substituted cycloalkyl, alkoxy, alkenyloxy, alkylthio, alkylsulfinyl, alkylsulfonyl, haloalkyl, haloalkoxy, haloalkenyloxy, nitro or cyano, Y and Z independently of one another represent hydrogen, alkyl, alkenyl, alkynyl, optionally substituted

TABLE

| | Structure | | Concentration | % Activity d (days) |
|---|---|---|---|---|
| prior art WO 2008/067911 Table 1 | (structure shown) | | PHAECO 20 g/ha<br>MYZUPE 20 g/ha<br>TETRUR 20 g/ha | 0 7 d<br>0 6 d<br>0 6 d |
| I-a-15 according to the invention | (structure shown) | | PHAECO 20 g/ha<br>MYZUPE 20 g/ha<br>TETRUR 20 g/ha | 67 7 d<br>100 6 d<br>90 6 d |

FIGURES

FIG. 1: ACC1 expression in tumor tissue and corresponding normal tissue
1: healthy breast tissue (2 samples)
2: breast tumor tissue (26 samples)
3: healthy colon tissue (30 samples)
4: colon tumor tissue (71 samples)
5: healthy lung tissue (27 samples)
6: lung tumor tissue (40 samples)
7: healthy pancreas tissue (22 samples)
8: pancreas tumor tissue (19 samples)

The invention claimed is:
1. A pesticide and/or herbicide and/or fungicide, wherein said pesticide and/or herbicide and/or fungicide comprises at least one compound of formula (I)

cycloalkyl, alkoxy, halogen, haloalkyl, haloalkoxy, cyano, nitro or in each case optionally substituted aryl or hetaryl, A represents halogen, B represents halogen or a bond to the adjacent carbon atom, with the proviso that A and B are located in the 3'- and/or 4'-position, D represents NH or oxygen, and G represents hydrogen (a) or represents one of the groups

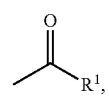

(b)

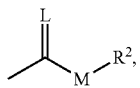
(c)

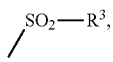
(d)

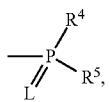
(e)

E, or (f)

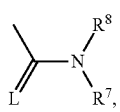
(g)

in which
E represents a metal ion or an ammonium ion,
L represents oxygen or sulfur,
M represents oxygen or sulfur,
$R^1$ represents in each case optionally halogen- or cyano-substituted alkyl, alkenyl, alkoxyalkyl, alkylthioalkyl or polyalkoxyalkyl or represents in each case optionally halogen-, alkyl- or alkoxy-substituted cycloalkyl or heterocyclyl or represents in each case optionally substituted phenyl, phenylalkyl, hetaryl, phenoxyalkyl or hetaryloxyalkyl,
$R^2$ represents in each case optionally halogen- or cyano-substituted alkyl, alkenyl, alkoxyalkyl or polyalkoxyalkyl or represents in each case optionally substituted cycloalkyl, phenyl or benzyl,
$R^3$, $R^4$ and $R^5$ independently of one another represent in each case optionally halogen-substituted alkyl, alkoxy, alkylamino, dialkylamino, alkylthio, alkenylthio or cycloalkylthio or represent in each case optionally substituted phenyl, benzyl, phenoxy or phenylthio, and
$R^6$ and $R^7$ independently of one another represent hydrogen, represent in each case optionally halogen- or cyano-substituted alkyl, cycloalkyl, alkenyl, alkoxy, alkoxyalkyl, represent in each case optionally substituted phenyl or benzyl, or together with the N atom to which they are attached form an optionally substituted cycle which optionally contains oxygen or sulfur.

2. The pesticide and/or herbicide and/or fungicide as claimed in claim 1, in which
W represents hydrogen, halogen, $C_1$-$C_6$-alkyl, $C_2$-$C_6$-alkenyl, $C_2$-$C_6$-alkynyl, $C_3$-$C_6$-cycloalkyl which is optionally mono- to disubstituted by $C_1$-$C_2$-alkyl, $C_1$-$C_2$-alkoxy, fluorine, chlorine, trifluoromethyl or $C_3$-$C_6$-cycloalkyl, $C_1$-$C_6$-alkoxy, $C_1$-$C_4$-haloalkyl, $C_1$-$C_4$-haloalkoxy or cyano,
X represents halogen, $C_1$-$C_6$-alkyl, $C_2$-$C_6$-alkenyl, $C_2$-$C_6$-alkynyl, $C_3$-$C_6$-cycloalkyl which is optionally mono- to disubstituted by $C_1$-$C_2$-alkyl, $C_1$-$C_2$-alkoxy, fluorine, chlorine, trifluoromethyl or $C_3$-$C_6$-cycloalkyl, $C_1$-$C_6$-haloalkyl, $C_1$-$C_6$-alkoxy, $C_3$-$C_6$-alkenyloxy, $C_1$-$C_6$-alkylthio, $C_1$-$C_6$-alkylsulfinyl, $C_1$-$C_6$-alkylsulfonyl, $C_1$-$C_6$-haloalkoxy, $C_3$-$C_6$-haloalkenyloxy, nitro or cyano,
Y and Z independently of one another represent hydrogen, halogen, $C_1$-$C_6$-alkyl, $C_2$-$C_6$-alkenyl, $C_2$-$C_6$-alkynyl, $C_3$-$C_6$-cycloalkyl which is optionally mono- to disubstituted by $C_1$-$C_2$-alkyl, $C_1$-$C_2$-alkoxy, fluorine, chlorine, trifluoromethyl or $C_3$-$C_6$-cycloalkyl, $C_1$-$C_6$-alkoxy, $C_1$-$C_6$-haloalkyl, $C_1$-$C_6$-haloalkoxy, cyano, or represent one of the (het)aryl radicals

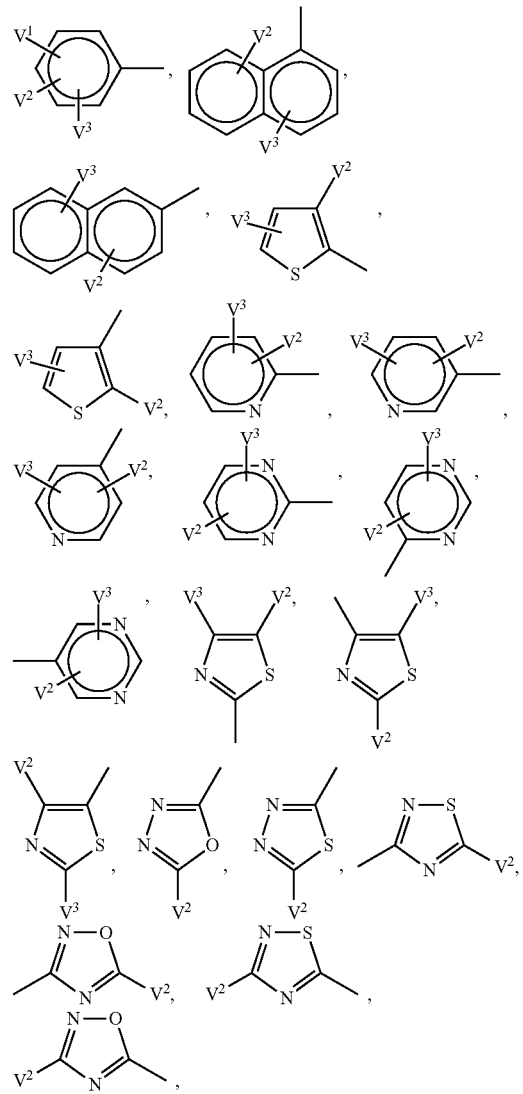

where in the case of (het)aryl only one of the radicals Y or Z may represent (het)aryl,
$V^1$ represents hydrogen, halogen, $C_1$-$C_{12}$-alkyl, $C_1$-$C_6$-alkoxy, $C_1$-$C_6$-alkylthio, $C_1$-$C_6$-alkylsulfinyl, $C_1$-$C_6$-alkylsulfonyl, $C_1$-$C_4$-haloalkyl, $C_1$-$C_4$-haloalkoxy, nitro, cyano or represents phenyl, phenoxy, phenoxy-$C_1$-$C_4$-alkyl, phenyl-$C_1$-$C_4$-alkoxy, phenylthio-$C_1$-$C_4$-alkyl or phenyl-$C_1$-$C_4$-alkylthio, each of which is optionally mono- or polysubstituted by halogen, $C_1$-$C_6$-alkyl, $C_1$-$C_6$-alkoxy, $C_1$-$C_4$-haloalkyl, $C_1$-$C_4$-haloalkoxy, nitro or cyano,
$V^2$ and $V^3$ independently of one another represent hydrogen, halogen, $C_1$-$C_6$-alkyl, $C_1$-$C_6$-alkoxy, $C_1$-$C_4$-haloalkyl $C_1$-$C_4$-haloalkoxy,
A represents halogen,
B represents halogen or a bond which is attached to the same carbon atom as A, with the proviso that A and B are located in the 3'- and/or 4'-position, D represents NH or oxygen, and
G represents hydrogen (a) or represents one of the groups

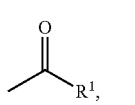 (b)

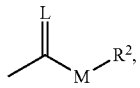 (c)

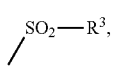 (d)

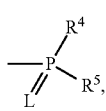 (e)

E, or (f)

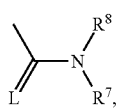 (g)

in which
E represents a metal ion or an ammonium ion,
L represents oxygen or sulfur,
M represents oxygen or sulfur,
$R^1$ represents in each case optionally halogen- or cyano-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl or poly-$C_1$-$C_8$-alkoxy-$C_1$-$C_8$-alkyl or represents optionally halogen-, $C_1$-$C_6$-alkyl- or $C_1$-$C_6$-alkoxy-substituted $C_3$-$C_8$-cycloalkyl in which optionally one or two not directly adjacent methylene groups are replaced by oxygen and/or sulfur,
represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulfonyl-substituted phenyl,
represents optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl,
represents optionally halogen- or $C_1$-$C_6$-alkyl-substituted 5- or 6-membered hetaryl having one or two heteroatoms from the group consisting of oxygen, sulfur and nitrogen, or
represents optionally halogen- or $C_1$-$C_6$-alkyl-substituted phenoxy-$C_1$-$C_6$-alkyl or represents optionally halogen-, amino- or $C_1$-$C_6$-alkyl-substituted 5- or 6-membered hetaryloxy-$C_1$-$C_6$-alkyl having one or two heteroatoms from the group consisting of oxygen, sulfur and nitrogen,
$R^2$ represents in each case optionally halogen- or cyano-substituted $C_1$-$C_{20}$-alkyl, $C_2$-$C_{20}$-alkenyl, $C_1$-$C_8$-alkoxy-$C_2$-$C_8$-alkyl or poly-$C_1$-$C_8$-alkoxy-$C_2$-$C_8$-alkyl,
represents optionally halogen-, $C_1$-$C_6$-alkyl- or $C_1$-$C_6$-alkoxy-substituted $C_3$-$C_8$-cycloalkyl or
represents phenyl or benzyl, each of which is optionally substituted by halogen, cyano, nitro, $C_1$-$C_6$-alkyl, $C_1$-$C_6$-alkoxy, $C_1$-$C_6$-haloalkyl or $C_1$-$C_6$-haloalkoxy,
$R^3$ represents optionally halogen-substituted $C_1$-$C_8$-alkyl or in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl,
$R^4$ and $R^5$ independently of one another represent in each case optionally halogen-substituted $C_1$-$C_8$-alkyl, $C_1$-$C_8$-alkoxy, $C_1$-$C_8$-alkylamino, di-($C_1$-$C_8$-alkyl)amino, $C_1$-$C_8$-alkylthio or $C_3$-$C_8$-alkenylthio or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio, and
$R^6$ and $R^7$ independently of one another represent hydrogen, represent in each case optionally halogen- or cyano-substituted $C_1$-$C_8$-alkyl, $C_3$-$C_8$-cycloalkyl, $C_1$-$C_8$-alkoxy, $C_3$-$C_8$-alkenyl or $C_1$-$C_8$-alkoxy-$C_2$-$C_8$-alkyl, represent in each case optionally halogen-, $C_1$-$C_8$-alkyl, $C_1$-$C_8$-haloalkyl- or $C_1$-$C_8$-alkoxy-substituted phenyl or benzyl or together represent an optionally $C_1$-$C_6$-alkyl-substituted $C_3$-$C_6$-alkylene radical in which optionally one methylene group is replaced by oxygen or sulfur.

3. The pesticide and/or herbicide and/or fungicide as claimed in claim 1, in which
W represents hydrogen, chlorine, bromine, $C_1$-$C_4$-alkyl, $C_2$-$C_4$-alkenyl, $C_2$-$C_4$-alkynyl, $C_3$-$C_6$-cycloalkyl which is optionally monosubstituted by methyl, ethyl, methoxy, fluorine, chlorine, trifluoromethyl or cyclopropyl, $C_1$-$C_4$-alkoxy, $C_1$-$C_2$-haloalkyl or $C_1$-$C_2$-haloalkoxy,
X represents chlorine, bromine, iodine, $C_1$-$C_4$-alkyl, $C_2$-$C_4$-alkenyl, $C_2$-$C_4$-alkynyl, $C_3$-$C_6$-cycloalkyl which is optionally monosubstituted by methyl, ethyl, methoxy, fluorine, chlorine, trifluoromethyl or cyclopropyl, $C_1$-$C_4$-alkoxy, $C_1$-$C_4$-haloalkyl, $C_1$-$C_4$-haloalkoxy or cyano,
Y and Z independently of one another represent hydrogen, fluorine, chlorine, bromine, iodine, $C_1$-$C_4$-alkyl, $C_2$-$C_4$-alkenyl, $C_2$-$C_4$-alkynyl, $C_3$-$C_6$-cycloalkyl which is optionally monosubstituted by methyl, ethyl, methoxy, fluorine, chlorine, trifluoromethyl or cyclopropyl, $C_1$-$C_6$-alkoxy, $C_1$-$C_4$-haloalkyl, $C_1$-$C_4$-haloalkoxy, cyano, or represent one of the (het)aryl radicals,

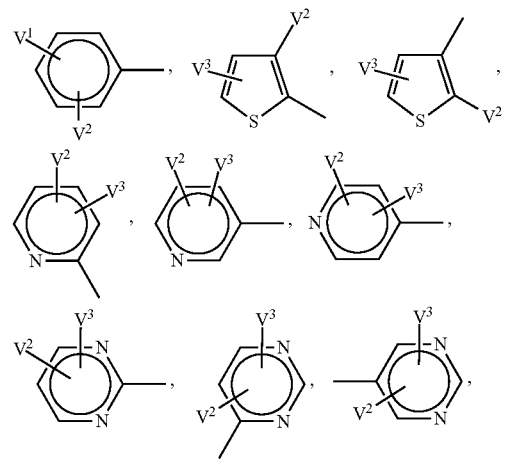

where in the case of (het)aryl only one of the radicals Y or Z may represent (het)aryl, V¹ represents hydrogen, fluorine, chlorine, bromine, $C_1$-$C_6$-alkyl, $C_1$-$C_4$-alkoxy, $C_1$-$C_2$-haloalkyl, $C_1$-$C_2$-haloalkoxy, nitro, cyano or phenyl which is optionally mono- or disubstituted by fluorine, chlorine, bromine, $C_1$-$C_4$-alkyl, $C_1$-$C_4$-alkoxy, $C_1$-$C_2$-haloalkyl, $C_1$-$C_2$-haloalkoxy, nitro or cyano, V² and V³ independently of one another represent hydrogen, fluorine, chlorine, bromine, $C_1$-$C_4$-alkyl, $C_1$-$C_4$-alkoxy, $C_1$-$C_2$-haloalkyl or $C_1$-$C_2$-haloalkoxy, A represents fluorine or chlorine, B represents fluorine, chlorine or a bond which is attached to the same carbon atom as A, with the proviso that A and B are located in the 3'- and/or 4'-position, D represents NH or oxygen, and G represents hydrogen (a) or represents one of the groups

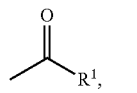
(b)

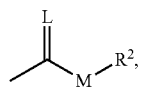
(c)

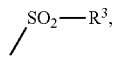
(d)

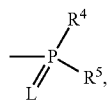
(e)

E, or
(f)

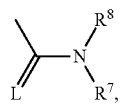
(g)

in which

E represents a metal ion or an ammonium ion,

L represents oxygen or sulfur and

M represents oxygen or sulfur,

R¹ represents $C_1$-$C_{16}$-alkyl, $C_2$-$C_{16}$-alkenyl, $C_1$-$C_6$-alkoxy-$C_1$-$C_4$-alkyl, $C_1$-$C_6$-alkylthio-$C_1$-$C_4$-alkyl or poly-$C_1$-$C_6$-alkoxy-$C_1$-$C_4$-alkyl, each of which is optionally mono- to trisubstituted by fluorine or chlorine, or represents $C_3$-$C_7$-cycloalkyl which is optionally mono- or disubstituted by fluorine, chlorine, $C_1$-$C_5$-alkyl or $C_1$-$C_5$-alkoxy and in which optionally one or two not directly adjacent methylene groups are replaced by oxygen and/or sulfur, represents phenyl which is optionally mono- to trisubstituted by fluorine, chlorine, bromine, cyano, nitro, $C_1$-$C_4$-alkyl, $C_1$-$C_4$-alkoxy, $C_1$-$C_3$-haloalkyl, $C_1$-$C_3$-haloalkoxy $C_1$-$C_4$-alkylthio or $C_1$-$C_4$-alkylsulfonyl, represents phenyl-$C_1$-$C_4$-alkyl, which is optionally mono- or disubstituted by fluorine, chlorine, bromine, $C_1$-$C_4$-alkyl, $C_1$-$C_4$-alkoxy, $C_1$-$C_3$-haloalkyl or $C_1$-$C_3$-haloalkoxy, represents pyrazolyl, thiazolyl, pyridyl, pyrimidyl, furanyl or thienyl, each of which is optionally mono- or disubstituted by fluorine, chlorine, bromine or $C_1$-$C_4$-alkyl, represents phenoxy-$C_1$-$C_5$-alkyl which is optionally mono- or disubstituted by fluorine, chlorine, bromine or $C_1$-$C_4$-alkyl, or represents pyridyloxy-$C_1$-$C_5$-alkyl, pyrimidyloxy-$C_1$-$C_5$-alkyl or thiazolyloxy-$C_1$-$C_5$-alkyl, each of which is optionally mono- or disubstituted by fluorine, chlorine, bromine, amino or $C_1$-$C_4$-alkyl, R² represents $C_1$-$C_{16}$-alkyl, $C_2$-$C_{16}$-alkenyl, $C_1$-$C_6$-alkoxy-$C_2$-$C_6$-alkyl or poly-$C_1$-$C_6$-alkoxy-$C_2$-$C_6$-alkyl, each of which is optionally mono- to trisubstituted by fluorine or chlorine, represents $C_3$-$C_7$-cycloalkyl which is optionally mono- or disubstituted by fluorine, chlorine, $C_1$-$C_4$-alkyl or $C_1$-$C_4$-alkoxy or represents phenyl or benzyl, each of which is optionally mono- to trisubstituted by fluorine, chlorine, bromine, cyano, nitro, $C_1$-$C_4$-alkyl, $C_1$-$C_3$-alkoxy, $C_1$-$C_3$-haloalkyl or $C_1$-$C_3$-haloalkoxy, R³ represents $C_1$-$C_6$-alkyl which is optionally mono- to trisubstituted by fluorine or chlorine or represents phenyl or benzyl, each of which is optionally mono- or disubstituted by fluorine, chlorine, bromine, $C_1$-$C_4$-alkyl, $C_1$-$C_4$-alkoxy, $C_1$-$C_2$-haloalkoxy, $C_1$-$C_2$-haloalkyl, cyano or nitro, R⁴ and R⁵ independently of one another represent $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio or $C_3$-$C_4$-alkenylthio, each of which is optionally mono- to trisubstituted by fluorine or chlorine, or represent phenyl, phenoxy or phenylthio, each of which is optionally mono- or disubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or $C_1$-$C_3$-haloalkyl, and R⁶ and R⁷ independently of one another represent hydrogen, represent $C_1$-$C_6$-alkyl, $C_3$-$C_6$-cycloalkyl, $C_1$-$C_6$-alkoxy, $C_3$-$C_6$-alkenyl or $C_1$-$C_6$-alkoxy-$C_2$-$C_6$-alkyl, each of which is optionally mono- to trisubstituted by fluorine or chlorine, represent phenyl or benzyl, each of which is optionally mono- to trisubstituted by fluorine, chlorine, bromine, $C_1$-$C_5$-haloalkyl, $C_1$-$C_5$-alkyl or $C_1$-$C_5$-alkoxy, or together represent an optionally $C_1$-$C_4$-alkyl-substituted $C_3$-$C_6$-alkylene radical in which optionally one methylene group is replaced by oxygen or sulfur.

4. The pesticide and/or herbicide and/or fungicide as claimed in claim 1, in which W represents hydrogen, chlorine, bromine, methyl, ethyl, vinyl, ethynyl, propynyl, cyclopropyl, methoxy, ethoxy or trifluoromethyl, X represents chlorine, bromine, methyl, ethyl, propyl, isopropyl, vinyl, ethynyl, propynyl, cyclopropyl, methoxy, ethoxy, trifluoromethyl, difluoromethoxy, trifluoromethoxy or cyano, Y and Z independently of one another represent hydrogen, fluorine, chlorine, bromine, iodine, methyl, ethyl, vinyl, ethynyl, propynyl, cyclopropyl, methoxy, trifluoromethyl, trifluoromethoxy, trifluoroethoxy, cyano or a phenyl radical,

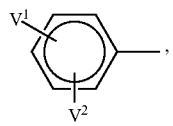

where in the case of phenyl only one of radicals Y or Z may represent phenyl,

V¹ represents hydrogen, fluorine or chlorine,
V² represents hydrogen, fluorine, chlorine, methyl, ethyl, n-propyl, isopropyl, methoxy, ethoxy or trifluoromethyl,
A represents fluorine,
B represents fluorine or a bond which is attached to the same carbon atom as A,
D represents NH or oxygen, and
G represents hydrogen (a) or represents one of the groups

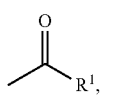  (b)

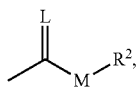  (c)

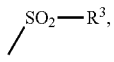  (d)

  (e)

E, or  (f)

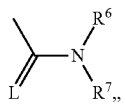  (g)

in which
E represents a metal ion or an ammonium ion,
L represents oxygen or sulfur,
M represents oxygen or sulfur,
$R^1$ represents $C_1$-$C_{10}$-alkyl, $C_2$-$C_{10}$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine, or represents $C_3$-$C_6$-cycloalkyl which is optionally monosubstituted by fluorine, chlorine, methyl, ethyl or methoxy,
represents phenyl which is optionally mono- or disubstituted by fluorine, chlorine, bromine, cyano, nitro, methyl, ethyl, n-propyl, isopropyl, methoxy, ethoxy, trifluoromethyl or trifluoromethoxy, or
represents furanyl, thienyl or pyridyl, each of which is optionally monosubstituted by chlorine, bromine or methyl,
$R^2$ represents $C_1$-$C_{10}$-alkyl, $C_2$-$C_{10}$-alkenyl or $C_1$-$C_4$-alkoxy-$C_2$-$C_4$-alkyl, each of which is optionally mono- to trisubstituted by fluorine or chlorine,
represents cyclopentyl or cyclohexyl
or represents phenyl or benzyl, each of which is optionally mono- or disubstituted by fluorine, chlorine, cyano, nitro, methyl, ethyl, methoxy, trifluoromethyl or trifluoromethoxy,
$R^3$ represents methyl, ethyl, propyl or isopropyl, each of which is optionally mono- to trisubstituted by fluorine or chlorine, or represents phenyl which is optionally monosubstituted by fluorine, chlorine, bromine, methyl, ethyl, isopropyl, tert-butyl, methoxy, ethoxy, isopropoxy, trifluoromethyl, trifluoromethoxy, cyano or nitro, $R^4$ and $R^5$ independently of one another represent $C_1$-$C_4$-alkoxy or $C_1$-$C_4$-alkylthio or represent phenyl, phenoxy or phenylthio, each of which is optionally monosubstituted by fluorine, chlorine, bromine, nitro, cyano, methyl, methoxy, trifluoromethyl or trifluoromethoxy, and
$R^6$ and $R^7$ independently of one another represent hydrogen, represent $C_1$-$C_4$-alkyl, $C_3$-$C_6$-cycloalkyl, $C_1$-$C_4$-alkoxy, $C_3$-$C_4$-alkenyl or $C_1$-$C_4$-alkoxy-$C_2$-$C_4$-alkyl, represent phenyl which is optionally mono- or disubstituted by fluorine, chlorine, bromine, methyl, methoxy or trifluoromethyl, or together represent a $C_5$-$C_6$-alkylene radical in which optionally one methylene group is replaced by oxygen or sulfur.

5. The pesticide and/or herbicide and/or fungicide as claimed in claim 1, in which
W represents hydrogen, chlorine, bromine, methyl, ethyl or methoxy,
X represents chlorine, bromine, methyl, ethyl, methoxy or ethoxy,
Y and Z independently of one another represent hydrogen, chlorine, bromine, methyl, trifluoroethoxy or represent the radical

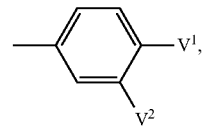

where in this case only one of radicals Y or Z may represent

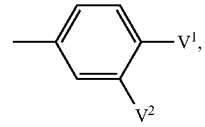

V¹ represents fluorine or chlorine,
V² represents hydrogen, fluorine or chlorine,
A represents fluorine,
B represents fluorine or a bond,
where A and B are attached to the same carbon atom in the 4'-position,
D represents NH or oxygen, and
G represents hydrogen (a) or represents one of the groups

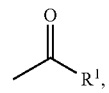  (b)

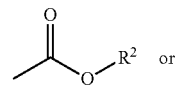  (c)

E,  (f)

in which
E represents a metal ion or an ammonium ion,
$R^1$ represents $C_1$-$C_{10}$-alkyl, $C_1$-$C_4$-alkoxy-$C_1$-$C_2$-alkyl, $C_3$-$C_6$-cycloalkyl, represents phenyl which is optionally monosubstituted by chlorine or represents thienyl, and
$R^2$ represents $C_1$-$C_{10}$-alkyl, $C_2$-$C_{10}$-alkenyl or represents benzyl.

6. A method for controlling animal pests and/or unwanted vegetation and/or fungi, comprising applying the pesticide and/or herbicide and/or fungicide as claimed in claim 1 to a pest and/or the habitat of said pest.

7. A pesticide and/or herbicide and/or fungicide as claimed in claim 1, capable of being used for controlling an animal pest and/or unwanted vegetation and/or fungi.

8. A composition comprising an effective amount of an active compound combination comprising:
(a') at least one pesticide and/or herbicide and/or fungicide as claimed in claim 1 and
(b') at least one crop plant compatibility-improving compound selected from the group consisting of
S1) a compound of the formula

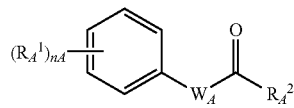

(S1)

where
$n_A$ is a natural number from 0 to 5,
$R_A^1$ is halogen, $(C_1-C_4)$-alkyl, $(C_1-C_4)$-alkoxy, nitro or $(C_1-C_4)$-haloalkyl,
$W_A$ is an unsubstituted or substituted divalent heterocyclic radical selected from the group consisting of the partially unsaturated or aromatic five-membered heterocycles having 1 to 3 ring heteroatoms of the N or O type, where at least one nitrogen atom and at most one oxygen atom is present in the ring,
$m_A$ is 0 or 1,
$R_A^2$ is $OR_A^3$, $SR_A^3$ or $NR_A^3R_A^4$ or a saturated or unsaturated 3- to 7-membered heterocycle having at least one nitrogen atom and up to 3 heteroatoms selected from the group consisting of O and S, which is joined to the carbonyl group in (S1) via the nitrogen atom and is unsubstituted or substituted by radicals selected from the group consisting of $(C_1-C_4)$-alkyl, $(C_1-C_4)$-alkoxy or optionally substituted phenyl,
$R_A^3$ is hydrogen or an unsubstituted or substituted aliphatic hydrocarbyl radical having a total of 1 to 18 carbon atoms,
$R_A^4$ is hydrogen, $(C_1-C_6)$-alkyl, $(C_1-C_6)$-alkoxy or substituted or unsubstituted phenyl,
$R_A^5$ is H, $(C_1-C_8)$-alkyl, $(C_1-C_8)$-haloalkyl, $(C_1-C_4)$-alkoxy-$(C_1-C_8)$-alkyl, cyano or $COOR_A^9$, where $R_A^9$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_{12})$-cycloalkyl or tri-$(C_1-C_4)$-alkylsilyl, and
$R_A^6$, $R_A^7$, and $R_A^8$ are identical or different and are hydrogen, $(C_1-C_8)$-alkyl, $(C_1-C_8)$-haloalkyl, $(C_3-C_{12})$-cycloalkyl or substituted or unsubstituted phenyl;
S2) a compound of the formula

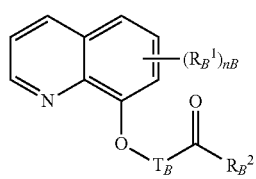

(S2)

where
$R_B^1$ is halogen, $(C_1-C_4)$-alkyl, $(C_1-C_4)$-alkoxy, nitro or $(C_1-C_4)$-haloalkyl,
$n_B$ is a natural number from 0 to 5,
$R_B^2$ is $OR_B^3$, $SR_B^3$ or $NR_B^3R_B^4$ or a saturated or unsaturated 3- to 7-membered heterocycle having at least one nitrogen atom and up to 3 heteroatoms selected from the group consisting of O and S, which is joined to the carbonyl group in (S2) via the nitrogen atom and is unsubstituted or substituted by radicals selected from the group consisting of $(C_1-C_4)$-alkyl, $(C_1-C_4)$-alkoxy or optionally substituted phenyl,
$R_B^3$ is hydrogen or an unsubstituted or substituted aliphatic hydrocarbyl radical having a total of 1 to 18 carbon atoms,
$R_B^4$ is hydrogen, $(C_1-C_6)$-alkyl, $(C_1-C_6)$-alkoxy or substituted or unsubstituted phenyl; and
$T_B$ is a ($C_1$ or $C_2$)-alkanediyl chain which is unsubstituted or substituted by one or two $(C_1-C_4)$-alkyl radicals or by $[(C_1-C_3)$-alkoxy]carbonyl;
S3) a compound of the formula

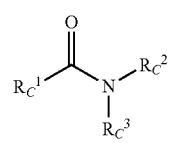

(S3)

where
$R_C^1$ is $(C_1-C_4)$-alkyl, $(C_1-C_4)$-haloalkyl, $(C_2-C_4)$-alkenyl, $(C_2-C_4)$-haloalkenyl or $(C_3-C_7)$-cycloalkyl, and
$R_C^2$ and $R_C^3$ are identical or different and are hydrogen, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_1-C_4)$-alkylcarbamoyl-$(C_1-C_4)$-alkyl, $(C_2-C_4)$-alkenylcarbamoyl-$(C_1-C_4)$alkyl, $(C_1-C_4)$-alkoxy-$(C_1-C_4)$-alkyl, dioxolanyl-$(C_1-C_4)$-alkyl, thiazolyl, furyl, furylalkyl, thienyl, piperidyl, or substituted or unsubstituted phenyl, or $R_C^2$ and $R_C^3$ together form a substituted or unsubstituted heterocyclic ring,
S4) a compound of the formula

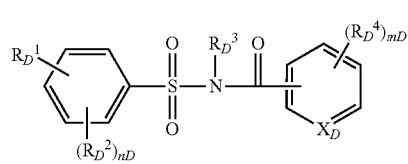

(S4)

where
$X_D$ is CH or N,
$R_D^1$ is $CO-NR_D^5R_D^6$ or $NHCO-R_D^7$,
$R_D^2$ is halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulfonyl, $(C_1-C_4)$-alkoxycarbonyl or $(C_1-C_4)$-alkylcarbonyl,
$R_D^3$ is hydrogen, $(C_1-C_4)$-alkyl, $(C_2-C_4)$-alkenyl or $(C_2-C_4)$-alkynyl,
$R_D^4$ is halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkylsulfinyl, $(C_1-C_4)$-alkylsulfonyl, $(C_1-C_4)$-alkoxycarbonyl or $(C_1-C_4)$-alkylcarbonyl, $R_D^5$ is hydrogen, $(C_1\text{-}C_6)$-alkyl, $(C_3\text{-}C_6)$-cycloalkyl, $(C_2\text{-}C_6)$-alkenyl, $(C_2\text{-}C_6)$-alkynyl, $(C_5\text{-}C_6)$-cycloalkenyl, phenyl or 3- to 6-membered heterocyclyl containing $v_D$ heteroatoms selected from the group consisting of nitrogen, oxygen and sulfur, where the seven latter radicals are each substituted by $v_D$ substituents selected from the group consisting of halogen, $(C_1\text{-}C_6)$-alkoxy, $(C_1\text{-}C_6)$-haloalkoxy, $(C_1\text{-}C_2)$-alkylsulfinyl, $(C_1\text{-}C_2)$-alkylsulfonyl, $(C_3\text{-}C_6)$-cycloalkyl, $(C_1\text{-}C_4)$-alkoxycarbonyl, $(C_1\text{-}C_4)$-alkylcarbonyl and phenyl, and in the case of cyclic radicals also $(C_1\text{-}C_4)$-alkyl and $(C_1\text{-}C_4)$-haloalkyl, $R_D^6$ is hydrogen, $(C_1\text{-}C_6)$-alkyl, $(C_2\text{-}C_6)$-alkenyl or $(C_2\text{-}C_6)$-alkynyl, where the three latter radicals are each substituted by $v_D$ radicals selected from the group consisting of halogen, hydroxyl, $(C_1\text{-}C_4)$-alkyl, $(C_1\text{-}C_4)$-alkoxy and $(C_1\text{-}C_4)$-alkylthio, or $R_D^5$ and $R_D^6$ together with the nitrogen atom which bears them form a pyrrolidinyl or piperidinyl radical, $R_D^7$ is hydrogen, $(C_1\text{-}C_4)$-alkylamino, di-$(C_1\text{-}C_4)$-alkylamino, $(C_1\text{-}C_6)$-alkyl, or $(C_3\text{-}C_6)$-cycloalkyl, where the 2 latter radicals are substituted by $v_D$ substituents selected from the group consisting of halogen, $(C_1\text{-}C_4)$-alkoxy, $(C_1\text{-}C_6)$-haloalkoxy and $(C_1\text{-}C_4)$-alkylthio, and in the case of cyclic radicals also $(C_1\text{-}C_4)$-alkyl and $(C_1\text{-}C_4)$-haloalkyl, $n_D$ is 0, 1 or 2, $m_D$ is 1 or 2, and $V_D$ is 0, 1, 2 or 3;

S5) a hydroxyaromatic or aromatic-aliphatic carboxylic acid derivative (S5) selected from the group consisting of ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicyclic acid, 2-hydroxycinnamic acid, 1,2-dihydro-2-oxo-6-trifluoromethylpyridine-3-carboxamide, and 2,4-dichlorocinnamic acid;

S6) a 1,2-dihydroquinoxalin-2-one (S6) selected from the group consisting of 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-[2-(diethylamino)ethyl]-6,7-dimethyl-3-thiophen-2-ylquinoxalin-2(1H)-one, and 1-(2-methylsulfonylaminoethyl)-3-(2-thienyl)-1,2-dihydroquinoxalin-2-one;

S7) a compound of the formula

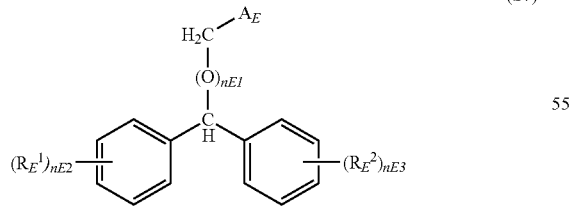

(S7)

where $R_E^1$, $R_E^2$ are each independently of one another halogen, $(C_1\text{-}C_4)$-alkyl, $(C_1\text{-}C_4)$-alkoxy, $(C_1\text{-}C_4)$-haloalkyl, $(C_1\text{-}C_4)$-alkylamino, di-$(C_1\text{-}C_4)$-alkylamino or nitro;

$A_E$ is $COOR_E^3$ or $COSR_E^4$, $R_E^3$, $R_E^4$ are each independently of one another hydrogen, $(C_1\text{-}C_4)$-alkyl, $(C_2\text{-}C_6)$-alkenyl, $(C_2\text{-}C_4)$-alkynyl, cyanoalkyl, $(C_1\text{-}C_4)$-haloalkyl, phenyl, nitrophenyl, benzyl, halobenzyl, pyridinylalkyl or alkylammonium, $n_E^1$ is 0 or 1, and $n_E^2$, $n_E^3$ are each independently of one another 0, 1 or 2;

S8) a compound of the formula

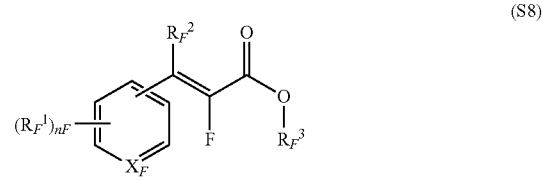

(S8)

where $X_F$ is CH or N, $n_E$ in the case that $X_F$=N is an integer from 0 to 4 and in the case that $X_F$=CH is an integer from 0 to 5, $R_F^1$ is halogen, $(C_1\text{-}C_4)$-alkyl, $(C_1\text{-}C_4)$-haloalkyl, $(C_1\text{-}C_4)$-alkoxy, $(C_1\text{-}C_4)$-haloalkoxy, nitro, $(C_1\text{-}C_4)$-alkylthio, $(C_1\text{-}C_4)$-alkylsulfonyl, $(C_1\text{-}C_4)$-alkoxycarbonyl, optionally substituted phenyl, or optionally substituted phenoxy, $R_F^2$ is hydrogen or $(C_1\text{-}C_4)$-alkyl, and $R_F^3$ is hydrogen, $(C_1\text{-}C_8)$-alkyl, $(C_2\text{-}C_4)$-alkenyl, $(C_2\text{-}C_4)$-alkynyl, or aryl, where each of the aforementioned carbon-containing radicals is unsubstituted or substituted by one or more identical or different radicals selected from the group consisting of halogen and alkoxy, or salts thereof;

S9) a 3-(5-tetrazolylcarbonyl)-2-quinolone (S9) selected from the group consisting of 1,2-dihydro-4-hydroxy-1-ethyl-3-(5-tetrazolylcarbonyl)-2-quinolone and 1,2-dihydro-4-hydroxy-1-methyl-3-(5-tetrazolylcarbonyl)-2-quinolone;

S10) a compound of the formula

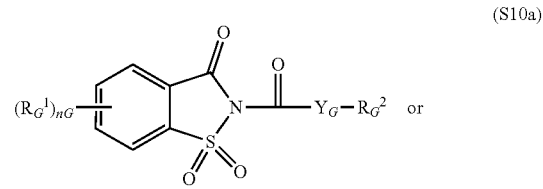

(S10a)

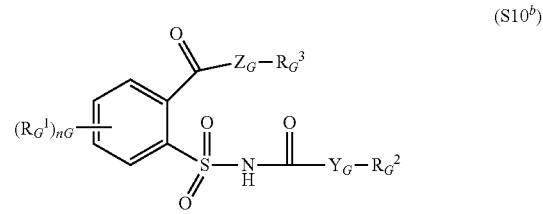

(S10b)

where $R_G^1$ is halogen, $(C_1\text{-}C_4)$-alkyl, methoxy, nitro, cyano, $CF_3$, or $OCF_3$, $Y_G$ and $Z_G$ are each independently of one another O or S, $n_G$ is an integer from 0 to 4, $R_G^2$ is $(C_1\text{-}C_{16})$-alkyl, $(C_2\text{-}C_6)$-alkenyl, $(C_3\text{-}C_6)$-cycloalkyl, aryl, benzyl, or halobenzyl, and $R_G^3$ is hydrogen or $(C_1\text{-}C_6)$-alkyl;

S11) an oxyimino compound (S11) seed dressing selected from the group consisting of oxabetrinil ((Z)-1,3-dioxolan-2-ylmethoxyimino(phenyl)acetonitrile) (S11-1) used as seed dressing safener for millet against metolachlor damage, fluxofenim (1-(4-chlorophenyl)-2,2,2-trifluoro-1-ethanone O-(1,3-dioxolan-2-ylmethyl) oxime) (S11-2) used as seed dressing safener for millet against metolachlor damage, and cyometrinil (CGA-43089, (Z)-cyanomethoxyimino(phenyl)acetonitrile) (S11-3) used as seed dressing safener for millet against metolachlor damage;

S12) an isothiochromanone (S12) that is methyl [(3-oxo-1H-2-benzothiopyran-4(3H)-ylidene)methoxy]acetate (S12-1);

S13) naphthalic anhydride (1,8-naphthalenedicarboxylic anhydride) (S13-1) used as seed dressing safener for corn against thiocarbamate herbicide damage, fenclorim (4,6-dichloro-2-phenylpyrimidine) (S13-2) used as safener for pretilachlor in sown rice, flurazole (benzyl 2-chloro-4-trifluoromethyl-1,3-thiazole-5-carboxylate) (S13-3) used as seed dressing safener for millet against alachlor and metolachlor damage, CL 304415 (4-carboxy-3,4-dihydro-2H-1-benzopyran-4-acetic acid) (S13-4) used as a safener for corn against damage by imidazolinones, MG 191 (2-dichloromethyl-2-methyl-1,3-dioxolane) (S13-5)) used as a safener for corn, MG-838 (2-propenyl 1-oxa-4-azaspiro[4.5]decane-4-carbodithioate) (S13-6), disulfoton (O,O-diethyl S-2-ethylthioethyl phosphorodithioate) (S13-7), dietholate (O,O-diethyl O-phenyl phosphorothioate) (S13-8), or mephenate (4-chlorophenyl methylcarbamate) (S13-9);

S14) an active compound which, in addition to herbicidal action against harmful plants, also has safener action on crop plants selected from the group consisting of dimepiperate (MY-93, S-1-methyl-1-phenylethylpiperidine-1-carbothioate) used as a safener for rice against damage by the herbicide molinate, daimuron (SK 23, 1-(1-methyl-1-phenylethyl)-3-p-tolylurea) used as a safener for rice against imazosulfuron herbicide damage, cumyluron (JC-940, 3-(2-chlorophenylmethyl)-1-(1-methyl-1-phenylethyl)urea) used as a safener for rice against damage by some herbicides, methoxyphenone (NK 049,3,3'-dimethyl-4-methoxybenzophenone) used as a safener for rice, and CSB (1-bromo-4-(chloromethylsulfonyl) benzene) used as a safener for rice;

S15) a compound of the formula

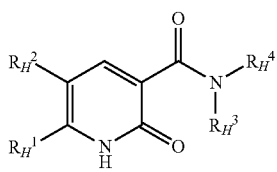

(S15)

where $R_H^1$ is a $(C_1-C_6)$-haloalkyl radical, $R_H^2$ is hydrogen or halogen, $R_H^3$ and $R_H^4$ are each independently hydrogen, $(C_1-C_{16})$-alkyl, $(C_2-C_{16})$-alkenyl or $(C_2-C_{16})$-alkynyl, where each of the latter 3 radicals is unsubstituted or substituted by one or more radicals selected from the group consisting of halogen, hydroxyl, cyano, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-$C_4$)-alkoxy]carbonyl, [$(C_1-C_4)$-haloalkoxy]-carbonyl, $(C_3-C_6)$-cycloalkyl which is unsubstituted or substituted, phenyl which is unsubstituted or substituted, and heterocyclyl which is unsubstituted or substituted, or $(C_3-C_6)$-cycloalkyl, $(C_4-C_6)$-cycloalkenyl, or $(C_3-C_6)$-cycloalkyl which is fused on one side of the ring to a 4 to 6-membered saturated or unsaturated carbocyclic ring, or $(C_4-C_6)$-cycloalkenyl which is fused on one side of the ring to a 4- to 6-membered saturated or unsaturated carbocyclic ring, where each of the latter 4 radicals is unsubstituted or substituted by one or more radicals selected from the group consisting of halogen, hydroxyl, cyano, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]carbonyl, [$(C_1-C_4)$-haloalkoxy]carbonyl, $(C_3-C_6)$-cycloalkyl which is unsubstituted or substituted, phenyl which is unsubstituted or substituted, and heterocyclyl which is unsubstituted or substituted, or $R_H^3$ is $(C_1-C_4)$-alkoxy, $(C_2-C_4)$-alkenyloxy, $(C_2-C_6)$-alkynyloxy or $(C_2-C_4)$-haloalkoxy and $R_H^4$ is hydrogen or $(C_1-C_4)$-alkyl, or $R_H^3$ and $R_H^4$ together with the directly bonded nitrogen atom are a four- to eight-membered heterocyclic ring which optionally contain further ring heteroatoms selected from the group consisting of N, O and S, and which is unsubstituted or substituted by one or more radicals selected from the group consisting of halogen, cyano, nitro, $(C_1-C_4)$-alkyl, $(C_1-C_4)$-haloalkyl, $(C_1-C_4)$-alkoxy, $(C_1-C_4)$-haloalkoxy and $(C_1-C_4)$-alkylthio; and S16) an active compound which is used primarily as an herbicide but also having safener action on crop plants selected from the group consisting of (2,4-dichlorophenoxy)acetic acid (2,4-D), (4-chlorophenoxy)acetic acid, (R,S)-2-(4-chloro-o-tolyloxy)propionic acid (mecoprop), 4-(2,4-dichlorophenoxy)butyric acid (2,4-DB), (4-chloro-o-tolyloxy)acetic acid (MCPA), 4-(4-chloro-o-tolyloxy)butyric acid, 4-(4-chlorophenoxy)butyric acid, 3,6-dichloro-2-methoxybenzoic acid (digamma), and 1-(ethoxycarbonyl)ethyl 3,6-dichloro-2-methoxybenzoate (lactidichlor-ethyl).

9. A method for controlling unwanted vegetation, comprising allowing a composition as claimed in claim 8 to act on a plant or surroundings thereof.

10. A composition as claimed in claim 8, capable of being used for controlling unwanted vegetation.

11. A method for controlling unwanted vegetation, comprising applying in close temporal succession on a plant or surroundings thereof a pesticide and/or herbicide and/or fungicide as claimed in claim 1 and at least one crop plant compatibility-improving compound selected from the group consisting of S1) a compound of the formula

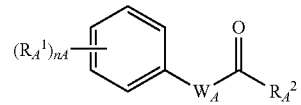

(S1)

where
- $n_A$ is a natural number from 0 to 5,
- $R_A^1$ is halogen, $(C_1\text{-}C_4)$-alkyl, $(C_1\text{-}C_4)$-alkoxy, nitro or $(C_1\text{-}C_4)$-haloalkyl,
- $W_A$ is an unsubstituted or substituted divalent heterocyclic radical selected from the group consisting of the partially unsaturated or aromatic five-membered heterocycles having 1 to 3 ring heteroatoms of the N or O type, where at least one nitrogen atom and at most one oxygen atom is present in the ring,
- $m_A$ is 0 or 1,
- $R_A^2$ is $OR_A^3$, $SR_A^3$ or $NR_A^3 R_A^4$ or a saturated or unsaturated 3- to 7-membered heterocycle having at least one nitrogen atom and up to 3 heteroatoms selected from the group consisting of O and S, which is joined to the carbonyl group in (S1) via the nitrogen atom and is unsubstituted or substituted by radicals selected from the group consisting of $(C_1\text{-}C_4)$-alkyl, $(C_1\text{-}C_4)$-alkoxy or optionally substituted phenyl,
- $R_A^3$ is hydrogen or an unsubstituted or substituted aliphatic hydrocarbyl radical having a total of 1 to 18 carbon atoms,
- $R_A^4$ is hydrogen, $(C_1\text{-}C_6)$-alkyl, $(C_1\text{-}C_6)$-alkoxy or substituted or unsubstituted phenyl,
- $R_A^5$ is H, $(C_1\text{-}C_8)$-alkyl, $(C_1\text{-}C_8)$-haloalkyl, $(C_1\text{-}C_4)$-alkoxy-$(C_1\text{-}C_8)$-alkyl, cyano or $COOR_A^9$, where is hydrogen, $(C_1\text{-}C_8)$-alkyl, $(C_1\text{-}C_8)$-haloalkyl, $(C_1\text{-}C_4$ alkoxy-$(C_1\text{-}C_4)$-alkyl, $(C_1\text{-}C_6)$-hydroxyalkyl, $(C_3\text{-}C_{12})$-cycloalkyl or tri-$(C_1\text{-}C_4)$-alkylsilyl, and
- $R_A^6$, $R_A^7$, and $R_A^8$ are identical or different and are hydrogen, $(C_1\text{-}C_8)$-alkyl, $(C_1\text{-}C_8)$-haloalkyl, $(C_3\text{-}C_{12})$-cycloalkyl or substituted or unsubstituted phenyl;

S2) a compound of the formula

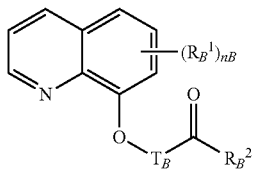

(S2)

where
- $R_B^1$ is halogen, $(C_1\text{-}C_4)$-alkyl, $(C_1\text{-}C_4)$-alkoxy, nitro or $(C_1\text{-}C_4)$-haloalkyl,
- $n_B$ is a natural number from 0 to 5,
- $R_B^2$ is $OR_B^3$, $SR_B^3$ or $NR_B^3 R_B^4$ or a saturated or unsaturated 3- to 7-membered heterocycle having at least one nitrogen atom and up to 3 heteroatoms selected from the group consisting of O and S, which is joined to the carbonyl group in (S2) via the nitrogen atom and is unsubstituted or substituted by radicals selected from the group consisting of $(C_1\text{-}C_4)$-alkyl, $(C_1\text{-}C_4)$-alkoxy or optionally substituted phenyl,
- $R_B^3$ is hydrogen or an unsubstituted or substituted aliphatic hydrocarbyl radical having a total of 1 to 18 carbon atoms,
- $R_B^4$ is hydrogen, $(C_1\text{-}C_6)$-alkyl, $(C_1\text{-}C_6)$-alkoxy or substituted or unsubstituted phenyl; and
- $T_B$ is a ($C_1$ or $C_2$)-alkanediyl chain which is unsubstituted or substituted by one or two $(C_1\text{-}C_4)$-alkyl radicals or by [$(C_1\text{-}C_3)$-alkoxy]carbonyl;

S3) a compound of the formula

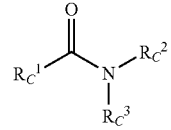

(S3)

where
- $R_C^1$ is $(C_1\text{-}C_4)$-alkyl, $(C_1\text{-}C_4)$-haloalkyl, $(C_2\text{-}C_4)$-alkenyl, $(C_2\text{-}C_4)$-haloalkenyl or $(C_3\text{-}C_7)$-cycloalkyl, and
- $R_C^2$ and $R_C^3$ are identical or different and are hydrogen, $(C_1\text{-}C_4)$-alkyl, $(C_2\text{-}C_4)$-alkenyl, $(C_2\text{-}C_4)$-alkynyl, $(C_1\text{-}C_4)$-haloalkyl, $(C_2\text{-}C_4)$-haloalkenyl, $(C_1\text{-}C_4)$-alkylcarbamoyl-$(C_1\text{-}C_4)$-alkyl, $(C_2\text{-}C_4)$-alkenylcarbamoyl-$(C_1\text{-}C_4)$alkyl, $(C_1\text{-}C_4)$-alkoxy-$(C_1\text{-}C_4)$-alkyl, dioxolanyl-$(C_1\text{-}C_4)$-alkyl, thiazolyl, furyl, furylalkyl, thienyl, piperidyl, or substituted or unsubstituted phenyl, or $R_C^2$ and $R_C^3$ together form a substituted or unsubstituted heterocyclic ring, S4) a compound of the formula

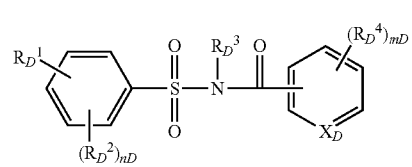

(S4)

where
- $X_D$ is CH or N,
- $R_D^1$ is CO—$NR_D^5 R_D^6$ or NHCO—$R_D^7$,
- $R_D^2$ is halogen, $(C_1\text{-}C_4)$-haloalkyl, $(C_1\text{-}C_4)$-haloalkoxy, nitro, $(C_1\text{-}C_4)$-alkyl, $(C_1\text{-}C_4)$-alkoxy, $(C_1\text{-}C_4)$-alkylsulfonyl, $(C_1\text{-}C_4)$-alkoxycarbonyl or $(C_1\text{-}C_4)$-alkylcarbonyl,
- $R_D^3$ is hydrogen, $(C_1\text{-}C_4)$-alkyl, $(C_2\text{-}C_4)$-alkenyl or $(C_2\text{-}C_4)$-alkynyl,
- $R_D^4$ is halogen, nitro, $(C_1\text{-}C_4)$-alkyl, $(C_1\text{-}C_4)$-haloalkyl, $(C_1\text{-}C_4)$-haloalkoxy, $(C_3\text{-}C_6)$-cycloalkyl, phenyl, $(C_1\text{-}C_4)$-alkoxy, cyano, $(C_1\text{-}C_4)$-alkylthio, $(C_1\text{-}C_4)$-alkylsulfinyl, $(C_1\text{-}C_4)$-alkylsulfonyl, $(C_1\text{-}C_4)$-alkoxycarbonyl or $(C_1\text{-}C_4)$-alkylcarbonyl,
- $R_D^5$ is hydrogen, $(C_1\text{-}C_6)$-alkyl, $(C_3\text{-}C_6)$-cycloalkyl, $(C_2\text{-}C_6)$-alkenyl, $(C_2\text{-}C_6)$-alkynyl, $(C_5\text{-}C_6)$-cycloalkenyl, phenyl or 3- to 6-membered heterocyclyl containing $v_D$ heteroatoms selected from the group consisting of nitrogen, oxygen and sulfur, where the seven latter radicals are each substituted by $v_D$ substituents selected from the group consisting of halogen, $(C_1\text{-}C_6)$-alkoxy, $(C_1\text{-}C_6)$-haloalkoxy, $(C_1\text{-}C_2)$-alkylsulfonyl, $(C_3\text{-}C_6)$-cycloalkyl, $(C_1\text{-}C_4)$-alkoxycarbonyl, $(C_1\text{-}C_4)$-alkylcarbonyl and phenyl, and in the case of cyclic radicals also $(C_1\text{-}C_4)$-alkyl and $(C_1\text{-}C_4)$-haloalkyl,
- $R_D^6$ is hydrogen, $(C_1\text{-}C_6)$-alkyl, $(C_2\text{-}C_6)$-alkenyl or $(C_2\text{-}C_6)$-alkynyl, where the three latter radicals are each substituted by $v_D$ radicals selected from the group consisting of halogen, hydroxyl, $(C_1\text{-}C_4)$-alkyl, $(C_1\text{-}C_4)$-alkoxy and $(C_1\text{-}C_4)$-alkylthio, or
- $R_D^5$ and $R_D^6$ together with the nitrogen atom which bears them form a pyrrolidinyl or piperidinyl radical, $R_D^7$ is hydrogen, $(C_1-C_4)$-alkylamino, di-$(C_1-C_4)$-alkylamino, $(C_1-C_6)$-alkyl, or $(C_3-C_6)$-cycloalkyl, where the 2 latter radicals are substituted by $v_D$ substituents selected from the group consisting of halogen, $(C_1-C_4)$-alkoxy, $(C_1-C_6)$-haloalkoxy and $(C_1-C_4)$-alkylthio, and in the case of cyclic radicals also $(C_1-C_4)$-alkyl and $(C_1-C_4)$-haloalkyl, $n_D$ is 0, 1 or 2, $m_D$ is 1 or 2, and $v_D$ is 0, 1, 2 or 3;

S5) a hydroxyaromatic or aromatic-aliphatic carboxylic acid derivative (S5) selected from the group consisting of ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicylic acid, 2-hydroxycinnamic acid, 1,2-dihydro-2-oxo-6-trifluoromethylpyridine-3-carboxamide, and 2,4-dichlorocinnamic acid;

S6) a 1,2-dihydroquinoxalin-2-one (S6) selected from the group consisting of 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-[2-(diethylamino)ethyl]-6,7-dimethyl-3-thiophen-2-ylquinoxalin-2(1H)-one, and 1-(2-methylsulfonylaminoethyl)-3-(2-thienyl)-1,2-dihydroquinoxalin-2-one;

S7) a compound of the formula

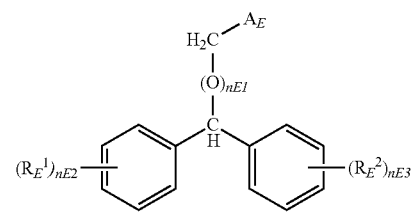

(S7)

where $R_E^1$, $R_E^2$ are each independently of one another halogen, $(C_1-C_4)$-alkyl, $(C_1-C_4)$-alkoxy, $(C_1-C_4)$-haloalkyl, $(C_1-C_4)$-alkylamino, di-$(C_1-C_4)$-alkylamino or nitro;

$A_E$ is $COOR_E^3$ or $COSR_E^4$, $R_E^3$, $R_E^4$ are each independently of one another hydrogen, $(C_1-C_4)$-alkyl, $(C_2-C_6)$-alkenyl, $(C_2-C_4)$-alkynyl, cyanoalkyl, $(C_1-C_4)$-haloalkyl, phenyl, nitrophenyl, benzyl, halobenzyl, pyridinylalkyl or alkylammonium, $n_E^1$ is 0 or 1, and $n_E^2$, $n_E^3$ are each independently of one another 0, 1 or 2;

S8) a compound of the formula

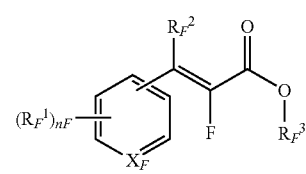

(S8)

where $X_F$ is CH or N, $n_F$ in the case that $X_F$=N is an integer from 0 to 4 and in the case that $X_F$=CH is an integer from 0 to 5, $R_F^1$ is halogen, $(C_1-C_4)$-alkyl, $(C_1-C_4)$-haloalkyl, $(C_1-C_4)$-alkoxy, $(C_1-C_4)$-haloalkoxy, nitro, $(C_1-C_4)$-alkylthio, $(C_1-C_4)$-alkylsulfonyl, $(C_1-C_4)$-alkoxycarbonyl, optionally substituted phenyl, or optionally substituted phenoxy, $R_F^2$ is hydrogen or $(C_1-C_4)$-alkyl, and $R_F^3$ is hydrogen, $(C_1-C_8)$-alkyl, $(C_2-C_4)$-alkenyl, $(C_2-C_4)$-alkynyl, or aryl, where each of the aforementioned carbon-containing radicals is unsubstituted or substituted by one or more identical or different radicals selected from the group consisting of halogen and alkoxy, or salts thereof;

S9) a 3-(5-tetrazolylcarbonyl)-2-quinolone (S9) selected from the group consisting of 1,2-dihydro-4-hydroxy-1-ethyl-3-(5-tetrazolylcarbonyl)-2-quinolone and 1,2-dihydro-4-hydroxy-1-methyl-3-(5-tetrazolylcarbonyl)-2-quinolone;

S10) a compound of the formula

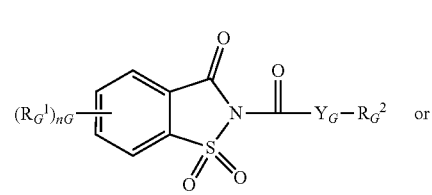

(S10a)

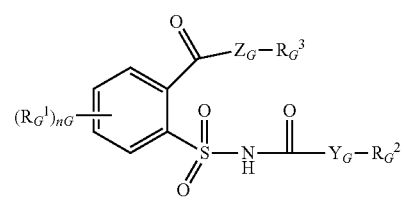

(S10b)

where $R_G^1$ is halogen, $(C_1-C_4)$-alkyl, methoxy, nitro, cyano, $CF_3$, or $OCF_3$, $Y_G$ and $Z_G$ are each independently of one another O or S, $n_G$ is an integer from 0 to 4, $R_G^2$ is $(C_1-C_{16})$-alkyl, $(C_2-C_6)$-alkenyl, $(C_3-C_6)$-cycloalkyl, aryl, benzyl, or halobenzyl, and $R_G^3$ is hydrogen or $(C_1-C_6)$-alkyl;

S11) an oxyimino compound (S11) seed dressing selected from the group consisting of oxabetrinil ((Z)-1,3-dioxolan-2-ylmethoxyimino(phenyl)acetonitrile) (S11-1) used as seed dressing safener for millet against metolachlor damage, fluxofenim (1-(4-chlorophenyl)-2,2,2-trifluoro-1-ethanone O-(1,3-dioxolan-2-ylmethyl) oxime) (S11-2) used as seed dressing safener for millet against metolachlor damage, and cyometrinil (CGA-43089, (Z)-cyanomethoxyimino(phenyl)acetonitrile) (S11-3) used as seed dressing safener for millet against metolachlor damage;

S12) an isothiochromanone (S12) that is methyl [(3-oxo-1H-2-benzothiopyran-4(3H)-ylidene)methoxy]acetate (S12-1);

S13) naphthalic anhydride (1,8-naphthalenedicarboxylic anhydride) (S13-1) used as seed dressing safener for corn against thiocarbamate herbicide damage, fenclorim (4,6-dichloro-2-phenylpyrimidine) (S13-2) used as safener for pretilachlor in sown rice, flurazole (benzyl 2-chloro-4-trifluoromethyl-1,3-thiazole-5-carboxylate)

(S13-3) used as seed dressing safener for millet against alachlor and metolachlor damage, CL 304415 (4-carboxy-3,4-dihydro-2H-1-benzopyran-4-acetic acid) (S13-4) used as a safener for corn against damage by imidazolinones, MG 191 (2-dichloromethyl-2-methyl-1,3-dioxolane) (S13-5)) used as a safener for corn, MG-838 (2-propenyl 1-oxa-4-azaspiro[4.5]decane-4-carbodithioate) (S13-6), disulfoton (O,O-diethyl S-2-ethylthioethyl phosphorodithioate) (S13-7), diethoate (O,O-diethyl 0-phenyl phosphorothioate) (S13-8), or mephenate (4-chlorophenyl methylcarbamate) (S13-9);

S14) an active compound which, in addition to herbicidal action against harmful plants, also has safener action on crop plants selected from the group consisting of dimepiperate (MY-93, S-1-methyl-1-phenylethylpiperidine-1-carbothioate) used as a safener for rice against damage by the herbicide molinate, daimuron (SK 23, 1-(1-methyl-1-phenylethyl)-3-p-tolylurea) used as a safener for rice against imazosulfuron herbicide damage, cumyluron (JC-940, 3-(2-chlorophenylmethyl)-1-(1-methyl-1-phenylethyl)urea) used as a safener for rice against damage by some herbicides, methoxyphenone (NK 049,3, 3'-dimethyl-4-methoxybenzophenone) used as a safener for rice, and CSB (1-bromo-4-(chloromethylsulfonyl)benzene) used as a safener for rice;

S15) a compound of the formula

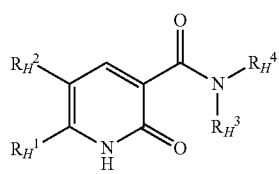

(S15)

where $R_H^1$ is a $(C_1-C_6)$-haloalkyl radical, $R_H^2$ is hydrogen or halogen, $R_H^3$ and $R_H^4$ are each independently hydrogen, $(C_1-C_{16})$-alkyl, $(C_2-C_{16})$-alkenyl or $(C_2-C_{16})$-alkynyl, where each of the latter 3 radicals is unsubstituted or substituted by one or more radicals selected from the group consisting of halogen, hydroxyl, cyano, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]carbonyl, [$(C_1-C_4)$-haloalkoxy]-carbonyl, $(C_3-C_6)$-cycloalkyl which is unsubstituted or substituted, phenyl which is unsubstituted or substituted, and heterocyclyl which is unsubstituted or substituted, or $(C_3-C_6)$-cycloalkyl, $(C_4-C_6)$-cycloalkenyl, or $(C_3-C_6)$-cycloalkyl which is fused on one side of the ring to a 4 to 6-membered saturated or unsaturated carbocyclic ring, or $(C_4-C_6)$-cycloalkenyl which is fused on one side of the ring to a 4- to 6-membered saturated or unsaturated carbocyclic ring, where each of the latter 4 radicals is unsubstituted or substituted by one or more radicals selected from the group consisting of halogen, hydroxyl, cyano, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]carbonyl, [$(C_1-C_4)$-haloalkoxy]carbonyl, $(C_3-C_6)$-cycloalkyl which is unsubstituted or substituted, phenyl which is unsubstituted or substituted, and heterocyclyl which is unsubstituted or substituted, or $R_H^3$ is $(C_1-C_4)$-alkoxy, $(C_2-C_4)$-alkenyloxy, $(C_2-C_6)$-alkynyloxy or $(C_2-C_4)$-haloalkoxy and $R_H^4$ is hydrogen or $(C_1-C_4)$-alkyl, or $R_H^3$ and $R_H^4$ together with the directly bonded nitrogen atom are a four- to eight-membered heterocyclic ring which optionally contain further ring heteroatoms selected from the group consisting of N, O and S, and which is unsubstituted or substituted by one or more radicals selected from the group consisting of halogen, cyano, nitro, $(C_1-C_4)$-alkyl, $(C_1-C_4)$-haloalkyl, $(C_1-C_4)$-alkoxy, $(C_1-C_4)$-haloalkoxy and $(C_1-C_4)$-alkylthio; and S16) an active compound which is used primarily as an herbicide but also having safener action on crop plants selected from the group consisting of (2,4-dichlorophenoxy)acetic acid (2,4-D), (4-chlorophenoxy)acetic acid, (R,S)-2-(4-chloro-o-tolyloxy)propionic acid (mecoprop), 4-(2,4-dichlorophenoxy)butyric acid (2,4-DB), (4-chloro-o-tolyloxy)acetic acid (MCPA), 4-(4-chloro-o-tolyloxy)butyric acid, 4-(4-chlorophenoxy)butyric acid, 3,6-dichloro-2-methoxybenzoic acid (digamma), and 1-(ethoxycarbonyl)ethyl 3,6-dichloro-2-methoxybenzoate (lactidichlor-ethyl).

12. The pesticide and/or herbicide and/or fungicide as claimed in claim 1, in which D is NH.

13. The pesticide and/or herbicide and/or fungicide as claimed in claim 1, in which W represents methyl,
X represents methyl,
Y represents hydrogen,
Z represents the radical

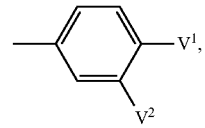

$V^1$ represents fluorine,
$V^2$ represents hydrogen,
A and B each represents fluorine attached to the same carbon atom in the 4'-position,
D represents NH, and
G represents hydrogen.

* * * * *